(12) United States Patent
Fairlie et al.

(10) Patent No.: US 9,586,914 B2
(45) Date of Patent: Mar. 7, 2017

(54) MODULATORS OF C3A RECEPTORS

(71) Applicant: THE UNIVERSITY OF QUEENSLAND, Queensland (AU)

(72) Inventors: David Fairlie, Mt Ommaney (AU); Robert C. Reid, Chelmer (AU)

(73) Assignee: THE UNIVERSITY OF QUEENSLAND, St. Lucia, Queensland (AU)

( * ) Notice: Subject to any disclaimer, the term of this patent is extended or adjusted under 35 U.S.C. 154(b) by 5 days.

(21) Appl. No.: 14/356,821

(22) PCT Filed: Nov. 7, 2012

(86) PCT No.: PCT/AU2012/001364
§ 371 (c)(1),
(2) Date: May 7, 2014

(87) PCT Pub. No.: WO2013/067578
PCT Pub. Date: May 16, 2013

(65) Prior Publication Data
US 2014/0302069 A1    Oct. 9, 2014

(30) Foreign Application Priority Data
Nov. 7, 2011 (AU) .............................. 2011904606

(51) Int. Cl.
| | |
|---|---|
| C07D 263/34 | (2006.01) |
| C07D 271/06 | (2006.01) |
| C07D 401/12 | (2006.01) |
| C07D 413/06 | (2006.01) |
| C07D 413/12 | (2006.01) |
| C07D 333/38 | (2006.01) |
| C07D 271/10 | (2006.01) |
| C07D 277/56 | (2006.01) |
| C07D 307/68 | (2006.01) |
| C07D 403/12 | (2006.01) |
| C07D 233/90 | (2006.01) |
| A61K 39/39 | (2006.01) |
| A61K 39/00 | (2006.01) |

(52) U.S. Cl.
CPC ............ *C07D 263/34* (2013.01); *A61K 39/39* (2013.01); *C07D 233/90* (2013.01); *C07D 271/06* (2013.01); *C07D 271/10* (2013.01); *C07D 277/56* (2013.01); *C07D 307/68* (2013.01); *C07D 333/38* (2013.01); *C07D 401/12* (2013.01); *C07D 403/12* (2013.01); *C07D 413/06* (2013.01); *C07D 413/12* (2013.01); *A61K 2039/55511* (2013.01)

(58) Field of Classification Search
CPC .. C07D 263/34; C07D 271/06; C07D 401/12; C07D 413/06; C07D 413/12; C07D 333/38; C07D 271/10; C07D 277/56; C07D 307/68; C07D 403/12; C07D 233/90
See application file for complete search history.

(56) References Cited

U.S. PATENT DOCUMENTS

| | | | |
|---|---|---|---|
| 2005/0147605 A1* | 7/2005 | Rosen ..................... | C07K 16/28 424/143.1 |
| 2008/0188528 A1* | 8/2008 | Biediger .............. | C07D 213/81 514/341 |

FOREIGN PATENT DOCUMENTS

| | | |
|---|---|---|
| WO | WO 00/20358 | 4/2000 |
| WO | WO 2008/079371 | 7/2008 |
| WO | WO 2008079371 A1 * | 7/2008 |

OTHER PUBLICATIONS

Denonne et al. Bioorg. Med. Chen. Lett. 2007, 17, 3258-3261.*
CAS Registry Entry for Registry No. 1038820-58-4, which entered STN on Aug. 5, 2008.*
Patani et al. Chem. Rev. 1996, 96, 3147-3176.*
IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins. ISBN 0-9678550-9-8. doi:10.1351/goldbook.*
CAS Registry No. 1039622-79-1, which entered STN on Aug. 8, 2008.*
CAS Regsitry No. 1039628-57-3, which entered STN on Aug. 8, 2008.*
International Search Report for PCT/AU2012/001364 mailed Dec. 11, 2012.
Denonne, F. et al."Discovery of New C3aR Ligands. Part 1: Arginine Derivatives", Bioorganic & medicinal Chemistry Letters (2007), 17 (12), pp. 3258-3326.
CAS Registry No. 1039750-92-9. STN Entry Date Aug. 10, 2008.
CAS Registry No. 1041857-88-8, STN Entry Date Aug. 19, 2008.
C. Scully et al., "Selective Hexapeptide Agonists and Antagonists for Human Complement C3a Receptor", J. Med. Chem. (2010), 53(13), pp. 4398-4948.
International Preliminary Report on Patentability dated Mar. 14, 2014.
Denonne, F., et al., "Discovery of New C3aR Ligands. Part 1: Arginine Derivatives," Bioorganic & Medicinal Chemistry Letters (2007), 17 (12), pp. 3258-3261.
CAS Registry No. 1039750-92-9. STN Entry Date Aug. 10, 2008 see compound.
CAS Registry No. 1041857-88-8, STN Entry Date Aug. 19, 2008 see compound.
Scully, C. et al., "Selective Hexapeptide Agonists and Antagonists for Human Complement C3a Receptor," J. Med. Chem. (2010), 53(13), pp. 4938-4948.
Boos, Laura et al., "Deletion of the Complement Anaphylatoxin C3a Receptor Attenuates, Whereas Ectopic Expression of C3a in the Brain Exacerbates, Experimental Autoimmune Encephalomyelitis," The Journal of Immunology 2004; vol. 173, pp. 4708-4714.

(Continued)

*Primary Examiner* — Matthew Coughlin
(74) *Attorney, Agent, or Firm* — Nixon & Vanderhye P.C.

(57) ABSTRACT

Heterocyclic compounds that modulate C3a receptors and their use in the treatment or prevention of inflammatory diseases, infectious diseases, cancers, metabolic disorders, obesity, type 2 diabetes, metabolic syndrome and associated cardiovascular diseases are described. The use of the compounds in stimulating or suppressing an immune response is also described together with pharmaceutical compositions comprising the compounds or their pharmaceutically acceptable salts.

26 Claims, 15 Drawing Sheets

(56) References Cited

OTHER PUBLICATIONS

Boos, Laura et al., "C3a Expressed in the Central Nervous System Protects Against LPS-Induced Shock," Neuroscience Letters 387 (2005), pp. 68-71.
Drouin, Scott M. et al., "Cutting Edge: The Absence of C3 Demonstrates a Role for Complement in Th2 Effector Functions in a Murine Model of Pulmonary Allergy," The Journal of Immunology 2001, vol. 167, pp. 4141-4145.
Drouin, Scott M. et al., "Absence of the Complement Anaphylatoxin C3a Receptor Suppresses Th2 Effector Functions in a Murine Model of Pulmonary Allergy," The Journal of Immunology 2002, vol. 169, pp. 5926-5933.
Engström, G. et al., "Weight Gain in Relation to Plasma Levels of Complement Factor 3: Results from a Population-Based Cohort Study," Diabetologia (2005) vol. 48, pp. 2525-2531.
Garrett, Matthew C. et al., "Synergistic Neuroprotective Effects of C3a and C5a Receptor Blockage Following Intracerebral Hemorrhage," Brain Research 1298 (2009), pp. 171-177.
Hernández, Delia et al., "Synthesis of IB-01211, a Cyclic Peptide Containing 2,4-Concatenated Thia- and Oxazoles, via Hantsch Macrocyclization," Organic Letters, vol. 9, No. 5, 2007, pp. 809-811.
Humbles, Alison A. et al., "A Role for the C3a Anaphylatoxin Receptor in the Effector Phase of Asthma," Nature, vol. 406, Aug. 31, 2000, pp. 998-1001.
Hutamekalin, Pilaiwanwadee et al., "Effect of the C3a-Receptor Antagonist SB 290157 on Anti-OVA Polyclonal Antibody-Induced Arthritis," Journal of Pharmacological Sciences, vol. 112, 2010, pp. 56-63.
Jacob, A. et al., "C3aR Inhibition Reduces Neurodegeneration in Experimental Lupus," Lupus 2010, vol. 19, Nov. 9, 2009, pp. 73-82.
Kawamoto, Seiji et al., "The Anaphylatoxin C3a Downregulates the Th2 Response to Epicutaneously Introduced Antigen," The Journal of Clinical Investigation, vol. 114, No. 3, Aug. 2004, pp. 399-407.
Kildsgaard, Jens et al., "Cutting Edge: Targeted Disruption of the C3a Receptor Gene Demonstrates a Novel Protective Anti-Inflammatory Role for C3a in Endotoxin-Shock," The Journal of Immunology 2000, vol. 165, pp. 5406-5409.
Kirschfink, Michael, "Targeting Complement in Therapy," Immunological Reviews 2001, vol. 180, pp. 177-189.
Malmsten, Martin et al., "Antimicrobial C3a—Biology, Biophysics, and Evolution," 2007, pp. 141-158.
Mamane, Yaël et al., "The C3a Anaphylatoxin Receptor is a Key Mediator of Insulin Resistance and Functions by Modulating Adipose Tissue Macrophage Infiltration and Activation," Diabetes, vol. 58, Sep. 2009, pp. 2006-2017.
Masters, Seth L. et al., "Horror Autoinflammaticus: The Molecular Pathophysiology of Autoinflammatory Disease," Annu. Rev. Immunol. 2009, vol. 27, pp. 621-668 and 3 Contents pages.
Mizutani, Nobuaki et al., "Complement C3a Regulates Late Asthmatic Response and Airway Hyperresponsiveness in Mice," The Journal of Immunology, vol. 183, Aug. 14, 2009, pp. 4039-4046.
Mocco, J. et al., "Complement Component C3 Mediates Inflammatory Injury Following Focal Cerebral Ischemia," Circulation Research, vol. 99, Jun. 15, 2006, pp. 209-217.
Mueller-Ortiz, Stacey L. et al., "Ablation of the Complement C3a Anaphylatoxin Receptor Causes Enhanced Killing of *Pseudomonas aeruginosa* in a Mouse Model of Pneumonia," Am. J. Physiol. Lung Cell Mol. Physiol., vol. 291, Feb. 3, 2006, pp. L157-L165.
Nordahl, Emma Andersson et al., "Activation of the Complement System Generates Antibacterial Peptides," Proceedings of the National Academy of Sciences of the United States of America, vol. 101, No. 48, Nov. 30, 2004, pp. 16879-16884.
Pasupuleti, Mukesh et al., "Rational Design of Antimicrobial C3a Analogues with Enhanced Effects Against Staphylococci Using an Integrated Structure and Function-Based Approach," Biochemistry 2008, Vo. 47, No. 35, pp. 9057-9070.
Patani, George A. et al., "Bioisosterism: A Rational Approach in Drug Design," Chemical Reviews, vol. 96, No. 8, 1996, pp. 3147-3176.
Péterfy, Hajna et al., "C3a-Derived Peptide Binds to the Type I FcεR and Inhibits Proximal-Coupling Signal Processes and Cytokine Secretion by Mast Cells," International Immunology, vol. 20, No. 10, Jul. 24, 2008, pp. 1239-1245.
Peterlin-Mašič et al., "Arginine Mimetics," Tetrahedron 57, 2001, pp. 7073-7105.
Phillips, Andrew J. et al., "Synthesis of Functionalized Oxazolines and Oxazoles with DAST and Deoxo-Fluor," Organic Letters, vol. 2, No. 8, 2000, pp. 1165-1168.
Phillips, Catherine M. et al., "Complement Component 3 Polymorphisms Interact with Polyunsaturated Fatty Acids to Modulate Risk of Metabolic Syndrome," The American Journal of Clinical Nutrition 2009, vol. 90, pp. 1665-1673.
Rahpeymai, Yalda et al., "Complement: A Novel Factor in Basal and Ischemia-Induced Neurogenesis," The EMBO Journal, vol. 25, No. 6, 2006, pp. 1364-1374.
Rynkowski, Michael A. et al., "C3a Receptor Antagonist Attenuates Brain Injury After Intracerebral Hemorrhage," Journal of Cerebral Blood Flow & Metabolism, vol. 29, 2009, pp. 98-107.
Sonesson, Andreas et al., "Antifungal Activity of C3a and C3a-Derived Peptides Against *Candida*," Biochimica et Biophysica Acta 1768, 2007, pp. 346-353.
Tang, Ziyong et al., "C3a Mediates Epithelial-to-Mesenchymal Transition in Proteinuric Nephropathy," Journal Am. Soc. Nephrol 20, 2009, pp. 593-603.
Van Oostrom, Antonie J.H.H.M. et al., "The Metabolic Syndrome in Relation to Complement Component 3 and Postprandial Lipemia in Patients From an Outpatient Lipid Clinic and Healthy Volunteers," Atherosclerosis 190, 2007, pp. 167-173.
Wagner, Björn et al., "Rational Design of Bacitracin A Derivatives by Incorporating Natural Product Derived Heterocycles," Journal Am. Chem. Soc., vol. 128, No. 32, 2006, pp. 10513-10520.
Wenderfer, Scott E. et al., "C3a Receptor Deficiency Accelerates the Onset of Renal Injury in the MRL/IPR Mouse," Molecular Immunology 46, 2009, pp. 1397-1404.
Zipfel, Peter F. et al., "Complement Regulators and Inhibitory Proteins," Nature Reviews Immunology, vol. 9, Oct. 2009, pp. 729-740.

* cited by examiner

A

B

A

B

C

A

B

A

A. 250 sec

B. 280 Sec

B. Antagonism

MODULATORS OF C3A RECEPTORS

This application is the U.S. national phase of International Application No. PCT/AU2012/001364 filed 7 Nov. 2012 which designated the U.S. and claims priority to AU 2011904606 filed 7 Nov. 2011, the entire contents of each of which are hereby incorporated by reference.

FIELD OF THE INVENTION

The present invention relates to heterocyclic compounds that modulate C3a receptors and their uses in the treatment or prevention of inflammatory diseases, infectious diseases, cancers, metabolic disorders, obesity, type 2 diabetes, metabolic syndrome and associated cardiovascular diseases or other conditions where C3a is a key mediator of pathogenesis. Their use in stimulating or suppressing an immune response is also described together with pharmaceutical compositions comprising the compounds or their pharmaceutically acceptable salts.

BACKGROUND OF THE INVENTION

Complement is a network of plasma proteins that mediates innate and adaptive immunity by effecting the recognition, opsonization, destruction, and removal of pathogens and infected or damaged cells. During host defense, inflammatory and cellular immune responses to foreign stimuli, infectious organisms, injury, radiation; and neoplasia are initiated by proteolytic activation of the complement network. Among complement activation products is the protein C3a that binds to a specific G protein-coupled receptor (C3aR) on immune cells and induces chemotaxis, inflammatory signaling, increased vasopermeability, vasodilation, release of cytokines and proinflammatory mediators, and immunological defense against infection, injury and cancer. Further, this protein is involved in non-immunological processes, such as hematopoiesis, tissue regeneration, angiogenesis, and lipid metabolism, as well as others.

Overexpression of C3a or its receptor C3aR has been implicated in the pathogenesis and progression of inflammatory diseases including asthma, allergies, sepsis, lupus erythematosus, type 2 diabetes, arthritis, psoriasis, nephropathy, autoimmune diseases, ischemia-reperfusion injury, multiple forms of shock, psoriasis, multiple sclerosis, fibrosis, glomerulonephritis, inflammatory bowel diseases, atherosclerosis, cystic fibrosis, stroke, metabolic syndrome (including obesity, type 2 diabetes and cardiovascular diseases) and others [Kildsgaard et al., 2000; Kawamoto et al., 2004; Wenderfer et al., 2009; Humbles et al., 2000; Mocco et al., 2006; Jacob et al., 2009; Mizutani et al., 2009; Mamane et al., 2009 (b); Garrett et al., 2009; Tang et al., 2009; Rynkowski et al., 2009, Hutamekalin et al., 2010]. C3a or the C3a receptor may also be important in immunological and autoimmune conditions that could lead to other chronic conditions including chronic inflammatory, neurodegenerative and cardiovascular diseases and cancers. For these and other inflammatory diseases, an antagonist of C3a receptor might be of therapeutic benefit if it blocks interaction of C3a with its G protein coupled receptor on the surface of immune cells and other cell types.

On the other hand, by virtue of the known induction of the release of proinflammatory cytokines, chemokines and other proinflammatory mediators, [Zipfel & Skerka, 2009; Masters et al., 2009; Kirschfink, 2001; Drouin et al., 2001; Drouin et al., 2002; Boos et al., 2004; Boos et al., 2005; Mueller-Ortiz et al., 2006; Rahpeymai et al., 2006; Kildsgaard et al., 2000; Kawamoto et al., 2004; Wenderfer et al., 2009; Humbles et al., 2000; Mocco et al., 2006; Jacob et al., 2009; Mizutani et al., 2009; Mamane et al., 2009 (b); Garrett et al., 2009; Tang et al., 2009; Rynkowski et al., 2009, Hutamekalin et al., 2010; Malmsten & Schtmdtchen, 2007]. C3a and small molecule agonists can be beneficial in a wide range of medical conditions. For example, a C3a agonist may act as an immunostimulant in promoting release of proinflammatory agents that contribute to the immune response. In individuals that are immunosuppressed or compromised by infection or disease, C3a agonists may exert beneficial inflammation that can augment under-performing immune systems. C3a agonists may therefore be valuable in regulating consequences of antibody-antigen interactions, stimulating or augmenting vaccine like responses associated with priming the immune response to infection, cell tissue damage or other inflammatory stimuli. In addition, antimicrobial and antifungal properties have also been reported for C3a derived peptides [Malmsten & Schtmdtchen, 2007]. The 21-residue C-terminus of C3a and the 20-residue C-terminus of C3adesArg are also antibacterial against *E. faecalis* and *P. aeruginosa*, [Nordahl et al., 2004] *Escherichia coli* and *Staphylococcus aureus*, [Pasupuleti et al., 2008] and antifungal against *Candida Albicans* [Sonesson et al., 2007]. Two nonapeptide derivatives of the C3a C-terminus interfere with intracellular $Ca^{2+}$ release and ERK 12 phosphorylation by binding to and promoting phosphorylation of type 1 Fc epsilon receptor in mast cells [Peterfy et al., 2008].

In another context, complement activation is also important for development of immunity in adipose tissue and endocrine organs, which express and secrete numerous inflammatory proteins including complement factors B, H and C3. Plasma C3 (but not C3a or C3a receptor) has even been suggested as a correlative biomarker for obesity, type 2 diabetes, cardiovascular disease, and postprandial increases in serum triglycerides [Engstrom et al., 2005; van Oostrom et al., 2007], while C3 polymorphisms affect metabolic dysfunction [Phillips et al. 2009]. Products of proteolytic cleavage of C3 are the chemotactic and proinflammatory protein C3a and its derivative C3a-desArg (acylation stimulation protein, ASP), which may influence energy storage in adipose tissue, although both the functional responses and receptor specificity of C3a-desArg remain controversial. The receptor for C3a has recently been suggested to be involved in insulin resistance [Mamane et al., 2009 (a)].

Adipose tissue, heart, liver, lung and other organs contain inflammatory cells that also express complement C3a receptor (e.g. macrophages, neutrophils, monocytes, eosinophils, dendritic cells, mast cells and T cells). Macrophages are very important cells in adipose tissue as they infiltrate adipose tissue during chronic obesity, perpetuating inflammation accompanying metabolic dysfunction (Lim et al., FASEB J., 1 Nov. 2012, epublication). T cells and neutrophils also contribute to obesity-associated inflammation but, unlike macrophages, they infiltrate adipose tissue during early obesity. Complement stimulates T cell proliferation and cytokine production independent of serum complement concentration, indicating that local complement production/activation is important in local inflammation and injury. Adipose macrophages in particular act indirectly on adipocytes and may potentially regulate weight changes. Modern diets high in carbohydrates and saturated fats are producing a global human epidemic in obesity, type II diabetes and cardiovascular disease. Metabolic syndrome, which predisposes people to these conditions, is characterized by abdominal obesity, glucose and insulin intolerance, elevated plasma triglycerides and cholesterol, and liver and cardiovascular abnormalities. Obesity and metabolic syndrome are becoming increasingly associated with a state of chronic low-grade inflammation, but the precise nature or importance of this association remains undefined. Energy deficiency through malnutrition or starvation impairs immune responses in mammals, while nutrient overload induces inflammatory responses through cellular stress in the mitochondria, endoplasmic reticulum and other organelles, with chronic inflammatory diseases often associated with premature or more severe metabolic dysfunction. Metabolic defects, such as insulin resistance in muscle and lipid accumulation in liver, can occur even, in pre-obese states without obvious systemic inflammation and even a single high carbohydrate, high fat meal induces oxidative and inflammatory responses in healthy lean people. Disruption of nutrient sensing in the gut alters gut microbiota and immune networks, affecting food intake, storage and metabolism of fatty acids in adipose tissue, and induces obesity and metabolic syndrome. These observations suggest that energy homeostasis is regulated and coordinated by signaling molecules and pathways that are common, or similar, to those in inflammatory networks.

While there has been much research into treatment and prevention of inflammatory diseases, metabolic disorders, obesity and metabolic syndrome, there is a need for new therapies that reduce or stimulate inflammation, reduce obesity and treat or prevent metabolic disorders, metabolic syndrome and associated cardiovascular diseases. C3a antagonists may have beneficial roles in the treatment of metabolic syndrome by virtue of regulating C3a-mediated proinflammatory actions in adipose tissue involving resident adipocytes or infiltrating immune cells such as macrophages, neutrophils, T cells and mast cells which are known to increase in numbers in adipose tissue during chronic obesity.

The present invention is predicted in part on the discovery of small molecule heterocyclic compounds that mimic the C-terminal sequence of human C3a, bind strongly and selectively to the human C3a receptor, and have agonist or antagonist activity at the C3a receptor.

SUMMARY OF THE INVENTION

In a first aspect of the present invention there is provided a compound of formula (I):

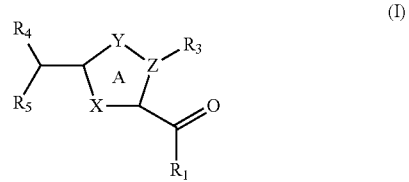

(I)

wherein the ring A is selected from one of the following:

wherein X is N or CH;

Y is O, S, NH, N(C$_{1-3}$alkyl) or CH$_2$; and
Z is N or C, provided that when Z is N, R$_3$ is absent;

wherein X is O, S, NH, N(C$_{1-3}$alkyl) or CH$_2$;
Y is N or CH; and
Z is N or C, provided that when Z is N, R$_3$ is absent;

wherein X is N or CH;
Y is N or CH; and
Z is O, S, N or CH, provided that when Z is O or S, R$_3$ is absent;
R$_1$ is selected from arginine or an arginine mimetic;
R$_3$ is selected from hydrogen, halogen, alkyl, alkenyl, cycloalkyl, cycloalkenyl, aryl, heterocyclyl or heteroaryl;
R$_4$ is selected from hydrogen, alkyl, alkenyl, —(CH$_2$)$_m$cycloalkyl, —(CH$_2$)$_m$aryl, —(CH)$_m$heterocyclyl, —(CH$_2$)$_m$heteroaryl, —(CH$_2$)$_m$NHC(=NH)NH$_2$, —(CF$_2$)$_m$CONH$_2$, —(CH$_2$)$_m$CO$_2$H, —(CH$_2$)$_m$SR$_6$, —(CH$_2$)$_m$NH$_2$ or —(CH$_2$)$_m$OR$_6$;
R$_5$ is selected from alkyl, alkenyl, cycloalkyl, cycloalkenyl, aryl, heterocyclyl, heteroaryl or —NHR$_7$;
R$_6$ is selected from hydrogen, alkyl, cycloalkyl, aryl, heterocyclyl or heteroaryl;
R$_7$ is selected from —C(O)R$_8$, —C(O)OR$_8$, —C(O)NHR$_8$ or —S(O)$_2$R$_8$;
R$_8$ is selected from alkyl, alkenyl, —(CHR$_9$)$_p$cycloalkyl, —(CHR$_9$)$_p$cycloalkenyl, —(CHR$_9$)$_p$aryl, —(CHR$_9$)$_p$heterocyclyl or —(CHR$_9$)$_p$heteroaryl;
R$_9$ is selected from hydrogen, alkyl, alkenyl, cycloalkyl, cycloalkenyl, aryl, heterocyclyl or heteroaryl;
m is 0 or an integer from 1 to 6; and
p is 0 or an integer from 1 to 6;
wherein each cycloalkyl, cycloalkenyl, aryl, heteroaryl and heterocyclyl group may be optionally substituted with one or more optional substituents;
or a pharmaceutically acceptable salt thereof.

In another aspect of the present invention there is provided a pharmaceutical composition comprising a compound of formula (I) or a pharmaceutically acceptable salt thereof and one or more pharmaceutically acceptable carriers, diluents or excipients.

In a further aspect of the invention there is provided a method of modulating C3a receptor comprising exposing the receptor to a compound of formula (I) or a pharmaceutically acceptable salt thereof.

In another aspect of the invention there is provided a method of treating or preventing inflammatory diseases comprising administering to a subject an effective amount of a compound of formula (I) or a pharmaceutically acceptable salt thereof.

In yet a further aspect of the invention there is provided a method of treating or preventing infectious diseases or inflammatory complications arising from infection comprising administering to a subject an effective amount of a compound of formula (I) or a pharmaceutically acceptable salt thereof.

In yet another aspect of the invention there is provided a method of treating or preventing obesity, type 2 diabetes, metabolic dysfunction, metabolic syndrome and associated metabolic and cardiovascular disorders comprising administering to a subject an effective amount of a compound of formula (I) or a pharmaceutically acceptable salt thereof.

In a further aspect of the invention there is provided a method of stimulating an immune response in a subject comprising administering to a subject an effective amount of a compound of formula (I) or a pharmaceutically acceptable salt thereof.

In yet another aspect of the invention there is provided a use of a compound of formula (I) or a pharmaceutically acceptable salt thereof as a vaccine adjuvant.

DESCRIPTION OF THE INVENTION

Definitions

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size or amount that varies by as much as 20%, 15%, 10% or 5% to a reference quantity, level, value, dimension, size or amount.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "alkyl" refers to a straight chain or branched saturated hydrocarbon group having 1 to 10 carbon atoms. Where appropriate, the alkyl group may have a specified number of carbon atoms, for example, $C_{1-6}$alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl, 3-ethylbutyl, heptyl, octyl, nonyl and decyl.

As used herein, the term "alkenyl" refers to a straight-chain or branched hydrocarbon group having one or more double bonds between carbon atoms and having 2 to 10 carbon atoms. Where appropriate, the alkenyl group may have a specified number of carbon atoms. For example, $C_2$-$C_6$ as in "$C_2$-$C_6$alkenyl" includes groups having 2, 3, 4, 5 or 6 carbon atoms in a linear or branched arrangement. Examples of suitable alkenyl groups include, but are not limited to, ethenyl, propenyl, isopropenyl, butenyl, butadienyl, pentenyl, pentadienyl, hexenyl, hexadienyl, heptenyl, octenyl, nonenyl and decenyl.

As used herein, the term "alkynyl" refers to a straight-chain or branched hydrocarbon group having one or more triple bonds and having 2 to 10 carbon atoms. Where appropriate, the alkenyl group may have a specified number of carbon atoms. For example, $C_2$-$C_6$ as in "$C_2$-$C_6$alkynyl" includes groups having 2, 3, 4, 5 or 6 carbon atoms in a linear or branched arrangement. Examples of suitable alkynyl groups include, but are not limited to ethynyl, propynyl, butynyl, pentynyl and hexynyl.

As used herein, the term "cycloalkyl" refers to a saturated cyclic hydrocarbon. The cycloalkyl ring may include a specified number of carbon atoms. For example, a 3 to 8 membered cycloalkyl group includes 3, 4, 5, 6, 7 or 8 carbon atoms. Examples of suitable cycloalkyl groups include, but are not limited to, cyclopropyl, cyclobutyl, cyclopentyl, cyclohexyl, cycloheptyl and cyclooctyl.

As used herein, the term "cycloalkenyl" refers to an unsaturated cyclic hydrocarbon. The cycloalkenyl ring may include a specified number of carbon atoms. For example, a 5 to 8 membered cycloalkenyl group includes 5, 6, 7 or 8 carbon atoms. The cycloalkenyl group has one or more double bonds and when more than one double bond is present, the double bonds may be unconjugated or conjugated, however the cycloalkenyl group is not aromatic. Examples of suitable cycloalkenyl groups include, but are not limited to, cyclopentenyl, cyclohexenyl, cyclohexadienyl, cycloheptenyl, cycloheptadienyl, cycloheptatrienyl, cyclooctenyl, cyclooctadienyl and cyclooctatrienyl rings.

As used herein, the term "aryl" is intended to mean any stable, monocyclic, bicyclic or tricyclic carbon ring system of up to 7 atoms in each ring, wherein at least one ring is aromatic. Examples of such aryl groups include, but are not limited to, phenyl, naphthyl, tetrahydronaphthyl, indanyl, fluorenyl, phenanthrenyl, biphenyl and binaphthyl.

As used herein, the terms "alkylene", "alkenylene" and "alkynylene" refer to a divalent hydrocarbon chain having 1 to 6 carbon atoms and contain no multiple bonds, or 2 to 6 carbon atoms and at least one double bond or at least one triple bond respectively.

As used herein, the term "halogen" or "halo" refers to fluorine (fluoro), chlorine (chloro), bromine (bromo) and iodine (iodo).

The term "heterocyclic" or "heterocyclyl" as used herein, refers to a cyclic hydrocarbon in which one to four carbon atoms have been replaced by heteroatoms independently selected from the group consisting of N, N(R), S, S(O), $S(O)_2$ and O. A heterocyclic ring may be saturated or unsaturated. Examples of suitable heterocyclyl groups include tetrahydrofuranyl, tetrahydrothiophenyl, pyrrolidinyl, pyrrolinyl, pyranyl, dioxolanyl, piperidinyl, pyrazolinyl, imidazolinyl, thiazolinyl, dithiolyl, oxathiolyl, dioxanyl, dioxinyl, dioxazolyl, oxathiozolyl, oxazolonyl, piperazinyl, morpholino, thiomorpholinyl, dithianyl, trithianyl and oxazinyl.

The term "heteroaryl" as used herein, represents a stable monocyclic, bicyclic or tricyclic ring of up to 7 atoms in each ring, wherein at least one ring is aromatic and at least one ring contains from 1 to 4 heteroatoms selected from the group consisting of O, N and S. Heteroaryl groups within the scope of this definition include, but are not limited to, acridinyl, carbazolyl, cinnolinyl, quinoxalinyl, quinazolinyl, pyrazolyl, indolyl, isoindolyl, 1H,3H-1-oxoisoindolyl, benzotriazolyl, furanyl, thienyl, thiophenyl, benzothienyl, benzofuranyl, benzodioxane, benzodioxin, quinolinyl, isoquinolinyl, oxazolyl, isoxazolyl, imidazolyl, pyrazinyl, pyridazinyl, pyridinyl, pyrimidinyl, pyrrolyl, tetrahydroquinolinyl, thiazolyl, isothiazolyl, 1,2,4-triazolyl, 1,2,4-oxadiazolyl, 1,2,4-thiadiazolyl, 1,3,5-triazinyl, 1,2,4-triazinyl, 1,2,4,5-tetrazinyl and tetrazolyl. Particular heteroaryl groups have 5- or 6-membered rings, such as pyrazolyl, furanyl, thienyl, oxazolyl, indolyl, isoindolyl, 1H,3H-1-oxoisoindolyl, isoxazolyl, imidazolyl, pyrazinyl, pyridazinyl, pyridinyl, pyrimidinyl, pyrrolyl, thiazolyl, isothiazolyl, 1,2,4-triazolyl and 1,2,4-oxadiazolyl and 1,2,4-thiadiazolyl.

Each alkyl, alkenyl, alkynyl, cycloalkyl, cyclohexenyl, aryl, heterocyclyl and heteroaryl whether an individual entity or as part of a larger entity may be optionally substituted with one or more optional substituents selected from the group consisting of $C_{1-6}$alkyl, $C_{2-6}$alkenyl, $C_{3-6}$cycloalkyl; oxo (=O), —OH, —SH, $C_{1-6}$alkylO-, $C_{2-6}$alkenylO-, $C_{3-6}$cycloalkylO-, $C_{1-6}$alkylS-, $C_{2-6}$alkenylS-, $C_{3-6}$cycloalkylS-, —CO$_2$H, —CO$_2$C$_{1-6}$alkyl, —NH$_2$, —NH(C$_{1-6}$alkyl), —N(C$_{1-6}$alkyl)$_2$, —NH(phenyl), —N(phenyl)$_2$, —CN, —NO$_2$, -halogen, —CF$_3$, —OCF$_3$, —SCF$_3$, -phenyl, -heterocyclyl, -heteroaryl, -Oheteroaryl, -Oheterocyclyl, -Ophenyl, —C(O)phenyl, —C(O)C$_{1-6}$alkyl. Examples of suitable substituents include, but are not limited to, methyl, ethyl, propyl, isopropyl, butyl, sec-butyl, tert-butyl, vinyl, methoxy, ethoxy, propoxy, isopropoxy, butoxy, methylthio, ethylthio, propylthio, isopropylthio, butylthio, hydroxy, hydroxymethyl, hydroxyethyl, hydroxypropyl, hydroxybutyl, fluoro, chloro, bromo, iodo, cyano, nitro, —CO$_2$H, —CO$_2$CH$_3$, trifluoromethyl, trifluoromethoxy, trifluoromethylthio, morpholino, amino, methylamino, dimethylamino, phenyl, phenylcarbonyl and acetyl.

The term "carboxylic acid bioisotere" refers to a group which is physiochemically or topologically similar to carboxylic acid or carboxylate group. Examples of suitable carboxylic acid or carboxylate isosteres include, but are not limited to, tetrazole, tetrazolate, —CONH-tetrazole, oxadiazole, phosphate (—PO$_3$H$_2$), —C(OH)(CF$_3$)$_2$, N-(aryl or heteroaryl)-sulfonamides, acylsulfonamides and sulfonic acid (—SO$_3$H) [See Patani and LaVoie, 1996]. Examples of sulfonamide isosteric equivalents of carboxy groups include —CONHSO$_2$R$_{11}$—SO$_2$NHCOR$_{11}$, —SO$_2$NHCONHR$_{11}$, —SO$_2$NHR$_{11}$ and —NHSO$_2$R$_{11}$, where R$_{11}$ is selected from the group consisting of $C_{1-6}$alkyl, $C_{2-6}$alkenyl, $C_{3-8}$cycloalkyl, aryl, heterocyclyl, heteroaryl and —CF$_3$.

The term "arginine mimetic" refers to a group that is physiochemically and topologically similar to an arginine residue. Arginine mimetics are described in detail in Peterlin-Mašič & Kikelj, 2001. Suitable mimietcs include α-amino acid arginine mimetics such as acyclic and cyclic N-alkyl arginines, electrophilic arginines, arginine mimetics with modified aliphatic side chains, and arginine mimetics with modified guanidine moieties, arginine mimetics with conformationally constrained guanidine moieties, amidine based arginine mimetics, benzamidine and heteroarylbenzamidine arginine side chain mimetics and heteroaromatic mimetics of arginine. The arginine mimetic may or may not contain the amino acid carboxylic acid or may have the carboxylic acid replaced by a carboxylic acid bioisostere. The arginine mimetic may also have a modified arginine side chain that includes an alkylene, alkenylene, alkynylene, cycloalkyl, heterocycloalkyl, aryl or heteroaryl group or a combination of these (or where one or more —CH$_2$— groups in the alkylene, alkenylene or alkynylene chains may be replaced by a heteroatom selected from —O—, —S—, —NH— or —N(alkyl)-) with one or more of amino, =NH, =Nalkyl, —NHC(=NH)NH$_2$, —NHC(=Nalkyl)NH$_2$, —NHC(=NH)NHalkyl or —NHC(=Nalkyl)NHalkyl substituents. The arginine mimetic may also include a guanidine mimetic.

The term "guanidine mimetic" as used herein refers to a group that is physiochemically or topologically similar to a guanidine group. Examples of suitable guanidine mimetics include but are not limited to:

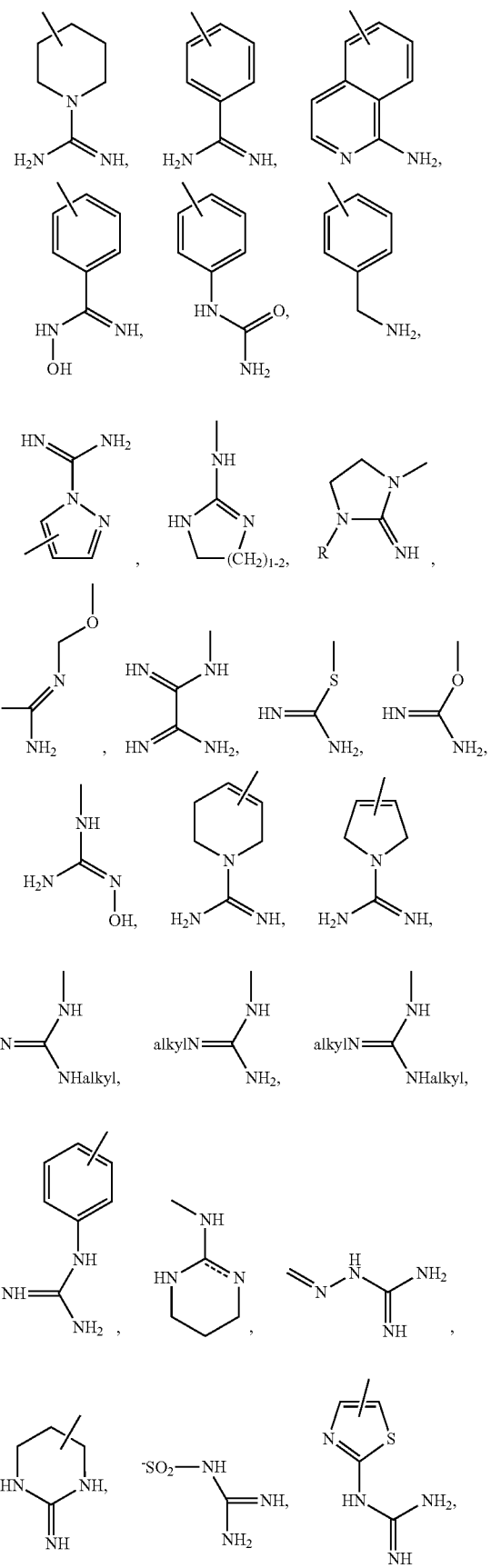

-continued

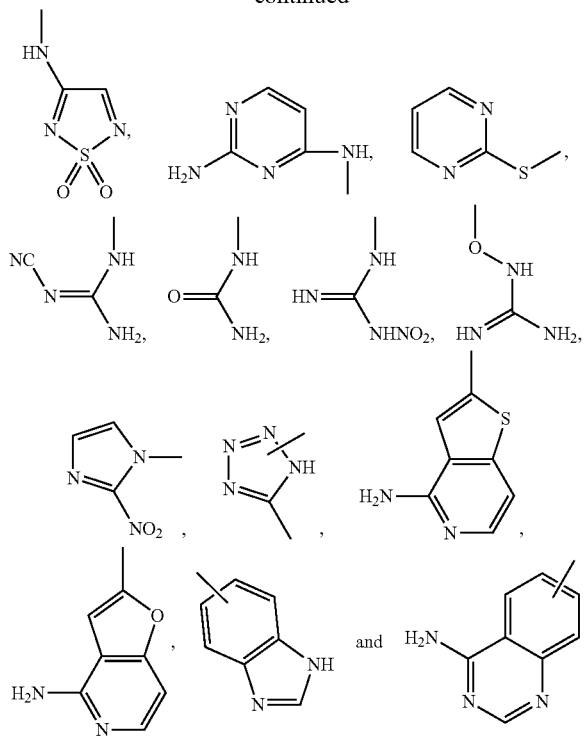

and the like.

The compounds of the invention may be in the form of pharmaceutically acceptable salts: It will be appreciated however that non-pharmaceutically acceptable salts also fall within the scope of the invention since these may be useful as intermediates in the preparation of pharmaceutically acceptable salts or may be useful during storage or transport. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicylic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quaternized with such agents as lower alkyl halide, such as methyl, ethyl, propyl, and butyl chlorides, bromides and iodides; dialkyl sulfates like dimethyl and diethyl sulfate; and others.

It will also be recognised that compounds of the invention may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution. The compounds of the invention may exist as geometric isomers. The invention also relates to compounds in substantially pure cis (Z) or trans (E) or mixtures thereof.

As used herein, the term "inflammatory disease" refers to a condition in which there is excessive inflammation leading to disease such as asthma, allergies, sepsis, lupus erythematosus, type 2 diabetes, arthritis, psoriasis, nephropathy, autoimmune disease, ischaemia-reperfusion injury, multiple forms of shock, psoriasis, multiple sclerosis, fibrosis, glomerlonephritis, inflammatory bowel disease, vascular inflammation, atherosclerosis, cystic fibrosis, stroke and the like.

As used herein, the term "inflammatory complications arising from infection" includes complications such as hemorrhagic fever that may occur during infection with viruses such as Dengue fever viruses.

As used herein the term "obesity" refers to an excessive accumulation of fat in a body. Causes of obesity include overeating, lack of exercise, poor nutritional health, inefficient lypolysis, infection, autoimmune conditions, medication or genetic factors.

The term "metabolic syndrome" as used herein refers to a combination of medical disorders that increase the risk of developing cardiovascular disorders. Obesity and diabetes mellitus Type 2 are risk factors of metabolic syndrome. Metabolic syndrome includes abdominal (central) obesity and at least two of the following:
  (i) impaired glucose tolerance,
  (ii) elevated fasting glucose,
  (iii) insulin resistance,
  (iv) conditions (i), (ii) and (iii) are often associated with Type 2 diabetes,
  (v) dyslipidemia (elevated triglycerides and/or reduced high density lipoprotein (HDL, cholesterol),
  (vi) vascular dysfunction,
  (vii) atherosclerotic plaques, and
  (viii) elevated (systolic or diastolic) blood pressure.

As used herein, the term "cardiovascular disorders associated with obesity and Type 2 diabetes and metabolic syndrome" refers to disorders such as hypertension, cardiac hypertrophy, cardiac fibrosis (collagen deposition, cardiac stiffness, cardiac remodeling), plasma and liver oxidative stress, lipid redistribution and metabolism, stroke and myocardial infarct.

The term "metabolic disorders" as used herein refer to disorders associated with the breakdown of food to component products such as proteins, fats and carbohydrates, and may be inherited (in-born) or may develop as a result of lifestyle. In-borne metabolic disorders are genetic and often caused by the absence or malfunction of an enzyme. Those metabolic disorders that may be acquired during a lifetime include diabetes type 2, atherosclerosis, dyslipdemia, muscle disorders, fatty liver disease, and those disorders related to illness such as cancer, autoimmune disease, liver or respiratory failure, chronic obstructive pulmonary disease, or organ failure.

Modulators of C3a Receptor

In a first aspect, the present invention provides a compound of formula (I):

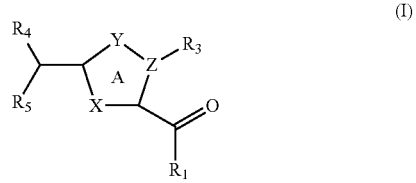

(I)

wherein the ring A is selected from one of the following:

wherein X is N or CH;
Y is O, S, NH, N($C_{1-3}$alkyl) or $CH_2$; and
Z is N or C, provided that when Z is N, $R_3$ is absent;

wherein X is O, S, NH, N($C_{1-3}$alkyl) or $CH_2$;
Y is N or CH; and
Z is N or C, provided that when Z is N, $R_3$ is absent;

wherein X is N or CH;
Y is N or CH; and
Z is O, S, N or CH, provided that when Z is O or S, $R_3$ is absent;

$R_1$ is selected from arginine or an arginine mimetic;
$R_3$ is selected from hydrogen, halogen, alkyl, alkenyl, cycloalkyl, cycloalkenyl, aryl, heterocyclyl or heteroaryl;
$R_4$ is selected from hydrogen, alkyl, alkenyl, —$(CH_2)_m$cycloalkyl, —$(CH_2)_m$aryl, —$(CH)_m$heterocyclyl, —$(CH_2)_m$heteroaryl, —$(CH_2)_m$NHC(=NH)$NH_2$, —$(CH_2)_m$$CONH_2$, $(CH_2)_m$$CO_2H$, —$(CH_2)_m$$SR_6$, —$(CH_2)_m$$NH_2$ or —$(CH_2)_m$$OR_6$;
$R_5$ is selected from alkyl, alkenyl, cycloalkyl, cycloalkenyl, aryl, heterocyclyl, heteroaryl or —$NHR_7$;
$R_6$ is selected from hydrogen, alkyl, cycloalkyl, aryl, heterocyclyl or heteroaryl;
$R_7$ is selected from —C(O)$R_8$, —C(O)O$R_8$, —C(O)NH$R_8$ or —S(O)$_2R_8$;
$R_8$ is selected from alkyl, alkenyl, —$(CHR_9)_p$cycloalkyl, —$(CHR_9)_p$cycloalkenyl, —$(CHR_9)_p$aryl, —$(CHR_9)_p$heterocyclyl or —$(CHR_9)_p$heteroaryl;
$R_9$ is selected from hydrogen, alkyl, alkenyl, cycloalkyl, cycloalkenyl, aryl, heterocyclyl or heteroaryl;
m is 0 or an integer from 1 to 6; and
p is 0 or an integer from 1 to 6;
wherein each cycloalkyl, cycloalkenyl, aryl, heteroaryl and heterocyclyl group may be optionally substituted with one or more optional substituents;
or a pharmaceutically acceptable salt thereof.

In one embodiment, the compound of formula (I) is a compound of formula (II):

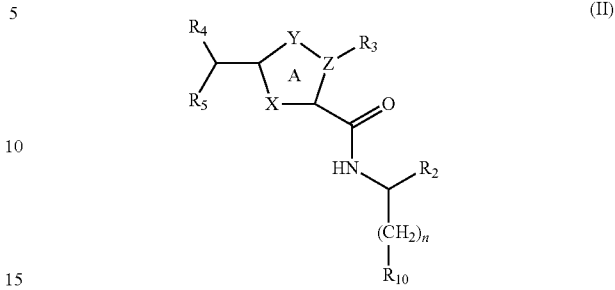

wherein the ring A is selected from one of the following:

wherein X is N or CH;
Y is O, S, NH, N($C_{1-3}$alkyl) or $CH_2$; and
Z is N or C, provided that when Z is N, $R_3$ is absent;

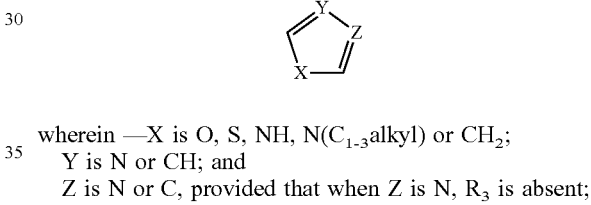

wherein —X is O, S, NH, N($C_{1-3}$alkyl) or $CH_2$;
Y is N or CH; and
Z is N or C, provided that when Z is N, $R_3$ is absent;

wherein X is N or CH;
Y is N or CH; and
Z is O, S, N or CH, provided that when Z is O or S, $R_3$ is absent;

$R_{10}$ is selected from guanidine (—NHC(=NH)$NH_2$) or a guanidine mimetic;
$R_2$ is selected from a carboxylic acid or a carboxylic acid bioisostere;
$R_3$ is selected from hydrogen, halogen, alkyl, alkenyl, cycloalkyl, cycloalkenyl, aryl, heterocyclyl or heteroaryl;
$R_4$ is selected from hydrogen, alkyl, alkenyl, —$(CH_2)_m$cycloalkyl, —$(CH_2)_m$aryl, —$(CH)_m$heterocyclyl, —$(CH_2)_m$heteroaryl, —$(CH_2)_m$NHC(=NH)$NH_2$, —$(CH_2)_m$$CONH_2$, —$(CH_2)_m$$CO_2H$, —$(CH_2)_m$$SR_6$, —$(CH_2)_m$$NH_2$ or —$(CH_2)_m$$OR_6$;
$R_5$ is selected from alkyl, alkenyl, cycloalkyl, cycloalkenyl, aryl, heterocyclyl, heteroaryl or —$NHR_7$;
$R_6$ is selected from hydrogen, alkyl, cycloalkyl, aryl, heterocyclyl or heteroaryl;
$R_7$ is selected from —C(O)$R_8$, —C(O)O$R_8$, —C(O)NH$R_8$ or —S(O)$_2R_8$;
$R_8$ is selected from alkyl, alkenyl, —$(CHR_9)_p$cycloalkyl, —$(CHR_9)_p$cycloalkenyl, —$(CHR_9)_p$aryl, —$(CHR_9)_p$heterocyclyl or —$(CHR_9)_p$heteroaryl;

$R_9$ is selected from hydrogen, alkyl, alkenyl, cycloalkyl, cycloalkenyl, aryl, heterocyclyl or heteroaryl;

n is an integer from 1 to 4;

m is 0 or an integer from 1 to 6; and p is 0 or an integer from 1 to 6;

wherein each cycloalkyl, cycloalkenyl, aryl, heteroaryl and heterocyclyl group may be optionally substituted with one or more optional substituents;

or a pharmaceutically acceptable salt thereof.

In some embodiments, the compounds of formulae (I) and (II) are compounds of formula (III):

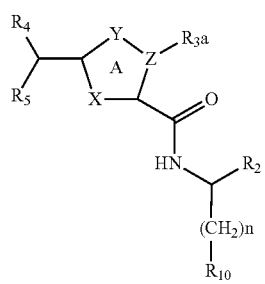

(III)

wherein ring A is selected from one of the following:

wherein X is N or CH;
Y is O, S, NH or N($C_{1-3}$alkyl); and
Z is C;

wherein X is O, S, NH or N($C_{1-3}$alkyl);
Y is N or CH; and
Z is C;

wherein X is N or CH;
Y is N or CH; and
Z is N or CH;

$R_{3a}$ is hydrogen and $R_{10}$, $R_2$, $R_5$ and n are as defined for formula (II).

In particular embodiments, the compounds of formula (III) are compounds of formula (IV):

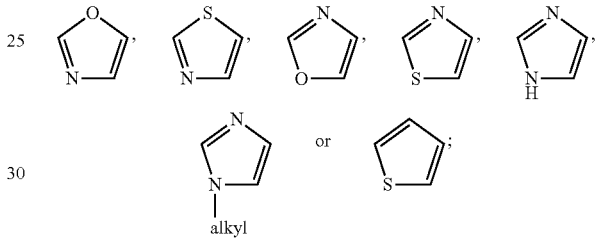

(IV)

wherein ring B is selected from one of the following:

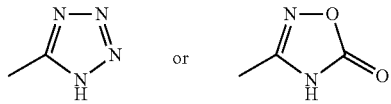

$R_2$ is selected from, $CO_2H$, —C(OH)(CF$_3$)$_2$, —C(O)NHSO$_2$aryl, —C(O)NHSO$_2$alkyl, $R_4$ is selected from hydrogen, —CH$_3$, cyclohexyl, phenyl, —(CH$_2$)$_2$NHC(=NH)NH$_2$, —CH$_2$—CONH$_2$, —CH$_2$CO$_2$H, —CH$_2$SH, —(CH$_2$)$_2$CONH$_2$, —(CH$_2$)$_2$CO$_2$H, —CH$_2$(4-imidazolyl), —CH(CH$_3$)CH$_2$CH$_3$, —CH$_2$CH(CH$_3$)$_2$, —(CH$_2$)$_4$NH$_2$, —(CH$_2$)$_2$SCH$_3$, —CH$_2$Ph, —CH, OH, —CH(CH$_3$)OH, —CH$_2$(3-indolyl), —CH$_2$(4-hydroxyphenyl), —CH(CH$_3$)$_2$ and —(CH$_2$)cyclohexyl;

$R_{20}$ is selected from —(CO)alkyl, —C(O)(CHR$_9$)$_p$cycloalkyl, —C(O)(CHR$_9$)$_p$cycloalkenyl, —C(O)(CHR$_9$)$_p$aryl, —C(O)(CHR$_9$)$_p$heterocyclyl, —C(O)(CHR$_9$)$_p$heteroaryl, —C(O)Oalkyl, —C(O)O(CHR$_9$)$_p$cycloalkyl, —C(O)O(CHR$_9$)$_p$cycloalkenyl, —C(O)NHalkyl, —C(O)NH(CHR$_9$)$_p$cycloalkyl, —C(O)NH(CHR$_9$)$_p$cycloalkenyl, —C(O)NH(CHR$_9$)$_p$aryl, —C(O)NH(CHR$_9$)$_p$heterocyclyl, —C(O)NH(CHR$_9$)$_p$heteroaryl, —S(O)$_2$alkyl, —S(O)$_2$(CHR$_9$)$_p$cycloalkyl, —S(O)$_2$(CHR$_9$)$_p$cycloalkenyl, —S(O)$_2$(CHR$_9$)$_p$aryl, —S(O)$_2$(CHR$_9$)$_p$heterocyclyl and —S(O)$_2$(CHR$_9$)$_p$heteroaryl; wherein each cycloalkyl, cycloalkenyl, aryl, heterocyclyl and heteroaryl group is optionally substituted with one or more of —$C_{1-6}$alkyl, —OC$_{1-6}$alkyl, —NHC$_{1-6}$alkyl, —N(C$_{1-6}$alkyl)$_2$, halogen, —C(O)phenyl, -Ophenyl, —CF$_3$, —N=N-phenyl and —OH;

R$_9$ selected from hydrogen, alkyl, alkenyl, cycloalkyl, cycloalkenyl, aryl, heterocyclyl and heteroaryl; and p is 0 or an integer from 1 to 4.

In other embodiments, the compounds of formulae (I) or (II) are compounds of formula (V):

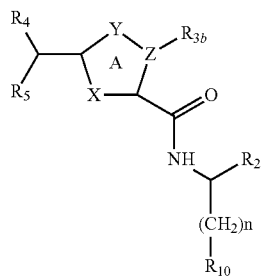

(V)

wherein ring A is selected from one of the following:

wherein X is N or CH;
Y is O, S, NH or N(C$_{1-3}$alkyl); and
Z is C;

wherein X is O, S, NH or N(C$_{1-3}$alkyl);
Y is N or CH; and
Z is C; and

wherein X is N or CH;
Y is N or CH; and
Z is N or CH;

R$_{3b}$ is selected from alkyl, alkenyl, cycloalkyl, cycloalkenyl, aryl, heterocyclyl, or heteroaryl, and R$_{10}$, R$_2$, R$_4$, R$_5$ and n are as defined in formula (II).

In particular embodiments, the compounds of formula (V) are compounds of formula (VI):

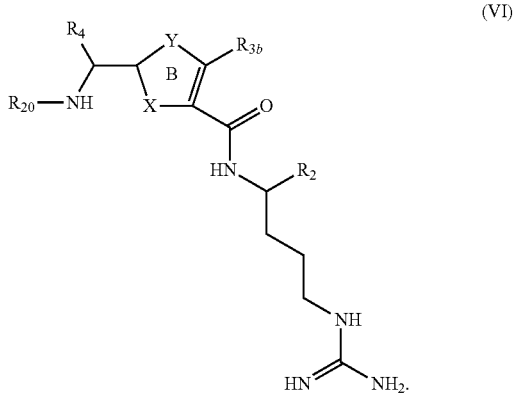

(VI)

wherein ring B is selected from one of the following:

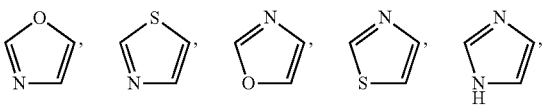

R$^2$ is selected from CO$_2$H, —C(OH)(CF$_3$)$_2$, —C(O)NHSO$_2$aryl, —C(O)NHSO$_2$alkyl,

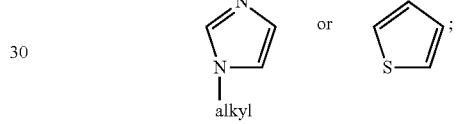

R$_{3b}$ is selected from —C$_{1-6}$alkyl, —C$_{3-6}$cycloalkyl, —C$_{5-6}$cycloalkenyl, phenyl or a 5 or 6 membered heterocyclyl or heteroaryl group;

R$_4$ is selected from hydrogen, —CH$_3$, cyclohexyl, phenyl, —(CH$_2$)$_2$NHC(=NH)NH$_2$, —CH$_2$—CONH$_2$, —CH$_2$CO$_2$H, —CH$_2$SH, —(CH$_2$)$_2$CONH$_2$, —(CH$_2$)$_2$CO$_2$H, —CH$_2$(4-imidazolyl), —CH(CH$_3$)CH$_2$CH$_3$, —CH$_2$CH(CH$_3$)$_2$, —(CH$_2$)$_4$NH$_2$, —(CH$_2$)$_2$SCH$_3$, —CH$_2$Ph, —CH, OH, —CH(CH$_3$)OH, —CH$_2$(3-indolyl), —CH$_2$(4-hydroxyphenyl), —CH(CH$_3$)$_2$ and —(CH$_2$)cyclohexyl;

R$_{20}$ is selected from —(CO)alkyl, —C(O)(CHR$_9$)$_p$cycloalkyl, —C(O)(CHR$_9$)$_p$cycloalkenyl, —C(O)(CHR$_9$)$_p$aryl, —C(O)(CHR$_9$)$_p$heterocyclyl, —C(O)(CHR$_9$)$_p$heteroaryl, —C(O)Oalkyl, —C(O)O(CHR$_9$)$_p$cycloalkyl, —C(O)O(CHR$_9$)$_p$cycloalkenyl, —C(O)NHalkyl, —C(O)NH(CHR$_9$)$_p$cycloalkyl, —C(O)NH(CHR$_9$)$_p$cycloalkenyl, —C(O)NH(CHR$_9$)$_p$aryl, —C(O)NH(CHR$_9$)$_p$heterocyclyl, —C(O)NH(CHR$_9$)$_p$heteroaryl, —S(O)$_2$alkyl, —S(O)$_2$(CHR$_9$)$_p$cycloalkyl, —S(O)$_2$(CHR$_9$)$_p$cycloalkenyl, —S(O)$_2$(CHR$_9$)$_p$aryl, —S(O)$_2$(CHR$_9$)$_p$heterocyclyl or —S(O)$_2$(CHR$_9$)$_p$heteroaryl; wherein each cycloalkyl, cycloalkenyl, aryl, heterocyclyl and heteroaryl group is optionally substituted with one or more of —C$_{1-6}$alkyl, —OC$_{1-6}$alkyl, —NHC$_{1-6}$alkyl, —N(C$_{1-6}$alkyl)$_2$, halogen, —C(O)phenyl, -Ophenyl, —CF$_3$, —N=N-phenyl or —OH;

R$_9$ selected from hydrogen, alkyl, alkenyl, cycloalkyl, cycloalkenyl, aryl, heterocyclyl and heteroaryl; and p is 0 or an integer from 1 to 4.

In other embodiments, the compounds of formulae (I) and (II) are compounds of formula (VII):

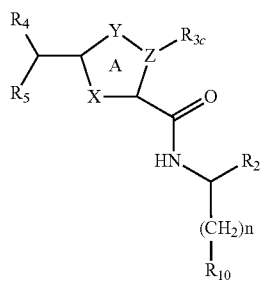

(VII)

wherein ring A is selected from the following:

wherein X is N or CH;
Y is O, S, NH, N(C$_{1-3}$alkyl) or CH$_2$;
Z is N;

wherein X is O, S, NH, N(C$_{1-3}$alkyl) or CH$_2$;
Y is N or CH; and
Z is N;

wherein X is N or CH;
Y is N or CH; and
Z is O or S;
R$_{3c}$ is absent; and
R$_{10}$, R$_2$, R$_4$, R$_5$ and n are as defined in formula (II).

In particular embodiments, the compounds of formula (VII) are compounds of formula (VIII);

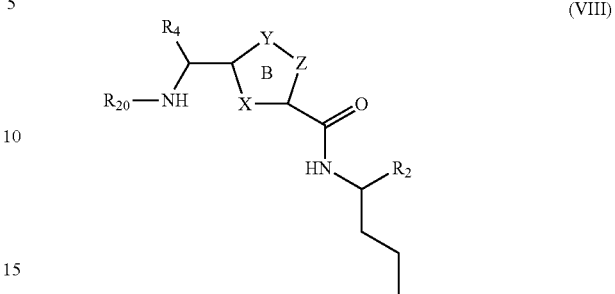

(VIII)

wherein ring B is selected from one of the following:

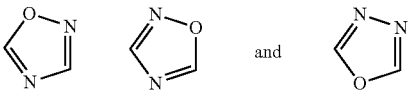 [SMILES: c1ncon1 ; c1ncon1 ; c1nnco1]

R$_2$ is selected from CO$_2$H, —C(OH)(CF$_3$)$_2$, —C(O)NHSO$_2$aryl, —C(O)NHSO$_2$alkyl,

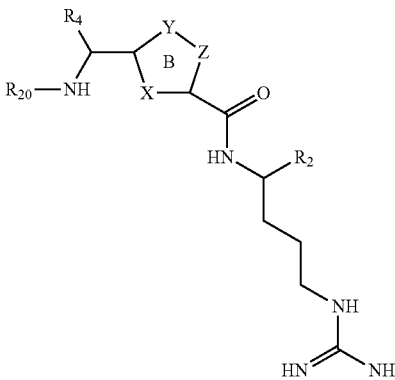

R$_4$ is selected from hydrogen, —CH$_3$, cyclohexyl, phenyl, —(CH$_2$)$_2$NHC(=NH)NH$_2$, —CH$_2$—CONH$_2$, —CH$_2$CO$_2$H, —CH$_2$SH, —(CH$_2$)$_2$CONH$_2$, —(CH$_2$)$_2$CO$_2$H, —CH$_2$(4-imidazolyl), —CH(CH$_3$)CH$_2$CH$_3$, —CH$_2$CH(CH$_3$)$_2$, —(CH$_2$)$_4$NH$_2$, —(CH$_2$)$_2$SCH$_3$, —CH$_2$Ph, —CH, OH, —CH(CH$_3$)OH, —CH$_2$(3-indolyl), —CH$_2$(4-hydroxyphenyl), —CH(CH$_3$)$_2$ and —(CH$_2$)cyclohexyl;

R$_{20}$ is selected from —(CO)alkyl, —C(O)(CHR$_9$)$_p$cycloalkyl, —C(O)(CHR$_9$)$_p$cycloalkenyl, —C(O)(CHR$_9$)$_p$aryl, —C(O)(CHR$_9$)$_p$heterocyclyl, —C(O)(CHR$_9$)$_p$heteroaryl, —C(O)Oalkyl, —C(O)O(CHR$_9$)$_p$cycloalkyl, —C(O)O(CHR$_9$)$_p$cycloalkenyl, —C(O)NHalkyl, —C(O)NH(CHR$_9$)$_p$cycloalkyl, —C(O)NH(CHR$_9$)$_p$cycloalkenyl, —C(O)NH(CHR$_9$)$_p$aryl, —C(O)NH(CHR$_9$)$_p$heterocyclyl, —C(O)NH(CHR$_9$)$_p$heteroaryl, —S(O)$_2$alkyl, —S(O)$_2$(CHR$_9$)$_p$cycloalkyl, —S(O)$_2$(CHR$_9$)$_p$cycloalkenyl, —S(O)$_2$(CHR$_9$)$_p$aryl, —S(O)$_2$(CHR$_9$)$_p$heterocyclyl and —S(O)$_2$(CHR$_9$)$_p$heteroaryl; wherein each cycloalkyl, cycloalkenyl, aryl, heterocyclyl and heteroaryl group is optionally substituted with one or more of —C$_{1-6}$alkyl, —OC$_{1-6}$alkyl, —N(C$_{1-6}$alkyl)$_2$, halogen, —C(O)phenyl, -Ophenyl, —CF$_3$, —N=N-phenyl and —OH;

R$_9$ selected from hydrogen, alkyl, alkenyl, cycloalkyl, cycloalkenyl, aryl, heterocyclyl and heteroaryl; and p is 0 or an integer from 1 to 4.

In particular embodiments of formulae (I) to (VIII), one or more of the following applies:

Ring A or ring B is selected from one of:

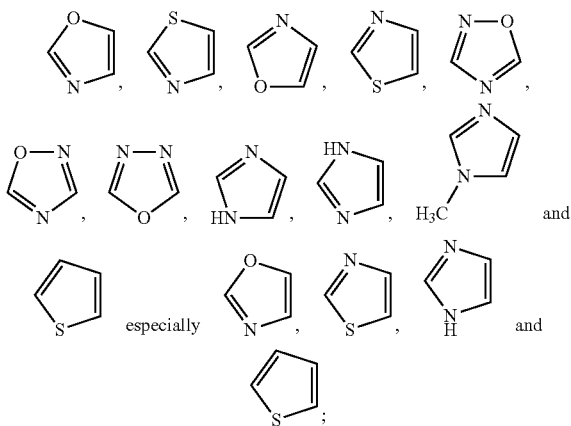

$R_1$ is arginine;

$R_{10}$ is selected from one of:

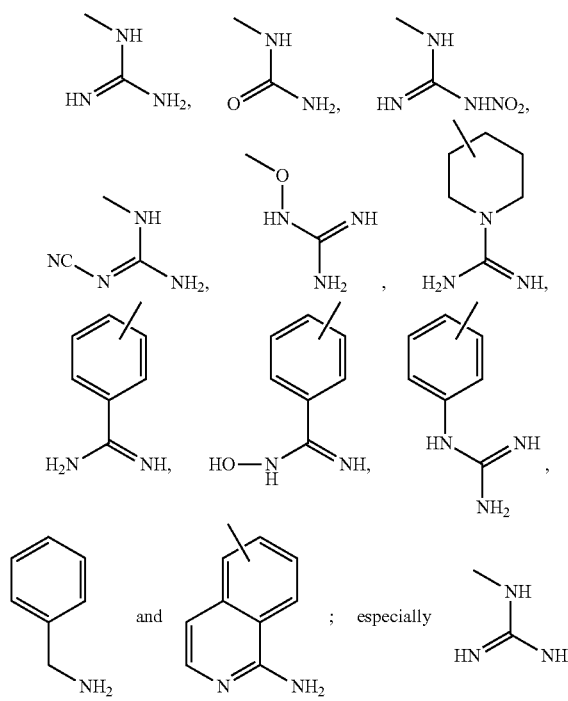

$R_2$ is selected from one of —$CO_2H$, —$C(OH)(CF_3)_2$, —$C(O)NHSO_2$aryl, —$C(O)NHSO_2$alkyl,

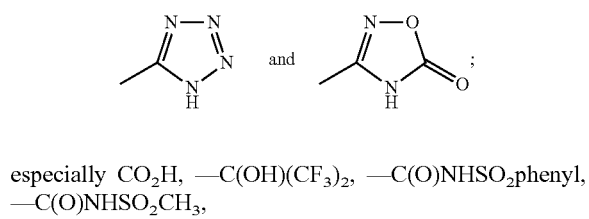

especially $CO_2H$, —$C(OH)(CF_3)_2$, —$C(O)NHSO_2$phenyl, —$C(O)NHSO_2CH_3$,

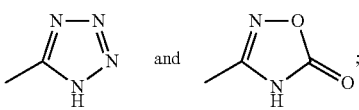

more especially —$CO_2H$;

$R_3$ is selected from hydrogen, —$C_{1-6}$alkyl, —$C_{2-6}$alkenyl, —$C_{5-6}$cycloalkyl, aryl, and 5 or 6 membered heterocyclyl and heteroaryl, especially hydrogen, methyl, ethyl, propyl, isopropyl, cyclohexyl, cyclohexenyl, cyclohexadienyl and phenyl, more especially hydrogen, methyl and phenyl;

$R_4$ is selected from hydrogen, —$CH_3$, cyclohexyl, phenyl, —$(CH_2)_2NHC(=NH)NH_2$, —$CH_2$—$CONH_2$, —$CH_2CO_2H$, —$CH_2SH$, —$(CH_2)_2CONH_2$, —$(CH_2)_2CO_2H$, —$CH_2$(4-imidazolyl), —$CH(CH_3)CH_2CH_3$, —$CH_2CH(CH_3)_2$, —$(CH_2)_4NH_2$, —$(CH_2)_2SCH_3$, —$CH_2Ph$, —CH, OH, —$CH(CH_3)OH$, —$CH_2$(3-indolyl), —$CH_2$(4-hydroxyphenyl), —$CH(CH_3)_2$ and —$(CH_2)$cyclohexyl; especially —$CH_3$, -cyclohexyl, phenyl, —$CH_2$phenyl, —$CH_2$cyclohexyl, —$CH_2CH(CH_3)_2$, —$CH(CH_3)CH_2CH_3$, —$CH_2$(3-indolyl) and —$CH(CH_3)_2$, more especially —$CH_2CH(CH_3)_2$, —$CH(CH_3)CH_2CH_3$, phenyl, —$CH_2$phenyl, —$CH_2$(3-indolyl) and —$CH_2$cyclohexyl, most especially phenyl, —$CH_2CH(CH_3)_2$ and —$CH(CH_3)CH_2CH_3$;

$R_5$ is selected from phenyl, —$NHC(O)R_8$, —$NHC(O)OR_8$, —$NHC(O)NHR_8$ and —$NHSO_2R_8$, especially —$NHC(O)R_8$ and —$NHC(O)OR_8$;

$R_8$ is selected from $C_{1-6}$alkyl, cycloalkyl, cycloalkenyl, aryl, heterocyclyl, heteroaryl, —$CH_2$cycloalkyl, —$CH_2$cycloalkenyl, —$CH_2$aryl, —$CH_2$heterocyclyl, —$CH_2$heteroaryl and —$CH(CH_3)$aryl, wherein each cycloalkyl, cycloalkenyl, aryl, heterocyclyl and heteroaryl are optionally substituted with one or more of $C_{1-6}$alkyl, —$OC_{1-6}$alkyl, —$NHC_{1-6}$alkyl, —$N(C_{1-6}$alkyl$)_2$, halogen, —$C(O)$phenyl, -Ophenyl, —$CF_3$, —N=N-phenyl and OH; especially

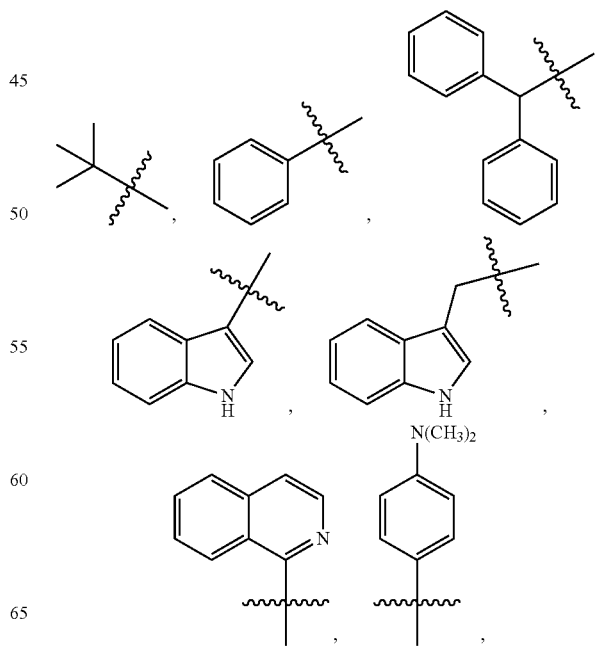

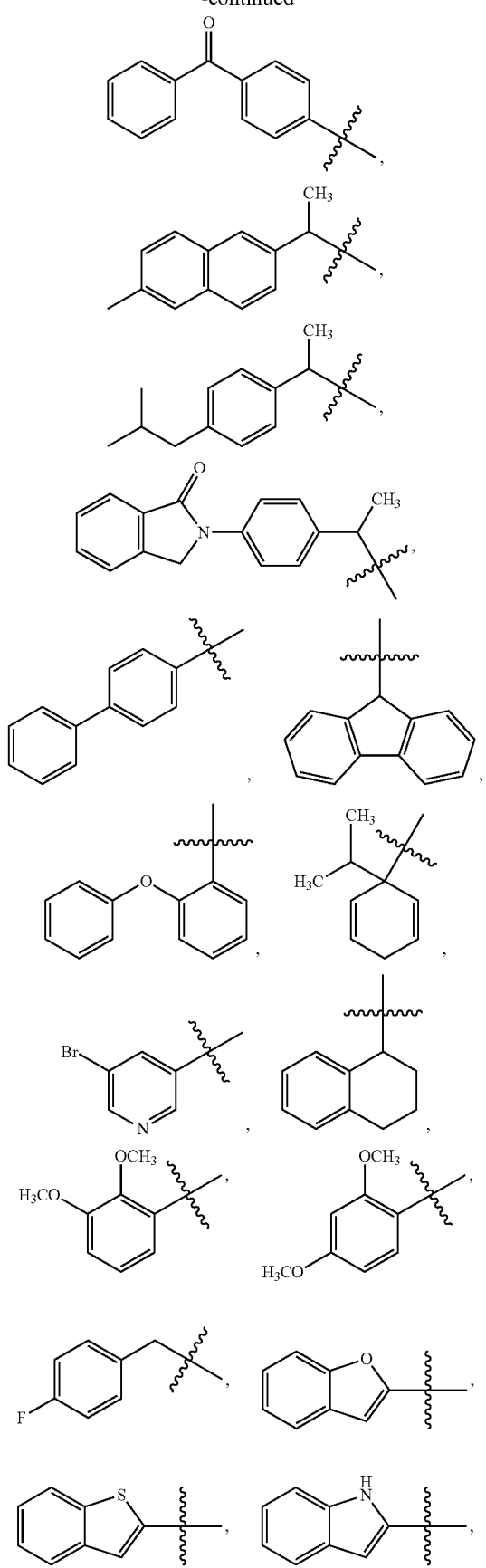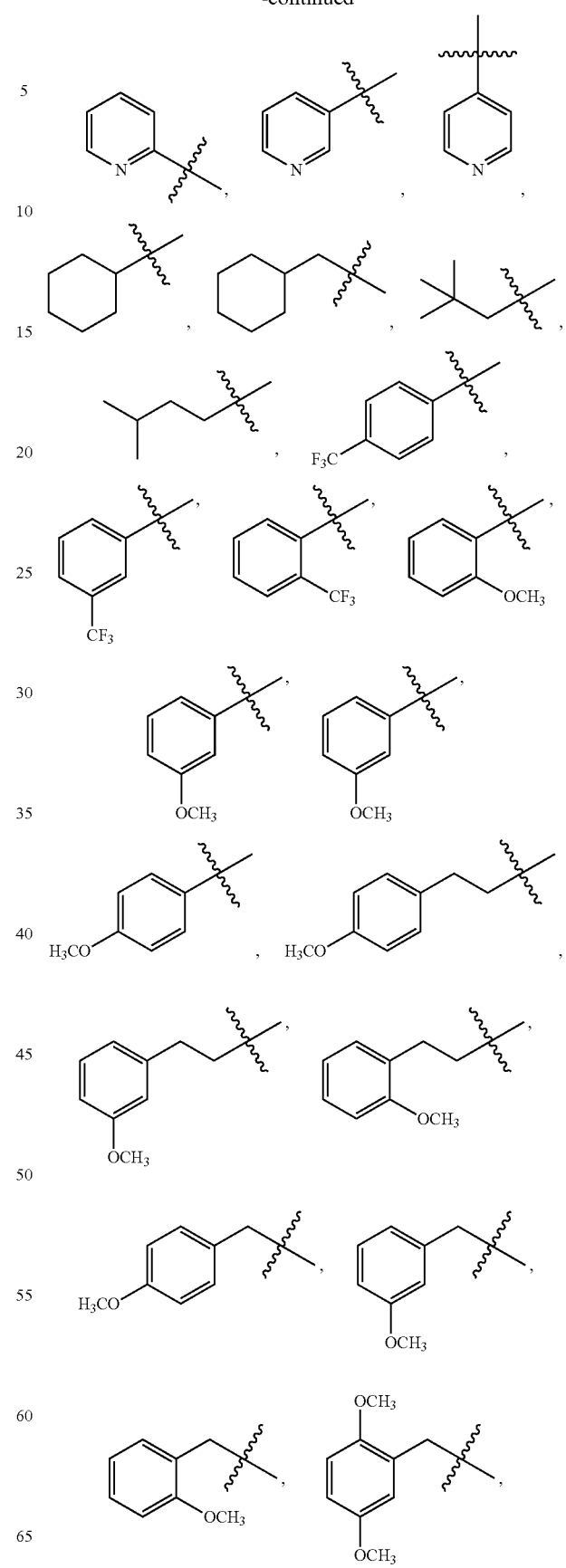

-continued

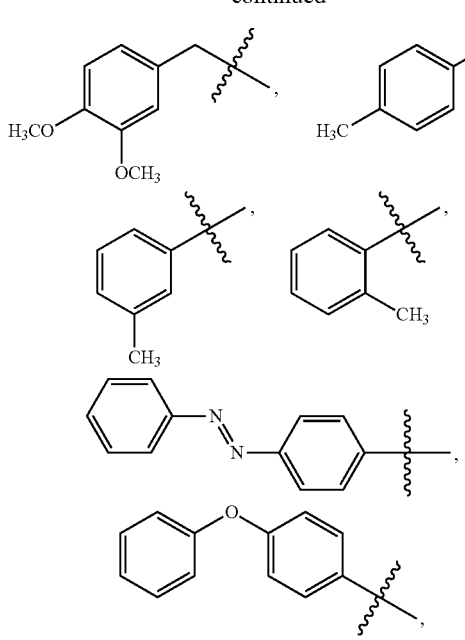
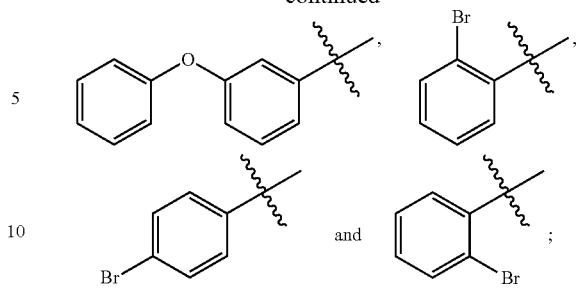

n is 2 or 3, especially 3;
m is 0, 1, 2 or 3;
p is 0, 1 or 2.

In particular embodiments of the invention, the stereochemistry of the carbon atoms bearing $R_2$ and $R_4$ conform with the stereochemistry of natural amino acids, that is the carbon atom bearing $R^2$ preferably has an S configuration and the carbon atom bearing $R_4$ preferably has an S configuration when $R_5$ is a substituted nitrogen atom, but may have an R configuration depending on the identity of the substituents $R_4$ and $R_5$.

Particular compounds of the present invention include those listed in Tables 1 to 5 below:

TABLE 1

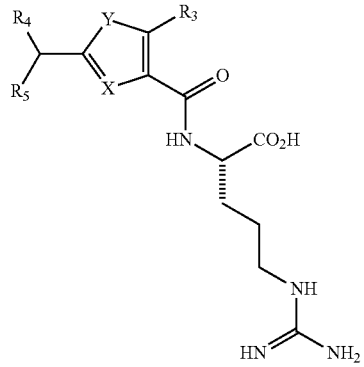

| Compound | X | Y | $R_3$ | $R_4$ | $R_5$ |
|---|---|---|---|---|---|
| 1 | N | O | H | —$CH_2CH(CH_3)_2$ | —NHC(O)OtBu |
| 2 | N | O | H | —$CH(CH_3)CH_2CH_3$ | —NHC(O)OtBu |
| 3 | N | O | H | —$CH_2$phenyl | —NHC(O)OtBu |
| 4 | N | O | H | —$CH_2$(3-indolyl) | —NHC(O)OtBu |
| 5 | N | O | H | —$CH_2$cyclohexyl | —NHC(O)OtBu |
| 6 | N | O | H | —$CH(CH_3)CH_2CH_3$ | —NHC(O)phenyl |
| 7 | N | O | H | —$CH(CH_3)CH_2CH_3$ | —NHC(O)CH(phenyl)$_2$ |
| 8 | N | O | H | —$CH_2CH(CH_3)_2$ | —NHC(O)-(3-indolyl) |
| 9 | N | O | H | —$CH(CH_3)CH_2CH_3$ | —NHC(O)$CH_2$-(3-indolyl) |
| 10 | N | O | H | —$CH(CH_3)CH_2CH_3$ | —NHC(O)-(1-isoquinoline) |
| 11 | N | O | H | —$CH(CH_3)CH_2CH_3$ | —NHC(O)-(4-N,N-dimethylamino)phenyl |
| 12 | N | O | H | —$CH(CH_3)CH_2CH_3$ | —NHC(O)(4-phenylcarbonyl)phenyl |
| 13 | N | O | H | —$CH(CH_3)CH_2CH_3$ | —NHC(O)CH($CH_3$)-2-(6-methoxy)naphthyl |
| 14 | N | O | H | —$CH_2CH(CH_3)_2$ | —NHC(O)CH($CH_3$)-4-(2-methylpropyl)-phenyl |
| 15 | N | O | H | —$CH_2CH(CH_3)_2$ | —NHC(O)CH($CH_3$)-4-(1H,3H-1-oxo-isoindol-2-yl)phenyl |
| 16 | N | O | H | —$CH(CH_3)CH_2CH_3$ | —NHC(O)—$CH_2CH_2$C(O)(4-phenyl)phenyl |
| 17 | N | O | H | —$CH_2CH(CH_3)_2$ | —NHC(O)-(9-fluorenyl) |
| 18 | N | O | H | —$CH(CH_3)CH_2CH_3$ | —NHC(O)-(2-phenoxy)-phenyl |
| 19 | N | O | H | —$CH_2CH(CH_3)_2$ | —NHC(O)$CH_2$CH(Ph)$_2$ |
| 20 | N | O | H | —$CH(CH_3)CH_2CH_3$ | —NHC(O)-3-(5-bromopyridyl) |

TABLE 1-continued

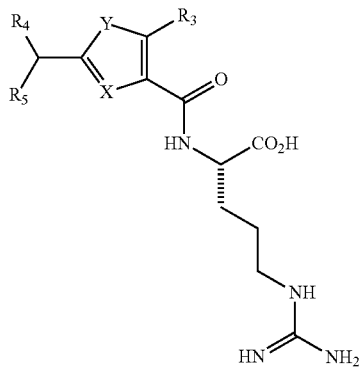

| Compound | X | Y | R₃ | R₄ | R₅ |
|---|---|---|---|---|---|
| 21 | N | O | H | —CH(CH₃)CH₂CH₃ | —NHC(O)-1-tetrahydronaphthylene |
| 22 | N | O | H | —CH(CH₃)CH₂CH₃ | —NHC(O)-(2,3-dimethoxy)phenyl |
| 23 | N | O | H | —CH(CH₃)CH₂CH₃ | —NHC(O)-(2,4-dimethoxy)phenyl |
| 24 | N | O | H | —CH₂CH(CH₃)₂ | —NHC(O)—CH₂-(4-fluoro)phenyl |
| 25 | N | O | CH₃ | —CH(CH₃)CH₂CH₃ | —NHC(O)OtBu |
| 26 | N | O | CH₃ | —CH₂CH(CH₃)₂ | —NHC(O)-2-benzofuranyl |
| 27 | N | O | CH₃ | —CH₂CH(CH₃)₂ | —NHC(O)-2-benzothiophene |
| 28 | N | O | CH₃ | —CH₂CH(CH₃)₂ | —NHC(O)-2-indolyl |
| 29 | N | O | CH₃ | —CH₂CH(CH₃)₂ | —NHC(O)-2-pyridinyl |
| 30 | N | O | CH₃ | —CH₂CH(CH₃)₂ | —NHC(O)-3-pyridinyl |
| 31 | N | O | CH₃ | —CH₂CH(CH₃)₂ | —NHC(O)-4-pyridinyl |
| 32 | N | O | CH₃ | —CH₂CH(CH₃)₂ | —NHC(O)cyclohexyl |
| 33 | N | O | CH₃ | —CH₂CH(CH₃)₂ | —NHC(O)—CH₂cyclohexyl |
| 34 | N | O | CH₃ | —CH₂CH(CH₃)₂ | —NHC(O)CH₂C(CH₃)₃ |
| 35 | N | O | CH₃ | —CH₂CH(CH₃)₂ | —NHC(O)—CH₂CH₂CH(CH₃)₂ |
| 36 | N | O | CH₃ | —CH₂CH(CH₃)₂ | —NHC(O)—CH₂-(4-fluoromethyl)phenyl |
| 37 | N | O | CH₃ | —CH₂CH(CH₃)₂ | —NHC(O)CH₂-(2-methoxy)phenyl |
| 38 | N | O | CH₃ | —CH₂CH(CH₃)₂ | —NHC(O)CH₂-(3-methoxy)phenyl |
| 39 | N | O | CH₃ | —CH₂CH(CH₃)₂ | —NHC(O)CH₂-(4-methoxy)phenyl |
| 40 | N | O | CH₃ | —CH₂CH(CH₃)₂ | —NHSO₂phenyl |
| 41 | N | O | CH₃ | —CH₂CH(CH₃)₂ | —NHC(O)CH₂CH₂-(4-methoxy)phenyl |
| 42 | N | O | CH₃ | —CH₂CH(CH₃)₂ | —NHC(O)-(3-methoxy)phenyl |
| 43 | N | O | CH₃ | —CH₂CH(CH₃)₂ | —NHC(O)CH₂-(3,4-dimethoxy)phenyl |
| 44 | N | O | CH₃ | —CH₂CH(CH₃)₂ | —NHC(O)CH₂-(2,5-dimethoxy)phenyl |
| 45 | N | O | CH₃ | —CH₂CH(CH₃)₂ | —NHC(O)NH-(4-methyl)phenyl |
| 46 | N | O | CH₃ | —CH₂CH(CH₃)₂ | —NHC(O)NH—CH₂phenyl |
| 47 | N | O | CH₃ | —CH₂CH(CH₃)₂ | —NHC(O)-4-CH₂-(N-phenyldiazeno)phenyl |
| 48 | N | O | CH₃ | —CH₂CH(CH₃)₂ | —NHC(O)-3-(5-bromo)pyridine |
| 49 | N | O | CH₃ | —CH₂CH(CH₃)₂ | —NHC(O)-(4-phenoxy)phenyl |
| 50 | N | O | Phenyl | —CH₂CH(CH₃)₂ | —NHC(O)OtBu |
| 51 | N | O | Phenyl | —CH₂CH(CH₃)₂ | —NHC(O)-3-(5-bromo)pyridine |
| 52 | N | O | Phenyl | —CH₂CH(CH₃)₂ | —NHC(O)—CH₂-(4-fluoro)phenyl |
| 53 | N | O | Phenyl | —CH₂CH(CH₃)₂ | —NHC(O)-2-benzothiophene |
| 54 | N | O | Phenyl | —CH₂CH(CH₃)₂ | —NHC(O)(3-methoxy)-phenyl |
| 55 | N | O | Phenyl | —CH₂CH(CH₃)₂ | —NHC(O)cyclohexyl |
| 56 | N | O | H | Phenyl | Phenyl |
| 70 | N | O | H | —CH(CH₃)CH₂CH₃ | —NHC(O)-1-isopropyl-cyclohexa-2,5-dienyl |
| 71 | N | S | H | —CH(CH₃)₂ | —NHC(O)OC(CH₃)₃ |
| 72 | N | NH | H | —CH(CH₃)₂ | —NHC(O)-(3-indolyl) |
| 73 | N | N(CH₃) | H | —CH(CH₃)₂ | —NHC(O)-3-(4-bromopyridyl) |
| 75 | N | N(CH₃) | H | —CH(CH₃)₂ | —NHC(O)—Ot-butyl |
| 79 | N | NH | CH₃ | —CH₂CH(CH₃)₂ | —NHC(O)-(3-indolyl) |
| 80 | N | NH | CH₃ | —CH₂CH(CH₃)₂ | —NHC(O)—Ot-butyl |
| 81 | N | N(CH₃) | CH₃ | —CH₂CH(CH₃)₂ | —NHC(O)—Ot-butyl |
| 97 | N | N(CH₃) | CH₃ | Phenyl | Phenyl |

TABLE 2

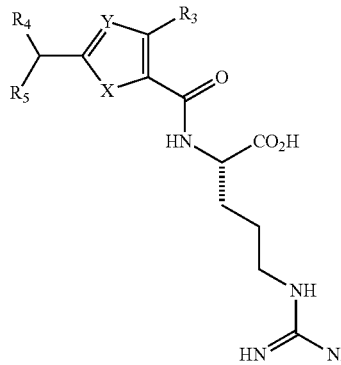

| Compound | X | Y | R3 | R4 | R5 |
|---|---|---|---|---|---|
| 57 | O | CH | H | Phenyl | Phenyl |
| 58 | O | N | CH3 | Phenyl | Phenyl |
| 59 | S | N | CH3 | Phenyl | Phenyl |
| 60 | S | CH | H | Phenyl | Phenyl |
| 61 | N | O | CH3 | Phenyl | Phenyl |
| 62 | NH | N | Phenyl | Phenyl | Phenyl |
| 63 | N(CH3) | N | Phenyl | Phenyl | Phenyl |
| 64 | NH | N | CH3 | Phenyl | Phenyl |
| 65 | S | N | Phenyl | Phenyl | Phenyl |
| 66 | O | N | Phenyl | Phenyl | Phenyl |
| 74 | N(CH3) | N | H | —CH(CH3)2 | —NHC(O)-3-methoxyphenyl |
| 76 | N(CH3) | N | H | —CH(CH3)2 | —NHC(O)—Ot-butyl |
| 77 | NH | N | H | Phenyl | Phenyl |
| 78 | S | N | H | Phenyl | Phenyl |
| 82 | S | N | CH3 | —CH2CH(CH3)2 | —NHC(O)—Ot-butyl |
| 98 | N(CH3) | N | CH3 | Phenyl | Phenyl |

TABLE 3

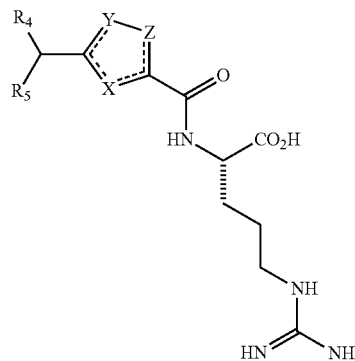

| Compound | X | Y | Z | R3 | R4 | R5 |
|---|---|---|---|---|---|---|
| 67 | =N | =N | O | — | Phenyl | Phenyl |
| 68 | =N | O | =N | — | Phenyl | Phenyl |
| 69 | O | =N | =N | — | Phenyl | Phenyl |
| 83 | O | =N | =N | — | —CH2CH(CH3)2 | —NHC(O)Ot-butyl |

TABLE 4

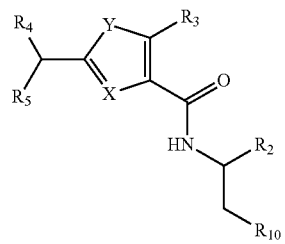

| Comp | X | Y | R10 | R2 | R3 | R4 | R5 |
|---|---|---|---|---|---|---|---|
| 84 | N | O | N-hydroxy-4-methyl-benzimidamide | CO2H | H | CH2CH(CH3)2 | NHC(O)OtBu |
| 85 | N | O | 4-methyl-benzimidamide | CO2H | H | CH2CH(CH3)2 | NHC(O)OtBu |
| 86 | N | O | 1-(p-tolyl)guanidine | CO2H | H | CH2CH(CH3)2 | NHC(O)OtBu |
| 87 | N | NH | p-tolylmethanamine | CO2H | CH3 | Phenyl | Phenyl |
| 88 | N | O | 1-ethylurea | CO2H | H | CH2CH(CH3)2 | NHC(O)OtBu |
| 89 | N | O | 1-ethyl-3-nitroguanidine | CO2H | H | CH2CH(CH3)2 | NHC(O)OtBu |
| 90 | N | O | 1-ethyl-3-cyanoguanidine | CO2H | H | CH2CH(CH3)2 | NHC(O)OtBu |
| 91 | N | O | 1-CH2O-guanidine | CO2H | H | CH2CH(CH3)2 | NHC(O)OtBu |
| 92 | N | O | 1-ethylguanidine | N-(phenylsulfonyl)-formyl | H | CH2CH(CH3)2 | NHC(O)OtBu |

TABLE 4-continued

| Comp | X | Y | R$_{10}$ | R$_2$ | R$_3$ | R$_4$ | R$_5$ |
|---|---|---|---|---|---|---|---|
| 93 | N | O | 1-ethylguanidine | N-(methanesulfonyl)-formyl | H | CH$_2$CH(CH$_3$)$_2$ | NHC(O)OtBu |

TABLE 5

| Compound | X | Y | R$_{10}$ | R$_2$ | R$_4$ | R$_5$ |
|---|---|---|---|---|---|---|
| 94 | S | CH | 1-ethylguanidine | N-(phenylsulfonyl)-formyl | Phenyl | Phenyl |
| 95 | S | CH | 1-ethyl-3-cyanoguanidine | CO$_2$H | Phenyl | Phenyl |
| 96 | S | CH | 1-ethyl-3-cyanoguanidine | N-(phenylsulfonyl)-formyl | Phenyl | Phenyl |

In particular embodiments, the compound of formula (I) is compound No. 1, 8, 9, 20, 50, 54, 59, 60, 64, 77, 78, 79, 80, 90, 92, 93 or 94. In some embodiments, a particular antagonist is compound 60. In other embodiments, particular agonists are selected from compounds 8 and 64.

The substituted oxazole compounds of the invention may be prepared by literature methods [Phillips et al., 2000; Wagner et al., 2006; Hernandez et al., 2007].

For example, an N-protected amino acid is coupled to an amino acid methyl ester bearing a hydroxyl group in its side chain and appropriate substitution to provide R$_3$. Suitable amino acids bearing a hydroxyl group in its side chain include serine methyl ester (R$_3$ is hydrogen), threonine methyl ester (R$_3$ is methyl) and β-phenylserine methyl ester (R$_3$ is phenyl) using known methods for peptide amide bond formation. For example, the carboxy group is activated by formation of a carbodiimide, triazole or a uronium or phosphonium salt of a non-nucleophilic anion. Suitable activating groups are well known in the art including dicyclohexylcarbodiimide (DCC), diisopropylcarbodiimide (DIC), 1-hydroxybenzotriazole (HOBt), 1-hydroxy-7-azabenzotriazole (HOAt), ethyl-2-cyano-2-cyano-2-(hydroxyimino)acetate (Oxyma Pure®), O-benzotriazole-N,N,N',N'-tetramethyluronium hexafluorophosphate (HBTU), O-(7-azabenzotriazol-1-yl)-N,N,N',N'-tetramethyluronium hexafluorophosphate (HATU), O-(6-chloro-1H-benzotriazol-1-yl)-1,1,3,3-tetramethyl tironitun tetrafluorophosphate (HCTU), O-benzotriazol-1-yl-N,N,N',N'-tetramethyluronium tetrafluoroborate (TBTU), (benzotriazol-1-yl oxy) tripyrrolidinophosphonium hexafluorophosphate (PyBOP); (benzotriazol-1-yloxy)-tris-(dimethylamino)phosphonium hexafluorophosphate (BOP), (1-cyano-2-ethoxy-2-oxoethyl idenaminooxy)-dimethylamino-morpholino-carbenium hexafluorophosphate (COMU) and O-[(ethoxycarbonyl)-cyanomethyleneamino]-N,N,N',N'-tetramethyluronium tetrafluoroborate (TOTU). In a particular embodiment, BOP is used to activate the carboxy group of the N-protected amino acid. The amide bond formation is done in the presence of a base such as diisopropylethyl amine (DIPEA).

The resulting dipeptides are cyclized to provide oxazolines using (dimethylamino)sulphur trifluoride (DAST) or Deoxo-Fluor followed by oxidation to the oxazole with bromotrichloromethane (BrCCl$_3$) and 1,8-diazabicyclo[5.4.0]undec-7-ene (DBU); The methyl ester is then hydrolyzed with aqueous methanolic sodium hydroxide or other suitable base to provide the carboxylic acid.

The N-protecting group may be removed if necessary and exchanged for another amino protecting group suitable for use in solid phase synthesis. Suitable N-protecting groups are known in the art, for example, those described in Greene & Wutz, Protective Groups in Organic Synthesis, 3$^{rd}$ Edition, Wiley Interscience. In some embodiments, the initial steps may use a t-butoxycarbonyl (BOC) protecting group which may be exchanged for a 9-fluoroenylmethoxycarbonyl (Fmoc) group.

The oxazole may then be reacted with an arginine substituted resin such as H-Arg-Wang resin to provide an Fmoc protected tripeptide oxazole derivative.

Using standard solid phase synthesis techniques, the Fmoc protecting group is then removed with 50% piperidine in dimethylformamide (DMF) and the free amino group reacted with a substituted carboxylic acid, substituted urea, substituted carbonate or substituted sulfonate group by methods known in the art. An exemplary synthetic method is shown in Scheme 1:

Scheme 1

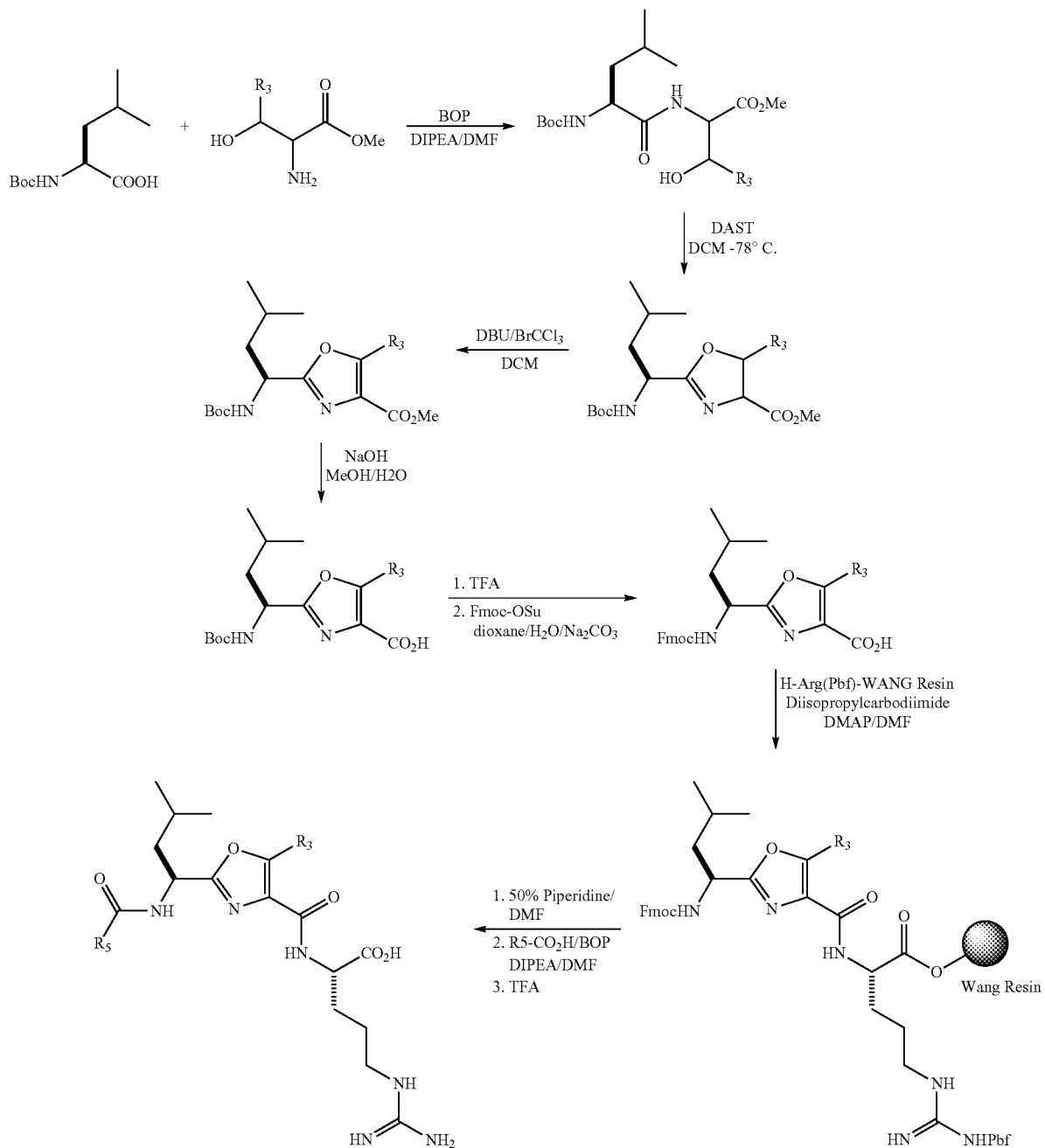

Arginine mimetics may be introduced by replacing arginine with an appropriately substituted non-natural amino acid. The arginine mimetic may be coupled to the heterocyclic or heteroaryl ring carboxy group using solid phase synthesis, such as with Wang resin as described above. Alternatively, the arginine mimetic may be coupled to the heterocyclic or heteroaryl ring carboxy group using solution phase synthesis and coupling reagents as are standard for formation of peptide bonds. In embodiments where the arginine mimetic includes a carboxylic acid bioisostere, solution phase synthesis may be preferred.

Compounds in which $R_4$ and $R_5$ are phenyl may be prepared by similar cyclization methods starting with ethyl-2-(2,2-diphenylacetoxy)-3-oxobutanoate or ethyl-2-(2,2-diphenylacetyl)-3-oxo-butanamide. Cyclization to provide the 5-substituted oxazole or imidazole may be achieved by treatment with freshly dried ammonium acetate ($NH_4OAc$) in glacial acetic acid at elevated temperature.

Hydrolysis of the ester may be achieved by standard methods such as acid or base hydrolysis.

Thiazoles may be prepared by condensing the appropriate thioamide with an α-chloro-β-ketoester using Hantzsch synthesis as outlined in Scheme 2. Additionally oxadiazoles may be prepared by condensing the appropriate amidoxime or hydrazine with an acid chloride as outlined in Scheme 2:

Scheme 2

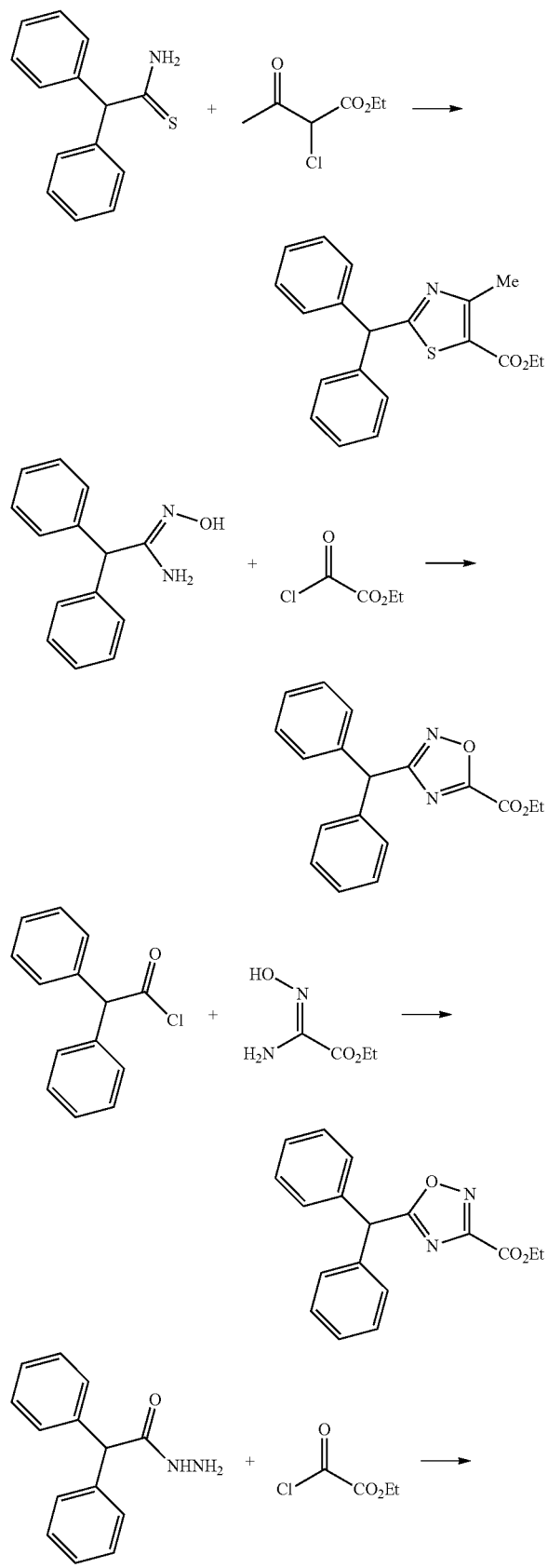
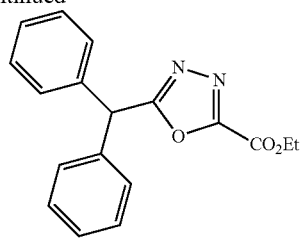

Similar synthetic methods were used to prepare oxadiazoles using appropriate acid chlorides and amidoximes as shown in Scheme 2.

After hydrolysis of the ester, the oxazole, oxadiazole and thiazole compounds may be reacted with an appropriate arginine amino acid or derivative thereof, for example, containing a shorter side chain, a guanidine mimetic or carboxy bioisostere by standard methods of peptide bond formation.

Methods of the Invention

In one aspect of the present invention, there is provided a method of modulating C3a receptor (C3aR) comprising exposing the C3a receptor to a compound of formula (I) or a pharmaceutically acceptable salt thereof.

In some embodiments, modulation causes agonism of the C3aR. In other embodiments, modulation causes antagonism of the C3aR.

In this aspect of the invention, the C3aR that is modulated may be located in vivo or may be located in vitro in an isolated cell. In some embodiments, when located in vitro, the modulation of the C3aR may be used in a competitive assay to identify other modulators, either agonists or antagonists, of C3aR.

In some embodiments of the invention the compound of formula (I) is an antagonist of C3aR. In these embodiments, the compounds of formula (I) or pharmaceutically acceptable salts thereof are useful in treating or preventing inflammatory diseases including the inflammatory complications of infection; obesity, Type 2 diabetes, metabolic syndrome, metabolic diseases and associated cardiovascular diseases.

The compounds of formula (I) are useful in treating or preventing inflammatory diseases, including but not limited to asthma, allergies, sepsis, lupus erythematosus, type 2 diabetes, arthritis, psoriasis, nephropathy, autoimmune disease, ischaemia-reperfusion injury, multiple forms of shock, psoriasis, multiple sclerosis, fibrosis, glomerulonephritis, inflammatory bowel disease, vascular inflammation, atherosclerosis, cystic fibrosis, neurodegenerative diseases, myocardial infarct, stroke and the like.

In some embodiments, the compounds of formula (I) are useful in treating or preventing complications of infection such as hemorrhagic fever that may occur once during viral infection such as Dengue fever.

In another aspect of the invention, there is provided a method of treating or preventing obesity, Type 2 diabetes, metabolic syndrome and associated metabolic and cardiovascular disorders comprising administering an effective amount of a compound of formula (I) or a pharmaceutically acceptable salt thereof.

In some embodiments, the obesity is obesity due to overeating, lack of exercise, poor nutritional health, inefficient lypolysis, infection, autoimmune conditions, medication or genetic factors.

In some embodiments, the metabolic disorders are related to diseases such as cancer, autoimmune disease such as HIV/AIDS, liver or respiratory failure, chronic obstructive pulmonary disease or organ failure. In some embodiments the metabolic disorder is diabetes type 2.

In some embodiments, the associated cardiovascular disorders are hypertension, cardiac hypertrophy, cardiac fibrosis, plasma or organ oxidative stress, stroke and myocardial infarct.

In some embodiments, the compound of formula (I) is an agonist of C3aR. In some embodiments, the agonist compound of formula (I) is a compound of formula (II) or pharmaceutically acceptable salt thereof may be used to stimulate an immune response due to proinflammatory mediation and/or attracting immune cells to the site of infection or injury. Because of its ability to stimulate immune responses, C3a agonists have considerable potential as anti-cancer, anti-viral agents or anti-neurodegenerative agents and have use in a number of clinical situations where patients are immune compromised. Primary immunodeficiencies result from genetic abnormalities, while secondary immunodeficiencies may arise as a result of malnutrition, infection (for example HIV and malaria), tumours (for example lymphoid, myeloma and other), trauma (for example burns, wounds and surgery), medical treatment (for example with drugs such as steroids, cyclosporin and cyclophosphamide), protein loss (such as in diarrhoea and burns), diabetes, neurodegenerative conditions, and old age.

Immunodeficiency causes increased susceptibility to a range of viral, protozoal, bacterial and fungal infections. Stimulating immune responses in such immunodeficient patients assists with the treatment or prevention of bacterial, viral, protozoal, parasitic or fungal infection.

Therefore in one aspect of the invention there is provided a method of treating or preventing an infectious disease comprising administering to a subject a compound of formula (I) or a pharmaceutically acceptable salt thereof.

In some embodiments the infectious disease is caused by a bacterial, viral, protozoal, parasitic or fungal pathogen.

While the compounds of the invention may be used to stimulate an immune response in a subject and therefore may be used to treat or prevent any disease causing bacteria, virus, protozoa, parasite or fungus, examples of suitable bacterial pathogens include but are not limited to *E. coli, E. faecalis, P. aerugenosa, S. aureus, B. pertussis, C. jejuni, C. pneumoMae, C. botulinum, C. tetani, C. diphtheriae, H. influenzae, L. pneumophilia, H. pylori, L. interrogans, L. monocytogenes, M leprae, M tuberculosis, N. gonorrhoeae, N. meningitides, S. typhi, S. typhimurium, S. sonnei, S. pyrogenes, S. pneumonia, V. cholerae* and *Y. pestis*. Examples of suitable viral pathogens include but are not limited to, hepatitis A, hepatitis B, hepatitis C, herpes simplex virus, human papilloma virus, adenovirus, Epstein-barr virus, human cytomegalovirus, Varicella-zoster virus, small pox virus, polio virus, coxsackievirus, rhinovirus, yellow fever virus, Dengue viruses, West Nile virus, rubella virus, HIV, measles virus, mumps virus, and rabies virus. Suitable protozoal pathogens include but are not limited to tropanosomiasis, giardia, malaria, toxoplasmosis and coccidiosis. Suitable fungi include *C. albicans, Microsporum* spp., *Epidermophyton floccosum, Madurella* spp., *Acremonium* spp., *Curvularia* spp., *Fusarium* spp. and *Asprgillus* spp.

In one aspect of the invention the compound of formula (I) or a pharmaceutically acceptable salt thereof may be used in a vaccine as an adjuvant to stimulate immune response, particularly where the compound of formula (I) is an agonist of the C3aR. In an embodiment of this aspect there is provided a vaccine comprising a compound of formula (I) or a pharmaceutically acceptable salt thereof, particularly a compound that is an agonist of C3aR.

The subjects, individuals or patients to be treated are mammalian subjects including but not limited to humans, primates, livestock animals such as sheep, cattle, pigs, horses, donkeys and goats; laboratory test animals such as mice, rats, rabbits and guinea pigs; companion animals such as cats and dogs or captive wild animals such as those kept in zoos. In a particular embodiment, the subject is a human.

An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials. An effective amount in relation to a human patient, for example, may lie in the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage. Dosage regimes may be adjusted to provide the optimum therapeutic response. For example, several divided doses may be administered daily, weekly, monthly or other suitable time intervals, or the dose may be proportionally reduced as indicated by the exigencies of the situation.

Reference herein to "treatment" and "prophylaxis" is to be considered in its broadest context. The term "treatment" does not necessarily imply that a subject is treated until total recovery. "Treatment" may also reduce the severity of an existing condition. The term "prophylaxis" does not necessarily mean that the subject will not eventually contract a disease condition. The term "prophylaxis" may be considered to include delaying the onset of a particular condition. Accordingly, treatment and prophylaxis include amelioration of the symptoms of a particular condition or preventing or otherwise reducing the risk of developing a particular condition.

In some embodiments, the compounds of formula (I) or their pharmaceutically acceptable salts thereof may be administered together with another therapy. Administration may be in a single composition or in separate compositions simultaneously or sequentially such that both compounds or therapies are active within the same time period in the body.

Compounds of formula (I) or their pharmaceutically acceptable salts that are antagonists may be administered with anti-inflammatory agents including steroids, such as cortisone, hydrocortisone, prednisolone, methylprednisolone, prednisone, budesonide, mometasone, triamcinolone and aclometasone, and non-steroidal anti-inflammatory drugs (NSAIDs) such as aspirin, diflunisal, salsalate, ibuprofen, napoxen, fenoprofen, ketoprofen, flubiprofen, oxaprozin, loxoprofen, indomethacin, sulindac, etodolac, ketorolac, diclofenac, nabumetone, piroxicam, meloxicam, tenoxicam, droxicam, lornoxicam, metenamic acid, meclofenamic acid, flufenamic acid, tolfenatnic acid, celecoxib, rofecoxib, valdecoxib, parecoxib, etoricoxib and ferocoxib.

In some embodiments, the compounds of formula (I) or their pharmaceutically acceptable salts that are agonists may be administered with immunostimulants such as deoxycholic acid, macrokine, imiquimod, resiquimod, cytokines (e.g. IL-2, GM-CSF, M-CSF, G-CSF), adjuvants (e.g. TLR agonists, alums, etc), toxins, β-glucans, as well as herbs, vitamins, probiotics and antioxidants; or proliferative agents such as erythropoietin (EPO), growth hormones and factors such as TGF-β, peptide hormones such as human chorionic gonadotrophin (hCG), glucagon like peptide (GLP-1), prolactin, gonadotropins, neupogen, and others.

In another aspect of the invention there is provided a compound of formula (I) or a pharmaceutically acceptable salt thereof for use in treating or preventing inflammatory disease and inflammatory complications of infection, infectious diseases, obesity, metabolic syndrome, associated metabolic disorders and cardiovascular disorders.

In yet a further aspect three is provided a use of a compound of formula (I) or a pharmaceutically acceptable salt thereof in the manufacture of a medicament for treating or preventing inflammatory disease and inflammatory complications of infection, infectious diseases, obesity, metabolic syndrome, associated metabolic disorders and cardiovascular disorders.

Compositions of the Invention

While it is possible that, for use in therapy, a compound of the invention may be administered as a neat chemical, it is preferable to present the active ingredient as a pharmaceutical composition.

Thus, in a further aspect of the invention, there is provided a pharmaceutical composition comprising a compound of formula (I) or a pharmaceutically acceptable salt thereof and at least one pharmaceutically acceptable carrier.

The carrier(s) must be "acceptable" in the sense of being compatible with the other ingredients of the composition and not deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier, excipient, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to two hundred (200) milligrams, per tablet, are accordingly suitable representative unit dosage forms. The compounds of the present invention can be administered in a wide variety of oral and parenteral dosage forms. It will be obvious to those skilled in the art that the following dosage forms may comprise, as the active component, either a compound of the invention or a pharmaceutically acceptable salt or derivative of the compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of, a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 1 to 10 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Figure 1:
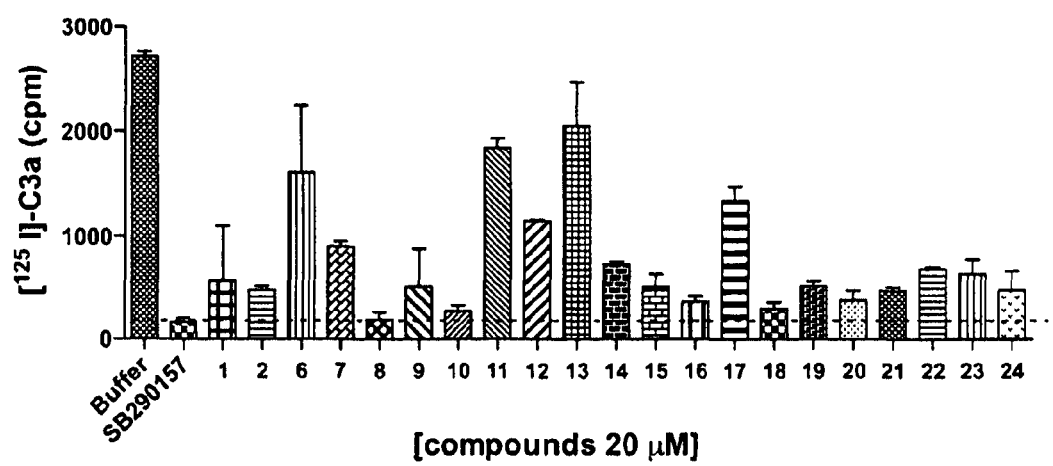
FIG. 1A is a graphical representation showing the competitive binding of compounds 1, 2 and 6-24 in the presence of [$^{125}$I]-C3a in human monocyte derived macrophages (HMDM). SB290157, a known compound with high affinity for the C3aR was used as a positive control. The buffer represents the total binding of [$^{125}$I]-C3a to HMDM.
FIG. 1B is a graphical representation showing the competitive binding of compounds 26-30, 32-34, 36-44 and 46-49 in the presence of [$^{125}$I]-C3a in human monocyte derived macrophages (HMDM). SB290157, a known compound with high affinity for the C3aR was used as a positive control. The buffer represents the total binding of [$^{125}$I]-C3a to HMDM.
Figure 1:
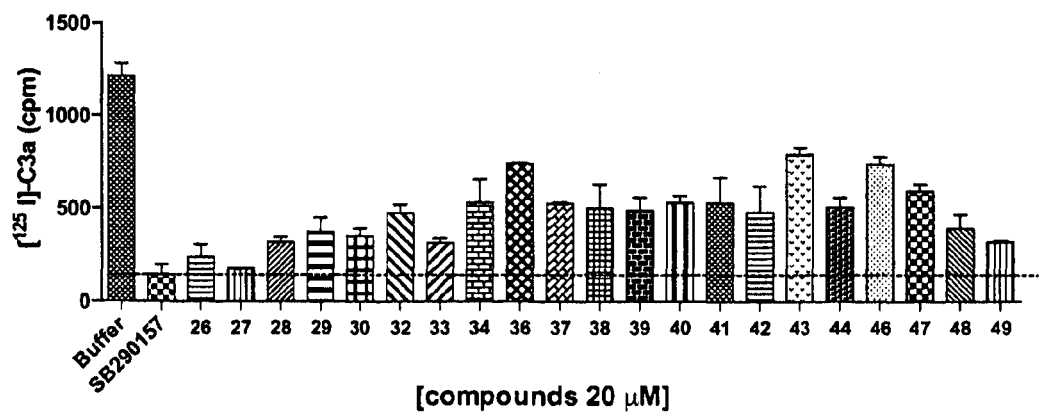
Figure 2:
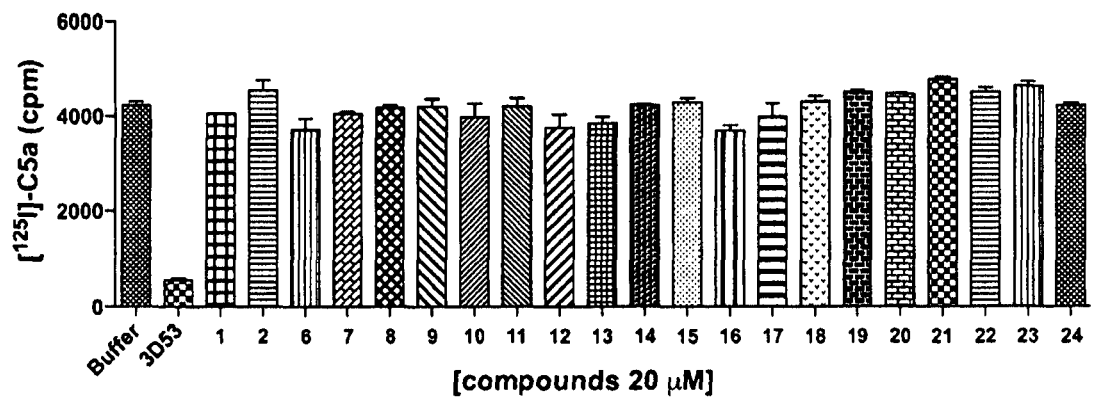
FIG. 2 provides graphical representations of competitive binding of various compounds between [$^{125}$I]-C5a and C3a ligands in HMDM. HMDM ($1.5 \times 10^6$ cells mL) were incubated 1 hr at rt with constant concentration of [$^{125}$I]-C5a (20 μM) and compound and 3D53 (20 μM). The buffer represents the total binding of [$^{125}$I]-C5a to HMDM (~4000 cpm). A: compounds 1, 2 and 6-24; B: compounds 26-28, 30-34, 36-44 and 46-49; C compounds 50-55; D: compounds 56-59.
Figure 2:
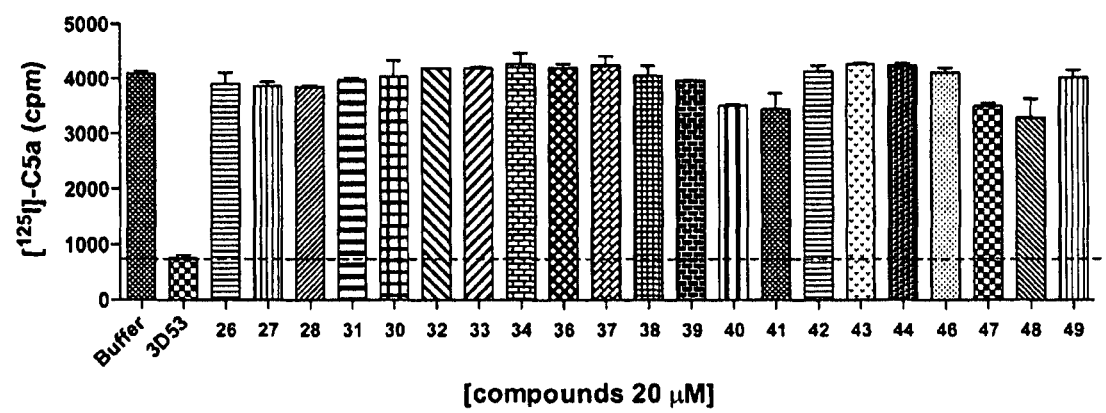
Figure 2:
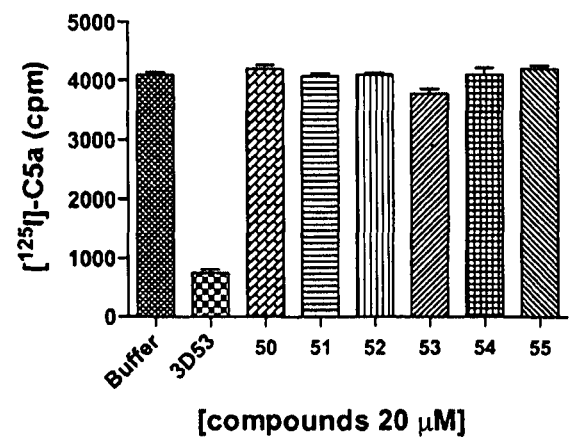
Figure 2D:
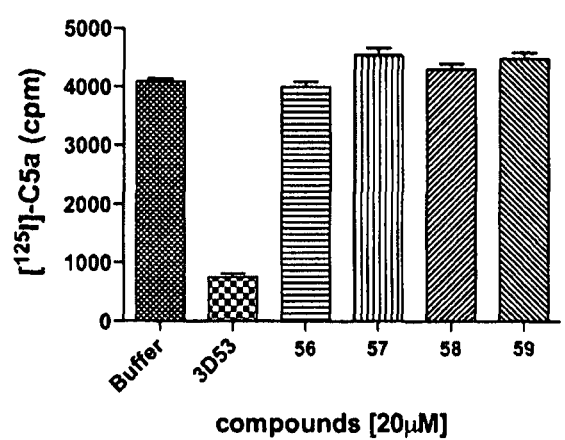

The invention will now be described with reference to the following Examples which illustrate some preferred aspects of the present invention. However, it is to be understood that the particularity of the following description of the invention is not to supersede the generality of the preceding description of the invention.

EXAMPLES

General Methods

Compounds of Formula (I) were Synthesized Using the Following General Methods:
Synthesis of Substitutes Oxazoles Compounds 156, 61

Procedures described in the literature were used to prepare substituted oxazoles [Phillips et al., 2000; Wagner et al., 2006; Hernandez et al., 2007]. A protected amino acid, for example Boc-L-Leucine, was coupled to either serine methyl ester, threonine methyl ester or β-phenylserine methyl ester using BOP. The resulting dipeptides were cyclized to provide oxazolines using (dimethylamino)sulphur trifluoride (DAST) or Deoxo-Fluor and then oxidized to the oxazoles using bromotrichloromethane and 1,8-Diazabicyclo[5.4.0]undec-7-ene (DBU). After hydrolysis of the methyl ester, the Boc group was exchanged with a Fmoc protecting group and the oxazole moiety was attached to H-Arg-Wang resin. Using standard solid phase peptide synthesis techniques, the Fmoc group was removed with 50% piperidine in DMF and an appropriate acid derivative was coupled onto the resin using BOP for activation. The product was deprotected and cleaved from resin using a mixture of 95% trifluoroacetic acid (TFA), 2.5% triisopylsilane and 2.5% water. Final compounds were purified by ion-exchange and/or reverse phase HPLC.

Synthesis of Oxazoles and Imidazoles Compounds 58, 62-64, 66, 72, 79, 97, 98

The appropriate oxazole or imidazole moiety was prepared as indicated below and then coupled to H-Arg(Pbf)-Wang resin. Elaboration using methods similar to those described for compounds 1-56, 61 and 71, afforded the final compounds 58, 62-64, 66, 72, 79, 97, 98.

Ethyl 2-(2,2-diphenylacetoxy)-3-oxobutanoate

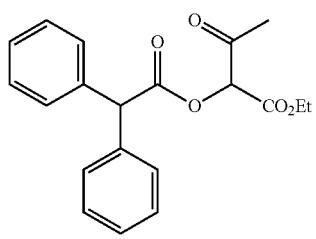 [SMILES: CCOC(=O)C(OC(=O)C(c1ccccc1)c1ccccc1)C(C)=O]

A solution of diphenylacetic acid (2.12 g, 10 mmol) and ethyl 2-chloroacetoacetate (1.88 g, 11 mmol) in dry DMF (5 mL) was treated with DIPEA (2 mL, 11 mmol) and stirred at rt 17 h. Ether (150 mL) was added and the solution was washed with 2M HCl, 1M NaHCO$_3$, brine and dried over MgSO$_4$. Removal of solvent gave a pale yellow oil 3.33 g, 98%. MS 363 [NNa]$^+$. $^1$H NMR (400 MHz, CDCl$_3$): δ 7.39-7.25 (m, 5H), 5.50 (s, 1H), 5.23 (s, 1H), 4.24 (q, J=7.2 Hz, 2H), 2.20 (s, 3H), 1.25 (t, J=7.2 Hz, 3H). $^{13}$C NMR (100 MHz, CDCl$_3$): δ 197.5, 171.1, 164.3, 137.8, 137.7, 128.7, 128.6, 127.54, 127.48, 78.2, 62.5, 56.4, 27.0, 13.9.

Ethyl 2-benzhydryl-4-methyloxazole-5-carboxylate

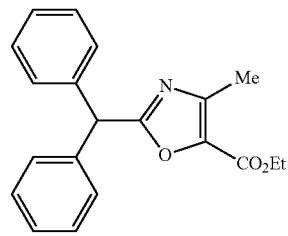 [SMILES: CCOC(=O)c1oc(C(c2ccccc2)c2ccccc2)nc1C]

A solution of ethyl 2-(2,2-diphenylacetoxy)-3-oxobutanoate (2.55 g, 7.5 mmol) and NH$_4$OAc (2.88 g 5 equiv. freshly dried under vacuum at 75° C. 1 h) in glacial acetic acid (12.5 mL) was stirred and heated until homogeneous then heated in a microwave reactor at 150° C. for 15 min. The mixture was diluted with EtOAc 200 mL and water 50 mL containing conc. NH$_3$ (15 mL, d 0.88, slight excess) and shaken well. The organic layer was washed with brine and dried over MgSO$_4$ and evaporated to an oil 2.45 g. Flash chromatography 25-40% EtOAc petrol afforded the oxazole as a pale yellow oil 1.56 g, 65% and the imidazole as a white powder 820 mg, 34%. $^1$H NMR (400 MHz, CDCl$_3$): δ 7.35-7.23 (m, 10H), 5.61 (s, 1H), 4.35 (q, J=7.1 Hz, 2H), 2.47 (s, 3H), 1.36 (t, J=7 Hz, 3H). $^{13}$C NMR (100 MHz, CDCl$_3$): δ 165.8, 158.7, 146.0, 139.1, 137.7, 128.7, 128.6, 127.4, 61.0, 51.0, 14.3, 13.5.

Ethyl 2-benzhydryl-4-methyl-1H-imidazole-5-carboxylate

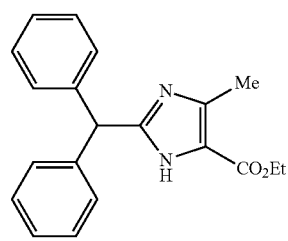 [SMILES: CCOC(=O)c1[nH]c(C(c2ccccc2)c2ccccc2)nc1C]

$^1$H NMR (400 MHz, CDCl$_3$): δ 9.03 and 8.76 (broad s, 1H), 7.36-7.22 (m, 6H), 7.18-7.08 (m, 4H), 5.73 and 5.62 (s, 1H), 4.29 (broad q, J=7.1 Hz, 2H), 2.47 (s, 3H), 1.34 (t, J=7.1 Hz, 3H). $^{13}$C NMR (150 MHz, CDCl$_3$): δ 160.9, 150.8, 146.4, 140.3, 128.9, 128.7, 127.4, 60.6, 51.2; 14.7, 14.4.

2-Benzhydryl-4-methyloxazole-5-carboxylic acid

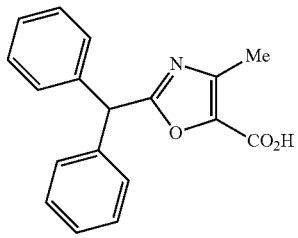 [SMILES: Cc1nc(C(c2ccccc2)c2ccccc2)oc1C(=O)O]

Hydrolysis of ethyl 2-benzhydryl-4-methyl-1H-imidazole-5-carboxylate with NaOH MeOH water gave the carboxylic acid after acidification with HCl.

$^1$H NMR (400 MHz, CDCl$_3$): δ 7.20-7.12 (m, 10H), 5.64 (s, 1H), 2.50 (s, 3H). $^{13}$C NMR (100 MHz, CDCl$_3$): δ 166.9, 162.8, 147.9, 138.6, 137.3, 12.8.7, 128.6, 127.5, 50.9, 13.3.

2-Benzhydryl-4-methyl-1H-imidazole-5-carboxylic acid

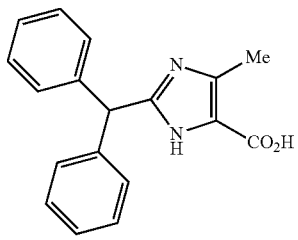 [SMILES: Cc1nc(C(c2ccccc2)c2ccccc2)[nH]c1C(=O)O]

$^1$H NMR (400 MHz, CDCl$_3$+DMSO-d$_6$): δ 7.34-7.17 (m, 10H), 5.61 (s, 1H), 2.48 (s, 3H).

Synthesis of Thiazoles 59, 65, 70, 71, 78 and Oxadiazoles 67, 68, 69

Thiazoles were prepared by condensing the appropriate thioamide and α-chloro-β-ketoester using the Hantzsch synthesis. Oxadiazoles were prepared by condensation of the appropriate amidoxime and acid chloride. The heterocyclic moieties were converted into the final products after amide bond formation with arginine.

Ethyl 2-diphenylmethyl-4-phenyl thiazole-5-carboxylate

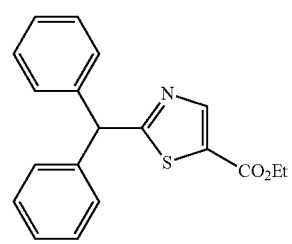 [SMILES: CCOC(=O)c1cnc(C(c2ccccc2)c2ccccc2)s1]

$^1$H NMR (400 MHz, CDCl$_3$): δ 7.77-7.71 (m, 2H), 7.43-7.25 (m, 13H), 5.85 (s, 1H), 4.23 (q, J=7.2 Hz, 2H), 1.24 (t, J=7.2 Hz, 3H).

$^{13}$C NMR (100 MHz, CDCl$_3$): δ 176.4, 161.5, 160.1, 141.3, 134.0, 129.9, 129.0; 128.9, 128.7, 127.7, 127.4; 123.1, 61.4, 55.4 and 14.1.

Ethyl 5-benzhydryl-1,2,4-oxadiazole-3-carboxylate

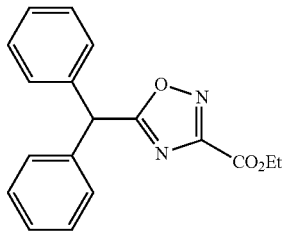 [SMILES: CCOC(=O)c1noc(C(c2ccccc2)c2ccccc2)n1]

$^1$H NMR (400 MHz, CDCl$_3$): δ 7.38-7.27 (m, 10H), 5.85 (s, 1H), 4.50 (q, J=7.1 Hz, 2H), 1.43 (t, J=7.1 Hz, 3H). $^{13}$C NMR (100 MHz. CDCl$_3$): δ 181.2, 161.8, 157.3, 137.2, 128.7, 128.3, 127.7, 62.7, 49.4, 13.8.

Ethyl 3-benzhydryl-1,2,4-oxadiazole-5-carboxylate

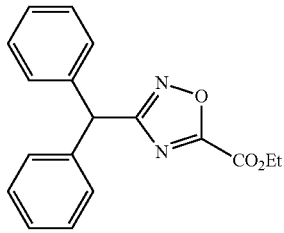 [SMILES: CCOC(=O)c1nc(C(c2ccccc2)c2ccccc2)no1]

$^1$H NMR (600 MHz, CDCl$_3$): δ 7.48-7.23 (m, 10H), 5.72 (s, 1H), 4.50 (q, J=7.1 Hz, 2H), 1.43 (t, J=7.1 Hz, 3H). $^{13}$C NMR (150 MHz, CDCl$_3$): δ 172.8, 166.6, 154.1, 138.8, 128.7, 128.7, 127.5, 63.8, 48.8, 14.0.

5-Benzhydryl-1,2,4-oxadiazole-3-carboxylic acid

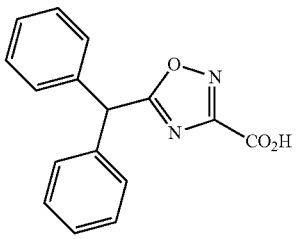 [SMILES: O=C(O)c1noc(C(c2ccccc2)c2ccccc2)n1]

$^1$H NMR (400 MHz, CDCl$_3$): δ 7.40-7.24 (m, 10H), 5.86 (s, 1H).

$^{13}$C NMR (100 MHz, CDCl$_3$): δ 181.8, 161.6, 158.9, 137.1, 136.6, 128.9, 128.8, 128.6, 128.4, 127.9, 127.8, 49.5.

Example 1

Boc-leucine oxazole-arginine-OH (Compound 1)

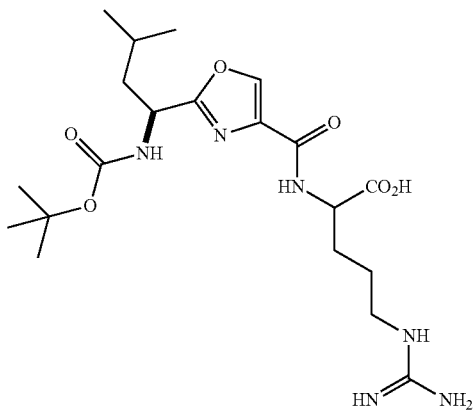 [SMILES: CC(C)C[C@H](NC(=O)OC(C)(C)C)c1nc(C(=O)NC(CCCNC(=N)N)C(=O)O)co1]

Analytical rt 7.736 (20% B to 100% B in 10 mins) 100% pure HRMS MH$^+$ C$_{20}$H$_{34}$N$_6$O$_6$$^+$ Calc 455.2613 found 455.2752. $^1$H NMR (400 MHz, DMSO-d$_6$): δ 8.58 (1H, s, Ox), 8.16 (1H, d, J=7.8 Hz, Leu-NH), 7.56-7.54 (2H, m, Arg-NHε), 4.76-4.70 (1H, m, Leu-Hα) 4.43-4.37 (1H, m, Arg-Hα), 3.46 (2H, q, J=7.2 Hz, Arg-Hδ), 1.89-1.45 (7H, m, Leu-Hγ, Leu-Hβ$_2$, Arg-Hβ$_2$, Arg-Hγ$_2$), 1.37 (9H, s, boc) 0.89 (6H, dd, J=12, 6.4 Hz, Leu-Hδ) $^{13}$C NMR (100 MHz DMSO-d$_6$) δ 173.5, 165.2, 160.4, 157.1, 155.7, 142.5, 135.8, 78.8, 51.6, 47.3, 41.6, 28.6, 28.3, 25.8, 24.6, 23.2, 21.9.

Example 2

(S)-2-(2-(((1S,2S)-1-(tert-butoxycarbonylamino)-2-methylbutyl)oxazole-4-carboxylic acid Arginine OH (Compound 2)

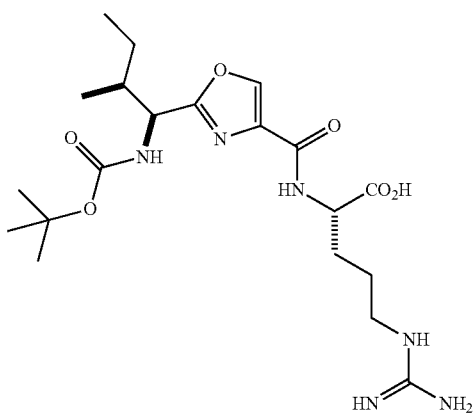 [SMILES: CC[C@H](C)[C@H](NC(=O)OC(C)(C)C)c1nc(C(=O)N[C@@H](CCCNC(=N)N)C(=O)O)co1]

Yield 11%, Analytical rt 7.638 (20% B to 100% B in 10 mins) 100% pure. HRMS (M+H) C$_{20}$H$_{35}$N$_6$O$_6$$^+$ Calc 455.2613 found 455.2616. $^1$H NMR (400 MHz, DMSO-d$_6$): δ 8.59 (1H, s, Ox), 8.17 (1H, d, J=5.2 Hz, Ile-NH), 7.58 (1H, d, J=5.6 Hz, Ile-NH), 7.46 (1H, t, J=3.8, εNH), 4.52 (1H, t, J=5.6 Hz, Ile-Hα), 4.41-4.38 (1H, m, Arg-Hα), 3.14-3.05 (2H, m, Arg-Hδ), 1.91-1.84 (2H, m, Ile-Hβ+Arg-Hβ$_1$), 1.80-1.38 (1H, m, Arg-Hβ$_2$), 1.52-1.46 (2H, m, Arg-Hγ), 1.36 (9H, s, Boc), 1.25-1.16 (2H, m, Ile-Hγ), 0.84 (3H, t, J=4.8 Hz, Ile-Hδ), 0.72 (3H, d, J 4.8 Hz, Ile-Hγ CH$_3$). $^{13}$C NMR (100 MHz DMSO-d$_6$) δ 173.0, 163.9, 159.9, 156.6, 153.3, 142.0, 135.2, 78.4, 53.3, 51.2, 37.1; 28.1, 25.3, 24.9, 153, 10.7.

Example 3

Boc-L-Phenylalanine-Oxazole-Arg (Compound 3)

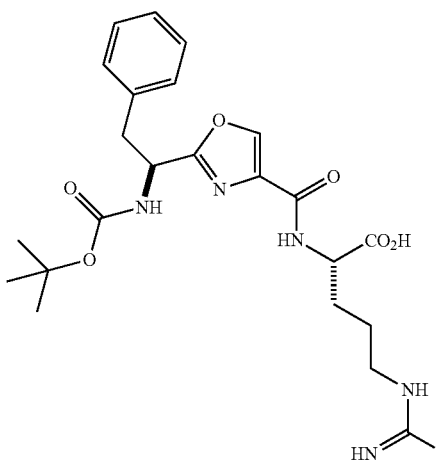

HRMS calc. for C$_{23}$H$_{33}$N$_6$O$_6$$^+$ 489.2456. found 489.2456. $^1$H NMR (600 MHz, DMSO-d$_6$): δ 8.60 (s, 1H), 8.17 (d, J=8.1 Hz, 1H), 7.64 (d, J=8.2 Hz, 1H), 7.53 (m, 1H), 7.32-7.14 (m, 7H), 4.91 (m, 1H), 4.41 (m, 1H), 3.23 (dd, J=13.7, 5.7 Hz, 1H), 3.16-3.04 (m, 3H), 1.88 (m, 1H), 1.78 (m, 1H), 1.56-1.45 (m, 2H), 1.30 (s, 9H).

Example 4

Boc-L-Tryptophan-Oxazole-Arg (Compound 4)

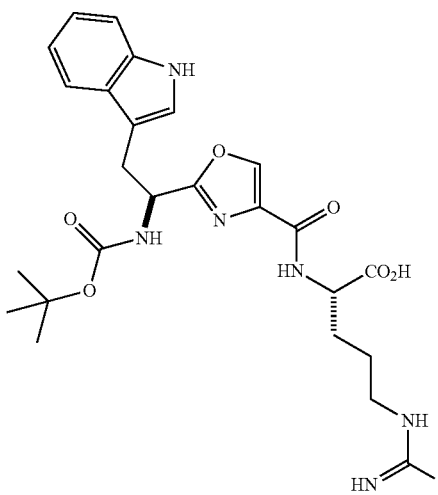

HRMS calc. for C$_{25}$H$_{34}$N$_7$O$_6$$^+$ 528.2565. found 528.2566. $^1$H NMR (600 MHz, DMSO-d$_6$): δ 10.97 and 10.84 (s, 1H), 8.57 (s, 1H), 8.19 (d, J=8.0 Hz, 1H), 7.63 (d, J=8.2 Hz, 1H), 7.55-7.50 (m, 2H), 7.32 (d, J=8.1 Hz, 1H), 7.09 (m, 1H), 7.06 (m, 1H), 6.98 (m, 1H), 4.95 (m, 1H), 4.39 (m, 1H), 3.22 (m, 1H), 3.15-3.06 (m, 2H), 1.87 (m, 1H), 1.77 (m, 1H), 1.56-1.44 (m, 2H), 1.33 (s, 9H). $^{13}$C NMR (150 MHz, DMSO-$d_6$): δ 173.0, 164.2, 160.0, 156.6, 155.1, 142.1, 136.0, 135.4, 127.1, 123.6, 120.9, 118.4, 118.1, 111.4, 109.5, 78.4, 51.2, 49.7, 28.5, 28.1, 27.9, 25.3.

Example 5

Boc-L-Cyclohexylalanine-Oxazole-Arg (Compound 5)

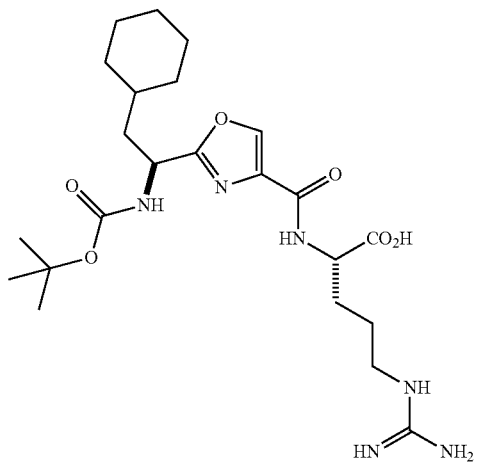 [SMILES: CC(C)(C)OC(=O)N[C@@H](CC1CCCCC1)c1nc(C(=O)N[C@@H](CCCNC(=N)N)C(=O)O)co1]

HRMS calculated for $C_{23}H_{39}N_6O_6^+$ 495.2926. found 495.2927. Retention time (20% B to 100% B in 10 minutes) is 8.456 minutes, purity 98%. $^1$H NMR (600 MHz, DMSO-$d_6$): δ 8.55 (1H, s, Ox), 8.11 (1H, d, J=7.9 Hz, Cha-NH), 4.37-4.80 (1H, m, Cha-Hα), 4.3-4.37 (1H, m, Arg-Hα), 3.04-3.13 (2H, m, Arg-Hδ), 1.91-1.81 (1H, m, Cha-Hγ), 1.81-1.69 (3H, m, Cha-β; Arg-Hβ1), 1.69-1.44 (7H, m, Arg-Hβ2, Arg-Hγ, Cha-CH) 1.37 (9H, s, Boc), 1.33-1.06 (6H, m, Cha-CH$_2$, Cha-CH).

Example 6

Benzoyl Isoleucine Oxazole Arginine-OH (Compound 6)

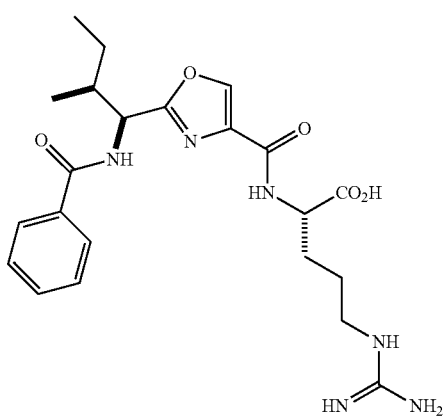 [SMILES: CC[C@H](C)[C@H](NC(=O)c1ccccc1)c1nc(C(=O)N[C@@H](CCCNC(=N)N)C(=O)O)co1]

Yield 26% Analytical rt 11.836 (5% B to 100% B in 20 min) 94% pure. HRMS (M+H) $C_{22}H_{31}N_6O_5^+$ Calc 459.2350 found 459.2349 $^1$H NMR (400 MHz, DMSO-$d_6$): δ 8.97 (1H, d, J=8 Hz, NH) 8.62 (1H, s, Ox), 8.20 (1H, d, J=8 Hz, Arg-NH), 7.88-7.86 (2H, m, Ile-NH, εNH), 7.56-7.44 (5H, m, Ar), 5.05 (1H, t, J=8.6 Hz, Ile-Hα), 4.42-4.37 (1H, m, Arg-Hα), 3.09 (2H, dd, J=13.6, 6.4 Arg-Hδ), 2.22-2.15 (1H, m, Ile-βH), 1.91-1.72 (2H, m, Arg-Hβ), 1.63-1.57 (1H, m, Ile-Hγ$_2$), 1.53-1.46 (2H, m, Arg-Hγ), 1.33-1.22 (1H, m, Ile-Hγ), 0.88 (3H, t, J=4.8 Hz, Ile-Hδ), 0.81 (3H, d, J=4.8 Hz, Ile-Hγ CH$_3$). $^{13}$C NMR (100 MHz DMSO-$d_6$) δ 173.5, 166.9, 164.0, 157.1, 142.6, 135.7, 134.2, 132.0, 128.7, 128.0, 52.5, 51.7, 37.0, 28.3, 25.8, 25.5, 16.0, 10.9.

Example 7

Diphenyl Acetic Acid Isoleucine Oxazole Arginine (Compound 7)

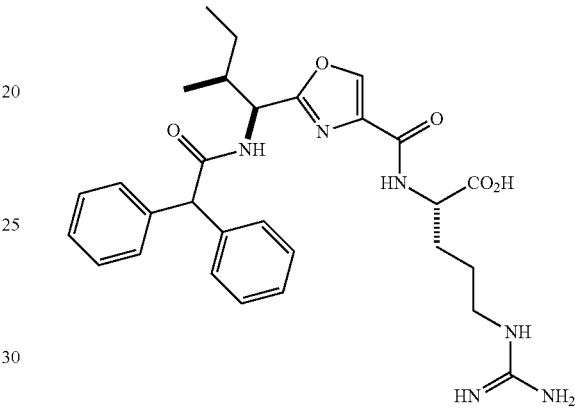

Analytical rt 14.026 (5% B to 100% B in 20 mins) 100% pure. HRMS (M+H) $C_{29}H_{37}N_6O_5^+$ Calc 549.2820 found 549.2819. $^1$H NMR (400 MHz, DMSO-$d_6$): δ 8.96 (1H, d, J 8 Hz, NH) 8.60 (1H, d, J=8 Hz, Arg-NH), 8.13 (1H, s, Ox), 7.54 (1H, t, J=5.6 Hz. Ile-NH), 7.31-7.19 (10H, m, Ar) 5.12 (1H, s, Ph$_2$CH) 4.89 (1H, t, J=8.6 Hz, Ile-Hα), 4.42-4.37 (1H, m, Arg-Hα), 3.09 (2H, q, J=6.8 Hz, Arg-Hδ), 2.00-1.71 (3H, m, Ile-βH, Arg-Hβ), 1.63-1.57 (1H, m, Ile-Hγ$_2$), 1.53-1.35 (3H, m, Arg-Hγ, Ile-Hγ), 1.17-1.10 (1H, m, Ile-Hγ), 0.80-0.73 (6H, m, Ile-Hδ, Ile-Hγ CH$_3$). $^{13}$C NMR (100 MHz DMSO-$d_6$) δ 173.4, 171.5, 163.7, 160.3, 157.1, 142.6, 140.6, 140.5, 135.7, 128.9, 128.7, 128.6, 56.3, 51.7, 37.7, 28.4, 25.8, 25.1, 15.8, 11.0.

Example 8

3-Indole Carboxylic Acid-Leucine-Oxazole-Arginine-OH (Compound 8)

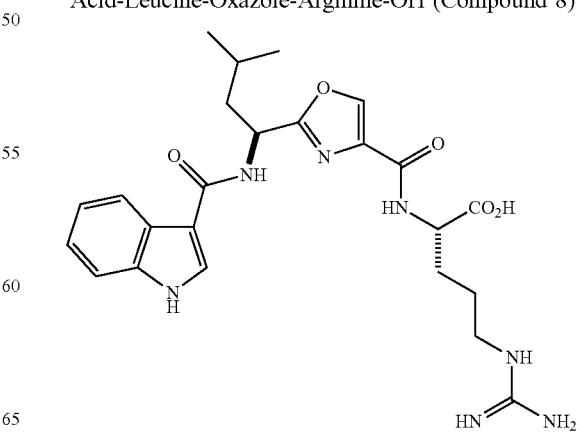

Analytical rt 7.331 (20% B to 100% B in 10 mins) 95% pure. HRMS (M+H) $C_{24}H_{32}N_7O_5^+$ Calc 498.2459 found 498.2461. $^1$H NMR (400 MHz, DMSO-d$_6$): δ 9.96 (1H, d, J=8.4 Hz, Arg-NH) 8.61 (1H, s, Ox), 8.19 (1H, d, J=7.8 Hz, Leu-NH), 7.87-7.85 (1H, m, Indole-NH) 7.54-7.46 (4H, m, Ar), 5.10-5.06 (1H, t, J=4.6 Hz, Leu-Hα) 4.42-4.36 (1H, m, Arg-Hα), 3.11-3.06 (2H, m, Arg-Hδ), 2.21-2.15 (1H, m, Leu-Hγ) 1.87-1.71 (2H, m, Arg-Hβ) 1.62-1.45 (3H, m, Leu-Hβ$_1$, Arg-Hγ$_2$), 1.32-1.21 (1H, m, Leu-Hβ, Leu-Hβ), 0.87 (3H, d, J=6.6 Hz, Leu-Hδ), 0.80 (3H, d, J=6.6 Hz, Leu-Hδ). $^{13}$C NMR (100 MHz DMSO-d$_6$): δ 173.0, 166.5, 163.6, 159.9, 156.6, 142.1, 135.3, 133.7, 131.5, 128.3, 127.6, 52.1, 52.0, 51.2, 36.5, 27.9, 25.3, 25.0, 15.6, 10.5.

Example 9

2-(1H-indol-3-yl)acetic acid-Isoleucine-Oxazole-Arginine-OH (Compound 9)

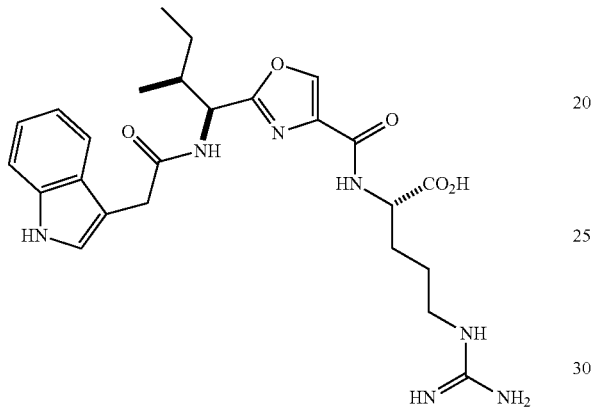

Analytical rt 12.002 (5% B to 100% B in 20 mins) 95% pure. HRMS (M+H) $C_{25}H_{34}N_7O_5^+$ Calc 512.2616 found 512.2615. $^1$H NMR (400 MHz, DMSO-d$_6$): δ 10.82 (1H, s, Ind), 8.67 (1H, d, J=8 Hz, NH) 8.61 (1H, s, Ox), 8.16 (1H, d, J=8 Hz, Arg-NH), 7.54-6.91 (8H, m, Ile-NH, Ar, guanidine NH), 4.86 (1H, t, J=8.4 Hz, Ile-Hα), 4.42-4.36 (1H, m, Arg-Hα), 3.58 (2H, dd, J=24, 14.8, Ind-CH$_2$), 3.09 (2H, q, J=6.8 Hz, Arg-Hδ), 1.99-1.71 (3H, m, Ile-βH, Arg-Hβ), 1.63-1.57 (1H, m, Ile-Hγ$_2$), 1.52-1.45 (3H, m, Arg-Hγ, Ile-Hγ), 1.24-1.13 (1H, m, Ile-Hγ), 0.82 (3H, t, J=4.8 Hz, Ile-Hδ), 0.76 (3H, d, J=4.8 Hz, Ile-Hγ CH$_3$). $^{13}$C NMR (100 MHz DMSO-d$_6$): δ 173.0, 170.8, 163.5, 159.9, 156.6, 142.0, 136.0, 135.3, 127.1, 123.7, 120.7, 118.6, 118.2, 111.3, 108.7, 51.3, 37.5, 32.2, 27.9, 25.3, 24.8, 15.4, 10.6.

Example 10

Isoquinoline-1-Isoleucine-Oxazole-Arginine-OH (Compound 10)

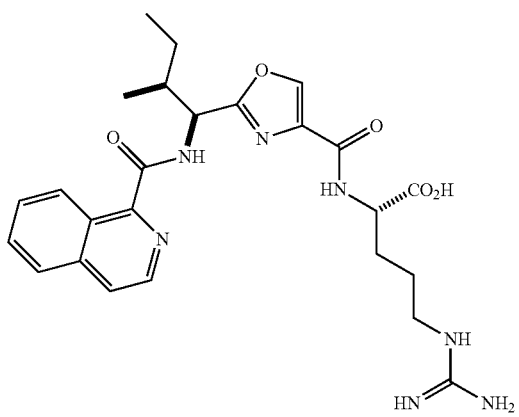 [SMILES: CC[C@H](C)[C@H](NC(=O)c1nccc2ccccc12)c1nc(C(=O)N[C@@H](CCCNC(=N)N)C(=O)O)co1]

Analytical rt 12.769 (5% B to 100% B in 20 mins) 88% pure. HRMS (M+H) $C_{25}H_{32}N_7O_5^+$ Calc 510.2459 found 510.2459. $^1$H NMR (400 MHz, DMSO-d$_6$): δ 9.35 (1H, d, J=8.4 Hz, ArNHCH) 8.70 (1H, dd, J=8.6, 1 Hz, NH) 8.68 (1H, s, Ox), 8.26 (1H, d, J=8 Hz, Arg-NH), 8.07-7.53 (4H, m, Ar), 5.18 (1H, t, J=8.4 Hz, Ile-Hα), 4.44-4.39 (1H, m, Arg-Hα), 3.13 (2H, q, J=6.8 Hz, Arg-Hδ), 2.23-2.16 (1H, m, Ile-βH), 1.92-1.74 (2H, m, Arg-Hβ) 1.65-1.57 (1H, m, Ile-Hγ$_2$), 1.55-1.47 (2H, m, Arg-Hγ), 1.36-1.22 (1H, m, Ile-Hγ), 0.91 (3H, t, J=4.8 Hz, Ile-Hδ), 0.86 (3H, d, J=4.8 Hz, Ile-Hγ CH$_3$), $^{13}$C NMR (100 MHz DMSO-d$_6$): δ 173.0, 166.2, 163.1, 159.9, 156.6, 151.1, 142.3, 141.0, 136.4, 135.4, 130.8, 128.6, 127.2, 126.1, 125.4, 123.4, 51.7, 36.9, 27.9, 25.4, 24.9, 15.4, 10.6.

Example 11

4-(Dimethylamino)benzoic acid-Isoleucine-Oxazole-Arginine-OH (Compound 11)

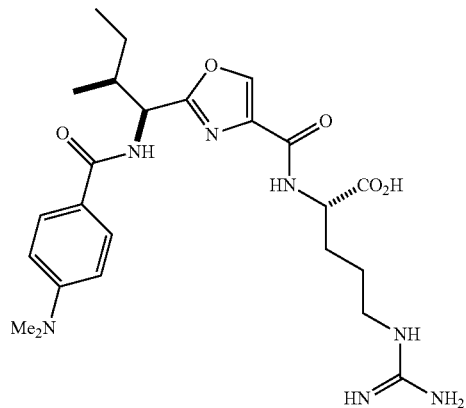 [SMILES: CC[C@H](C)[C@H](NC(=O)c1ccc(N(C)C)cc1)c1nc(C(=O)N[C@@H](CCCNC(=N)N)C(=O)O)co1]

Analytical rt 11.196 (5% B to 100% B in 20 mins) 90% pure. HRMS (M+H$^+$) $C_{24}H_{36}N_7O_5^+$ Calc 502.2772 found 251.6422 (M+2H$^+$) $^1$H NMR (400 MHz, DMSO-d$_6$): δ 8.60 (1H, s, Ox), 8.53 (1H, d, J=8 Hz, Arg-NH), 7.78-7.75 (2H, d, J=9.2 Hz, Ar), 7.49 (1H, t, J=5.6 Hz, Ile-NH), 6.69 (2H, d, J=9.2 Hz, Ar) 5.03 (1H, t, J=8.8 Hz, Ile-Hα), 4.43-4.37 (1H, m, Arg-Hα), 3.12-3.06 (2H, m, Arg-Hδ), 2.96 (6H, s, NCH$_3$) 2.21-2.14 (1H, m, Ile-βH), 1.91-1.72 (2H, m, Arg-Hβ), 1.65-1.45 (3H, m, Arg-Hγ, Ile-Hγ$_2$), 1.55-1.47 (2H, m, Arg-Hγ), 1.28-1.21 (1H, m, Ile-Hγ), 0.87 (3H, t, J=7.4 Hz, Ile-Hδ), 0.78 (3H, d, J=5.2 Hz, Ile-Hγ CH$_3$). $^{13}$C NMR (100 MHz DMSO-d$_6$): δ 173.0, 166.2, 164.0, 160.0, 156.6, 152.3, 142.0, 135.2, 135.2, 130.9, 129.0, 120.2, 110.7, 51.9, 51.8, 51.2, 36.5, 27.9, 25.3, 25.1, 15.6, 10.5.

Example 12

4-Benzoylbenzoic acid-Isoleucine-Oxazole-Arginine-OH (Compound 12)

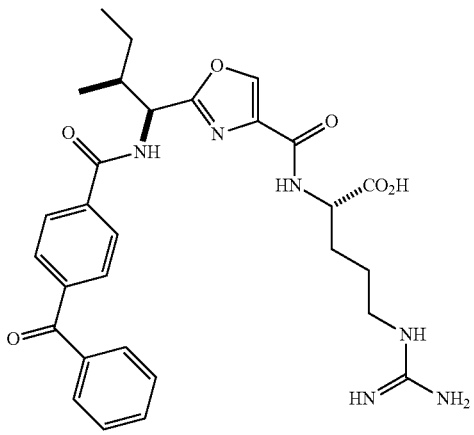 [SMILES: CC[C@H](C)[C@H](NC(=O)c1ccc(C(=O)c2ccccc2)cc1)c1nc(C(=O)N[C@@H](CCCNC(=N)N)C(=O)O)co1]

Analytical rt 8.287 (20% B to 100% B in 10 mins) 100% pure. (HRMS) (M+H) $C_{29}H_{34}N_6O_6^+$ Calc 563.2613 found 563.2608 $^1$H NMR (400 MHz, DMSO-$d_6$): δ 9.21 (1H, d, J=8 Hz, NH) 8.64 (1H, s, Ox), 8.23-7.55 (9H, m, Ar), 5.08 (1H, t, J=8.6 Hz, Ile-Hα), 4.43-4.37 (1H, m, Arg-Hα), 3.10 (2H, q, J=6.8 Hz, Arg-Hδ), 2.24-2.17 (1H, m, Ile-βH), 1.90-1.73 (2H, m, Arg-Hβ) 1.65-1.59 (1H, m, Ile-Hγ$_2$), 1.54-1.46 (2H, m, Arg-Hγ), 1.35-1.23 (1H, m, Ile-Hγ), 0.89 (3H, t, J=4.8 Hz, Ile-Hδ), 0.83 (3H, d, J=4.8 Hz, Ile-Hγ CH$_3$).

$^{13}$C NMR (100 MHz DMSO-$d_6$): δ 195.4, 173.0, 165.8, 163.3, 159.9; 156.6, 142.2, 139.5, 137.0, 136.6, 135.3, 133.1, 129.7, 129.4, 128.7, 127.8, 52.2, 51.3, 36.6, 27.9, 25.3, 25.0, 15.5, 10.5.

Example 13

2-(6-methoxynaphthalen-2-yl)propanoic acid Isoleucine Oxazole Arginine OH (Compound 13)

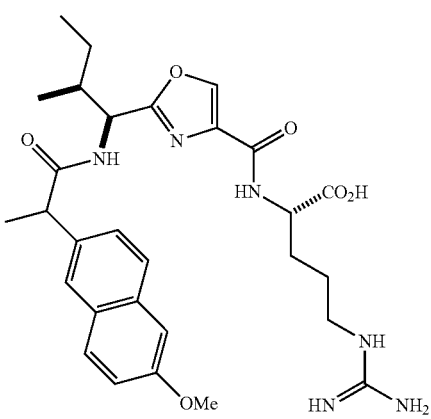 [SMILES: CC[C@H](C)[C@H](NC(=O)C(C)c1ccc2cc(OC)ccc2c1)c1nc(C(=O)N[C@@H](CCCNC(=N)N)C(=O)O)co1]

Analytical rt 8.47 (20% B to 100% B in 10 mins) 97% pure. HRMS (M+H) $C_{29}H_{39}N_6O_6^+$ Calc 567.2926 found 567.2922. $^1$H NMR (400 MHz, DMSO-$d_6$): δ 8.71 (1H, d, J=8 Hz, Arg-NH) 8.52 (1H, s, Ox), 8.10 (1H, d, J=8 Hz, Ile-NH), 7.73-7.09 (6H, m, Ar), 4.88 (1H, t, J=8.6 Hz, Ile-Hα), 4.39-4.33 (1H, m, Arg-Hα), 3.90 (1H, q, J=7.2 Hz, ArCH) 3.84 (3H, s, OMe) 3.06 (2H, q, J=6.4 Hz, Arg-Hδ), 2.01-1.95 (1H, m, Ile-βH), 1.88-1.68 (2H, m, Arg-Hβ) 1.56-1.41 (6H, m, Ile-Hγ$_1$, Arg-Hγ$_2$, ArCHCH$_3$), 1.26-1.18 (1H, m, Ile-Hγ), 0.87 (3H, t, J=4.8 Hz, Ile-Hδ), 0.77 (H, d, J=4.8 Hz, Ile-Hγ CH$_3$). $^{13}$C NMR (100 MHz DMSO-$d_6$): δ 173.6, 173.0, 163.3, 159.8, 157.0, 156.6, 142.0, 136.8, 135.2, 133.0, 129.1, 129.0, 128.3, 126.5, 125.2, 118.5, 105.6, 55.1, 51.3, 51.2, 37.2, 27.9, 25.3, 24.8, 18.7, 15.4, 10.6.

Example 14

2-(4-isobutylphenyl)propanoic acid Leucine-Oxazole-Arginine-OH (Compound 14)

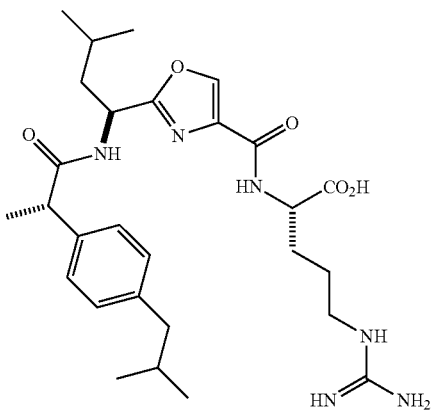 [SMILES: CC(C)Cc1ccc([C@H](C)C(=O)N[C@@H](CC(C)C)c2nc(C(=O)N[C@@H](CCCNC(=N)N)C(=O)O)co2)cc1]

Analytical rt 9.238 (20% B to 100% B in 10 mins) 96% pure. HRMS (M+H) $C_{28}H_{43}N_6O_5^+$ Calc 543.3289 found 543.3290. $^1$H NMR (400 MHz, DMSO-$d_6$): δ 8.58 (1H, d, J=8 Hz Arg-NH) 8.49 (1H, s, Ox) 8.12 (1H, d, J=7.8 Hz, Leu-NH), 7.48 (1H, t, J=5.8 Hz Arg-NH) 7.10 (4H, dd, J=45.6, 8.4 Hz, Ar), 5.06-5.01 (1H, m, Leu-Hα) 4.41-4.35 (1H, m, Arg-Hα), 3.63 (1H, q, J=7 Hz, COCH) 3.10-3.05 (2H, m, Arg-Hδ), 2.37 (2H, d, J=6.8 Hz, isobutyl CH$_2$), 1.86-1.45 (7H, m, Leu-Hγ, Leu-Hβ$_2$, Arg-Hβ$_2$, Arg-Hγ$_2$), 1.31 (3H, d, J=7.2 Hz, COCHCH$_3$), 0.88 (6H, dd, J=17.6, 6.4 Hz, PhCH$_2$CHCH$_3$) 0.82 (6H, d, J=6.8 Hz, Leu-Hδ). $^{13}$C NMR (100 MHz DMSO-$d_6$): δ 173.5, 173.0, 164.2, 159.9, 156.6, 142.0, 139.2, 138.9, 135.2, 128.7, 126.9, 51.2, 45.1, 45.0, 44.9, 44.4, 44.3, 44.2, 41.1, 29.6, 27.9, 25.3, 24.2, 22.7; 22.2, 21.4, 18.7.

Example 15

2-(4-(1-oxoisoindolin-2-yl)phenyl)propanoic acid Leucine-Oxazole-Arginine-OH (Compound 15)

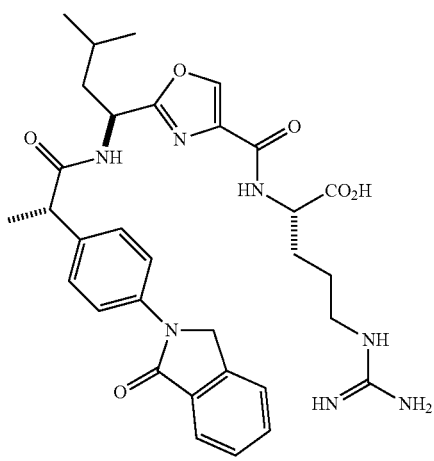 [SMILES: CC(C)C[C@H](NC(=O)[C@@H](C)c1ccc(N2Cc3ccccc3C2=O)cc1)c1nc(C(=O)N[C@@H](CCCNC(=N)N)C(=O)O)co1]

Analytical rt 8.089 (20% B to 100% B in 10 mins) 97% pure. HRMS (M+H) $C_{32}H_{40}N_7O_6^+$ Calc 618.3035 found 618.3046. $^1$H NMR (400 MHz, DMSO-$d_6$): δ 8.64 (1H, m, Arg-NH) 8.60 (1H, s, Ox), 8.16 (1H, d, J=7.8 Hz, Leu-NH), 7.84 (9H, m, Arg-NH, Ar), 5.09-4.98 (2H, m, Leu-Hα, isoindolinNCH) 4.44-4.35 (1H, m, Arg-Hα), 3.72-3.66 (1H, m, PhCH) 3.09 (2H, q, J=Arg-Hδ), 1.89-1.31 (7H, m, Leu-Hγ, Leu-Hβ$_2$, Arg-Hβ$_2$, Arg-Hγ$_2$), 0.90 (3H, dd, 18, 6.4 Hz, PhCHCH$_3$) 0.78 (6H, dd, J=12, 6.4 Hz, Leu-Hδ). $^{13}$C NMR (100 MHz DMSO-$d_6$): δ 173.3, 173.0, 166.5, 164.2, 159.9, 156.6, 142.2, 142.1, 141.9, 141.0, 138.0, 137.7, 135.4, 132.4, 132.2, 128.2, 127.7, 123.3, 123.2, 119.3, 51.2, 50.5, 49.0, 45.1, 44.3, 41.2, 27.9, 25.3, 24.2, 24.1, 22.7, 22.6, 21.4, 21.3, 18.4.

Example 16

4-(biphenyl-4-yl)-4-oxobutanoic acid-Isoleucine-Oxazole-Arginine-OH (Compound 16)

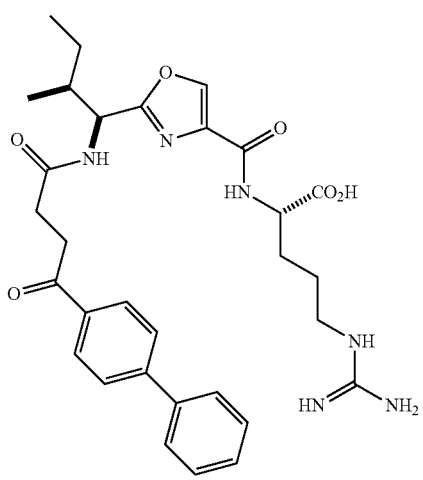 [SMILES: CC[C@H](C)[C@H](NC(=O)CCC(=O)c1ccc(-c2ccccc2)cc1)c1nc(C(=O)N[C@@H](CCCNC(=N)N)C(=O)O)co1]

Analytical rt 6.08 (20% B to 100% B in 10 mins) 100% pure. HRMS (M+H) $C_{31}H_{38}N_6O_6^+$ Calc 591.2926 found 591.2989. $^1$H NMR (400 MHz, DMSO-$d_6$): δ 8.62 (1H, s, Ox), 8.57 (1H, d, J=8.4 Hz, Arg-NH) 8.18 (1H, d, J=8 Hz, Ile-NH), 8.04-7.40 (9H, m, Ar), 4.87 (1H, t, J=8.6 Hz, Ile-Hα), 4.43-4.37 (1H, m, Arg-Hα), 3.33-3.21 (2H, m, butyl CH$_2$) 3.11 (2H, q, J=6.4 Hz, Arg-Hδ), 2.68-2.51 (2H, m, butyl CH$_2$) 1.98-1.72 (3H, m, Ile-βH, Arg-Hβ$_2$) 1.55-1.46 (3H, m, Ile-Hγ$_1$, Arg-Hγ$_2$), 0.86 (3H, t, J=4.8 Hz, Ile-Hδ), 0.77 (H, d, J=4.8 Hz, Ile-Hγ CH$_3$). $^{13}$C NMR (100 MHz DMSO-$d_6$): δ 198.3, 173.0, 171.3, 163.5, 160.0, 156.6, 144.4, 142.1, 138.9, 135.4, 135.3, 129.1, 128.6, 128.4, 127.0, 126.9, 51.3, 37.4, 33.2, 28.9, 27.9, 25.3, 24.8, 15.4, 10.7.

Example 17

9-Fluorenecarboxylic acid-Leu-Oxazole-Arginine-OH (Compound 17)

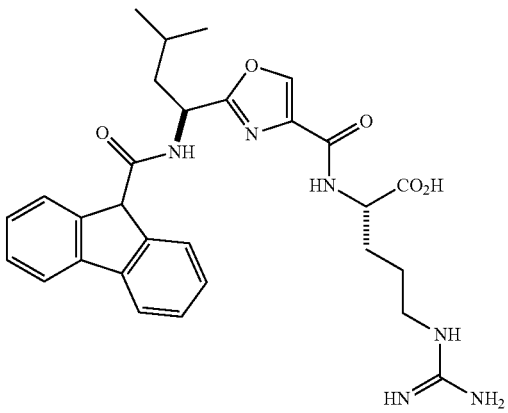 [SMILES: CC(C)C[C@H](NC(=O)C1c2ccccc2-c2ccccc21)c1nc(C(=O)N[C@@H](CCCNC(=N)N)C(=O)O)co1]

Analytical rt 8.42 (20% B to 100% B in 10 mins) 100% pure. HRMS (M+H) Calc $C_{29}H_{34}N_6O_5^+$ Calc 547.2663 found 547.2685. $^1$H NMR (600 MHz, DMSO-$d_6$): δ 9.27 (1H, d, J=8.4 Hz, Arg-NH) 8.65 (1H, s, Ox), 8.16 (1H, d, J=7.8 Hz, Leu-NH), 7.87 (1H, t, J=7.2 Hz, Fmoc-H) 7.49-7.28 (8H, m, Ar), 5.10-5.06 (1H, m, Leu-H) 4.44-4.40 (1H, m, Arg-Hα), 3.10-3.06 (2H, m, Arg-Hδ), 1.95-1.84 (2H, m, Arg-Hβ) 1.80-1.71 (3H, m, Leu-Hβ$_1$, Arg-Hγ$_2$), 1.51-1.46 (2H, m, Let-Hβ, Leu-Hγ), 0.98 (3H, d, J=6.6 Hz, Leu-Hβ), 0.90 (3H, d, J=6.6 Hz, Leu-H$_8$CH$_3$).

Example 18

2-phenoxy benzoic acid-isoleucine-oxazole-arginine-OH (Compound 18)

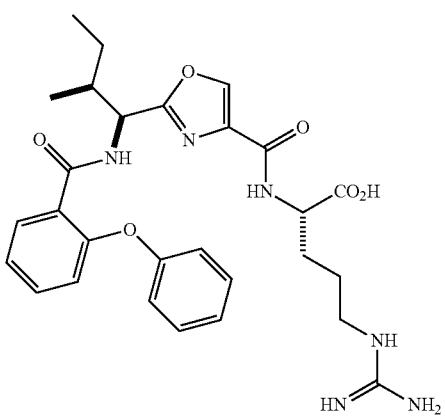 [SMILES: CC[C@H](C)[C@H](NC(=O)c1ccccc1Oc1ccccc1)c1nc(C(=O)N[C@@H](CCCNC(=N)N)C(=O)O)co1]

Analytical rt 8.526 (20% B to 100% B in 10 mins) 100% pure. HRMS (M+H) $C_{28}H_{35}N_6O_6^+$ Calc 551.2613 found 551.2606. $^1$H NMR (400 MHz, DMSO-d$_6$): 8.81 (1H, d, J=8.4 Hz, Arg-NH) 8.56 (1H, s, Ox), 8.17 (1H, d, J=8 Hz, Ile-NH), 7.59 (1H, dd, J=6.8, 1.6 Hz, Ar) 7.51 (1H, m, Arg-Nhε) 7.49-6.93 (9H, m, Ar), 4.99 (1H, t, J=8.6 Hz, Ile-Hα), 4.42-4.37 (1H, m, Arg-Hα), 3.09 (2H, m, Arg-Hδ), 2.02-1.72 (3H, m, Ile-βH, Arg-Hβ$_2$) 1.54-1.44 (3H, m, Ile-Hγ$_1$, Arg-Hγ$_2$), 1.18-1.11 (1H, m, Ile-Hγ$_1$) 0.78-0.73 (6H, m, Ile-Hδ, Ile-Hγ CH$_3$). $^{13}$C NMR (100 MHz DMSO-d$_6$): δ 173.0, 165.3, 163.1, 159.9, 156.6, 135.2, 129.9, 127.7, 119.3, 118.3, 51.7, 51.3, 37.2, 27.9, 25.3, 24.7, 15.3, 10.6.

Example 19

3,3-diphenylpropanoic acid-Leucine-Oxazole-Arginine-OH (Compound 19)

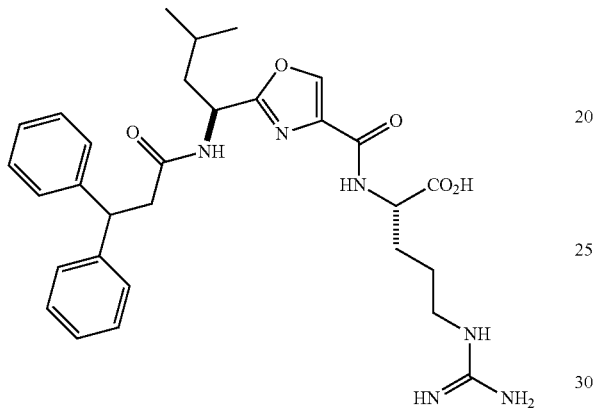

Analytical rt 8.582 (20% B to 100% B in 10 mins) 100% pure. HRMS (M+H) $C_{30}H_{39}N_6O_5^+$ Calc 563.2976 found 563.2977. $^1$H NMR (400 MHz, DMSO-d$_6$): δ 8.50-8.48 (2H, m, Arg-NH, Ox-H) 8.14 (1H, d, J=7.8 Hz, Leu-NH), 7.55 (1H, t, J=6 Hz, Arg-NH) 7.25-7.11 (10H, m, Ar), 4.96-4.90 (1H, t, J 4.6 Hz, Leu-Hα) 4.47-4.37 (2H, m, Arg-Hα, Ph$_2$CH), 3.11-3.06 (2H, m, Arg-Hδ), 2.97 (1H, dd, J=14.4, 9.2 Hz, Ph$_2$CHCH$_2$) 2.80 1H, dd, J=14.4, 9.2 Hz, Ph$_2$CHCH$_2$) 2.21-2.15 (1H, m, Leu-Hγ) 1.87-1.71 (2H, m, Arg-Hβ) 1.62-1.45 (3H, m, Leu-Hβ$_1$, Arg-Hγ$_2$), 1.32-1.21 (1H, m, Leu-Hβ, Leu-Hβ), 0.87 (3H, d, J=6.6 Hz, Leu-Hδ), 0.80 (3H, d, J=6.6 Hz, Leu-Hδ). $^{13}$C NMR (100 MHz DMSO-d$_6$): δ 173.0, 171.1, 163.0, 159.9, 156.6, 142.1, 140.1, 140.0, 135.3, 128.4, 128.2, 126.7, 126.6, 55.9, 55.8, 51.5, 51.4, 51.2, 37.3, 27.9, 25.3, 24.7, 15.3, 10.2.

Example 20

5-bromonicotinic acid-leucine-oxazole-arginine-OH (Compound 20)

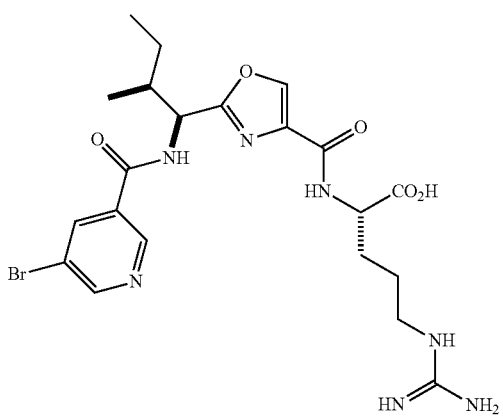 [SMILES: CC[C@H](C)[C@H](NC(=O)c1cncc(Br)c1)c1nc(C(=O)N[C@@H](CCCNC(=N)N)C(=O)O)co1]

Analytical rt 7.168 (20% B to 100% B in 10 mins) 96% pure. HRMS (M+H) $C_{21}H_{29}{}^{79}BrN_7O_5^+$ Calc 538.1408 found 538.1405. $^1$H NMR (400 MHz, DMSO-d$_6$): δ) 9.29 (1H, d, J=8 Hz, Arg-NH) 8.98 (1H, d, J=1.6 Hz, Ar), 8.87 (1H, d, J=2 Hz, Ar), 8.64 (1H, s, Ox), 8.48 (1H, t, J=2 Hz, Ar) 8.22 (1H, d, J=8 Hz, Ile-NH), 7.53 (1H, t, J=5.6 Hz, Arg-Nhε), 5.06 (1H, t, J=8.6 Hz, Ile-Hα), 4.42-4.36 (1H, m, Arg-Hα), 3.09 (2H, q, J=6.4 Hz, Arg-Hδ), 2.19-2.12 (1H, m, Ile-Hβ), 1.92-1.72 (2H, m, Arg-Hβ$_2$) 1.62-1.46 (3H, m, Ile-Hγ$_1$, Arg-Hγ$_2$), 1.31-1.23 (1H, m, Ile-Hγ$_1$), 0.88 (3H, t, J=4.8 Hz, Ile-Hδ), 0.82 (2H, d, J=4.8 Hz, Ile-Hγ, Isopropyl CH$_3$). $^{13}$C NMR (100 MHz DMSO-d$_6$): δ 173.0, 163.7, 163.0, 159.9, 156.6, 152.8, 147.4, 147.3, 142.3, 137.6, 135.3, 130.7, 120.0, 52.2, 52.1, 51.3, 36.7, 27.9, 25.4, 25.0, 15.5, 10.6.

Example 21

Tetrahydronapthalene-isoleucine-oxazole-arginine-OH (Compound 21)

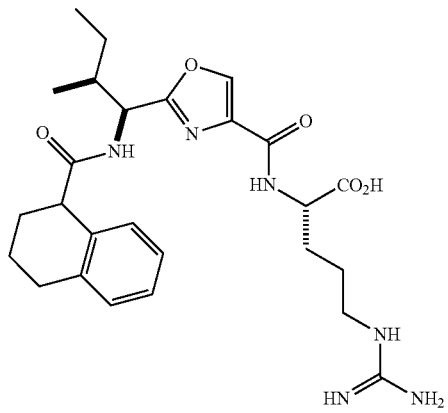 [SMILES: CC[C@H](C)[C@H](NC(=O)C1CCCc2ccccc21)c1nc(C(=O)N[C@@H](CCCNC(=N)N)C(=O)O)co1]

Analytical rt 8.019 (20% B to 100% B in 10 mins) 100% pure. HRMS (M+H) $C_{26}H_{37}N_6O_5^+$ Calc 513.2820 found 513.2816. $^1$H NMR (400 MHz, DMSO-d$_6$): 8.72 (1H, d, J=8.4 Hz, Arg-NH), 8.62 (1H, s, Ox), 8.17 (1H, d, J=8 Hz, Ile-NH), 7.54 (1H, m, Arg-Nhε), 7.11-6.94 (4H, m, Ar), 4.87 (1H, t, J=8.6 Hz, Ile-Hα), 4.45-4.37 m, Arg-Hα), 3.79 (1H, t, J=6.4 Hz, tetrahydronapthalene), 3.09 (2H, m, Arg-Hδ), 2.74-2.64 (2H, m, tetrahydronapthalene), 2.02-1.72 (7H, m, tetrahydro, Ile-βH, Arg-Hβ$_2$) 1.61-1.48 (3H, m, Ile-Hγ$_1$, Arg-Hγ$_2$), 1.32-1.21 (1H, m, Ile-Hγ$_1$) 0.87 (3H, t, J=4.8 Hz, Ile-Hδ), 0.82-0.80 (3H, m, Ile-Hγ CH$_3$). $^{13}$C NMR (100 MHz DMSO-d$_6$): δ 174.3, 173.0, 163.7, 163.5, 159.9, 156.6, 142.1, 137.2, 137.0, 135.3, 1325.3, 5.0, 134.9, 129.0, 128.9, 128.2, 126.1, 126.0, 125.5, 51.3, 44.7, 37.2, 28.8, 28.0, 26.9, 24.9, 20.7, 20.5, 15.5, 15.4, 10.6.

Example 22

2,3-dimethoxybenzoic acid-isoleucine-oxazole-arginine-OH (Compound 22)

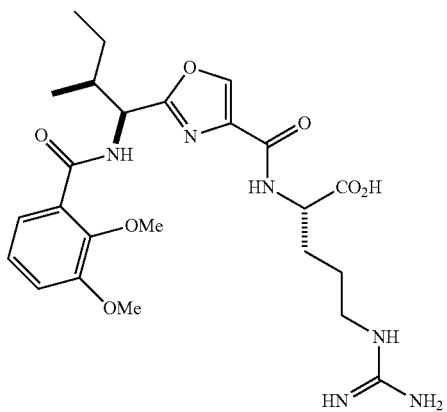 [SMILES: CC[C@H](C)[C@H](NC(=O)c1cccc(OC)c1OC)c1nc(C(=O)N[C@@H](CCCNC(=N)N)C(=O)O)co1]

Analytical rt 7.659 (20% B to 100% B in 10 mins) 100% pure. HRMS (M+H) $C_{24}H_{35}N_6O_7^+$ Calc 519.2562 found 519.2561. $^1$H NMR (400 MHz, DMSO-$d_6$): 8.84 (1H, d, J=8.4 Hz, Arg-NH) 8.63 (1H, s, Ox), 8.16 (1H, d, J=8 Hz, Ile-NH), 7.55 (1H, m, Arg-Nhε), 7.20-7.11 (3H, m, Ar), 5.09 (1H, t, J=8.6 Hz, Ile-Hα), 4.42-4.36 (1H, m, Arg-Hα), 3.83 (3H, s, OMe), 3.78 (3H, s, OMe), 3.09 (2H, q, J=6.8 Hz, Arg-Hδ), 2.09-2.02 (1H, m, Ile-βH), 1.91-1.72 (2H, m, Arg-Hβ$_2$) 1.58-1.46 (3H, m, Ile-Hγ$_1$, Arg-Hγ$_2$), 1.31-1.201 (1H, m, Ile-Hγ$_1$), 0.89 (3H, t, J=4.8 Hz, Ile-Hδ), 0.83 (3H, d, J=6.8 Hz, Ile-Hγ CH$_3$).
$^{13}$C NMR (100 MHz DMSO-$d_6$) δ 165.4, 163.3, 159.8, 156.7, 152.5, 146.3, 142.2, 135.4, 128.8, 124.2, 120.7, 115.2, 61.1, 56.1, 51.5, 37.4, 28.2, 25.3, 24.9, 15.4, 10.8.

Example 23

2,4-Dimethoxybenzoic acid-isoleucine-oxazole-arginine-OH (Compound 23)

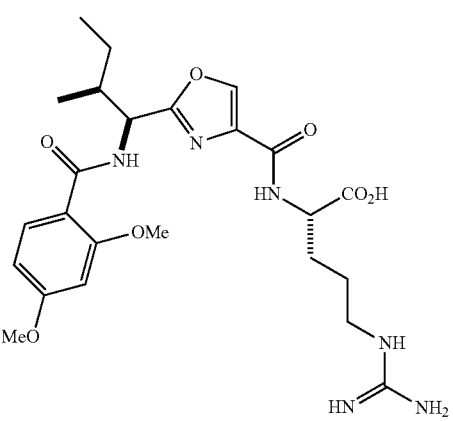 [SMILES: CC[C@H](C)[C@H](NC(=O)c1ccc(OC)cc1OC)c1nc(C(=O)N[C@@H](CCCNC(=N)N)C(=O)O)co1]

Analytical rt 7.722 (20% B to 100% B in 10 mins) 99% pure. HRMS (M+H) $C_{24}H_{35}N_6O_7^+$ Calc 519.2562 found 519.2565. $^1$H NMR (400 MHz, DMSO-$d_6$): 8.61 (1H, s, Ox), 8.47 (1H, d, J=8.0 Hz, Arg-NH) 8.21 (1H, d, J=8 Hz, Ile-NH),) 7.76 (1H, d, J=8.8 Hz, Ar) 7.51 (1H, t, J=5.6 Hz, Arg-Nhε), 6.69-6.62 (2H, m, Ar), 5.11 (1H, t, J=8.6 Hz, Ile-Hα), 4.43-4.37 (1H, m, Arg-Hα), 3.95 (3H, s, OMe) 3.82 (3H, s, OMe), 3.09 (2H, q, J=6.8 Hz, Arg-Hδ), 2.10-2.03 (1H, m, Ile-(H)), 1.91-1.72 (2H, m, Arg-Hβ$_2$) 1.55-1.46 (3H, m, Ile-Hγ$_1$, Arg-Hγ$_2$), 1.28-1.17 (1H, m, Ile-Hγ$_1$) 0.90 (3H, t, J=4.8 Hz, Ile-Hδ), 0.85 (3H, d, J=6.8 Hz, Ile-Hγ CH$_3$). $^{13}$C NMR (100 MHz DMSO-$d_6$) δ 173.0, 164.2, 163.4, 163.2, 159.9, 158.8, 156.6, 142.1, 135.4, 132.4, 114.0, 106.0, 98.7, 56.4, 55.6, 55.5, 51.8, 51.7, 51.3, 37.7, 27.9, 25.3, 24.9, 15.4, 11.0.

Example 24

2-(4-fluorophenyl)acetic acid-Leucine-Oxazole-Arginine-OH (Compound 24)

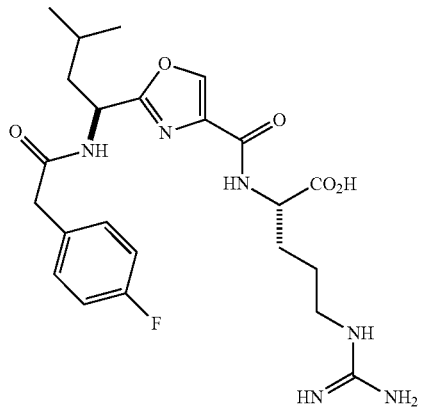 [SMILES: CC(C)C[C@H](NC(=O)Cc1ccc(F)cc1)c1nc(C(=O)N[C@@H](CCCNC(=N)N)C(=O)O)co1]

Analytical rt 7.538 (20% B to 100% B in 10 mins) 95% pure. HRMS (M+H) $C_{23}H_{32}FN_6O_5^+$ Calc 491.2413 found 491.2410. $^1$H NMR (400 MHz, DMSO-$d_6$): δ 8.74 (1H, d, J=8 Hz, Arg-NH) 8.58 (1H, s, Ox), 8.16 (1H, d, J=7.8 Hz, Leu-NH), 7.48-7.08 (9H, m, Arg-NH, Ar), 5.05-4.99 (1H, m, Leu-Hα) 4.43-4.37 (1H, m, Arg-Hα), 3.46 (2H, q, J=19.2 11.2 Hz, Ph CH$_2$), 1.91-1.45 (7H, m, Leu-Hγ, Leu-Hβ$_2$, Arg-Hβ$_2$, Arg-Hγ$_2$), 0.86 (6H, dd, J=12, 6.4 Hz, Leu-Hδ).

Example 25

Boc-isoleucine-5-methyl-oxazole-arginine-OH (Compound 25)

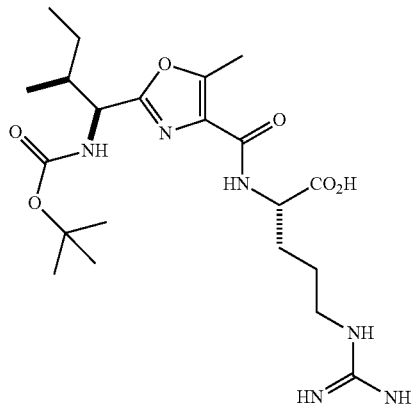

$^1$H NMR (600 MHz, DMSO-$d_6$): δ 7.95 (d, J=8.0 Hz, 1H); 7.57 (t, J=5.3 Hz, 1H); 7.51 (d, J=8.4 Hz, 1H); 4.46 (m,

1H); 4.39 (m, 1H); 3.15-3.05 (m, 2H); 2.54 (s, 3H); 1.93-1.83 (m, 2H); 1.83-1.72 (m, 1H); 1.56-1.45 (m, 3H); 1.37 (s, 9H); 1.19 (m, 1H); 0.85 (t, J=7.4 Hz, 3H); 0.74 (d, J=6.8 Hz, 3H).

Example 26

Benzofuran carboxylic acid-Leucine-5-Methyl-Oxazole-Arginine (Compound 26)

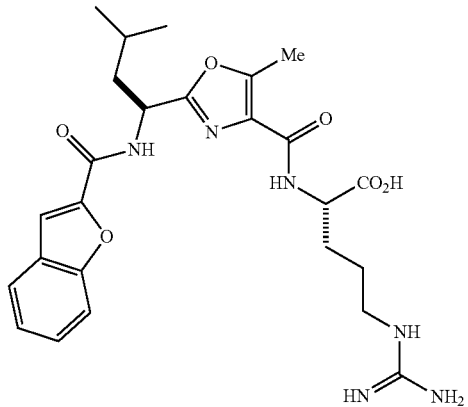 [SMILES: Cc1oc([C@H](CC(C)C)NC(=O)c2cc3ccccc3o2)nc1C(=O)N[C@@H](CCCNC(=N)N)C(=O)O]

HRMS calculated for $C_{25}H_{33}N_6O_6^+$ Calc 513.2456. found 513.2456. Retention time (20% B to 100% B in 10 minutes) is 8.359 minutes, purity 97.4%. $^1$H NMR (600 MHz, DMSO-d$_6$): δ 9.28 (1H, d, J=8.3 Hz, Arg-NH), 8.01 (1H, d, J=8.3 Hz, Leu-NH), 7.78 (1H, d, J=7.6, Ar), 7.67-7.63 (2H, m, Ar), 7.50-7.46 (1H, m, Ar), 7.35-7.33 (1H, m, Ar), 5.29-5.25 (1H, m, Leu-Hα), 4.41-4.37 (1H, m, Arg-Hα), 3.10-3.06 (2H, m, Arg-Hδ), 2.53 (3H, s, CH$_3$), 2.05-2.00 (1H, m, Leu-Hγ), 1.89-1.74 (3H, m, Leu-β1, Arg-Hβ), 1.69-1.63 (1H, m, Leu-Hβ2), 1.50-1.45 (2H, m, Arg-Hγ), 0.95 (3H, d, J=6.6 Hz, Leu-Hβ), 0.92 (3H, d, J=6.6 Hz, Leu-Hδ).

Example 27

Benzothiophene-2-carboxylic acid-Leucine-5-Methyl-Oxazole-Arginin (Compound 27)

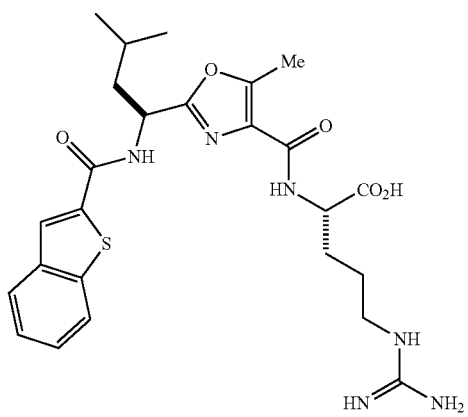

HRMS calculated for $C_{25}H_{33}N_6O_5S^+$ Calc 529.2228. found 529.2228. Retention time (20% B to 100% B in 20 minutes) is 12.68 minutes, purity 100%. $^1$H NMR (600 MHz, DMSO-d$_6$): δ 9.28 (1H, d, J=8.1 Hz, Arg-NH), 8.23 (1H, s, Ar), 8.02 (1H, d, J=8.3 Hz, Leu-NH), 7.96-7.95 (1H, d, J=7.8 Hz, Ar), 7.50-7.43 (3H, m, Ar), 5.28-5.24 (1H, m, Leu-Hα), 4.41-4.37 (1H, m, Arg-Hα), 3.11-3.07 (2H, m, Arg-Hδ), 2.54 (3H, s, CH$_3$), 2.02-1.97 (1H, m, Leu-Hγ), 1.89-1.74 (3H, m, Leu-β1, Arg-Hβ), 1.71-1.66 (1H, m, Leu-Hβ2), 1.51-1.45 (2H, m, Arg-Hγ), 0.96 (3H, d, J=6.7 Hz, Leu-Hδ), 0.92 (3H, d, J=6.5 Hz, Leu-Hδ).

Example 28

Indole-2-carboxylic acid-Leucine-5-Methyl-Oxazole-Arginine (Compound 28)

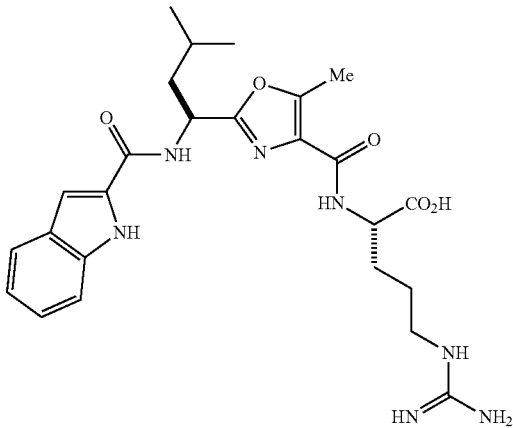 [SMILES: Cc1oc([C@H](CC(C)C)NC(=O)c2cc3ccccc3[nH]2)nc1C(=O)N[C@@H](CCCNC(=N)N)C(=O)O]

HRMS calculated $C_{25}H_{34}N_7O_5^+$ Calc 512.2616. found 512.2621. Retention time (20% B to 100B in 10 minutes) is 8.343 minutes, purity 100%. $^1$H NMR (600 MHz, DMSO-d$_6$): δ 8.94 (1H, d, J=8.5 Hz, Arg-NH), 8.0 (1H, d, J=8.2 Hz, Leu-NH), 7.61 (1H, d, J=7.6 Hz, Ar), 7.50-7.40 (2H, m, Ar), 7.24-7.17 (3H, m, Ar), 7.05-7.02 (1H, m, Ar), 5.33-5.29 (1H, m, Leu-Hα), 4.41-4.37 (1H, m, Arg-Hα), 3.10-3.06 (2H, m, Arg-Hδ), 2.53 (3H, s, CH$_3$), 2.01-1.96 (1H, m, Leu-Hγ), 1.90-1.73 (3H, m, Leu-β1, Arg-Hβ), 1.71-1.65 (1H, m, Leu-Hβ2), 1.51-1.45 (2H, m, Arg-Hγ), 0.95 (3H, d, J=6.7 Hz, Leu-Hδ), 0.93 (3H, d, J=6.5 Hz, Leu-Hδ).

Example 29

Picolinic acid-Leucine-5-Methyl-Oxazole-Arginine (Compound 29)

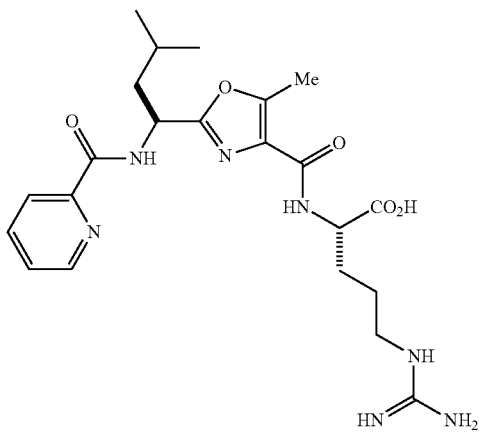 [SMILES: Cc1oc([C@H](CC(C)C)NC(=O)c2ccccn2)nc1C(=O)N[C@@H](CCCNC(=N)N)C(=O)O]

HRMS calculated for $C_{22}H_{32}N_7O_5^+$ Calc 474.2459. found 474.2459. Retention time (20% B to 100B in 20 minutes) is 10.105 minutes, purity 100%. $^1$H NMR (600 MHz, DMSO-$d_6$): δ 9.20 (1H, d, J=8.7 Hz, Arg-NH), 8.67 (1H, d, J=8.3 Hz, Leu-NH), 8.06-7.99 (3H, m, Ar), 7.64-7.62 (1H, m, Ar), 5.30-5.25 (1H, m, Leu-Hα), 4.41-4.36 (1H, m, Arg-Hα), 3.12-3.04 (2H, m, Arg-Hδ), 2.51 (3H, s, CH$_3$), 2.11-2.05 (1H, m, Leu-Hγ), 1.89-1.73 (3H, m, Leu-β1, Arg-Hβ), 1.65-1.57 (1H, m, Leu-Hβ2), 1.51-1.43 (2H, m, Arg-Hγ), 0.93 (3H, d, J=6.6 Hz, Leu-Hδ), 0.91 (3H, d, J=6.7 Hz, Leu-Hδ).

Example 30

Nicotinic acid-Leucine-5-Methyl-Oxazole-Arginine
(Compound 30)

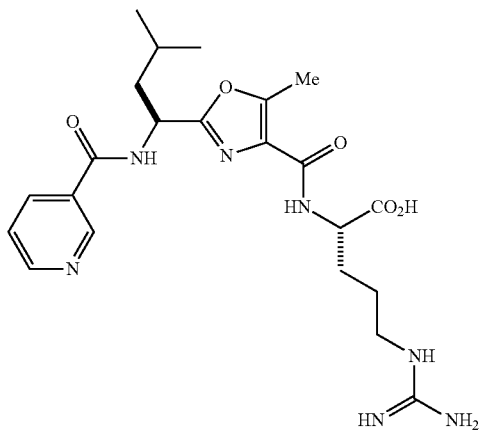 [SMILES: Cc1oc([C@H](CC(C)C)NC(=O)c2cccnc2)nc1C(=O)N[C@@H](CCCNC(=N)N)C(=O)O]

HRMS calculated for $C_{22}H_{32}N_7O_5^+$ Calc 474.2459. found 474.2460. Retention time (20% B to 100B in 10 minutes) is 6.932 minutes, purity 100%. $^1$H NMR (600 MHz, DMSO-$d_6$): δ 9.19 (1H, d, J=8.2 Hz, Arg-NH), 9.04 (1H, m, Ar), 8.73 (1H, m, Ar), 8.24 (1H, m, Ar) 7.54 (1H, m, Ar), 8.00 (1H, d, J=8.2 Hz, Leu-NH), 5.30-5.26 (1H, m, Leu-Hα), 4.41-4.37 (1H, m, Arg-Hα), 3.13-3.06 (2H, m, Arg-Hδ), 2.53 (3H, s, CH$_3$), 2.00-1.94 (1H, m, Leu-Hγ), 1.90-1.74 (3H, m, Leu-β1, Arg-Hβ), 1.70-1.63 (1H, m, Leu-Hβ2), 1.51-1.45 (2H, m, Arg-Hγ), 0.95 (3H, d, J=6.7 Hz, Leu-Hβ), 0.91 (3H, d, J=6.6 Hz, Leu-Hδ).

Example 31

Isonicotinic acid-Leucine-5-Methyl-Oxazole-Arginine
(Compound 31)

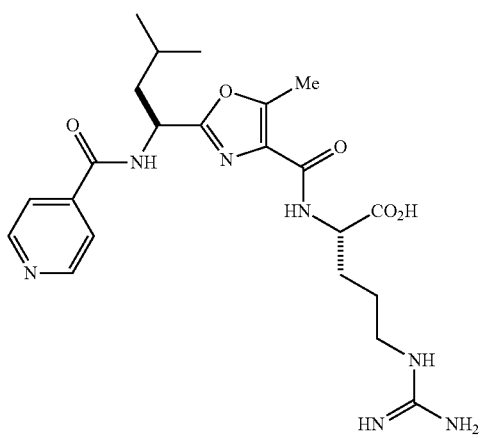 [SMILES: Cc1oc([C@H](CC(C)C)NC(=O)c2ccncc2)nc1C(=O)N[C@@H](CCCNC(=N)N)C(=O)O]

HRMS calculated $C_{22}H_{32}N_7O_5^+$ Calc 474.2459. found 474.2455. Retention time (20% B to 100B in 20 minutes) is 6.843 minutes, purity 100%. $^1$H NMR (600 MHz, DMSO-$d_6$): δ 9.29 (1H, d, J=8.2 Hz, Arg-NH), 8.75 (2H, m, Ar), 8.00 (1H, d, J=8.2 Hz, Leu-NH), 7.8 (2H, m, Ar), 5.29-5.25 (1H, m, Leu-Hα), 4.41-4.37 (1H, m, Arg-Hα), 3.14-3.04 (2H, m, Arg-Hδ), 2.53 (3H, s, CH$_3$), 2.00-1.94 (1H, m, Leu-Hγ), 1.91-1.70 (3H, m, Leu-β1, Arg-Hβ3), 1.69-1.62 (1H, m, Leu-Hβ2), 1.50-1.45 (2H, m, Arg-Hγ), 0.94 (3H, d, J=6.7 Hz, Leu-Hδ), 0.91 (3H, d, J=6.7 Hz, Leu-Hδ).

Example 32

Cyclohexane carboxylic acid-Leucine-5-Methyl-Oxazole-Arginine
(Compound 32)

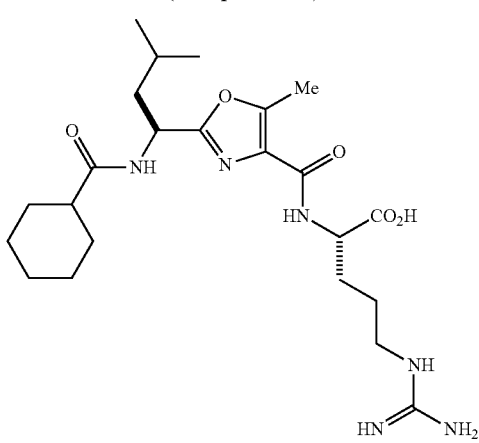

HRMS calculated for $C_{23}H_{39}N_6O_5^+$ Calc 479.2976. found 479.2975. Retention time (20% B to 100B in 10 minutes) is 8.343 minutes, purity 100%. $^1$H NMR (600 MHz, DMSO-$d_6$): δ 8.27 (1H, d, J=8.2 Hz, Arg-NH), 7.94 (1H, d, J=8.2 Hz, Leu-NH), 5.00-4.96 (1H, m, Leu-Hα), 4.41-4.37 (1H, m, Arg-Hα), 3.13-3.06 (2H, m, Arg-Hδ), 2.51 (3H, s, CH$_3$), 2.12-2.18 (1H, m, Leu-Hγ), 1.90-1.06 (17H, m, CH$_2$, Leu-β, Arg-Hβ, Arg-Hγ), 0.90 (3H, d, J=6.2 Hz, Leu-Hδ), 0.85 (3H, d, J=6.0 Hz, Leu-Hδ).

Example 33

Cyclohexyl acetic acid-Leucine-5-Methyl-Oxazole-Arginine
(Compound 33)

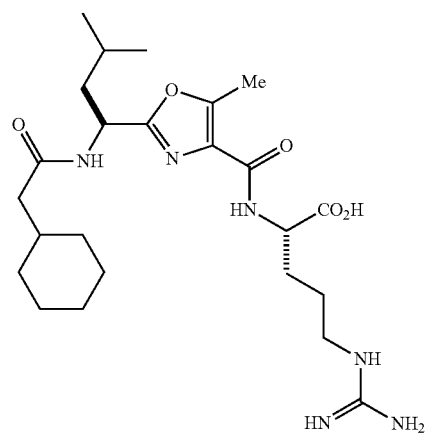 [SMILES: Cc1oc([C@H](CC(C)C)NC(=O)CC2CCCCC2)nc1C(=O)N[C@@H](CCCNC(=N)N)C(=O)O]

HRMS calculated for $C_{24}H_{41}N_6O_5^+$ Calc 493.3133. found 493.3130. Retention time (20% B to 100B in 20 minutes) is 11.881 minutes, purity 100%. $^1$H NMR (600 MHz, DMSO-d$_6$): δ8.37 (1H, d, J=8.1 Hz, Arg-NH), 7.93 (1H, d, J=8.1 Hz, Leu-NH), 5.00-4.96 (1H, m, Leu-Hα), 4.41-4.36 (1H, m, Arg-Hα), 3.12-3.06 (2H, m, Arg-Hδ), 2.51 (3H, s, CH$_3$), 2.00-1.02 (20H, m, CH$_2$, Leu-Hγ, Leu-β, Arg-Hβ, Arg-Hγ), 0.90 (3H, d, J=6.3 Hz, Leu-Hα), 0.85 (3H, d, J=6.0 Hz, Leu-Hδ).

Example 34

3,3-Dimethylbutanoic acid-Leucine-5-Methyl-Oxazole-Arginine (Compound 34)

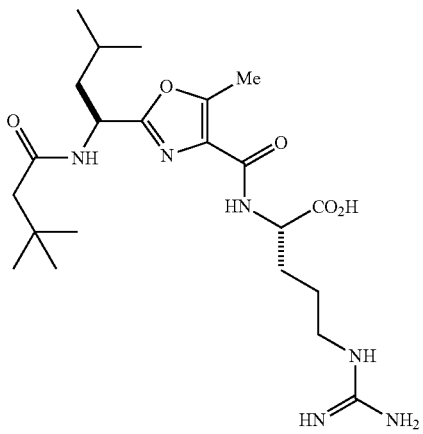 [SMILES: Cc1oc([C@H](CC(C)C)NC(=O)CC(C)(C)C)nc1C(=O)N[C@@H](CCCNC(=N)N)C(=O)O]

HRMS calculated for $C_{22}H_{39}N_6O_5^+$ Calc 467.2976. found 467.2978. Retention time (20% B to 100B in 10 minutes) is 7.898 minutes, purity 100%. $^1$H NMR (600 MHz, DMSO-d$_6$): δ 8.33 (1H, d, J=8.3 Hz, Arg-NH), 7.92 (1H, d, J=8.3 Hz, Leu-NH), 5.00-4.95 (1H, m, Leu-Hα), 4.41-4.36 (1H, m, Arg-Hα), 3.13-3.06 (2H, m, Arg-Hδ), 2.50 (3H, s, CH$_3$), 2.00 (2H, s, CH$_2$), 1.90-1.80 (1H, m, Leu-Hγ), 1.80-1.70 (2H, m, Arg-Hβ), 1.66-1.56 (1H, m, Leu-Hβ), 1.52-1.43 (2H, m, Arg-Hγ), 0.93 (9H, s, 3×CH$_3$), 0.90 (3H, d, J=6.3 Hz, Leu-Hδ), 0.86 (3H, d, J=6.0 Hz, Leu-Hδ).

Example 35

4-Methyl valeric acid-Leucine-5-Methyl-Oxazole-Arginine (Compound 35)

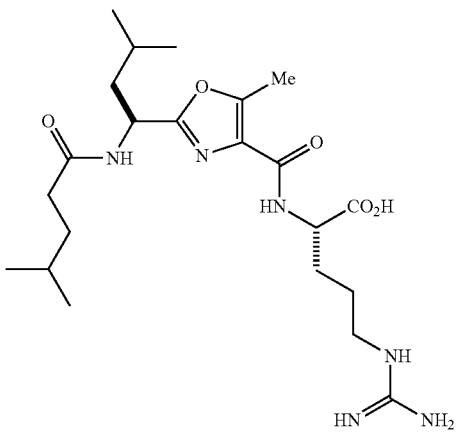 [SMILES: Cc1oc([C@H](CC(C)C)NC(=O)CCC(C)C)nc1C(=O)N[C@@H](CCCNC(=N)N)C(=O)O]

HRMS calculated for $C_{22}H_{39}N_6O_5^+$ Calc 467.2976. found 467.2972. Retention time (20% B to 100B in 10 minutes) is 8.092 minutes, purity 100%. $^1$H NMR (600 MHz, DMSO-d$_6$): δ 8.39 (1H, d, J=8.3 Hz, Arg-NH), 7.90 (1H, d, J=8.0 Hz, Leu-NH), 5.02-4.97 (1H, m, Leu-Hα), 4.32-4.27 (1H, m, Arg-Hα), 3.11-3.06 (2H, m, Arg-Hδ), 2.51 (3H, s, CH$_3$), 2.17-2.06 (2H, m, COCH$_2$), 1.87-1.79 (1H, m, Leu-Hγ), 1.79-1.69 (2H, m, Leu-β), 1.64-1.55 (2H, m, Arg-Hβ), 1.52-1.42 (3H, m, CH, Arg-Hγ), 1.42-1.32 (2H, m, COCH$_2$CH$_2$), 1.92-1.82 (12H, m, 2×CH$_3$, 2×Leu-Hδ).

Example 36

4-(Trifluoromethyl)-phenylacetic acid-Leucine-5-Methyl-Oxazole-Arginine (Compound 36)

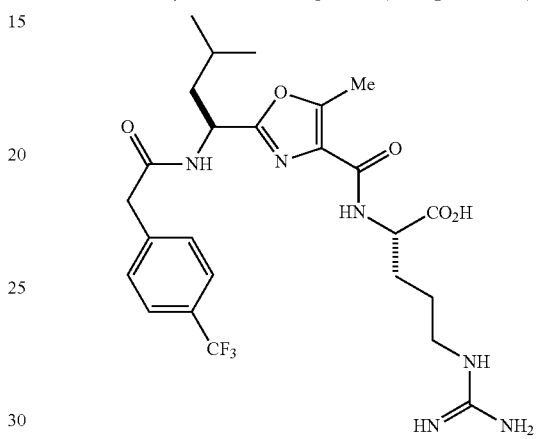

HRMS calculated for $C_{25}H_{34}F_3N_6O_5^+$ Calc 555.2537. found 555.2535. Retention time (20% B to 100B in 10 minutes) is 8.676 minutes, purity 100%. $^1$H NMR (600 MHz, DMSO-d$_6$): δ8.8 (1H, d, J=8.3 Hz, Arg-NH), 7.96 (1H, d, J=8.2 Hz, Leu-NH), 7.66 (2H, d, J=8.0 Hz, Ar), 7.46 (2H, d, J=8.0 Hz, Ar), 5.00-4.96 (1H, m, Leu-Hα), 4.40-4.36 (1H, m, Arg-Hα), 3.13-3.04 (2H, m, Arg-Hδ), 2.50 (3H, s, CH$_3$), 1.91-1.81 (1H, m, Leu-Hγ), 1.80-1.61 (3H, m, Leu-β1, Arg-Hβ), 1.60-1.52 (1H, m, Leu-Hβ2), 1.51-1.42 (2H, m, Arg-Hγ), 0.89 (3H, d, J=6.7 Hz, Leu-Hδ), 0.82 (3H, d, J=6.6 Hz, Leu-Hδ).

Example 37

2-Methoxy-phenylacetic acid-Leucine-5-Methyl-Oxazole-Arginine (Compound 37)

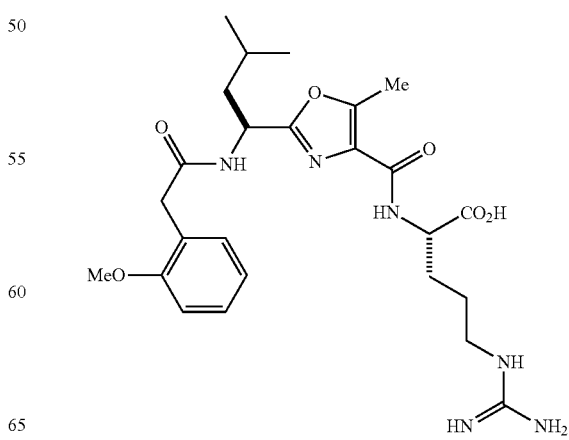

HRMS calculated for $C_{25}H_{37}N_6O_6^+$ Calc 517.2769. found 517.2768. Retention time (20% B to 100B in 10 minutes) is 7.893 minutes, purity 100%. $^1$H NMR (600 MHz, DMSO-d$_6$): δ 8.52 (1H, d, J=8.1 Hz, Arg-NH), 7.96 (1H, d, J=8.2 Hz, Leu-NH), 7.20-6.83 (4H, m, Ar), 5.0-4.89 (1H, m, Leu-Hα), 4.42-4.37 (1H, m, Arg-Hα), 3.70 (3H, s, OCH$_3$), 3.12-3.06 (2H, m, Arg-Hδ), 2.53 (3H, s, CH$_3$), 1.90-1.72 (3H, m, Leu-Hγ, Arg-Hβ), 1.69-1.60 (2H, m, Leu-Hβ), 1.51-1.43 (2H, m, Arg-Hγ), 0.92 (3H, d, J=6.3 Hz, Leu-Hδ), 0.86 (3H, d, J=6.3, Hz, Leu-Hδ).

Example 38

3-Methoxy-phenylacetic acid-Leucine-5-Methyl-Oxazole-Arginin (Compound 38)

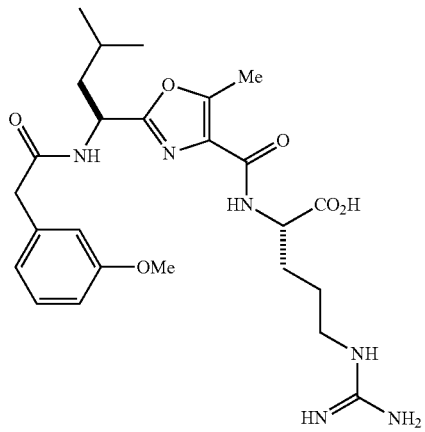 [SMILES: COc1cccc(CC(=O)N[C@@H](CC(C)C)c2nc(C(=O)N[C@@H](CCCNC(=N)N)C(=O)O)c(C)o2)c1]

HRMS calculated for $C_{25}H_{37}N_6O_6^+$ Calc 517.2769. found 517.2762. Retention time (20% B to 100B in 20 minutes) is 10.728 minutes, purity 98.6%. $^1$H NMR (600 MHz, DMSO-d$_6$): δ 8.7 (1H, d, J=8.2 Hz, Arg-NH), 7.97 (1H, d, J=8.2 Hz, Leu-NH), 7.51-7.47 (2H, m, Ar), 7.21-7.18 (1H, m, Ar), 7.81-7.77 (4H, m, Ar), 5.00-4.96 (1H, m, Leu-Hα), 4.41-4.37 (1H, m, Arg-Hα), 3.61 (3H, s, OCH$_3$), 3.11-3.06 (2H, m, Arg-Hδ), 2.51 (3H, s, CH$_3$), 1.89-1.82 (1H, m, Leu-Hγ), 1.80-1.73 (2H, m, Arg-Hβ), 1.69-1.54 (2H, m, Leu-Hβ), 1.50-1.44 (2H, m, Arg-Hγ), 0.90 (3H, d, J=6.5 Hz, Leu-Hδ), 0.83 (3H, d, J=6.6 Hz, Leu-Hδ).

Example 39

4-Methoxy-phenylacetic acid-Leucine-5-Methyl-Oxazole-Arginine (Compound 39)

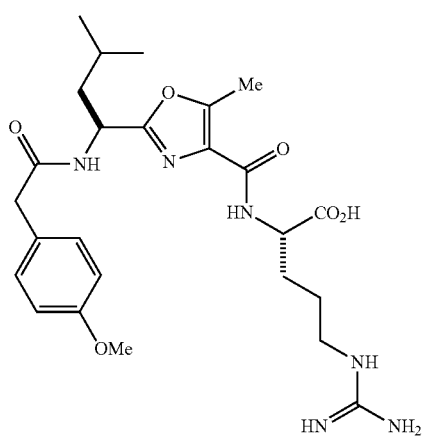 [SMILES: COc1ccc(CC(=O)N[C@@H](CC(C)C)c2nc(C(=O)N[C@@H](CCCNC(=N)N)C(=O)O)c(C)o2)cc1]

HRMS calculated $C_{25}H_{37}N_6O_6^+$ Calc 517.2769. found 517.2770. Retention time (20% B to 100B in 10 minutes) is 7.752 minutes, purity 97.2%. $^1$H NMR (600 MHz, DMSO-d$_6$): δ 8.65 (1H, d, J=8.2 Hz, Arg-NH), 7.95 (1H, d, J=8.3 Hz, Leu-NH), 7.50-7.48 (1H, m, Ar), 7.14 (3H, d, J=8.7 Hz, Ar), 6.86-6.83 (3H, m, Ar), 5.00-4.94 (1H, m, Leu-Hα), 4.41-4.37 (1H, m, Arg-Hα), 3.70 (3H, s, OCH$_3$), 3.11-3.05 (2H, m, Arg-Hδ), 2.99 (3H, s, CH$_3$), 1.89-1.82 (1H, m, Leu-Hγ), 1.80-1.72 (2H, m, Leu-β), 1.67-1.53 (2H, m, Leu-Hβ), 1.50-1.44 (2H, m, Arg-Hγ), 0.89 (3H, d, J=6.6 Hz, Leu-Hδ), 0.82 (3H, d, J=6.5 Hz, Leu-Hδ).

Example 40

Phenyl sulfonamide-Leucine-5-Methyl-Oxazole-Arginine (Compound 40)

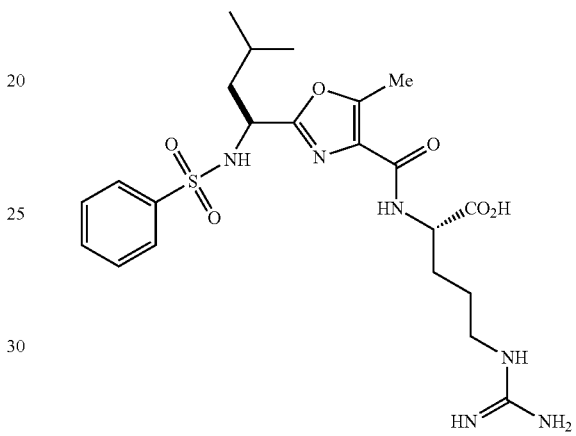

HRMS calculated for $C_{22}H_{33}N_6O_6S^+$ Calc 509.2177. found 509.2172. Retention time (20% B to 100B in 20 minutes) is 10.366 minutes, purity 100%. $^1$H NMR (600 MHz, DMSO-d$_6$): δ 8.58 (1H, d, J=8.7 Hz, Arg-NH), 7.81 (1H, d, J=8.3 Hz, Leu-NH), 7.64-7.39 (5H, m, Ar), 4.40-4.30 (2H, m, Leu-Hα, Arg-Hα), 3.16-3.09 (2H, m, Arg-Hδ), 2.23 (3H, s, CH$_3$), 1.89-1.80 (1H, m, Leu-Hγ), 1.79-1.71 (1H, m, Leu-β1), 1.69-1.62 (1H, m, Leu-Hβ2), 1.57-1.44 (4H, m, Arg-Hβ, Arg-Hγ), 0.83 (3H, d, J=6.4 Hz, Leu-Hβ), 0.76 (3H, d, J=6.3 Hz, Leu-Hδ).

Example 41

3-(4-Methoxyphenyl)propionic acid-Leucine-5-Methyl-Oxazole-Arginine (Compound 41)

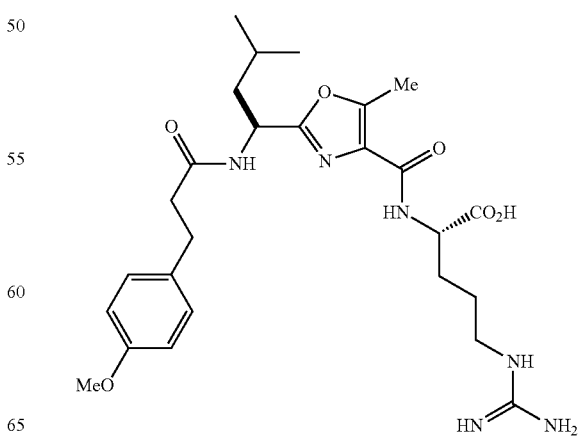

HRMS calculated for $C_{26}H_{39}N_6O_6^+$ Calc 531.2926. found 531.2927. Retention time (20% B to 100B in 10 minutes) is 7.903 minutes, purity 100%. $^1$H NMR (600 MHz, DMSO-$d_6$): δ 8.38 (1H, d, J=8.3 Hz, Arg-NH), 7.96 (1H, d, J=8.3 Hz, Leu-NH), 7.88 (2H, d, J=8.4, Ar), 7.78 (2H, d, J=8.6, Ar), 5.02-4.97 (1H, m, Leu-Hα), 4.41-4.36 (1H, m, Arg-Hα), 3.69 (3H, s, OCH$_3$), 3.13-3.05 (2H, m, Arg-Hδ), 2.76-2.71 (2H, m, PheCH$_2$), 2.51 (3H, s, CH$_3$), 2.43-2.33 (2H, m, PheCH$_2$CH$_2$), 1.90-1.81 (1H, m, Leu-Hγ), 1.81-1.65 (2H, m, Leu-β), 1.60-1.52 (1H, m, Arg-Hβ1), 1.52-1.36 (3H, m, Arg-Hβ2, Arg-Hγ), 0.86 (3H, d, J=6.7 Hz, Leu-Hβ), 0.81 (3H, d, J=6.5 Hz, Leu-Hδ).

Example 42 m-Anisic acid-Leucine-5-Methyl-Oxazole-Arginine
(Compound 42)

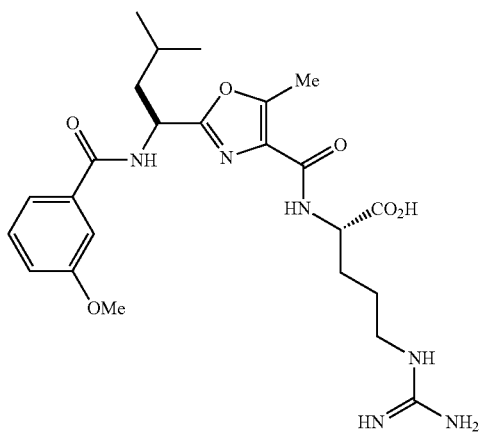 [SMILES: COc1cccc(C(=O)N[C@@H](CC(C)C)c2nc(C(=O)N[C@@H](CCCNC(=N)N)C(=O)O)c(C)o2)c1]

HRMS calculated for $C_{24}H_{35}N_6O_6^+$ Calc 503.2613. found 503.2614. Retention time (20% B to 100B in 10 minutes) is 7.937 minutes, purity 100%. $^1$H NMR (600 MHz, DMSO-$d_6$): δ 8.94 (1H, d, J=8.2 Hz, Arg-NH), 7.99 (1H, d, J=8.2 Hz, Leu-NH), 7.49-7.36 (4H, m, Ar), 5.30-5.24 (1H, m, Leu-Hα), 4.42-4.37 (1H, m, Arg-Hα), 3.79 (3H, s, OCH$_3$), 3.14-3.03 (2H, m, Arg-Hδ), 2.76-2.71 (2H; m, PheCH$_2$), 2.53 (3H, s, CH$_3$), 2.02-1.93 (1H, m, Leu-Hγ), 1.91-1.73 (3H, m, Leu-01, Arg-Hβ), 1.69-1.60 (1H, m, Leu-β2), 1.53-1.43 (2H, m, Arg-Hγ), 0.94 (3H, d, J=6.7 Hz, Leu-Hβ), 0.91 (3H, d, J=6.5 Hz, Leu-Hδ).

Example 43

3,4-Dimethoxy-phenyl acetic
acid-Leucine-5-Methyl-Oxazole-Arginine
(Compound 43)

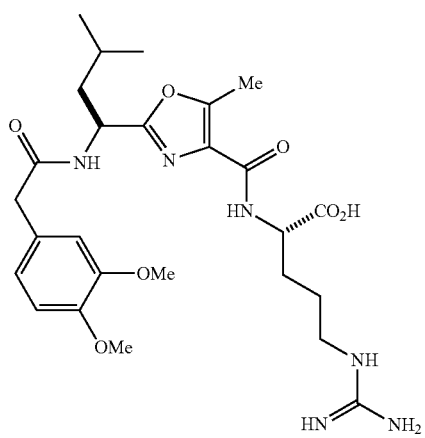 [SMILES: COc1ccc(CC(=O)N[C@@H](CC(C)C)c2nc(C(=O)N[C@@H](CCCNC(=N)N)C(=O)O)c(C)o2)cc1OC]

HRMS calculated for $C_{26}H_{39}N_6O_7^+$ Calc 547.2875. found 547.2872. Retention time (20% B to 100B in 10 minutes) is 7.358 minutes, purity 100%. $^1$H NMR (600 MHz, DMSO-$d_6$): δ 8.66 (1H, d, J=8.3 Hz, Arg-NH), 7.96 (1H, d, J=8.0 Hz, Leu-NH), 6.8 (2H, m, Ar), 6.74 (1H, m, Ar), 5.00-4.96 (1H, m, Leu-Hα), 4.41-4.36 (1H, m, Arg-Hα), 3.70 (6H, s, 2×OCH$_3$), 3.13-3.05 (2H, m, Arg-Hδ), 2.51 (3H, s, CH$_3$), 1.90-1.80 (1H, m, Leu-Hγ), 1.80-1.70 (2H, m, Arg-Hβ), 1.67-1.52 (1H, m, Leu-Hβ), 1.52-1.43 (2H, m, Arg-Hγ), 0.90 (3H, d, J=6.6 Hz, Leu-Hβ), 0.82 (3H, d, J=6.5 Hz, Leu-Hδ).

Example 44

2,5-Dimethoxy-phenyl acetic
acid-Leucine-5-Methyl-Oxazole-Arginine
(Compound 44)

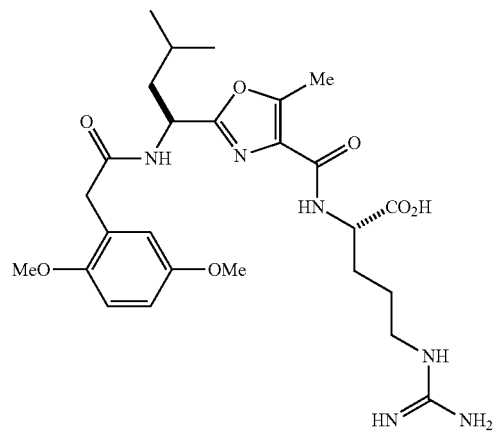 [SMILES: COc1ccc(OC)c(CC(=O)N[C@@H](CC(C)C)c2nc(C(=O)N[C@@H](CCCNC(=N)N)C(=O)O)c(C)o2)c1]

HRMS calculated for $C_{26}H_{39}N_6O_7^+$ Calc 547.2875. found 547.2879. Retention time (20% B to 100B in 10 minutes) is 7.895 minutes, purity 100%. $^1$H NMR (600 MHz, DMSO-$d_6$): δ 8.53 (1H, d, J=8.2 Hz, Arg-NH), 7.97 (1H, d, J=8.2 Hz, Leu-NH), 6.86-6.74 (3H, m, Ar), 5.04-4.99 (1H, m, Leu-Hα), 4.41-4.36 (1H, m, Arg-Hα), 3.65 (6H, s, 2×OCH$_3$), 3.13-3.04 (2H, m, Arg-Hδ), 2.53 (3H, s, CH$_3$), 1.91-1.82 (1H, m, Leu-Hγ), 1.81-1.70 (2H, m, Arg-Hβ), 1.68-1.59 (1H, m, Leu-Hβ), 1.51-1.44 (2H, m, Arg-Hγ), 0.92 (3H, d, J=6.2 Hz, Leu-Hβ), 0.86 (3H, d, J=6.2 Hz, Leu-Hδ).

Example 45 p-Tolyl
isocyanate-Leucine-5-Methyl-Oxazole-Arginine
(Compound 45)

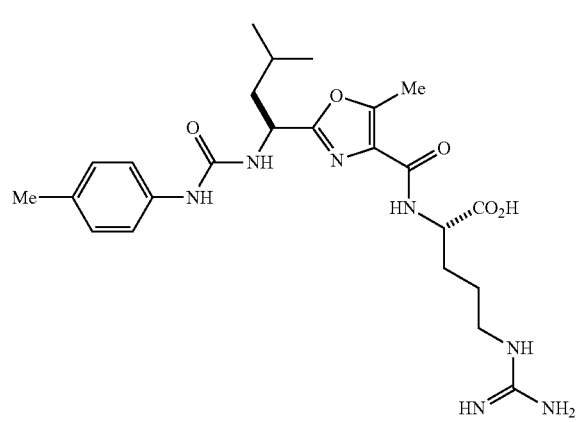 [SMILES: Cc1ccc(NC(=O)N[C@@H](CC(C)C)c2nc(C(=O)N[C@@H](CCCNC(=N)N)C(=O)O)c(C)o2)cc1]

HRMS calculated for $C_{24}H_{36}N_7O_5^+$ Calc 502.2772. found 502.2777. Retention time (20% B to 100B in 10 minutes) is 7.980 minutes, purity 100%. $^1$H NMR (600 MHz, DMSO-$d_6$): δ 8.44 (1H, s, PheNH), 7.97 (1H, d, J=8.0 Hz, Arg-NH), 7.25 (2H, d, J=8.3, Ar), 7.01 (2H, d, J 8.2 Hz, Ar), 6.77 (1H, d, J=8.0 Hz, Leu-NH), 4.95-4.90 (1H, m, Leu-Hα), 4.37-4.30 (1H, m, Arg-Hα), 3.13-3.06 (2H, m, Arg-Hδ), 2.54 (3H, s, CH$_3$), 2.20 (3H, s, PheCH$_3$), 1.88-1.80 (1H, m, Leu-Hγ), 1.80-1.58 (4H, m, Leu-β, Arg-Hβ), 1.51-1.45 (2H, m, Arg-Hγ), 0.93 (3H, d, J=6.1 Hz, Leu-Hδ), 0.90 (3H, d, J=6.0 Hz, Leu-Hδ).

Example 46

Benzylisocyanate-Leucine-5-Methyl-Oxazole-Arginine (Compound 46)

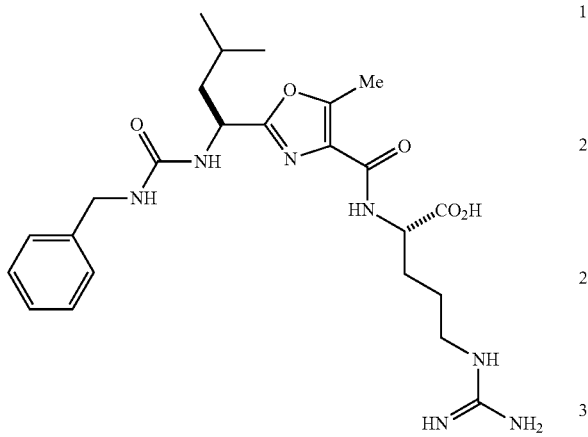

HRMS calculated for $C_{24}H_{36}N_7O_5^+$ Calc 502.2772. found 502.2774. Retention time (20% B to 100B in 10 minutes) is 7.681 minutes, purity 100%. $^1$H NMR (600 MHz, DMSO-$d_6$): δ 7.95 (1H, d, J=8.2 Hz, Arg-NH), 7.31-7.28 (2H, m, Ar), 7.23-7.19 (3H, m, Ar), 6.60 (1H, d, J=8.3 Hz, Leu-NH), 4.91-4.86 (1H, m, Leu-Hα), 4.42-4.37 (1H, m, Arg-Hα), 4.2 (2H, m, PheCH$_2$), 3.13-3.06 (2H, m, Arg-Hδ), 2.53 (3H, s, CH$_3$), 1.90-1.82 (1H, m, Leu-Hγ), 1.81-1.64 (2H, m, Leu-β), 1.64-1.54 (2H, m, Arg-Hβ), 1.53-1.44 (2H, m, Arg-Hγ), 0.91 (3H, d, J=6.0 Hz, Leu-Hδ), 0.88 (3H, d, J=6.0 Hz, Leu-Hδ).

Example 47

Phenyl hydrazine-Benzeneacetic acid-Leucine-5-Methyl-Oxazole-Arginine (Compound 47)

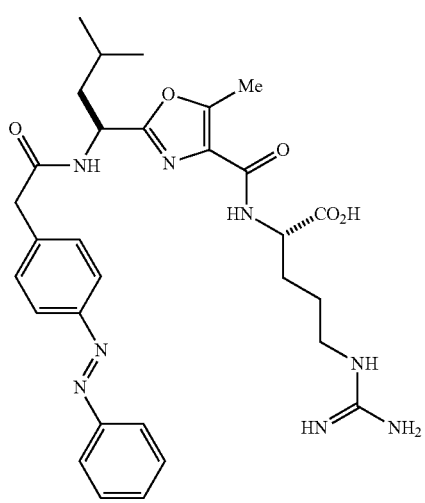 [SMILES: Cc1oc([C@H](CC(C)C)NC(=O)Cc2ccc(/N=N/c3ccccc3)cc2)nc1C(=O)N[C@@H](CCCNC(=N)N)C(=O)O]

HRMS calculated for $C_{30}H_{39}N_8O_5^+$ Calc 591.3038. found 591.3040. Retention time (20% B to 100B in 10 minutes) is 8.268 minutes, purity 97%. $^1$H NMR (600 MHz, DMSO-$d_6$): δ 8.80 (1H, d, J=8.2 Hz, Arg-NH), 7.97 (1H, d, J=8.2 Hz, Leu-NH), 7.89-7.82 (4H, m, Ar), 7.61-7.54 (3H, m, Ar), 7.48-7.45 (2H, d, J=8.3 Hz, Ar), 5.03-4.98 (1H, m, Leu-Hα), 4.41-4.37 (1H, m, Arg-Hα), 3.60 (2H, d, J=4.7 Hz, PheCH$_2$), 3.13-3.05 (2H, m, Arg-Hδ), 2.53 (3H, s, CH$_3$), 1.90-1.82 (1H, m, Leu-Hγ), 1.82-1.63 (3H, m, Leu-β1, Arg-Hβ), 1.63-1.55 (1H, m, Leu-β2), 1.52-1.44 (2H, m, Arg-Hγ), 0.91 (3H, d, J=6.6 Hz, Leu-Hβ), 0.84 (3H, d, J=6.5 Hz, Leu-Hδ).

Example 48

5-Bromonicotinic acid-Leucine-5-Methyl-Oxazole-Arginine (Compound 48)

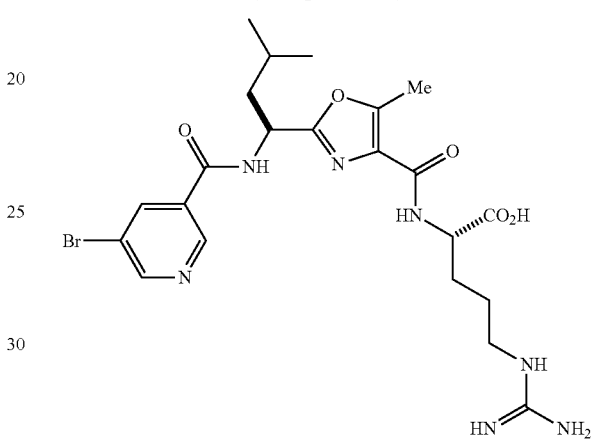

HRMS calculated for $C_{22}H_{31}BrN_7O_5^+$ Calc 552.1565. found 552.1568. Retention time (20% B to 100B in 10 minutes) is 7.682 minutes, purity 95%. $^1$H NMR (600, MHz, DMSO-$d_6$): δ 9.28 (1H, d, J=8.2 Hz, Arg-NH), 9.00 (1H, d, J=1.7 Hz, Ar), 8.88 (1H, d, J=2.0 Hz, Ar), 8.48 (1H, t, J=2.1 Hz, Ar), 8.00 (1H, d, J=8.0 Hz, Leu-NH), 5.29-5.24 (1H, m, Leu-Hα), 4.41-4.37 (1H, m, Arg-Hα), 3.69 (3H, s, OCH$_3$), 3.13-3.06 (2H, m, Arg-Hδ), 2.53 (3H, s, CH$_3$), 1.99-1.91 (1H, m, Leu-Hγ), 1.90-1.72 (3H, m, Leu-β1, Arg-Hβ), 1.71-1.60 (1H, m, Leu-β2), 1.52-1.44 (2H, m, Arg-Hγ), 0.94 (3H, d, J=6.6 Hz, Leu-Hβ), 0.91 (3H, d, J=6.6 Hz, Leu-Hδ).

Example 49

4-Phenoxybenzoic acid-Leucine-5-Methyl-Oxazole-Arginine (Compound 49)

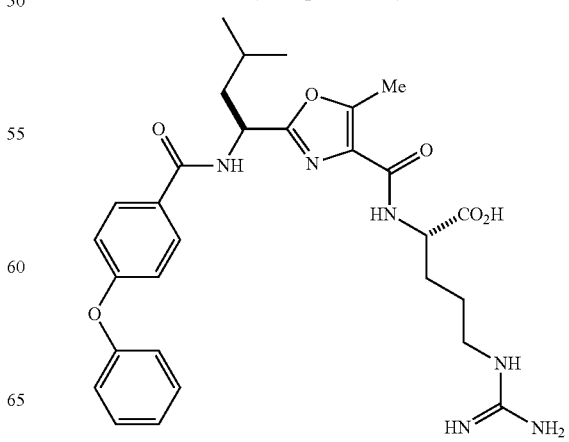

HRMS calculated for $C_{29}H_{37}N_6O_6^+$ Calc 565.2769. found 565.2766. Retention time (20% B to 100B in 10 minutes) is 9.263 minutes, purity 100%. $^1$H NMR (600 MHz, DMSO-d$_6$): δ 8.90 (1H, d, J=8.2 Hz, Arg-NH), 8.00 (1H, d, J=8.3 Hz, Leu-NH), 7.92 (1H, d, J=8.7, Ar), 7.50-7.49 (1H, m, Ar), 7.45-7.42 (2H, m, Ar), 7.22-7.20 (1H, m, Ar), 7.04-7.08 (4H, m, Ar), 5.29-5.25 (1H, m, Leu-Hα), 4.41-4.37 (1H, m, Arg-Hα), 3.11-3.07 (2H, m, Arg-Hδ), 2.53 (3H, s, CH$_3$), 2.0-1.94 (1H, m, Leu-Hγ), 1.90-1.73 (3H, m, Leu-Hβ1, Arg-Hβ), 1.69-1.62 (1H, m, Leu-Hβ2), 1.51-1.45 (2H, m, Arg-Hγ), 0.94 (3H, d, J=6.7 Hz, Leu-Hβ), 0.91 (3H, d, J=6.5 Hz; Leu-Hδ).

Example 50

Boc-Leucine-5-Phenyl-Oxazole-Arginine
(Compound 50)

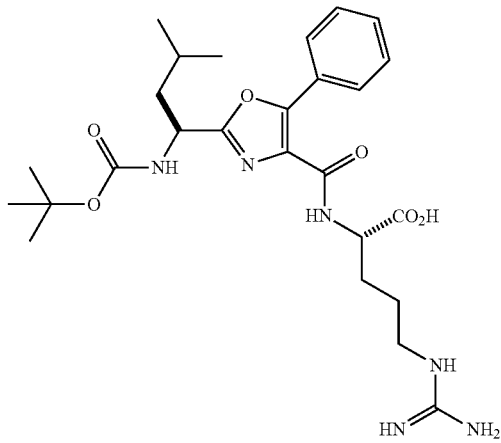 [SMILES: CC(C)C[C@H](NC(=O)OC(C)(C)C)c1nc(C(=O)N[C@@H](CCCNC(=N)N)C(=O)O)c(-c2ccccc2)o1]

HRMS calculated for $C_{26}H_{39}N_6O_6^+$ Calc 531.2926. found 531.2927. Retention time (20% B to 100% B in 20 minutes) is 13.753 minutes, purity 93.8%. $^1$H NMR (600 MHz, DMSO-d$_6$): δ 8.24 (1H, d, J=8.0 Hz, Arg-NH), 8.17-8.14 (2H, m, Ar), 7.64 (1H, d, J=8.4 Hz, Leu-NH), 7.53-7.45 (3H, m, Ar), 4.82-4.75 (1H, m, Leu-Hα), 4.46-4.40 (1H, m, Arg-Hα), 3.14-3.06 (2H, m, Arg-Hδ), 1.95-1.85 (1H, m, Leu-Hγ), 1.84-1.75 (2H, m, Leu-β), 1.73-1.60 (2H, m, Arg-Hβ), 1.56-1.45 (2H, m, Arg-Hγ), 0.94 (3H, d, J=6.4 Hz, Leu-Hβ), 0.90 (3H, d, J=6.4 Hz, Leu-Hδ).

Example 51

5-Bromonicotinic
acid-Leucine-5-Phenyl-Oxazole-Arginine
(Compound 51)

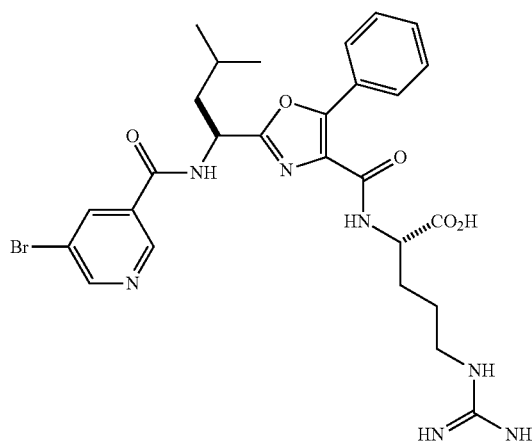

HRMS calculated for $C_{27}H_{33}^{79}BrN_7O_5^+$ Calc 614.1721. found 614.1722. Retention time (20% B to 100B in 10 minutes) is 8.782 minutes, purity 100%. $^1$H NMR (600 MHz, DMSO-d$_6$): δ 9.36 (1H, d, J=8.0 Hz, Arg-NH), 9.02 (1H, d, J=2.0 Hz, Ar), 8.89 (1H, d, J=2.3 Hz, Ar), 8.50 (1H, t, J=2.0 Hz, Ar), 8.30 (1H, d, J=7.9 Hz, Leu-NH), 8.15-8.12 (2H, m, Ar), 7.49-7.46 (3H, m, Ar), 5.40-5.34 (1H, m, Leu-Hα), 4.46-4.40 (1H, m, Arg-Hα), 3.13-3.08 (2H, m, Arg-Hδ), 2.03-1.99 (1H, m, Leu-Hγ), 1.94-1.76 (3H, m, Leu-β1, Arg-Hβ), 1.76-1.66 (1H, m, Leu-β2), 1.54-1.49 (2H, m, Arg-Hγ), 0.98 (3H, d, J=6.6 Hz, Leu-Hδ), 0.95 (3H, d, J=6.6 Hz, Leu-Hδ).

Example 52

4-Fluorophenylacetic
acid-Leucine-5-Phenyl-Oxazole-Arginine
(Compound 52)

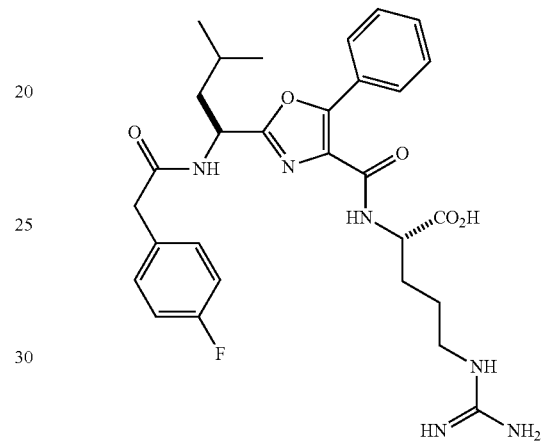

HRMS calculated for $C_{29}H_{36}FN_6O_5^+$ Calc 567.2726. found 567.2726. Retention time (20% B to 100B in 10 minutes) is 8.904 minutes, purity 100%. $^1$H NMR (600 MHz, DMSO-d$_6$): δ 8.82 (1H, d, J=8.0 Hz, Arg-NH), 8.24 (1H, d, J=8.0 Hz, Leu-NH), 8.05-8.00 (2H, m, Ar), 7.49-7.40 (4H, m, Ar), 7.32-7.28 (2H, m, Ar), 7.11-7.06 (2H, m, Ar), 5.08-5.03 (1H, m, Leu-Hα), 4.45-4.40 (1H, m, Arg-Hα), 3.49 (2H, q, J=7.8, 14.1, PhCH2), 3.13-3.07 (2H, m, Arg-Hδ), 1.93-1.72 (4H, m, Leu-Hγ, Leu-β, Arg-Hβ1), 1.69-1.60 (1H, m, Arg-Hβ2), 1.54-1.45 (2H, m, Arg-Hγ), 0.94 (3H, d, J=6.6 Hz, Leu-Hβ), 0.87 (3H, d, J=6.5 Hz, Leu-Hδ).

Example 53

Thianaphthene carboxylic
acid-Leucine-5-Phenyl-Oxazole-Arginine
(Compound 53)

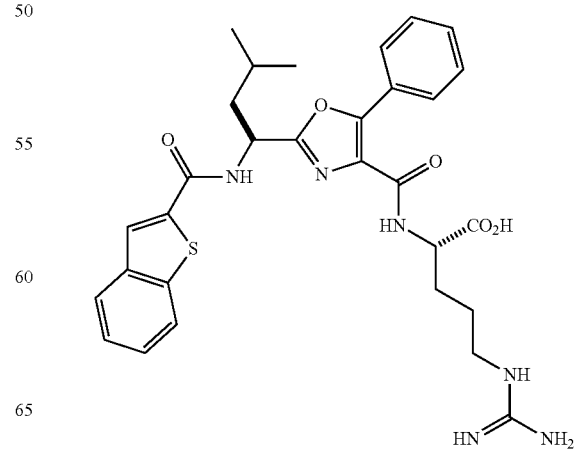

HRMS calculated for $C_{30}H_{35}N_6O_5S^+$ Calc 591.2384. found 591.2384. Retention time (20% B to 100B in 10 minutes) is 9.719 minutes, purity 100%. $^1$H NMR (600 MHz, DMSO-$d_6$): δ 9.38 (1H, d, J=8.3 Hz, Arg-NH), 8.31 (1H, d, J=7.9 Hz, Leu-NH), 8.24 (1H, s, Ar), 8.15-8.11 (2H, m, Ar), 8.02 (1H, d, J=8.0 Hz, Ar), 5.38-5.33 (1H, m, Leu-Hα), 4.45-4.41 (1H, m, Arg-Hα), 3.12-3.07 (2H, m, Arg-Hδ), 2.10-2.03 (1H, m, Leu-Hγ), 1.93-1.69 (4H, m, Leu-β, Arg-Hβ), 1.55-1.47 (2H, m, Arg-Hγ), 0.99 (3H, d, J=6.7 Hz, Leu-Hβ), 0.95 (3H, d, J=6.6 Hz, Leu-Hδ).

Example 54 m-Anisic acid-Leucine-5-Phenyl-Oxazole-Arginine (Compound 54)

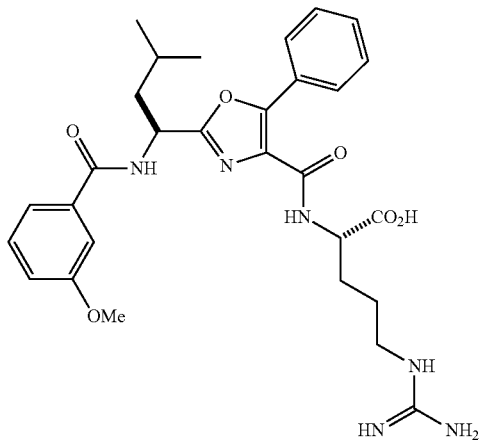 [SMILES: COc1cccc(C(=O)N[C@@H](CC(C)C)c2nc(C(=O)N[C@@H](CCCNC(=N)N)C(=O)O)c(-c3ccccc3)o2)c1]

HRMS calculated for $C_{29}H_{37}N_6O_6^+$ Calc 565.2769. found 565.2768. Retention time (20% B to 100B in 10 minutes) is 8.095 minutes, purity 100%. $^1$H NMR (600 MHz, DMSO-$d_6$): δ 9.04 (1H, d, J=8.0 Hz, Arg-NH), 8.28 (1H, d, J=8.0 Hz, Leu-NH), 8.14-8.11 (2H, m, Ar), 7.50-7.38 (7H, m, Ar), 5.40-5.34 (1H, m, Leu-Hα), 4.46-4.31 (1H, m, Arg-Hα), 3.79 (3H, s, OCH$_3$), 3.13-3.07 (2H, m, Arg-Hδ), 2.09-1.97 (1H, m, Leu-Hγ), 1.94-1.70 (4H, m, Leu-β, Arg-Hβ), 1.55-1.47 (2H, m, Arg-Hγ), 0.98 (3H, d, J=6.7 Hz, Leu-Hβ), 0.95 (3H, d, J=6.6 Hz, Leu-Hδ).

Example 55

Cyclohexane carboxylic acid-Leucine-5-Phenyl-Oxazole-Arginine (Compound 55)

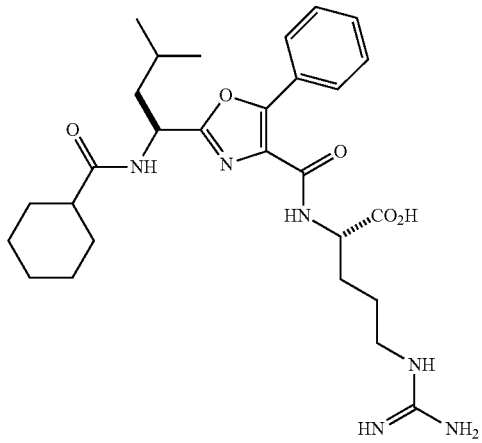 [SMILES: CC(C)C[C@H](NC(=O)C1CCCCC1)c1nc(C(=O)N[C@@H](CCCNC(=N)N)C(=O)O)c(-c2ccccc2)o1]

HRMS calculated for $C_{28}H_{41}N_6O_5^+$ Calc 541.3133. found 541.3132. Retention time (20% B to 100B in 10 minutes) is 8.095 minutes, purity 100%. $^1$H NMR (600 MHz, DMSO-$d_6$): δ 8.38 (1H, d, J=8.1 Hz, Arg-NH), 8.24 (1H, d, J=8.1 Hz, Leu-NH), 8.15-8.12 (2H, m, Ar), 7.50-7.23 (3H, m, Ar), 5.10-5.05 (1H, m, Leu-Hα), 4.45-4.41 (1H, m, Arg-Hα), 3.13-3.08 (2H, m, Arg-Hδ), 2.23-2.17 (1H, m, Leu-Hγ), 1.93-1.09 (17H, m, CH$_2$, Leu-β, Arg-Hβ, Arg-Hγ), 0.90 (3H, d, J=6.2 Hz, Leu-Hβ), 0.85 (3H, d, J=6.0 Hz, Leu-Hδ).

Example 56

2-Diphenylmethyl-oxazole-4-carboxyl-Arg-OH (Compound 56)

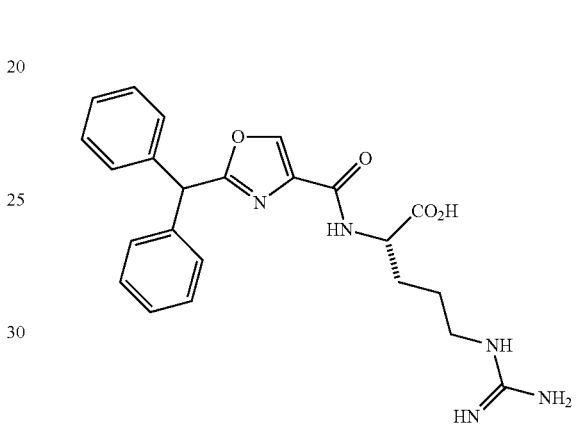

HRMS calculated for $C_{23}H_{26}N_5O_4^+$ Calc 436.1979. found 436.1979. $^1$H NMR (600 MHz, DMSO-$d_6$): δ 8.64 (s, 1H), 8.25 (d, J=8.1 Hz, 1H), 7.51 (t, J=5.6 Hz, 1H), 7.40-7.26 (m, 10H), 5.87 (s, 1H), 4.39 (m, 1H), 3.14-3.04 (m, 2H), 1.86 (m, 1H), 1.77 (m, 1H), 1.55-1.44 (m, 2H).

Example 57

5-Diphenylmethyl-furan-2-carboxyl-Arg-OH (Compound 57)

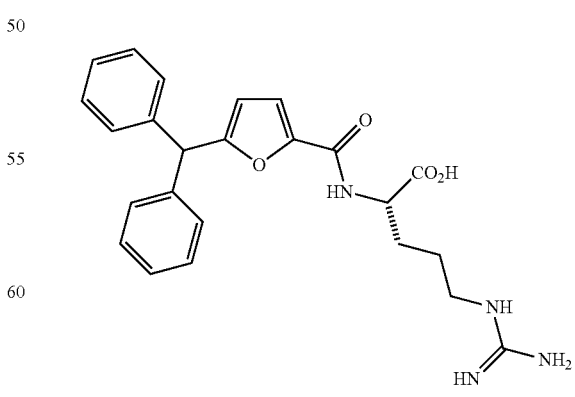

HRMS calculated for $C_{24}H_{27}N_4O_4^+$ Calc 435.2027. found 435.2025. $^1$H NMR (600 MHz, DMSO-$d_6$): δ 8.41 (d, J=8.0 Hz, 1H), 7.51 (t, J=5.6 Hz, 1H), 7.34 (t, J=7.6 Hz, 4H), 7.28-7.21 (m, 6H), 7.18 (d, J=3.4 Hz, 1H), 6.15 (d, J=3.4 Hz, 1H), 5.65 (s, 1H), 4.33 (m, 1H), 3.14-3.04 (m, 2H), 1.84 (m, 1H), 1.71 (m, 1H), 1.57-1.43 (m, 2H).

Example 58

2-Diphenylmethyl-4-methyl oxazole-5-carboxyl-Arg-OH (Compound 58)

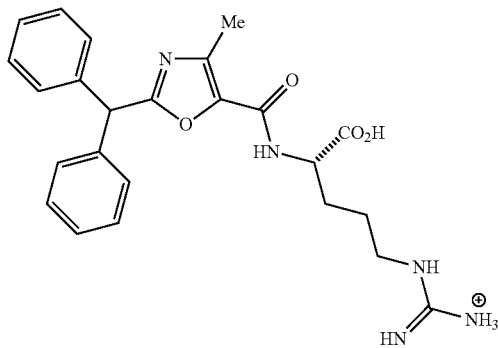 [SMILES: Cc1nc(C(c2ccccc2)c2ccccc2)oc1C(=O)N[C@@H](CCCNC(=N)[NH3+])C(=O)O]

HRMS calculated for $C_{24}H_{28}N_5O_4^+$ Calc 450.2136. found 450.2132. $^1$H NMR (600 MHz, DMSO-$d_6$): δ 8 46 (d, J=8.0 Hz, 1H), 7.52 (t, J=5.6 Hz, 1H), 7.39-7.20 (m, 13H), 5.75 (s, 1H), 4.33 (m, 1H), 3.13-3.04 (m, 2H), 2.36 (s, 3H), 1.85 (m, 1H), 1.74 (m, 1H), 1.56-1.40 (m, 2H).

Example 59

2-Diphenylmethyl-4-methyl thiazole-5-carboxyl-Arg-OH (Compound 59)

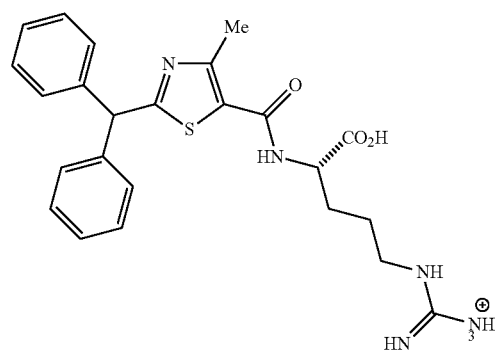 [SMILES: Cc1nc(C(c2ccccc2)c2ccccc2)sc1C(=O)N[C@@H](CCCNC(=N)[NH3+])C(=O)O]

HRMS calculated for $C_{24}H_{28}N_5O_3S^+$ Calc 466.1907. found 466.1907. $^1$H NMR (600 MHz, DMSO-$d_6$): δ 8.41 (d, J=7.8 Hz, 1H), 7.52 (t, J=5.6 Hz, 1H), 7.39-7.26 (m, 10H), 5.94 (s, 1H), 4.29 (m, 1H), 3.13-3.04 (m, 2H), 2.52 (s, 3H), 1.81 (m, 1H), 1.67 (m, 1H), 1.57-1.44 (m, 2H). $^{13}$C NMR (150 MHz, DMSO-$d_6$): δ 173.1, 172.6, 161.4, 156.6, 154.9, 141.7, 128.7, 127.2, 125.5, 53.7, 52.2, 40.3, 27.5, 25.4, 17.0.

Example 60

5-Diphenylmethyl-thiophene-2-carboxyl-Arg-OH (Compound 60)

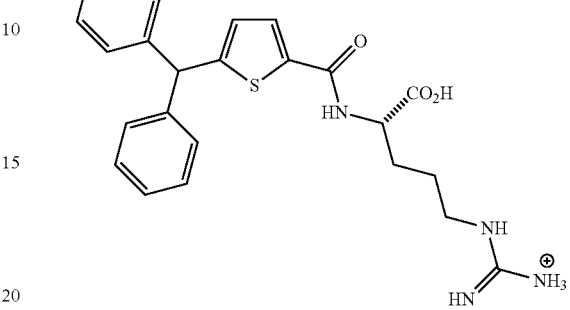

Thiophene-2-carboxylic acid was brominated in the 5-position with $Br_2$. The 5-bromo-thiophene-2-carboxylic acid was treated with n-butyllithium (2 equiv) in THF at −78° C. followed by reaction with PhC(O)Ph to provide 5-diphenylhydroxymethyl-thiophene-2-carboxylic acid. The carboxylic acid was then treated with H-Arg(pbf)-Wang resin in DMF in the presence of BOP and DIPEA. The Wang resin and pbf protecting group were removed by treatment with triethylsilane ($Et_3SiH$) and trifluoroacetic acid (TFA) for 2 hours, to produce Compound 60.

HRMS calculated for $C_{24}H_{27}N_4O_3S^+$ Calc 451.1798. found 451.1798. $^1$H NMR (600 MHz, DMSO-$d_6$): δ 8.60 (d, J=8.0 Hz, 1H), 7.73 (d, J=3.8 Hz, 1H), 7.58 (t, J=5.5 Hz, 1H), 7.37-7.22 (m, 11H), 6.79 (dd, J=3.8, 0.8 Hz, 1H), 5.83 (s, 1H), 4.32 (m, 1H), 3.16-3.04 (m, 2H), 1.85 (m, 1H), 1.70 (m, 1H), 1.61-1.46 (m, 2H), $^{13}$C NMR (150 MHz, DMSO-$d_6$): δ 173.4, 161.2, 156.7, 153.0, 143.2, 137.8, 128.6, 128.5, 126.9, 51.9, 51.2, 40.3, 27.7, 25.4.

Example 61

2-Diphenylmethyl-5-methyl oxazole-4-carboxyl-Arg-OH (Compound 61)

HRMS calculated for $C_{24}H_{28}N_5O_4^+$ Calc 450.2136. found 450.2136. $^1$H NMR (600 MHz, DMSO-$d_6$): δ 8.02 (d, J=8.1 Hz, 1H), 7.59 (t, J=5.6 Hz, 1H), 7.39-7.55 (m, 10H), 5.79 (s, 1H), 4.38 (m, 1H), 3.10 (m, 1H), 2.54 (s, 3H), 1.86 (m, 1H), 1.77 (m, 1H), 1.54-1.44 (m, 2H). $^{13}$C NMR (150

MHz, DMSO-d$_6$): δ 173.1, 161.3, 161.1, 156.7, 153.1, 139.7, 139.7, 128.7, 128.7, 128.4, 128.4, 127.2, 51.2, 49.5, 40.3, 28.0, 25.4, 11.4.

Example 62

2-Diphenylmethyl-4-phenyl imidazole-5-carboxyl-Arg-OH (Compound 62)

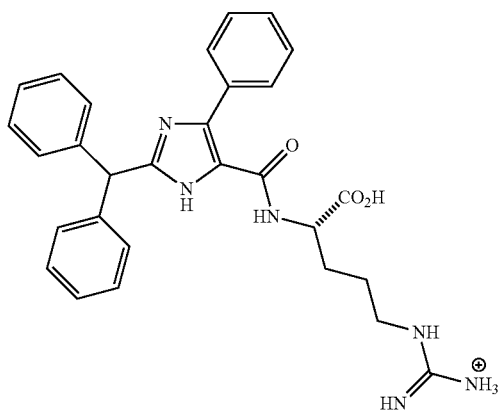 [SMILES: N=C([NH3+])NCCC[C@H](NC(=O)c1[nH]c(C(c2ccccc2)c2ccccc2)nc1-c1ccccc1)C(=O)O]

HRMS calculated for C$_{29}$H$_{31}$N$_6$O$_3$$^+$ Calc 511.2452. found 511.2453. $^1$H NMR (600 MHz, DMSO-d$_6$): δ 7.98 (d, J=7.9 Hz, 1H), 7.78 (d, J=7.8 Hz, 2H), 7.55 (t, J=5.6 Hz, 1H), 7.40 (m, 6H), 7.34 (m, 5H), 7.26 (m, 2H), 5.64 (s, 11H), 4.38 (m, 1H), 3.17-3.05 (m, 2H), 1.85 (m, 1H), 1.74 (m, 1H), 1.55-1.46 (m, 2H). $^{13}$C NMR (150 MHz, DMSO-d$_6$): δ 173.4, 162.1, 156.7, 148.2, 141.3, 141.3, 51.2, 49.6, 40.3, 28.6, 25.3.

Example 63

1-Methyl-2-diphenylmethyl-4-phenyl imidazole-5-carboxyl-Arg-OH (Compound 63)

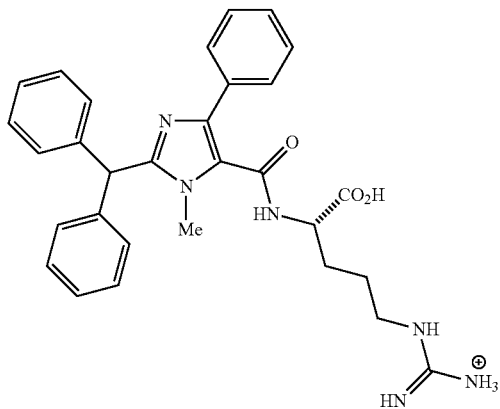 [SMILES: Cn1c(C(c2ccccc2)c2ccccc2)nc(-c2ccccc2)c1C(=O)N[C@@H](CCCNC(=N)[NH3+])C(=O)O]

HRMS calculated for C$_{30}$H$_{33}$N$_6$O$_3$$^+$ Calc 525.2609. found 525.2609. $^1$H NMR (400 MHz, DMSO-d$_6$): δ 8.90 (d, J=7.3 Hz, 1H), 7.70 (m, 2H), 7.50 (t, J=5.5 Hz, 1H), 7.45-7.19 (m, 15H), 5.82 (s, 1H), 4.33 (m, 1H), 3.57 (s, 3H), 3.08 (m, 2H), 1.79 (m, 1H), 1.62 (m, 1H), 1.54-1.42 (m, 2H).

Example 64

2-Diphenylmethyl-4-methyl imidazole-5-carboxyl-Arg-OH (Compound 64)

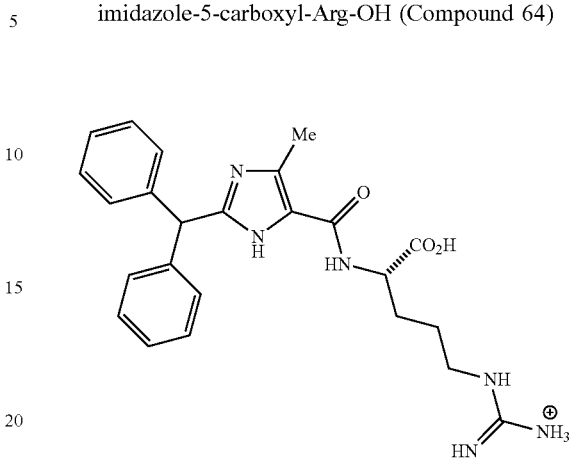

HRMS calculated for C$_{24}$H$_{29}$N$_6$O$_3$$^+$ Calc 449.2296. found 449.2295. $^1$H NMR (600 MHz, DMSO-d$_6$): δ 7.84 (d, J=7.5 Hz, 1H), 7.61 (t, J=5.6 Hz, 1H), 7.38-7.25 (m, 10H), 5.65 (s, 1H), 4.39 (m, 1H), 3.16-3.06 (m, 2H), 2.41 (s, 3H), 1.84 (m, 1H), 1.73 (m, 1H), 1.55-1.46 (m, 2H). $^{13}$C NMR (150 MHz, DMSO-d$_6$): δ 173.4, 162.1, 156.7, 146.6, 140.7, 132.3, 128.6, 127.0, 51.0, 49.6, 40.3, 36.5, 36.4, 28.6, 25.3, 10.6.

Example 65

2-Diphenylmethyl-4-phenyl thiazole-5-carboxyl-Arg-OH (Compound 65)

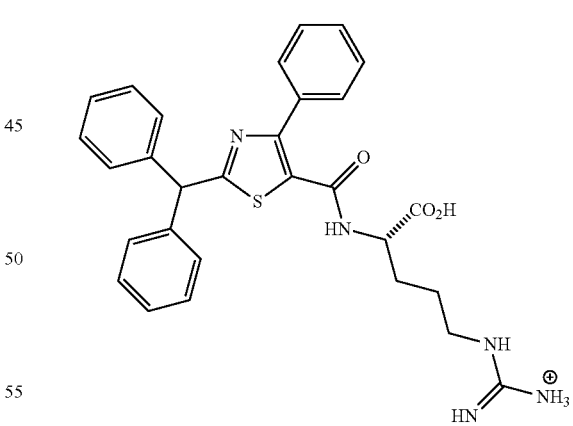

HRMS calculated for C$_{29}$H$_{30}$N$_5$O$_3$S$^+$ Calc 528.2064. found 528.2065. $^1$H NMR (600 MHz, DMSO-d$_6$): δ 8.82 (d, J=7.5 Hz, 1H), 7.75 (m, 2H), 7.55 (t, J=5.6 Hz, 1H), 7.41-7.34 m, 11H), 7.32-7.27 (m, 2H), 6.05 (s, 1H), 4.25 (m, 1H), 3.11-3.01 m, 2H), 1.76 (m, 1H), 1.60 (m, 1H), 1.50-1.40 (m, 2H). $^{13}$C NMR (100 MHz, DMSO-d$_6$): δ 172.8, 171.5, 161.8, 156.7, 152.6, 141.7, 133.6, 128.69, 128.66, 128.5, 128.4, 128.3, 127.2, 126.4, 53.5, 52.5, 40.2, 27.4, 25.2.

Example 66

2-Diphenylmethyl-4-phenyl oxazole-5-carboxyl-Arg-OH (Compound 66)

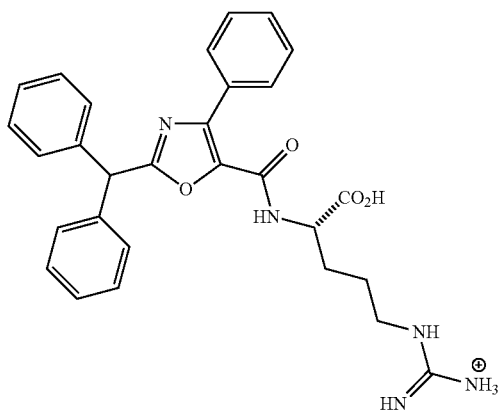 [SMILES: N=C([NH3+])NCCC[C@H](NC(=O)c1oc(C(c2ccccc2)c2ccccc2)nc1-c1ccccc1)C(=O)O]

HRMS calculated for $C_{29}H_{30}N_5O_4^+$ Calc 512.2292. found 512.2292. $^1$H NMR (600 MHz, DMSO-$d_6$): δ 8.69 (d, J=7.7 Hz, 1H), 8.11 (m, 2H), 7.57 (t, J=5.6 Hz, 1H), 7.51-7.35 (m, 12H), 7.33-7.27 (m, 2H), 5.85 (s, 1H), 4.36 (m, 1H), 3.14-3.06 (m, 2H), 1.88 (m, 1H), 1.76 (m, 1H), 1.58-1.47 (m, 2H). $^{13}$C NMR (150 MHz, DMSO-$d_6$): δ 172.9, 163.5, 157.7, 156.7, 141.8, 139.6, 139.5, 138.8, 130.1, 129.2, 128.7, 128.5, 128.4, 128.1, 127.3, 127.3, 51.9, 49.6, 40.3, 27.5, 25.4.

Example 67

3-Diphenylmethyl-1-oxa-2,4-diazole-5-carboxyl-Arginine-OH (Compound 67)

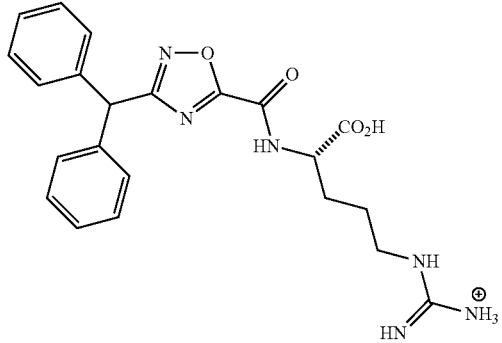 [SMILES: N=C([NH3+])NCCC[C@H](NC(=O)c1nc(C(c2ccccc2)c2ccccc2)no1)C(=O)O]

HRMS calculated for $C_{22}H_{25}N_6O_4^+$ Calc 437.1932. found 437.1932. $^1$H NMR (600 MHz, DMSO-$d_6$): δ 9.62 (d, J=7.9 Hz, 1H), 7.61 (t, J=5.6 Hz, 1H), 7.38-7.33 (m, 8H), 7.31-7.26 (m, 2H), 5.88 (s, 1H), 4.37 (m, 1H), 3.15-3.04 (m, 2H), 1.89 (m, 1H), 1.78 (m, 1H), 1.59-1.46 (m, 2H).

Example 68

5-Diphenylmethyl-1-oxa-2,4-diazole-3-carboxyl-Arginine-OH (Compound 68)

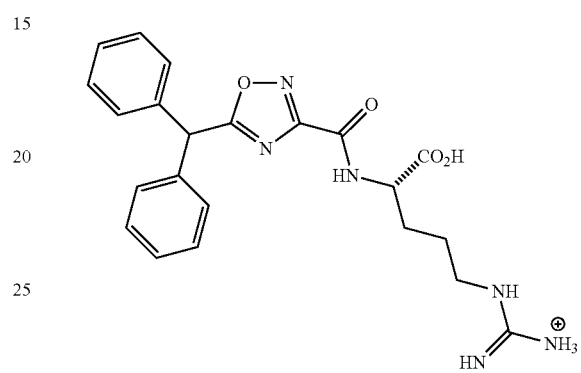

HRMS calculated for $C_{22}H_{25}N_6O_4^+$ Calc 437.1932. found 437.1934. $^1$H NMR (600 MHz, DMSO-$d_6$): δ 9.19 (d, J=7.9 Hz, 1H), 7.58 (t, J=5.6 Hz, 1H), 7.42-7.29 (m, 10H), 6.19 (s, 1H), 4.38 (m, 1H), 3.14-3.05 (m, 2H), 1.88 (m, 1H), 1.77 (m, 1H), 1.58-1.47 (m, 2H).

Example 69

2-Diphenylmethyl-1-oxa-3,4-diazole-5-carboxyl-Arginine-OH (Compound 69)

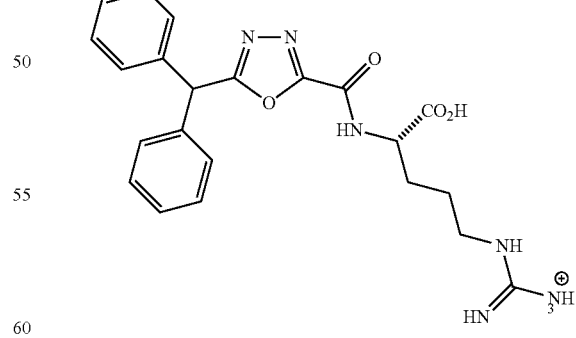

HRMS calculated for $C_{22}H_{25}N_6O_4^+$ Calc 437.1932. found 437.1932. $^1$H NMR (600 MHz, DMSO-$d_6$): δ 9.53 (d, J=7.8 Hz, 1H), 7.61 (t, J=5.6 Hz, 1H), 7.41-7.28 (m, 11H), 6.08 (s, 1H), 4.35 (m, 1H), 3.14-3.05 (m, 2H), 1.88 (m, 1H), 1.79 (m, 1H), 1.60-1.46 (m, 2H).

Example 70

1-isopropylcyclohexa-2,5-dienecarboxylic acid
(Compound 70)

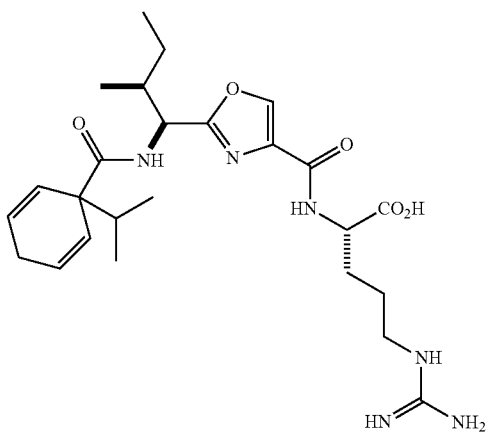 [SMILES: CC[C@H](C)[C@H](NC(=O)C1(C(C)C)C=CCC=C1)c1nc(C(=O)N[C@@H](CCCNC(=N)N)C(=O)O)co1]

Analytical rt 8.359 (20% B to 100% B in 10 mins) 84% pure. FIRMS (M+H) $C_{25}H_{39}N_6O_5^+$ Calc 503.2976 found 503.2974. $^1$H NMR (400 MHz, DMSO-$d_6$): δ 8.59 (1H, s, Ox), 8.12 (1H, d, J=8.4 Hz, Arg-NH) 7.62 (1H, d, J=8 Hz, Ile-NH), 7.53 (1H, t, J=5.6 Hz, Arg-Nhε), 5.92-5.88 (3H, m, Ar), 5.72 (2H, d, J=10 Hz, Ar), 4.82 (1H, t, J=8.6 Hz, Ile-Hα), 4.42-4.36 (1H, m, Arg-Hα), 3.10 (2H, q, J=6.4 Hz, Arg-Hδ), 2.57 (1H, s, C$\underline{H}$(CH$_3$)$_2$), 2.17-2.08 (1H, m, Ile-βH), 1.87-1.73 (2H, m, Arg-Hβ$_2$) 1.53-1.45 (3H, m, Ile-Hγ$_1$, Arg-Hγ$_2$), 1.20-1.12 (1H, m, Ile-Hγ), 0.83 (3H, t, J=4.8 Hz, Ile-Hδ), 0.75-0.69 (9H, m, Ile-HγCH$_3$). $^{13}$C NMR (100 MHz DMSO-$d_6$) δ 173.6, 173.0, 163.5, 159.9, 156.6, 142.1, 135.1, 126.5, 126.4, 126.3, 51.7, 51.2, 36.2, 34.2, 28.0, 26.2, 25.3, 24.8, 17.2, 17.1, 15.5, 10.3.

Example 71

Boc-Valine-Thiazole-Arginine-OH (Compound 71)

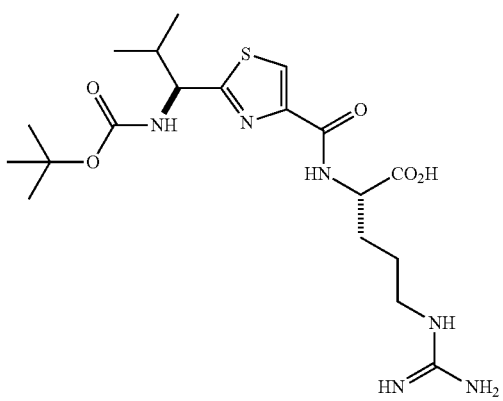 [SMILES: CC(C)[C@H](NC(=O)OC(C)(C)C)c1nc(C(=O)N[C@@H](CCCNC(=N)N)C(=O)O)cs1]

yield 29% Analytical rt 7.475 (20% B to 100% B in 10 mins) 100% pure HRMS (M+H) $C_{19}H_{35}N_6O_5S^+$ Calc 457.2228 found 457.2319. $^1$H NMR (400 MHz, DMSO-$d_6$): δ 8.27 (1H, d, J=8 Hz, Arg-NH) 8.18 (1H, s, Thiazole), 7.72 (1H, d, J=8.4 Hz, Val-NH), 7.49 (1H, t, J=5.6 Hz, Arg-NH), 4.66 (1H, t, J=7.4 Hz, Val-Ha) 4.44-4.38 (1H, m, Arg-Hα), 3.13-3.08 (2H, m, Arg-Hδ), 2.26-2.17 (1H, m, Val-Hβ) 1.93-1.76 (2H, m, Arg-Hβ$_2$), 1.54-1.47 (2H, m, Arg-Hγ); 1.39 (9H, s, Boc), 0.88 (6H, dd, 9, 5.6 Hz, Val-Hδ). $^{13}$C NMR (100 MHz DMSO-$d_6$) δ 174.8, 173.0, 160.4, 156.6, 155.6, 148.8, 124.0, 78.5, 58.5, 51.5, 32.4, 28.2, 28.0, 25.3, 19.3, 18.0.

Example 72

2-Diphenylmethyl-thiazole-4-carboxyl-Arg-OH
(Compound 77)

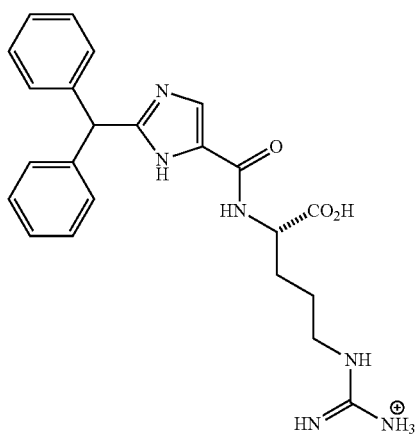 [SMILES: N=C([NH3+])NCCC[C@H](NC(=O)c1cnc(C(c2ccccc2)c2ccccc2)[nH]1)C(=O)O]

$^1$H NMR (DMSO-$d_6$), δ 1.47-1.55 (m, 2H), 1.68-1.76 (m, 1H), 1.81-1.88 (m, 1H), 3.06-3.14 (m, 2H), 4.36-4.41 (m, 2H), 5.78 (s, 1H), 7.24-7.29 (m, 7H), 7.33-7.36 (m, 5H), 7.68-7.70 (t, 1H, J=5.3 Hz), 7.88 (s, 1H), 8.35 (br s, 1H). HRMS: [MH]$^+$ 435.2139 (calc. for $C_{23}H_{27}N_6O_3^+$) 435.2139 (found); Rt=9.3 min (0-100% B 15 min gradient).

Example 73

2-Diphenylmethyl-thiazole-4-carboxyl-Arg-OH
(Compound 78)

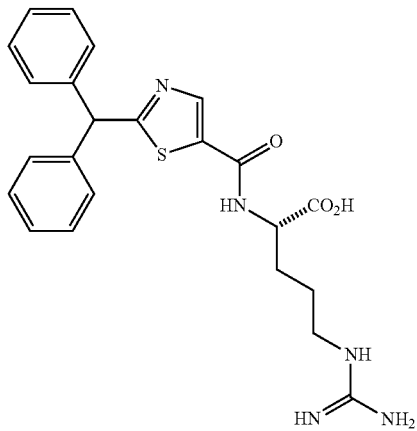 [SMILES: N=C(N)NCCC[C@H](NC(=O)c1cnc(C(c2ccccc2)c2ccccc2)s1)C(=O)O]

$^1$H NMR (DMSO-$d_6$), δ 1.49-1.59 (m, 2H), 1.67-1.73 (m, 1H), 1.82-1.88 (m, 1H), 3.08-3.15 (m, 2H), 4.32-4.35 (m, 1H), 6.00 (s, 1H), 7.29-7.37 (m, 10H), 7.60-7.62 (t, 1H,

J=5.5 Hz), 8.43 (s, 1H), 8.84-8.85 (d, 1H, J=7.8 Hz). HRMS: [MH]⁺ 452.1751 (calc. for $C_{23}H_{26}N_5O_3S^+$) 452.1751 (found); Rt=9.4 min (20-100% B 15 min gradient).

Example 74

3-Indole carboxylic acid-Leucine-5-methyl-imidazole-Arginine-OH (Compound 79)

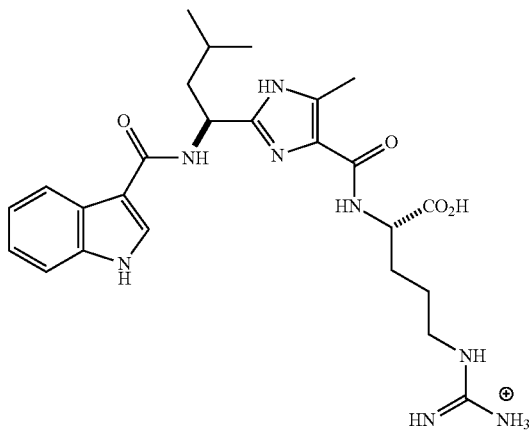 [SMILES: Cc1[nH]c([C@H](CC(C)C)NC(=O)c2c[nH]c3ccccc23)nc1C(=O)N[C@@H](CCCNC(=N)[NH3+])C(=O)O]

¹H NMR (DMSO-d₆), δ 0.92-0.96 (dd, 6H, J=6.6, 15.5 Hz), 1.49-1.56 (m, 2H), 1.63-1.80 (m, 3H), 1.82-1.96 (m, 2H), 2.43 (s, 3H), 3.08-3.17 (m, 2H), 4.39-4.44 (m, 1H), 5.24-5.29 (m, 1H), 7.09-7.11 (t, 1H, J=7.6 Hz), 7.14-7.16 (t, 1H, J=7.8 Hz), 7.43-7.44 (d, 1H, J=7.7 Hz), 7.59 (br s, 1H), 8.02 (br s, 1H), 8.11-8.12 (d, 1H, J=7.7 Hz), 8.17-8.18 (t, 1H, J=3 Hz), 8.25 (br s, 1H). HRMS: [MH]⁺ 511.2776 (calc. for $C_{25}H_{35}N_8O_4^+$) 511.2774 (found); Rt=7.9 min (0-100% B 10 min gradient).

Example 75

Boc-Leucine-imidazole-Arginine-OH (Compound 80)

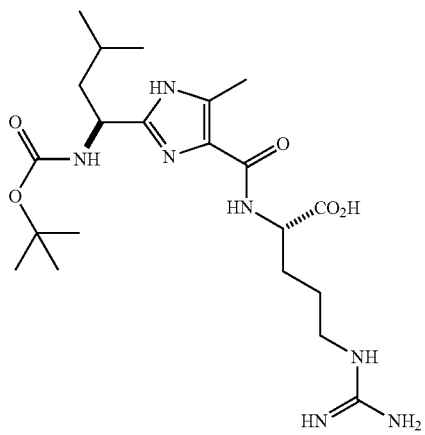 [SMILES: Cc1[nH]c([C@H](CC(C)C)NC(=O)OC(C)(C)C)nc1C(=O)N[C@@H](CCCNC(=N)N)C(=O)O]

Acetoacetic acid ethyl ester was treated with NaNO₂ in acetic acid/H₂O followed by reduction with H₂ (15 psi) in the presence of 10% PdC in ethanol to give α-amino-acetoacetic acid ethyl ester hydrochloric salt. The α-amino-acetoacetic acid ethyl ester hydrochloric salt was then reacted with Cbz-L-Leu-OH in the presence of HBTU and DIPEA in DMF, which formed an amide bond between the leucine carboxy group and the α-amino group of the acetoacetic acid ethyl ester. A 5-methyl-imidazole ring was formed by reaction with NH₄OAc in Acetic acid under microwave condition (150° C.) for 30 minutes. The Cbz group was removed by reduction with H₂ (40 psi) in the presence of 10% PdC in methanol and replaced with a Boc group by reaction with Boc₂O in dichloromethane. The ethyl ester was then hydrolysed with sodium hydroxide in H₂O/EtOH at 100° C. and the free carboxylic acid reacted with H-Arg-OEt in DMF in the presence of HBTU and DIPEA. The ethyl ester was then removed with sodium hydroxide in H₂O/EtOH at room temperature to afford Compound 80.

¹H NMR (600 MHz, DMSO-d₆), δ 0.86-0.90 (2 sets of d, 6H, J=6.4 Hz), 1.36 (s, 9H), 1.47-1.61 (m, 4H), 1.66-1.74 (m, 2H), 1.81-1.87 (m, 1H), 2.41 (s, 3H), 3.06-3.15 (m, 2H), 4.37-4.42 (m, 1H), 4.64-4.71 (m, 1H), 7.29 (br s, 1H), 7.63-7.68 (m, 1H), 8.00 (br s, 1H).

Example 76

Boc-Leucine-1-methylimidazole-Arginine-OH (Compound 81)

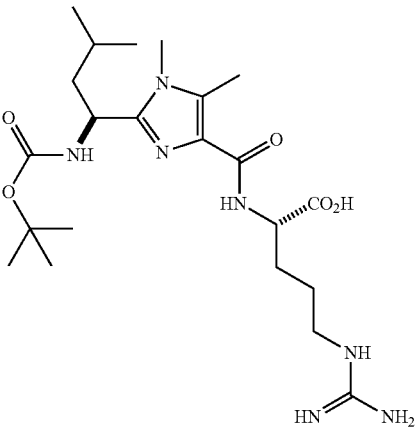 [SMILES: Cc1c(C(=O)N[C@@H](CCCNC(=N)N)C(=O)O)nc([C@H](CC(C)C)NC(=O)OC(C)(C)C)n1C]

Boc-Leu-5-methylimidazole ethyl ester, prepared from the Cbz-Leu-5-imidazole ethyl ester in Example 75 by removal of Cbz and replacement with Boc, was treated with sodium hydride and methyl iodide to give two N-methyl-imidazole isomers which were separated by flash chromatography. The desired isomer was then hydrolysed to reveal the carboxylic acid which was coupled to H-Arg-OEt under standard peptide bond forming conditions. The ethyl ester of the arginine was then hydrolysed to give Compound 81.

¹H NMR (600 MHz, DMSO-d6), δ 0.85-0.94 (m, 6H), 1.36 (s, 9H), 1.43-1.50 (m, 2H), 1.55-1.62 (m, 2H), 1.66-1.74 (m, 1H), 1.76-1.88 (m, 2H), 2.43 (s, 1H), 3.06-3.15 (m, 2H), 3.50 (s, 3H), 4.39-4.44 (m, 1H), 4.72-4.78 (m, 1H), 7.27-7.30 (t, 1H, J=8.2 Hz), 7.58-7.60 (m, 1H), 7.64-7.70 (m, 1H).

Example 77

Boc-Leucine-thiazole-Arginine-OH (Compound 82)

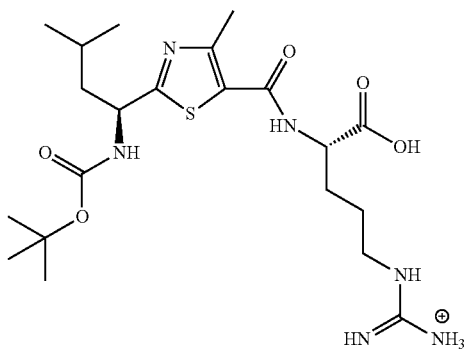 [SMILES: Cc1nc([C@H](CC(C)C)NC(=O)OC(C)(C)C)sc1C(=O)N[C@@H](CCCNC(=N)[NH3+])C(=O)O]

Compound 82 was prepared from Boc-Leu-4-methylthiazole-5-carboxylic acid by reaction with H-Arg-OEt under standard peptide bond forming conditions. The ethyl ester of the arginine was then hydrolysed to give Compound 82.

$^1$H NMR (600 MHz, $d_6$-DMSO): δ 8.42 (m, 1H), 7.75 (m, 1H), 7.54 (m, 1H), 4.74 (m, 1H), 4.30 (m, 1H), 3.11 (m, 2H), 2.51 (s, 3H), 1.83 (m, 1H), 1.66-1.73 (m, 4H), 1.51-1.57 (m, 2H), 1.40 (s, 9H), 0.90 (m, 6H).

Example 78

Boc-Leucine-1-oxa-3,4-diazole-Arginine-OH (Compound 83)

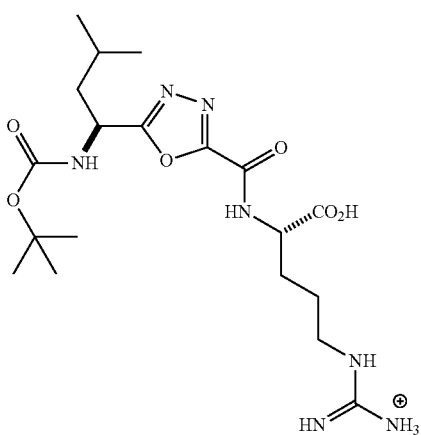 [SMILES: CC(C)C[C@H](NC(=O)OC(C)(C)C)c1nnc(C(=O)N[C@@H](CCCNC(=N)[NH3+])C(=O)O)o1]

Boc-Leu-methyl ester was treated with $N_2H_2$ in ethanol (EtOH) at room temperature to give an acyl hydrazine which was then reacted with ClC(O)CO$_2$Et in the presence of triethylamine (Et$_3$N) in dichloromethane (DCM). The resulting N-α-ketoester was cyclised with tosyl chloride in the presence of Et$_3$N in DCM to provide Boc-Leu-1-oxadiazole-2-carboxylic acid ethyl ester which was hydrolysed and the free carboxylic acid reacted with H-Arg-OEt in DMF in the presence of HBTU and DIPEA. The carboxylic acid ester was then hydrolysed at room temperature with sodium hydroxide in H$_2$O/EtOH to give Compound 83.

$^1$H NMR (600 MHz, DMSO-$d_6$), δ 0.88-0.93 (2 sets of d, 6H, J=6.4 Hz), 1.38 (s, 9H), 1.50-1.59 (m, 2H), 1.61-1.72 (m, 2H), 1.77-1.83 (m, 2H), 1.87-1.92 (m, 1H), 3.08-3.14 (m, 2H), 4.34-4.40 (m, 1H), 4.82-4.91 (m, 1H), 7.63-7.65 (t, 1H, J=5.5 Hz), 7.69-7.71 (d, 1H, J=8.3 Hz), 9.50-9.52 (d, 1H, J=7.3 Hz).

Example 79

(S)-2-(2-((S)-1-((tert-butoxycarbonyl)amino)-3-methylbutyl)oxazole-4-carboxamido)-3-(4-(N-hydroxycarbamimidoyl)phenyl)propanoic acid (Compound 84)

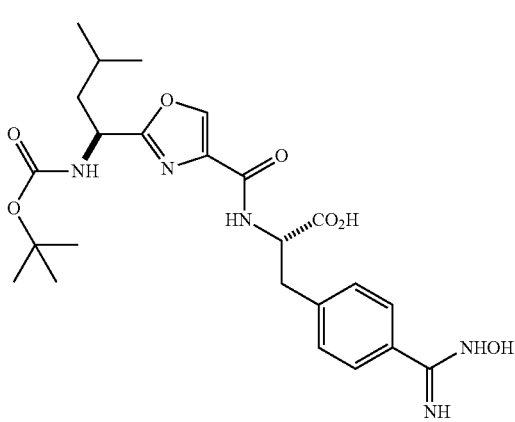

4-Cyanophenylalanine methyl ester was coupled with Boc-Leu-oxazole-4-carboxylic acid in the presence of BOP and DIPEA in DMF. The cyano group was then treated with NH$_2$OH.HCl in ethanol in the presence of DIPEA at 60° C. to provide the N-hydroxycarbamimidoyl group. The methyl ester was then hydrolysed with sodium hydroxide in methanol/H$_2$O to give Compound 84.

$^1$H NMR (DMSO $d_6$), δ 0.84-0.91 (m, 6H), 1.23-1.27 (br s, 1H), 1.36 (s, 9H), 1.55-1.62 (m, 2H), 1.68-1.75 (m, 1H), 3.20-3.31 (m, 3H), 4.67-4.76 (m, 2H), 7.41-7.48 (m, 2H), 7.51-7.56 (m, 1H), 7.56-7.61 (m, 2H), 8.28-8.33 (m, 1H), 8.50 (s, 1H). Rt=9.0 min (Method I); HRMS: [MH]$^+$ 504.2453 (calc. for $C_{24}H_{34}N_5O_7^+$) 504.2452 (found).

Example 80

(S)-2-(2-((S)-1-((tert-butoxycarbonyl)amino)-3-methylbutyl)oxazole-4-carboxamido)-3-(4-carbamimidoylphenyl)propanoic acid (Compound 85)

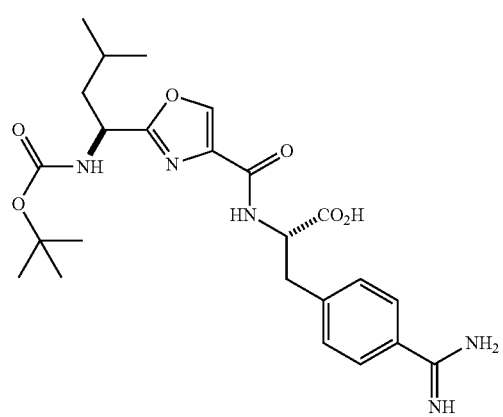 [SMILES: CC(C)C[C@H](NC(=O)OC(C)(C)C)c1nc(C(=O)N[C@@H](Cc2ccc(C(=N)N)cc2)C(=O)O)co1]

(S)-2-(2-((S)-1-((tert-butoxycarbonyl)amino)-3-methylbutyl)oxazole-4-carboxamido)-3-(4-(N-hydroxycarbamimidoyl)phenyl)propanoic acid methyl ester from Example 79 was reduced to proved (S)-2-(2-((S)-1-((tert-butoxycarbonyl)amino)-3-methylbutyl)oxazole-4-carboxamido)-3-(4-(carbamimidoyl)phenyl)propanoic acid methyl ester. The ester was then hydrolysed as described in Example 79.

Rt=9.0 min (100% A to 100% B linear gradient over 10 minutes followed by 10 minutes 100% B. A=$H_2O$+0.1% TFA. B=MeCN+0.1% TFA); HRMS: $[MH]^+$ 488.2504 (calc. for $C_{24}H_{34}N_5O_6^+$) 488.2505 (found); $^1$H NMR (DMSO $d_6$), δ 0.84-0.91 (m, 6H), 1.22-1.28 (br s, 1H), 1.36 (s, 9H), 1.54-1.63 (m, 2H), 1.68-1.75 (m, 1H), 3.22-3.34 (m, 2H), 4.67-4.77 (m, 2H), 7.46-7.50 (m, 2H), 7.51-7.55 (m, 1H), 7.67-7.71 (m, 2H), 8.29-8.34 (m, 1H), 8.50 (s, 1H), 8.98-9.06 (m, 2H), 9.20 (s, 2H).

Example 81

(S)-2-(2-((S)-1-((tert-butoxycarbonyl)amino)-3-methylbutyl)oxazole-4-carboxamido)-3-(4-guanidinophenyl)propanoic acid (Compound 86)

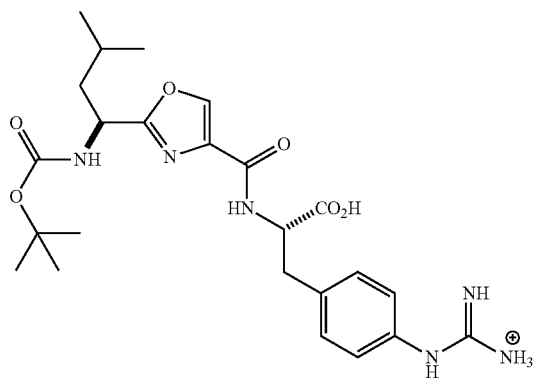 [SMILES: CC(C)C[C@H](NC(=O)OC(C)(C)C)c1nc(C(=O)N[C@@H](Cc2ccc(NC(=N)[NH3+])cc2)C(=O)O)co1]

4-N-Boc-N-Boc-α-Fmoc-guanidinophenylalanine was converted to a methyl ester with methyl iodide in DMF in the presence of $Na_2CO_3$. The Boc groups were removed in the presence of 20% TFA in dichloromethane and the Fmoc group with 20% piperidine in DMF. The α-amino group was then reacted with Boc-Leu-oxazolyl-4-carboxylic acid in DMF in the presence of BOP and DIPEA. The methyl ester was then hydrolysed as described in Example 79 to give Compound 86.

Rt=9.2 min (80% A:20% B to 100% B linear gradient over 15 minutes followed by 5 minutes at 100% B. A=$H_2O$+0.1% TFA. B=MeCN+0.1% TFA); HRMS: $[MH]^+$ 503.2613 (calc. for $C_{24}H_{35}N_6O_6^+$) 503.2614 (found); $^1$H NMR (DMSO $d_6$), δ 0.84-0.91 (m, 6H), 1.23-1.28 (br s, 1H), 1.36 (s, 9H), 1.53-1.64 (m, 2H), 1.68-1.75 (m, 1H), 3.14-3.19 (m, 2H), 4.62-4.73 (m, 2H), 7.08-7.14 (m, 2H), 7.26-7.32 (m, 2H), 7.33-7.44 (m, 4H), 7.50-7.56 (m, 1H), 8.18-8.25 (m, 1H), 8.52 (s, 1H), 9.59-9.72 (m, 1H).

Example 82

(S)-3-(4-(aminomethyl)phenyl)-2-(2-benzhydryl-4-methyl-1H-imidazole-5-carboxamido)propanoic acid (Compound 87)

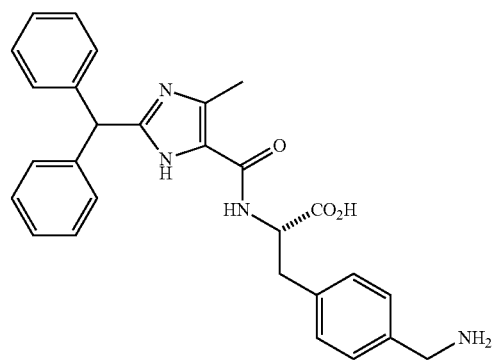 [SMILES: Cc1nc(C(c2ccccc2)c2ccccc2)[nH]c1C(=O)N[C@@H](Cc1ccc(CN)cc1)C(=O)O]

4-(Boc-aminomethyl)-Fmoc-phenylalanine was treated with Wang-resin, DIC, 5% DMAP, DCM/DMF (1:1) and then the Fmoc group was removed with 20% piperidine in DMF. The resulting resin attached amino acid was reacted with 2-Benzhydryl-4-methyl-1H-imidazole-5-carboxylic acid in the presence of BOP and DIPEA in DMF. The resulting, compound was removed from the resin and concomitantly the Boc protecting group removed by treatment with 95% TFA, 2.5% TIPS and 2.5% water, to give Compound 87

Rt=9.4 min (100% A to 100% B linear gradient over 15 minutes followed by 5 minutes at 100% B. A=$H_2O$+0.1% TFA. B=MeCN+0.1% TFA); HRMS: $[MH]^+$ 469.2234 (calc. for $C_{28}H_{29}N_4O_3^+$) 469.2234 (found); $^1$H NMR (DMSO $d_6$), δ 2.34 (s, 3H), 3.09-3.17 (m, 2H), 3.94-3.98 (q, 2H, J=5.52 Hz), 5.50 (s, 1H), 7.21-7.35 (m, 14H), 7.67-7.68 (d, 1H, J=10.1 Hz), 8.09 (br s, 2H).

Example 83

(S)-2-(2-((S)-1-((tert-butoxycarbonyl)amino)-3-methylbutyl)oxazole-4-carboxamido)-5-ureidopentanoic acid (Compound 88)

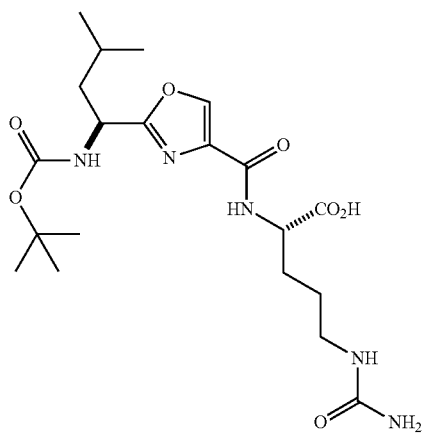 [SMILES: CC(C)C[C@H](NC(=O)OC(C)(C)C)c1nc(C(=O)N[C@@H](CCCNC(N)=O)C(=O)O)co1]

The carboxylic acid of 2-amino-5-urea-pentanoic acid was methylated with methyl iodide in the presence of $Na_2CO_3$ in DMF. The resulting ester was coupled with Boc-Leu-oxazole-4-carboxylic acid in the presence of BOP and DIPEA in DMF. The methyl ester was then removed with sodium hydroxide in methanol/$H_2O$ to give Compound 88.

Rt=8.3 min (80% A:20% B to 100% B linear gradient over 15 minutes followed by 10 minutes at 100% B. A=$H_2O$+0.1% TFA. B=MeCN+0.1% TFA); HRMS: $[MH]^+$ 456.2453 (calc. for $C_{20}H_{34}N_5O_7^+$) 456.2457 (found); $^1H$ NMR (DMSO $d_6$), δ 0.86-0.90 (2 sets of d, 6H, J=6.0 Hz), 1.25-1.28 (br s, 1H), 1.36 (s, 9H), 1.55-1.65 (m, 2H), 1.69-1.75 (m, 2H), 1.77-1.83 (m, 1H), 2.91-2.96 (m, 2H), 4.34-4.37 (m, 1H), 4.71-4.75 (m, 1H), 5.96-5.98 (br s, 1H), 7.53-7.54 (d, 1H, J=8.4 Hz), 8.08-8.09 (d, 1H, J=7.8 Hz), 8.55 (s, 1H).

Example 84

(S)-2-(2-((S)-1-((tert-butoxycarbonyl)amino)-3-methylbutyl)oxazole-4-carboxamido)-5-(3-nitroguanidino)pentanoic acid (Compound 89)

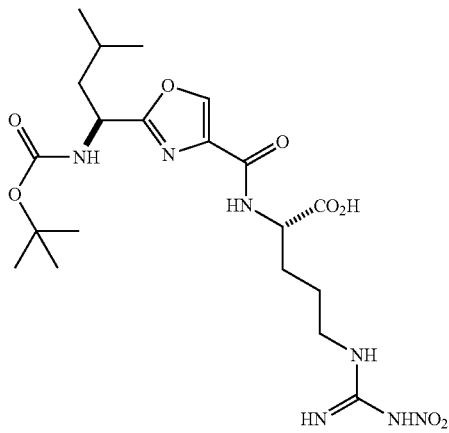

The carboxylic acid of 2-(Boc-amino)-5-(3-$NO_2$-guanidino)-pentanoic acid was methylated with methyl iodide in the presence of $Na_2CO_3$ in DMF. The Boc group was then removed using 20% TFA in DCM. The resulting free amino group was reacted with Boc-Leu-oxazole-4-carboxylic acid in the presence of BOP and DIPEA in DMF. The methyl ester was then removed with sodium hydroxide in methanol/$H_2O$ to give Compound 89.

Rt=11.6 min (100% A to 100% B linear gradient over 15 minutes followed by 5 minutes at 100% B. A=$H_2O$+0.1% TFA. B=MeCN+0.1% TFA); HRMS: $[MH]^+$ 500.2463 (calc. for $C_{20}H_{34}N_7O_8^+$) 500.2463 (found); $^1H$ NMR (DMSO $d_6$), δ 0.84-0.90 (2 sets of d, 6H, J=6.6 Hz), 1.24-1.30 (br s, 1H), 1.36 (s, 9H), 1.46-1.54 (m, 2H), 1.55-1.66 (m, 2H), 1.70-1.81 (m, 2H), 1.82-1.89 (m, 1H), 3.11-3.20 (m, 2H), 4.34-4.41 (m, 1H), 4.71-4.75 (m, 1H), 7.52-7.54 (d, 1H, J=8.4 Hz), 8.15-8.18 (d, 1H, J=7.8 Hz), 8.55 (s, 1H).

Example 85

(S)-2-(2-((S)-1-((tert-butoxycarbonyl)amino)-3-methylbutyl)oxazole-4-carboxamido)-5-((Z)-2-cyanoguanidino)pentanoic acid (Compound 90)

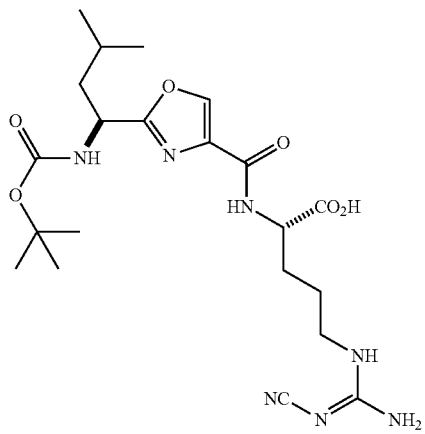 [SMILES: CC(C)C[C@H](NC(=O)OC(C)(C)C)c1nc(C(=O)N[C@@H](CCCN/C(N)=N\C#N)C(=O)O)co1]

The carboxylic acid of 2-(Boc-amino)-5-(2-N-cyanoguanidino)-pentanoic acid was methylated with methyl iodide in the presence of $Na_2CO_3$ in DMF. The Boc group was then removed using 20% TFA in DCM. The resulting free amino group was reacted with Boc-Leu-oxazole-4-carboxylic acid in the presence of BOP and DIPEA in DMF. The methyl ester was then removed with sodium hydroxide in methanol/$H_2O$ to give Compound 90.

Rt=10.1 min (80% A:20% B to 100% B linear gradient over 15 minutes followed by 5 minutes at 100% B. A=$H_2O$+0.1% TFA. B=MeCN+0.1% TFA); HRMS: $[MH]^+$480.2565 (calc. for $C_{21}H_{34}N_7O_6$) 480.2565 (found); $^1H$ NMR (DMSO $d_6$), δ 0.86-0.90 (2 sets of d, 6H, J=6.6 Hz), 1.24-1.30 (br s, 1H), 1.36 (s, 9H), 1.41-1.47 (m, 2H), 1.53-1.65 (m, 3H); 1.71-1.89 (m, 3H), 3.01-3.04 (q, 2H, J=6 Hz), 4.33-4.39 (m, 1H), 4.71-4.75 (m, 1H), 7.53-7.54 (d, 1H, J=7.8 Hz), 8.11-8.12 (d, 1H, J=7.8 Hz), 8.55 (s, 1H).

Example 86

(S)-2-(2-((S)-1-((tert-butoxycarbonyl)amino)-3-methylbutyl)oxazole-4-carboxamido)-4-(guanidinooxy)butanoic acid (Compound 91)

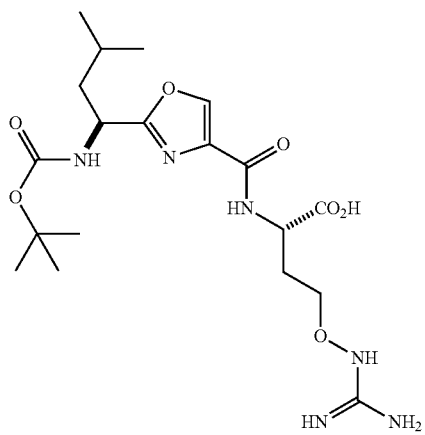 [SMILES: CC(C)C[C@H](NC(=O)OC(C)(C)C)c1nc(C(=O)N[C@@H](CCONC(=N)N)C(=O)O)co1]

2-Amino-4-O-guanidino-butanoic acid methyl ester was reacted with Boc-Leu-oxazole-4-carboxylic acid in the presence of BOP and DIPEA in DMF. The methyl ester was then removed with sodium hydroxide in methanol/H$_2$O to give Compound 91.

Rt=9.0 min (80% A:20% B to 100% B linear gradient over 15 minutes followed by 5 minutes at 100% B. A=H$_2$O+ 0.1% TFA. B=MeCN+0.1% TFA); HRMS: [MH]$^+$457.2405 (calc. for C$_{19}$H$_{33}$N$_6$O$_7^+$) 457.2407 (found); $^1$H NMR (DMSO d$_6$), δ 0.86-0.90 (2 sets of d, 6H, J=6.6 Hz), 1.24-1.30 (br s, 1H), 1.38 (s, 9H), 1.56-1.66 (m, 2H), 1.72-1.76 (m, 1H), 2.06-2.11 (m, 1H), 2.16-2.20 (m, 1H), 3.82-3.84 (t, 2H, J=6 Hz), 4.41-4.45 (m, 1H), 4.72-4.76 (m, 1H), 6.56 (s, 2H), 7.43-7.57 (m, 5H), 8.27-8.28 (d, 1H, J=6.6 Hz), 8.56 (s, 1H).

Example 87 tert-butyl ((S)-1-(4-(((S)-5-guanidino-1-oxo-1-(phenylsulfonamido)pentan-2-yl)carbamoyl)oxazol-2-yl)-3-methylbutyl)carbamate (Compound 92)

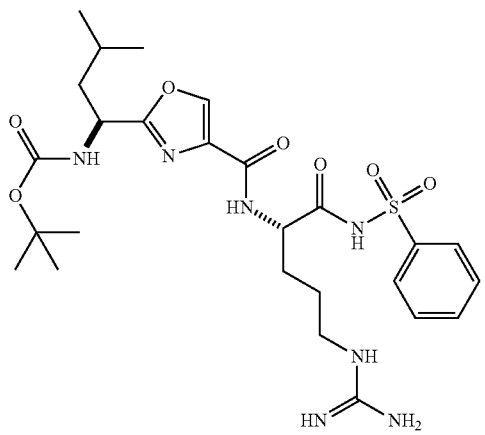

2-Boc-amino-5-Cbz-amino-pentanoic acid was reacted with NH$_2$SO$_2$phenyl in the presence of CDI and DBU in DMF to give a sulphonamide. The Cbz group was then removed with H$_2$ in the presence of 10% PdC in methanol. The 5-amino group was reacted with BocNHC(=NBoc)SCH$_3$ in the presence of HgCl$_2$ and triethylamine. The Boc groups were then removed with 20% TFA in DCM. The resulting arginine mimetic was reacted with Boc-Leu-oxazole-4-carboxylic acid in the presence of BOP and DIPEA in DMF to provide Compound 92.

Rt=10.6 min (80% A:20% B to 100% B linear gradient over 15 minutes followed by 5 minutes at 100% B. A=H$_2$O+ 0.1% TFA. B=MeCN+0.1% TFA); HRMS: [MH]$^+$594.2704 (calc. for C$_{26}$H$_{40}$N$_2$O$_7$S$^+$) 594.2704 (found); $^1$H NMR (DMSO d$_6$), δ 0.85-0.89 (2 sets of d, 6H, J=6.0 Hz), 1.24-1.30 (br s, 1H), 1.35 (s, 9H), 1.51-1.56 (m, 2H), 1.64-1.73 (m, 2H), 3.02-3.06 (q, 2H, J=7.2 Hz), 4.39-4.42 (m, 1H), 4.69-4.73 (m, 1H), 7.52-7.54 (m, 1H), 7.60-7.62 (t, 3H, J=7.8 Hz), 7.68-7.71 (t, 1H, J=7.2 Hz), 7.89-7.91 (d, 2H, J=7.2 Hz), 8.12-8.14 (d, 1H, J=7.8 Hz), 8.55 (s, 1H).

Example 88 tert-butyl ((S)-1-(4-(((S)-5-guanidino-1-(methylsulfonamido)-1-oxopentan-2-yl)carbamoyl)oxazol-2-yl)-3-methylbutyl)carbamate (Compound 93)

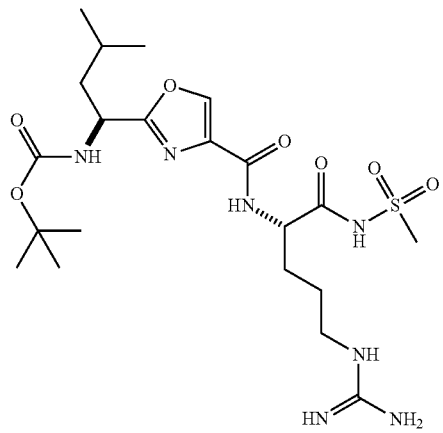

2-Boc-amino-5-Cbz-amino-pentanoic acid was reacted with NH$_2$SO$_2$methyl in the presence of CDI and DBU in DMF to give a sulphonamide. The Cbz group was then removed with H$_2$ in the presence of 10% PdC in methanol. The 5-amino group was reacted with BocNHC(=NBoc)SCH$_3$ in the presence of HgCl$_2$ and triethylamine. The Boc groups were then removed with 20% TFA in DCM. The resulting arginine mimetic was reacted with Boc-Leu-oxazole-4-carboxylic acid in the presence of BOP and DIPEA in DMF to provide Compound 93.

Rt=11.4 min (160% A to 100% B linear gradient over 15 minutes followed by 5 minutes at 100% B. A=H$_2$O+0.1% TFA. B=MeCN+0.1% TFA); HRMS: [MH]$^+$ 532.2548 (calc. for C$_{21}$H$_{38}$N$_7$O$_7$S$^+$) 532.2548 (found); $^1$H NMR (DMSO d$_6$), δ 0.86-0.90 (2 sets of d, 6H, J=6.0 Hz), 1.25-1.30 (br s, 1H), 1.36 (s, 9H), 1.54-1.65 (m, 2H), 1.70-1.80 (m, 2H), 3.08-3.11 (q, 2H, J=7.2 Hz), 3.24 (s, 3H), 4.44-4.48 (m, 1H), 4.71-4.75 (m, 1H), 7.50-7.53 (m, 2H), 8.21-8.22 (d, 1H, J=7.8 Hz), 8.59 (s, 1H), 12.01 (s, 1H).

Example 89

(S)-5-benzhydryl-N-(5-guanidino-1-oxo-1-(phenylsulfonamido)pentan-2-yl)thiophene-2-carboxamide (Compound 94)

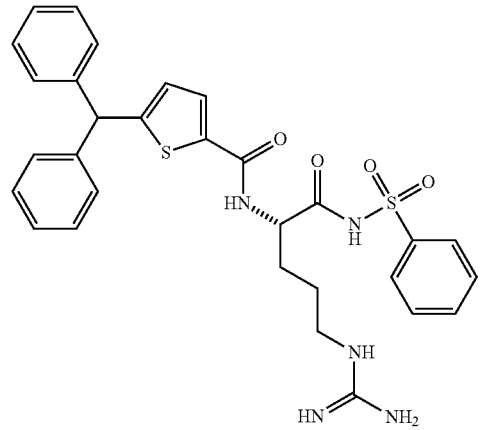

2-Boc-amino-5-Cbz-amino-pentanoic acid was reacted with NH$_2$SO$_2$phenyl in the presence of CDI and DBU in DMF to give a sulphonamide. The Cbz group was then removed with H$_2$ in the presence of 10% PdC in methanol. The 5-amino group was reacted with BocNHC(=NBoc)SCH$_3$ in the presence of HgCl$_2$ and triethylamine. the Boc groups were then removed with 20% TFA in DCM. The resulting arginine mimetic was coupled with 5-diphenylmethyl-thiophene-2-carboxylic acid in the presence of BOP and DIPEA in DMF to provide Compound 94.

Rt=13.1 min (100% A to 100% B linear gradient over 15 minutes followed by 5 minutes at 100% B. A=H$_2$O+0.1% TFA. B=MeCN+0.1% TFA); HRMS: [MH]$^+$ 590.1890 (calc. for C$_{30}$H$_{32}$N$_5$O$_4$S$_2^+$) 590.1890 (found); $^1$H NMR (DMSO d$_6$), δ 1.32-1.39 (m, 1H), 1.41-1.48 (m, 1.54-1.60 (m, 1H), 1.65-1.70 (m, 1H), 3.03-3.06 (q, 2H, J=7.2 Hz), 4.31-4.35 (m, 1H), 5.81 (s, 1H), 6.75-6.76 (d, 1H, J=3.6 Hz), 7.21-7.25 (m, 6H), 7.30-7.33 (t, 4H, J=7.2 Hz), 7.54-7.56 (t, 1H, J=6 Hz), 7.58-7.61 (t, 2H, J=8.4 Hz), 7.67-7.70 (m, 2H), 7.88-7.90 (m, 2H), 8.52-8.54 (d, 1H, J=7.2 Hz)

Example 90

(S)-2-(5-benzhydrylthiophene-2-carboxamido)-5-(2-cyanoguanidino)pentanoic acid (Compound 95)

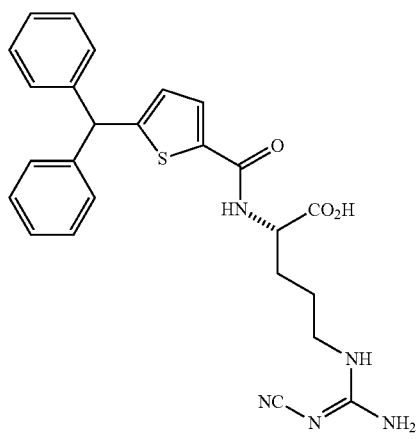

5-diphenylmethyl-thiophene-2-carboxylic acid was coupled with 2-amino-5-(2-cyanoguanidino)-pentanoic acid methyl ester in the presence of BOP and DIPEA in DMF. The methyl ester was then hydrolysed with NaOH in MeOH/H$_2$O to provide Compound 95.

Rt=10.7 min (100% A to 100% B linear gradient over 10 minutes followed by 10 minutes 100% B. A=H$_2$O+0.1% TFA. B=MeCN+0.1% TFA); HRMS: [MH]$^+$ 476.1751 (calc. for C$_{25}$H$_{26}$N$_6$O$_3$S$^+$) 476.1751 (found); $^1$H NMR (DMSO d$_6$), δ 1.41-1.42 (m, 2H), 1.62-1.69 (m, 1H), 1.75-1.80 (m, 1H), 3.01-3.05 (q, 2H, J=6.6 Hz), 4.25-4.29 (m, 1H), 5.81 (s, 1H), 6.75-6.77 (d, 1H, J=3.6 Hz), 7.22-7.25 (m, 6H), 7.31-7.34 (m, 4H), 7.71-7.72 (d, 1H, J=3.6 Hz), 8.53-8.55 (d, 1H, J=7.8 Hz).

Example 91

(S)-5-benzhydryl-N-(5-(2-cyanoguanidino)-1-oxo-1-(phenylsulfonamido)pentan-2-yl)thiophene-2-carboxamide (Compound 96)

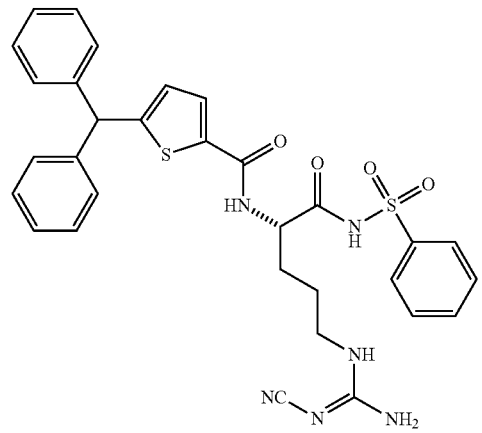

5-amino-2-Boc-amino-pentanoic acid phenyl sulphonamide was heated with diphenyl N-cyanocarbonimidate in isopropanol and the resulting compound treated with saturated ammonia in ethanol to give the 5-(2-cyano-guanidino)-2-amino-pentanoic acid phenyl sulphonamide. The α-amino group was then coupled with 5-diphenyl-thiophene-2-carboxylic acid in the presence of BOP and DIPEA in DMF to give Compound 96.

Rt=11.6 min (100% A to 100% B linear gradient over 10 minutes followed by 10 minutes 100% B. A=H$_2$O+0.1% TFA. B=MeCN+0.1% TFA); HRMS: [MH]$^+$ 615.1843 (calc. for C$_{31}$H$_{31}$N$_6$O$_4$S$_2^+$) 615.1839 (found); $^1$H NMR (DMSO d$_6$), δ 1.27-1.34 (m, 1H), 1.37-1.43 (m, 1H), 1.50-1.56 (m, 1H), 1.60-1.65 (m, 1H), 2.97-3.00 (q, 2H, J=6.6 Hz), 4.28-4.31 (m, 1H), 5.80 (s, 1H), 6.74-6.75 (d, 1H, J=3.6 Hz), 7.21-7.25 (m, 6H), 7.30-7.33 (m, 4H), 7.58-7.61 (t, 2H, J=7.8 Hz), 7.67-7.70 (m, 2H), 7.87-7.89 (m, 2H), 8.48-8.50 (d, 1H, J=7.2 Hz), 12.34 (s, 1H).

Example 92

2-Benzhydryl-1,5-Dimethyl imidazole-4-carboxyl-Arginine (Compound 97)

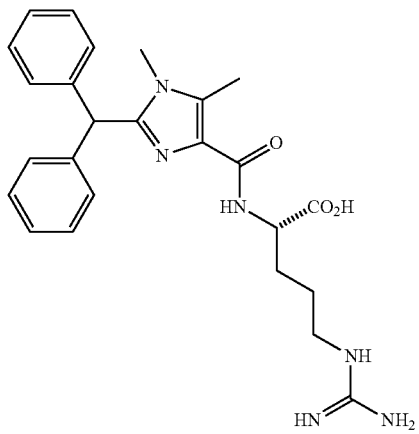 [SMILES: Cc1c(C(=O)N[C@@H](CCCNC(=N)N)C(=O)O)nc(C(c2ccccc2)c2ccccc2)n1C]

$^1$H NMR (600 MHz, DMSO-d$_6$): δ 7.72, (m, 1H); 7.43-7.19 (m, 10H); 6.08 (broad s, 1H); 4.34 (m, 1H); 3.61 (broad s, 3H); 3.17-3.06 (m, 2H); 2.31 (s, 3H); 1.85 (m, 1H); 1.70 (m, 1H); 1.62-1.51 (m, 2H). HRMS Calculated for $C_{25}H_{31}N_6O_3^+$ 463.2452. found 463.2447.

Example 93

2-Benzhydryl-1,4-Dimethyl imidazole-5-carboxyl-Arginine (Compound 98)

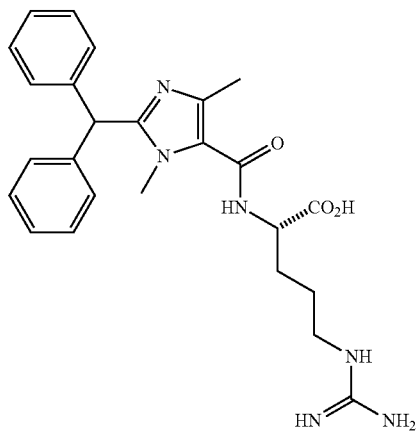 [SMILES: Cc1nc(C(c2ccccc2)c2ccccc2)n(C)c1C(=O)N[C@@H](CCCNC(=N)N)C(=O)O]

$^1$H NMR (600 MHz, DMSO-d$_6$): δ 7.60, (d, J=7.9 Hz, 1H); 7.56 (t, J=5.7 Hz, 1H); 7.35-7.28 (m, 8H), 7.25-7.20 (m, 2H); 5.79 (s, 1H); 4.39 (m, 1H); 3.39 (s, 3H); 3.17-3.05 (m, 2H); 2.45 (s, 3H); 1.83 (m, 1H); 1.71 (m, 1H); 1.53-1.42 (m, 2H). HRMS Calculated for $C_{25}H_{31}N_6O_3^+$ 463.2452. found 463.2447.

Example 94

C3a Receptor Binding of Compounds of Formula (I)

Macrophage Cell Culture and Differentiation.

Human monocyte-derived macrophage (HMDM) cells were kept in complete media, consisting of Iscove's Modified Dulbecco's Medium (IMDM) with 10% FBS, 10 Um/L penicillin, 10 U/mL streptomycin and 2 mM L-glutamine (Invitrogen). Cells were cultured at 37° C., with 5% $CO_2$. For HMDM, peripheral blood mononuclear cells were isolated from buffy coat (obtained from Australian Red Cross Blood Service, Kelvin Grove) using Ficoll-paque density centrifugation (GE Healthcare Bio-Science, Uppsala, Sweden). CD$^{14+}$ monocytes were positively selected using CD$^{14+}$ MACS magnetic beads (Miltenyi Biotech, Auburn, Calif., USA). Monocytes were differentiated to HMDM in complete media containing 104 U/mL (100 ng/mL) recombinant human macrophage colony stimulating factor (M-CSF) (PeptroTech Inc, Rocky Hill, N.J., USA) at 1.5× 10$^6$ monocytes/mL. HMDM were supplemented with 50% fresh complete medium containing CSF-1 on Day 5 after seeding. Cells were harvested by gentle scraping in saline solution and replated for use on Day 7.

Receptor Binding Assay.

The receptor binding assay was performed using [$^{125}$I]-C3a 80 pM (2200 Ci/mmol; Perkin Elmer, Torrance, Calif., USA), HMDM cells (1.5×10$^6$ cells/mL and in the absence or presence of various concentrations of unlabelled C3a or compound of formula (I) for 60 mins at room temperature with shaking in 50 mM Tris, 3 mM MgCl$_2$, 0.1 mM CaCl$_2$, 0.5% (w/v) bovine serum albumin, pH 7.4. Unbound radioactivity was removed by filtration through glass microfiber filters GF/B (Whatman Iner. Ltd, England) that had been soaked in 0.6% polyethylenimine to reduce non-specific binding. The filter was washed 3 times with cold buffer (50 mM Tris-HCl) pH 7.4. Bound [$^{125}$I]-C3a was then assessed by scintillation counting on a β-counter. Specific [$^{125}$I]-C3a binding is defined as a difference between total binding and non-specific binding as determined in the presence of 1 μM unlabeled C3a. The IC$_{50}$ value is the concentration of compounds of formula (I) to inhibit the binding of labelled ligand by 50 percent.

Nonlinear regression analysis (GraphPad Prism 5, USA) was performed on concentration response curves to determine IC$_{50}$ and −log IC$_{50}$. The −log IC$_{50}$ for each compound was calculated for separate experiments and express as an arithmetic mean standard error (SE). IC$_{50}$ values were expressed as a geometric mean.

The results are shown in Tables 6 to 8 and in FIG. 1.

TABLE 6

Activity of compounds of formula (I) on competitive binding with [$^{125}$I]-C3a in isolated human monocyte derived macrophage cells (HMDM).

| Compound | n | pIC$_{50}$ ± SEM | IC$_{50}$ (nM) |
|---|---|---|---|
| hC3a | 12 | 9.64 ± 0.04 | 0.23 |
| SB290157 | 11 | 7.42 ± 0.06 | 38 |
| 1 | 3 | 7.71 ± 0.08 | 20 |
| 2 | 3 | 7.53 ± 0.10 | 30 |
| 3 | 1 | 6.29 ± 0.14 | 509 |
| 4 | 1 | 5.64 ± 0.31 | 2286 |
| 5 | 3 | 7.09 ± 0.11 | 82 |
| 6 | 2 | 7.58 ± 0.07 | 26 |
| 7 | 1 | 6.86 ± 0.08 | 137 |
| 8 | 3 | 8.03 ± 0.05 | 9 |
| 9 | 4 | 6.82 ± 0.10 | 152 |
| 10 | 3 | 6.91 ± 0.09 | 123 |
| 11 | 1 | 6.10 ± 0.16 | 800 |
| 12 | 1 | 6.80 ± 0.15 | 157 |
| 13 | 2 | 7.14 ± 0.19 | 72 |
| 14 | 2 | 5.99 ± 025 | 1031 |
| 15 | 2 | 6.35 ± 0.17 | 451 |
| 16 | 3 | 6.81 ± 0.07 | 155 |
| 17 | 1 | 6.85 ± 0.15 | 142 |
| 18 | 3 | 7.26 ± 0.09 | 55 |
| 19 | 1 | 6.12 ± 0.13 | 754 |
| 20 | 3 | 8.30 ± 0.10 | 5 |
| 21 | 5 | 6.98 ± 0.11 | 104 |
| 22 | 5 | 6.15 ± 0.14 | 712 |
| 23 | 5 | 6.06 ± 0.13 | 872 |
| 24 | 6 | 6.99 ± 0.10 | 102 |
| 25 | 3 | 7.86 ± 0.08 | 14 |
| 50 | 4 | 7.43 ± 0.10 | 37 |
| 56 | 4 | 7.43 ± 0.10 | 1 |
| 57 | 3 | 5.88 ± 0.11 | 302 |
| 58 | 3 | 6.22 ± 0.15 | 12 |
| 59 | 3 | 7.04 ± 0.12 | 38 |
| 79 | 3 | 7.9 ± 0.3 | 12 |
| 80 | 3 | 7.4 ± 0.4 | 38 |
| 82 | 3 | 6.4 ± 00.3 | 375 |
| 83 | 3 | — | 1220 |
| 84 | 3 | — | 76 |
| 89 | 3 | — | 129 |
| 90 | 3 | — | 41 |
| 91 | 3 | — | 93 |
| 92 | 3 | — | 7.5 |
| 93 | 3 | — | 30 |
| 94 | 3 | — | 35 |
| 95 | 3 | — | 853 |
| 96 | 3 | — | 888 |
| 97 | 3 | 5.9 ± 0.3 | 1,144 |
| 98 | 3 | 7.5 ± 0.2 | 31 | n = number of experiments performed

TABLE 7

Activity of Compounds of formula (I) on competitive binding with [$^{125}$I]-C3a in isolated human monocyte derived macrophage cells (HMDM).

| compound | %[$^{125}$I]-C3a binding[a] | % agonist[b] | compound | %[$^{125}$I]-C3a binding[a] | % agonist[b] |
|---|---|---|---|---|---|
| 26 | 19 | 84 | 38 | 41 | 87 |
| 27 | 14 | 62 | 39 | 40 | 26 |
| 28 | 26 | 56 | 40 | 44 | 103 |
| 29 | 31 | 77 | 41 | 44 | 44 |
| 30 | 29 | 68 | 42 | N/A | 134 |
| 31 | N/A | 109 | 43 | 65 | 67 |
| 32 | 39 | 107 | 44 | 42 | 69 |
| 33 | 26 | 69 | 45 | N/A | 64 |
| 34 | 44 | 70 | 46 | 61 | 50 |
| 35 | N/A | 95 | 47 | 49 | 48 |
| 36 | 61 | 50 | 48 | 32 | 68 |
| 37 | 43 | 81 | 49 | N/A | 105 |

[a] % binding of [$^{125}$I]-C3a at compounds concentration 20 μM; compared to the binding of [$^{125}$I]-C3a with cells in the absence of compound (or Buffer) as 100%
[b] % Response to 100 nM C3a activity. The compounds tested at [10 μM]. Buffer at 100%

TABLE 8

Activity of Compounds of formula (I) on competitive binding with [$^{125}$I]-C3a in isolated human monocyte derived macrophage cells (HMDM).

| Compound | X | Y | Z | Receptor Binding Affinity $^{125}$I IC$_{50}$ (nM) | n |
|---|---|---|---|---|---|
| 56 | N | O | CH | 1 | 3 |
| 57 | O | CH | CH | 302 | 3 |
| 58 | O | N | C—Me | 12 | 3 |
| 59 | S | N | C—Me | 38 | 3 |
| 60 | S | CH | CH | 140 | 3 |
| 61 | N | O | C—Me | 740 | 3 |
| 62 | N | NH | C—Ph | 46 | 3 |
| 64 | N | NH | C—Me | 7.6 | 3 |
| 65 | S | N | C—Ph | 3369 | 4 |
| 66 | O | N | C—Ph | 123 | 3 |
| 67 | N | N | O | 11 | 3 |
| 68 | N | O | N | 447 | 4 |
| 69 | O | N | N | 2575 | 3 |
| SB290157 | | | | 11 | 5 |
| hC3a | | | | 0.07 | 4 |

The compounds showed high affinity for the C3aR.

Example 95

Calcium Mobilization Assay

Harvested HMDM cells were washed with 0.9% NaCl solution by centrifugation at 2500 rpm for 5 min, followed by resuspension of the cell pellet with complete media. Cells were seeded at 5×10$^4$ cells/well in a 96-well black-wall, clear bottom plate (DKSH, Zurich), and left overnight to adhere at 37° C. On the day of the experiment, supernatant was removed and cells were incubated in dye loading buffer (Hank's Balanced Salt Solution (HBSS) with 4 μM Fluo-3, 25 μL pluronic acid, 1% fetal bovine serum (FBS) and 2.5 mM probenecid) for one hour at 37° C. Cells were then washed twice with HBSS and transferred to a Fluorostar spectrofluorimeter (BMG, Durham N.C.) for oxazole compound injection and fluorescence measurements.

The results are shown in Tables 9 and 10.

TABLE 9

Activity of non-peptide agonists on Ca$^{2+}$ mobilization from isolated human monocyte derived macrophage cells (HMDM).

| Compound | n | pEC$_{50}$ ± SEM | EC$_{50}$ (nM) |
|---|---|---|---|
| hC3a | 3 | 7.19 ± 0.06 | 65 |
| SB290157 | 7 | 5.52 ± 0.08 | 3050(IC$_{50}$) |
| 1 | 4 | 7.72 ± 0.27 | 19 |
| 2 | 4 | 7.57 ± 0.11 | 27 |
| 5 | 2 | 6.87 ± 0.18 | 135 |
| 6 | 1 | 5.30 ± 0.18 | 5000 |
| 7 | 2 | 5.25 ± 0.31 | 5600 |
| 8 | 3 | 8.15 ± 0.10 | 7.2 |
| 9 | 3 | 7.14 ± 0.19 | 73 |
| 10 | 7 | 7.39 ± 0.12 | 41 |
| 11 | | — | |
| 12 | | — | |
| 13 | 2 | 6.30 ± 0.90 | 498 |
| 14 | | — | |
| 15 | | — | |
| 16 | 7 | 8.12 ± 0.21 | 8 |
| 17 | | — | |
| 18 | 3 | 7.26 ± 0.08 | 54 |
| 19 | 3 | 6.13 ± 0.11 | 744 |
| 20 | 3 | 7.76 ± 0.36 | 17 |
| 21 | 3 | 6.62 ± 0.28 | 240 |
| 22 | 2 | ∞ | ∞ |
| 23 | 1 | 6.07 ± 0.13 | 849 |
| 24 | 3 | 6.28 ± 0.16 | 527 |
| 25 | 3 | 7.35 ± 0.18 | 45 |
| 56 | 4 | 8.2 ± 0.15 | 6.6 |
| 57 | 3 | 6.19 ± 0.2 | 645 |
| 59 | 3 | 4.13 ± 2.7 | 74800 |
| 79 | 3 | 7.8 ± 0.3 | 15 |
| 80 | 3 | 6.9 ± 0.1 | 120 |
| 81 | 3 | 7.2 ± 0.1 | 60 |
| 90 | 3 | | 250 |
| 91 | 3 | | 370 |
| 98 | 3 | | 40 |

TABLE 10

| Compound | X | Y | Z | Antagonist Activity Ca$^{2+}$ IC$_{50}$ (uM) | n | Agonist Activity EC$_{50}$ (uM) | n |
|---|---|---|---|---|---|---|---|
| 56 | N | O | CH | 0.02 | 4 | partial agonist | 4 |
| 57 | O | CH | CH | 1.8 | 3 | N.A | |
| 58 | O | N | C-Me | 2.9 | 3 | N.A | |
| 59 | S | N | C-Me | 1 | 3 | N.A greater than 100 | 7 |
| 60 | S | CH | CH | 0.07 | 5 | micromolar | 5 |
| 61 | N | O | C-Me | 0.03 | 4 | partial agonist greater than 100 micromolar | 5 |
| 62 | N | NH | C-Ph | 0.6 | 4 | | |
| 63 | N-Me | N | C-Ph | | | | |
| 64 | N | NH | C-Me | N.A. | — | 0.024 | 4 |
| 65 | S | N | C-Ph | 67 | 5 | N.A. | |
| 66 | O | N | C-Ph | 2 | 3 | N.A. | |
| 67 | N | N | O | 1.3 | 3 | N.A. | |
| 68 | N | O | N | 1.2 | 3 | N.A. | |
| 69 | O | N | N | 24 | 3 | N.A. | |
| SB290157 | | | | 1.3 | 8 | | |
| hC3a | | | | | | 45 | 1 |

N.A. = not applicable

Example 96

Competitive Radio-Ligand Binding Assays: [$^{125}$I]-C5a Binding

The competitive radio-labelled C5a assay was used to evaluate whether the compounds bound to C3aR over C5a receptor (C5aR). HMDM cells (1.5×10$^6$ cells/mL) were incubated for 1 hour at room temperature with 20 pM of [$^{125}$I]-C5a and ligand [20 μM]. Unbound radioactivity was removed by filtration through glass microfiber filters GF/B (Whatman Iner. Ltd, England) that had been soaked in 0.6% polyethylenimine to reduce non-specific binding. The filter was washed 3 times with cold buffer (50 mM Tris-HCl) pH 7.4. Bound [$^{125}$I]-C3a was then assessed by scintillation counting on a β-counter. Specific [$^{125}$I]-C3a binding is defined as a difference between total binding and non-specific binding as determined in the presence of 1 μM unlabeled C3a. The IC$_{50}$ value is the concentration of compounds of formula (I) to inhibit the binding of labelled ligand by 50 percent.

A single concentration screen (ligands at 20 μM) for C5aR binding affinity shows none of the compounds have affinity for C5aRs on human macrophages (HMDM). The binding affinity was compared to 3D53, a known selective C5aR antagonist with no cross reactivity to C3aR. The results are shown in FIG. 2A to 2D.

The results indicate that the compounds are selective for C3aR over C5aR.

Example 97

Dose Response Curves for Competitive Binding at C5a Receptor

Using the assay described in Example 94, full dose response curves were obtained by incubation of cells with increasing concentrations of non-labelled C3a [1 pM to 0.3 μM] and selected ligands [0.1 nM to 100 μM].

Figure 3:
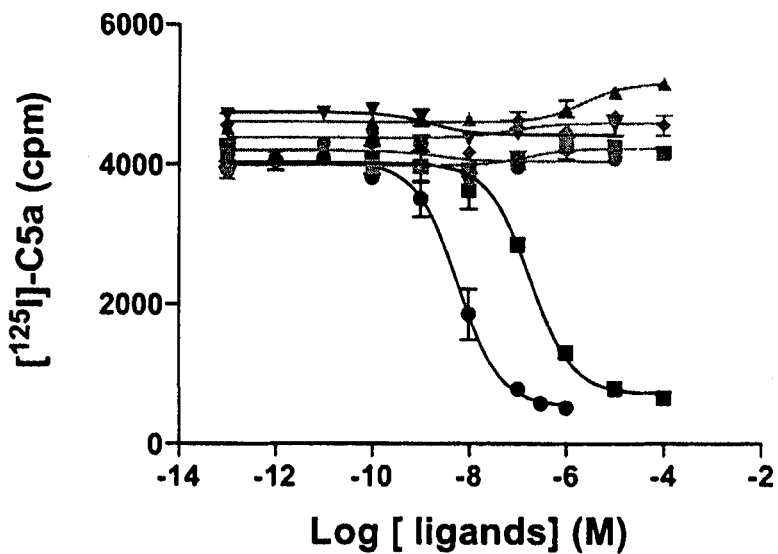
FIG. 3 is a dose response curve of competitive binding of compounds (0.1 nM to 100 μM) and [$^{125}$I]-C5a (20 pM). A: hC5a (●), 3D5e (■), 8 (♦), 2 (▼), 20 (▲), 25 (■), 26 (●); B: hC5a (●), 3D5e (■), 50 (▲), 54 (▼).
Figure 3:
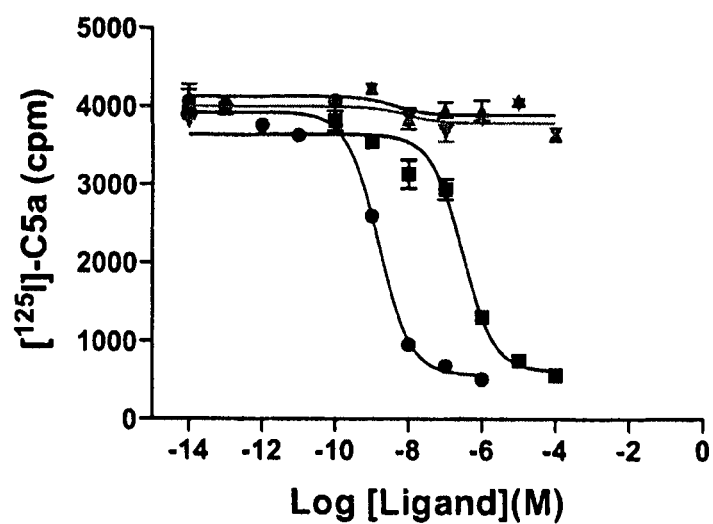

The results are shown in FIGS. 3A and 3B. These results confirm that the compounds are selective for C3aR over C5aR.

Example 98

Desensitization Experiments

Desensitization experiments were used to measure the selectivity of various ligands for C3aR, since this can help to clarify whether the non-peptidic ligands bind selectively to C3aR over other GPCRs that signal through intracellular calcium release.

Figure 4:
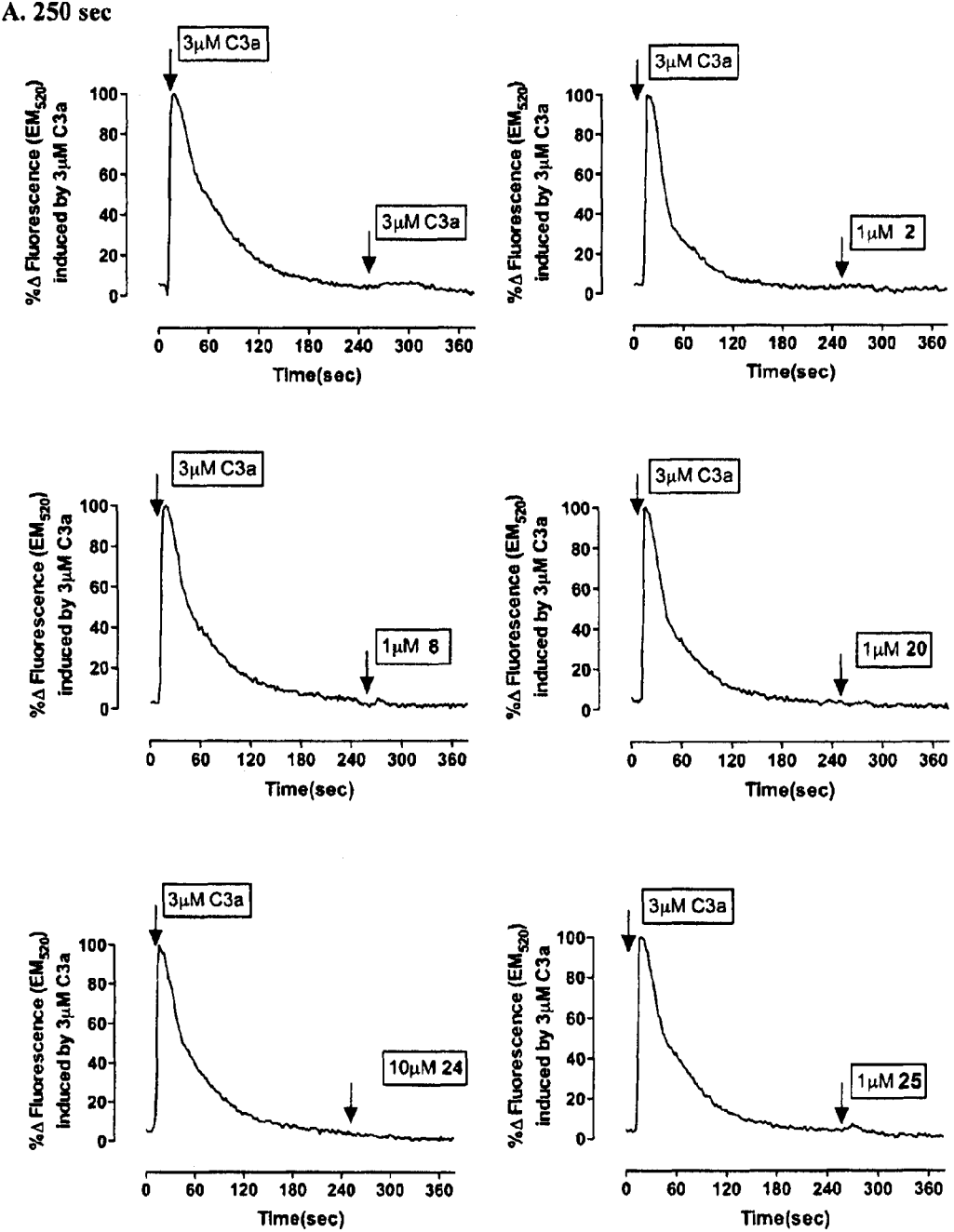
FIG. 4 provides spectrophotometric graphs showing C3aR desensitization of Calcium mobilization on HMDM for compounds of the invention. A. compounds 2, 8, 20, 24 and 25; B: compounds 10, 16, 1 and 18; C: compounds 50 and 54; D: compounds 56, 57, 58 and 59.
Figure 4B:
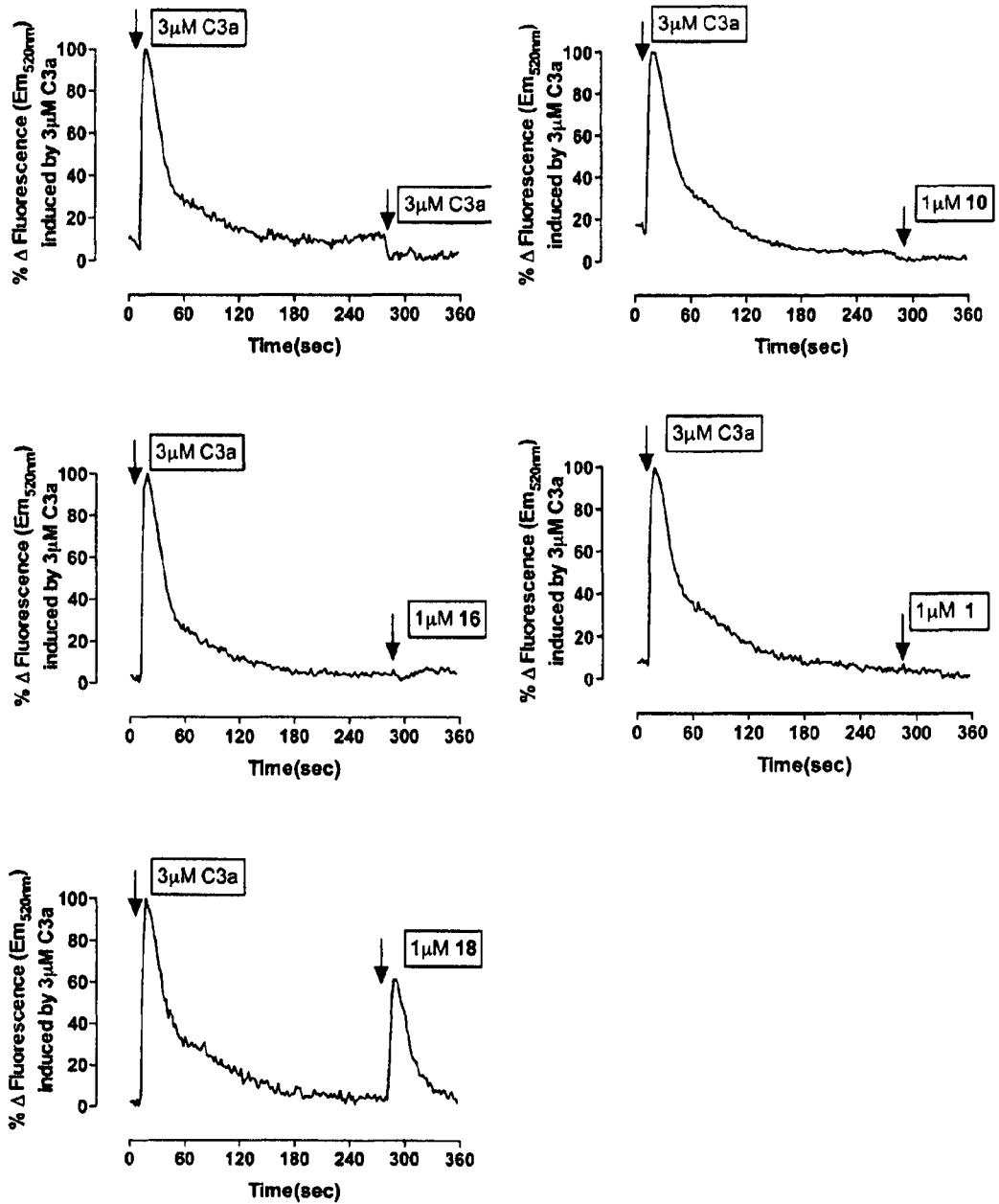
Figure 4C:
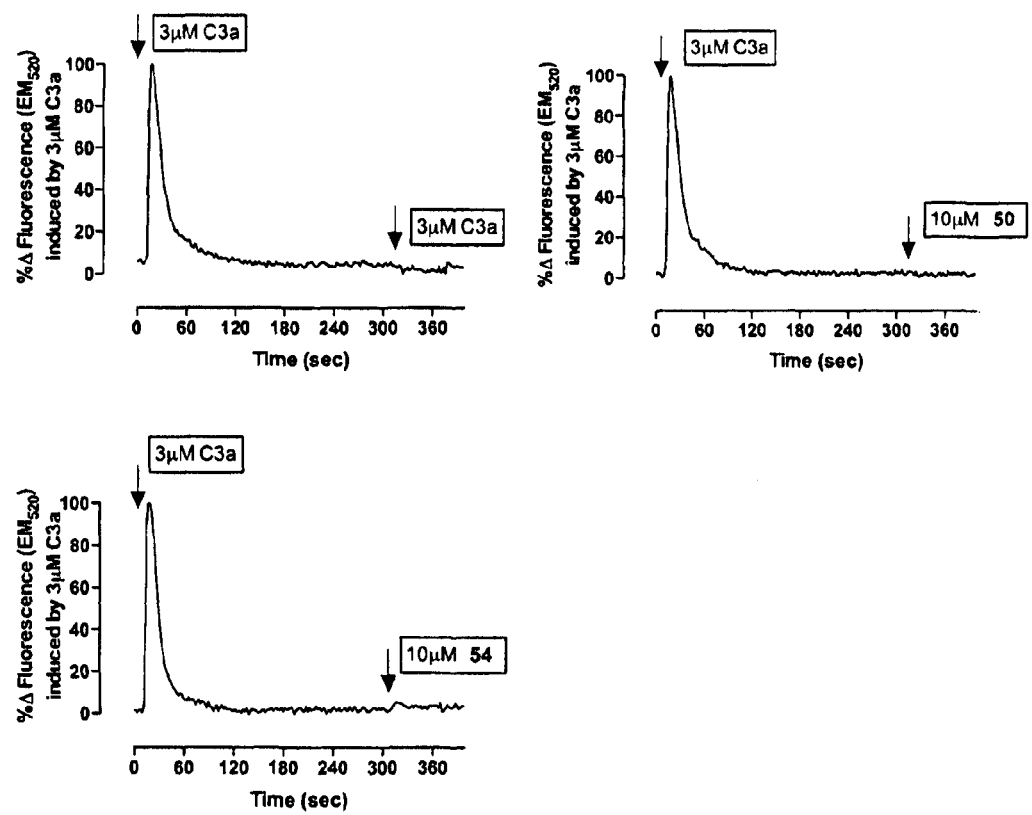
Figure 4D:
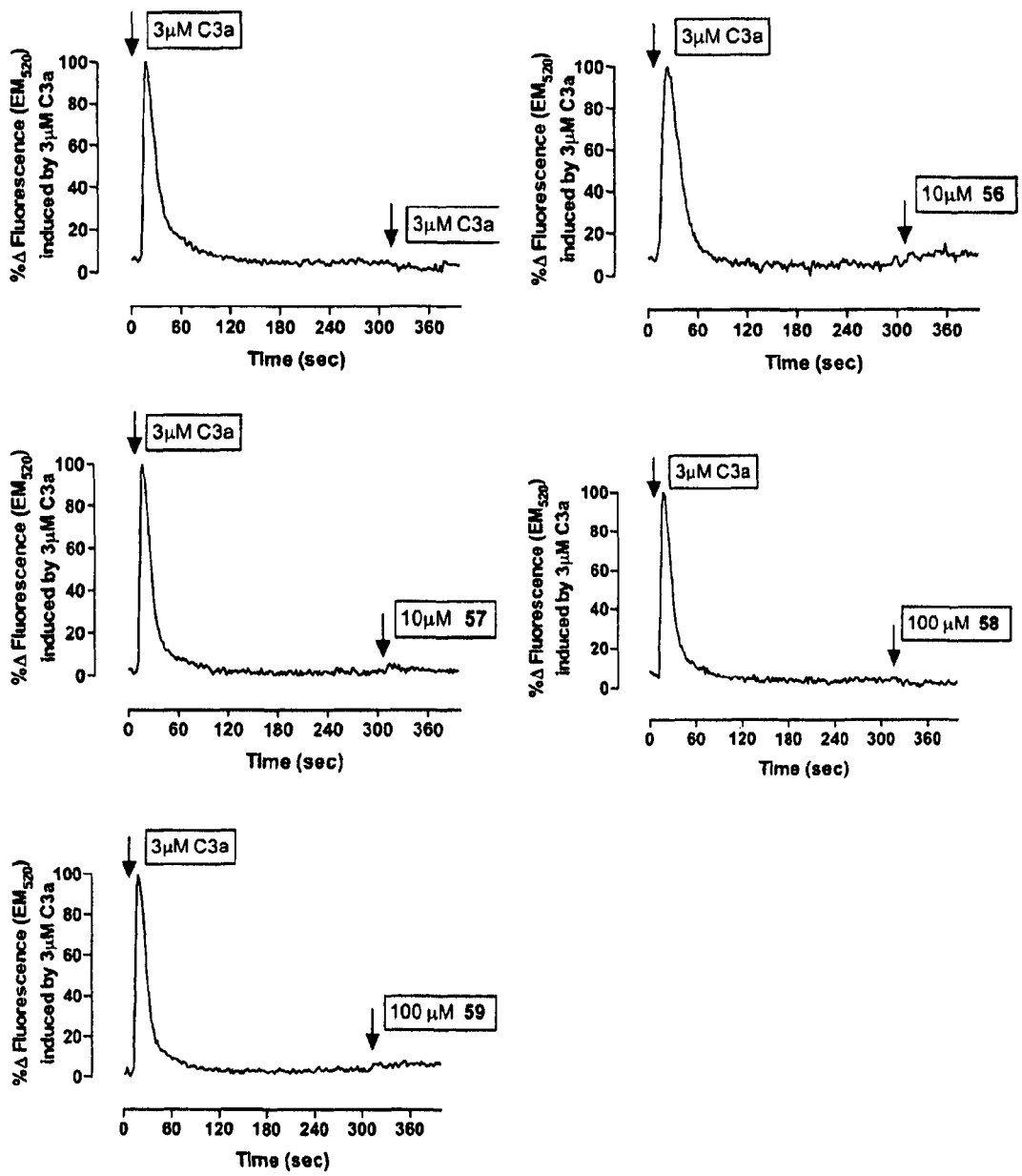
Figure 5A:
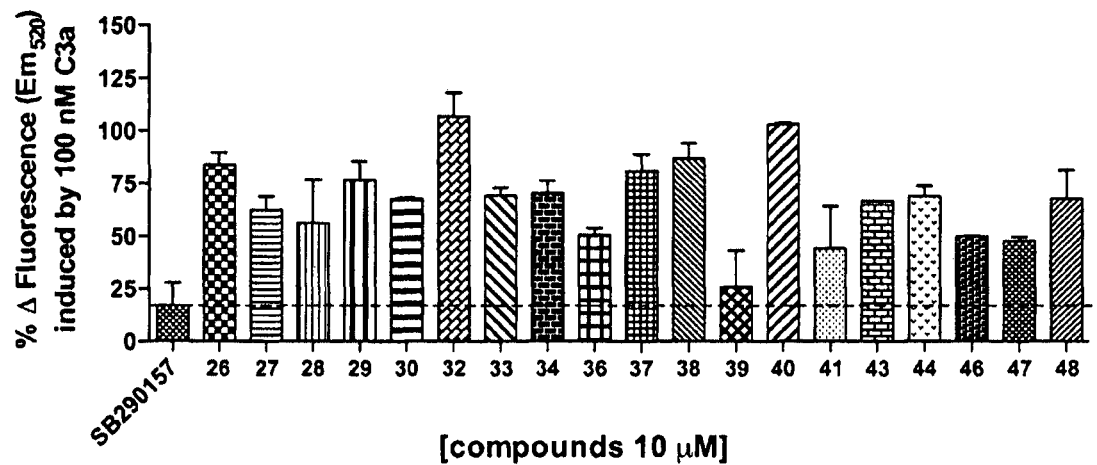
FIG. 5 shows graphical representation of the ability of compounds to induce or inhibit the induction of mobilization of Ca$^{++}$ inside human monocyte derived macrophages. Agonists stimulate Ca$^{++}$ efflux, while antagonist inhibit calcium efflux. A: compounds 26-30, 32-34, 36-41, 43, 44 and 46-48; B: compounds 2, 6, 7, 9-13 and 16, and compounds 1, 8, 14, 15 and 17-24; C: compounds 50, 51, 54 and 55 and compounds 52, 53, 55 and 54.
Figure 5B:
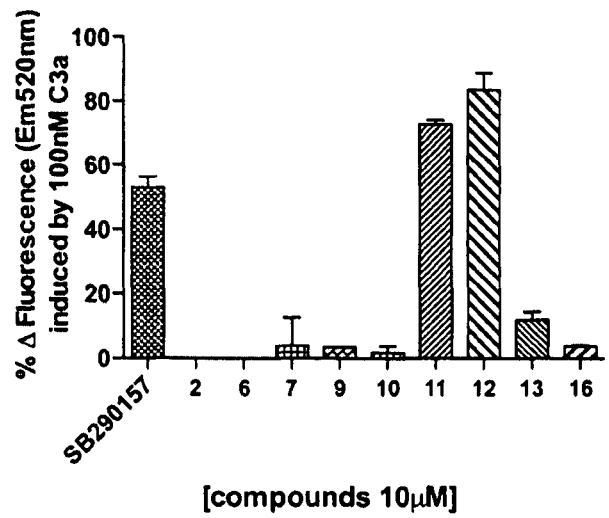
Figure 5B:
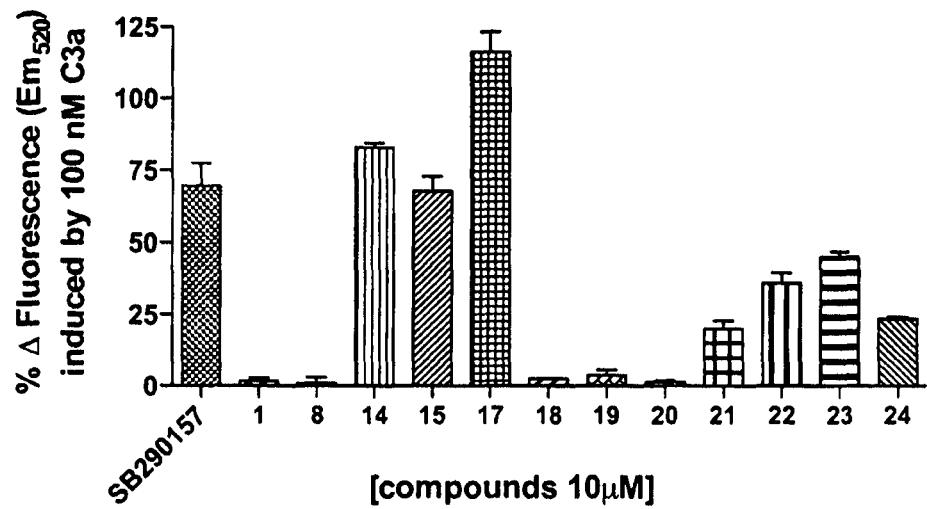
Figure 5C:
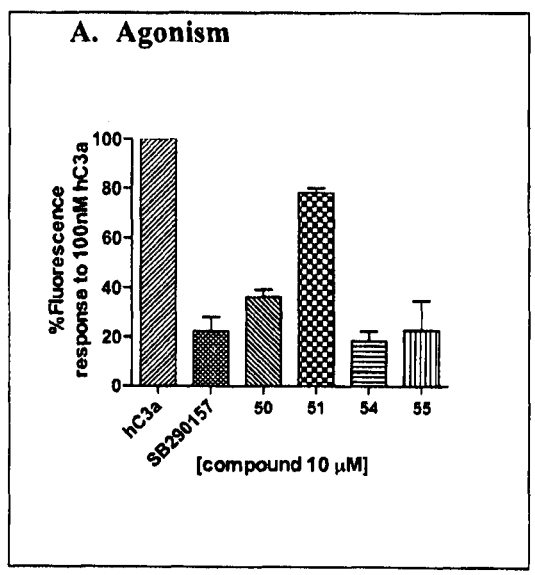
Figure 5C:
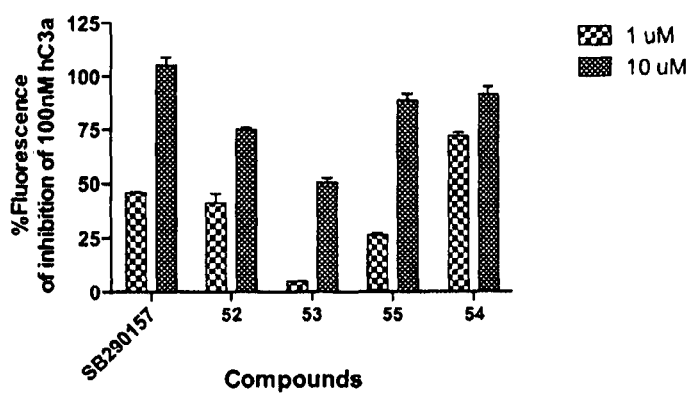

The hC3a (3 μM) was administered to human monocyte derived macrophage cells, which produces an efflux of intracellular Ca$^{2+}$ that dissipates after 4-5 mins (FIGS. 4A and 4B). A second addition of 3 μM hC3a after 5 mins has no effect, due to desensitization of the receptor through either receptor (C3a receptor) phosphorylation or receptor internalization from the cell surface. FIGS. 4A and 4B shows that compounds 8, 18 and 25 caused a second efflux of intracellular Ca$^{2+}$. This suggests that these non-peptidic ligands are not purely selective for C3aR, which is desensitized upon the first addition of agonist. In contrast, compounds 2, 10, 16 and 1 (EC$_{50}$=27, 41, 8 and 19 nM, respectively) appear to be selective for C3aR as a second addition of 1 μM of these compounds, following first desensitization with C3a did not produce calcium efflux from macrophage cells. Similar results were obtained for compounds 105, 109, 143, 144, 145 and 146 (FIGS. 4C and 4D) showing these compounds are selective for C3aR over other GPCRs.

Example 99

Effect of Compounds on Calcium Release from HMDM

Various compounds were examined in the calcium mobilization assay for agonist or antagonist activity compared to hC3a and to the known antagonist SB290157. The results are shown in Tables 11 to 13 and FIGS. 5A to 5D.

TABLE 11

SAR of acyl-leucine-5-phenyl-oxazole-arginine (50) comparison to boc-leucine-oxazole-arginine (1) and acyl-leucine-5-methyl-oxazole-arginine (25) on competitive binding with [$^{125}$I]-C3a and Ca$^{2+}$ mobilisation from HMDM cells.

| | | Receptor Binding Affinity | | Apparent Antagonist Activity | | Apparent Antagonist Activity | |
|---|---|---|---|---|---|---|---|
| Agonist/ Antagonist | n | pIC$_{50}$ ± SE | IC$_{50}$ (nM) | n | pEC$_{50}$ ± SE | EC$_{50}$ (nM) | n | pIC$_{50}$ ± SE | IC$_{50}$ (nM) |
| hC3a | 12 | 9.64 ± 0.04 | 0.23 | 3 | 7.2 ± 0.06 | 65 | — | — | — |
| SB290157 | 11 | 7.42 ± 0.06 | 38 | 4 | * | * | 9 | 5.6 ± 0.09 | 2700 |

TABLE 11-continued

SAR of acyl-leucine-5-phenyl-oxazole-arginine (50)
comparison to boc-leucine-oxazole-arginine (1) and acyl-leucine-5-methyl-oxazole-
arginine (25) on competitive binding with [$^{125}$I]-C3a and Ca$^{2+}$ mobilisation from HMDM cells.

| Agonist/Antagonist | Receptor Binding Affinity | | | Apparent Antagonist Activity | | | Apparent Antagonist Activity | | |
|---|---|---|---|---|---|---|---|---|---|
| | n | pIC$_{50}$ ± SE | IC$_{50}$ (nM) | n | pEC$_{50}$ ± SE | EC$_{50}$ (nM) | n | pIC$_{50}$ ± SE | IC$_{50}$ (nM) |
| 1 | 3 | 7.71 ± 0.06 | 20 | 4 | 7.7 ± 0.27 | 19 | — | — | — |
| 25 | 3 | 7.86 ± 0.08 | 15 | 2 | 7.4 ± 0.18 | 45 | — | — | — |
| 50 | 4 | 7.43 ± 0.10 | 37 | 4 | * | * | 4 | 7.8 ± 0.17 | 16.5 |

* The compounds show no agonist activity in calcium mobilisation assays up to 100 μM.

TABLE 12

SAR data: Heterocycles at the linker.

| Agonist | n | pIC$_{50}$ ± SE | IC$_{50}$ (nM) | n | pEC$_{50}$ ± SE | EC$_{50}$ (nM) |
|---|---|---|---|---|---|---|
| 56 | 4 | 7.43 ± 0.10 | 37 | 4 | 8.2 ± 0.15 | 6.6 |
| 57 | 3 | 5.88 ± 0.11 | 1300 | 2 | 6.19 ± 0.2 | 645 |
| 58 | 3 | 6.22 ± 0.15 | 606 | 2 | φ | φ |
| 59 | 3 | 7.04 ± 0.12 | 91 | 2 | 4.13 ± 2.7 | 74800 |

φ compound showed no agonist activity up to 100 μM.

TABLE 13

Antagonist Activity

| Compound | n | IC$_{50}$ (μM) |
|---|---|---|
| 82 | 3 | 0.2 |
| 92 | 3 | 1.3 |
| 93 | 3 | 2.0 |
| 94 | 3 | 0.3 |
| 95 | 3 | 0.9 |
| 96 | 3 | 2.0 |

Example 100

Correlation Between Binding Affinity and H-Bond Interaction Energy

Figure 6:
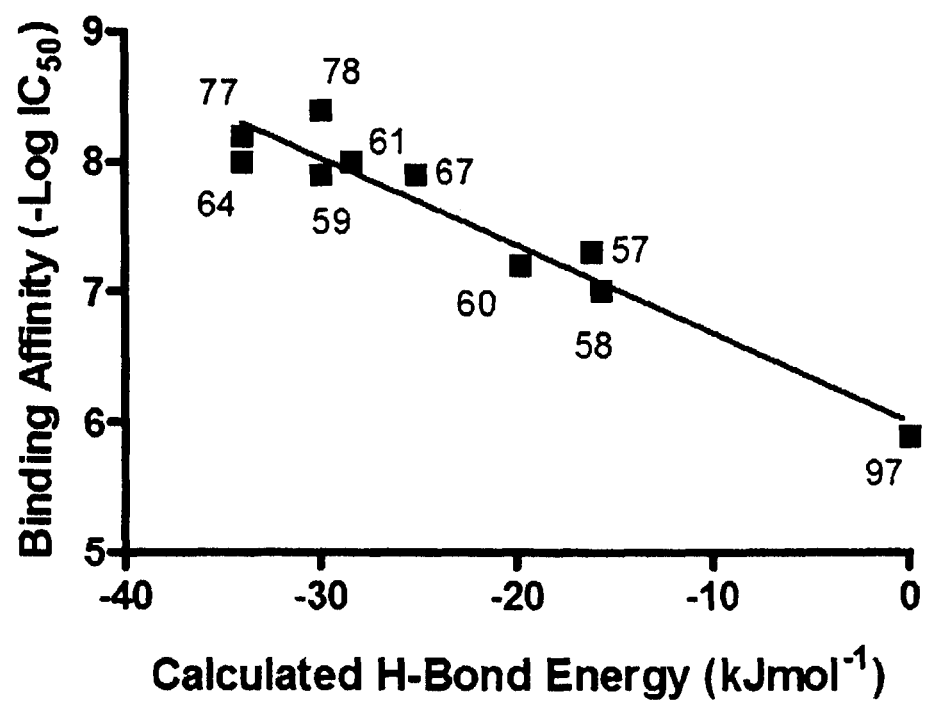
FIG. 6 shows a graphical representation of the linear relationship between binding affinity (–Log IC$_{50}$) of compounds for the C3a receptor C3aR on human monocyte derived macrophages and the calculated hydrogen bond interaction energy (kJmol$^{-1}$) between water and a specific heteroatom in compounds 57, 58, 59, 60, 61, 64, 67, 77, 78 and 97.
Figure 7:
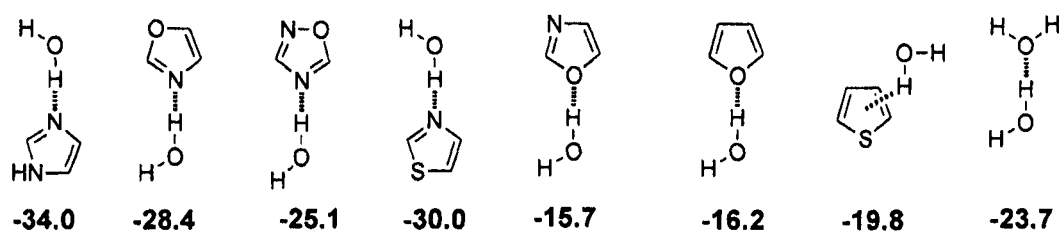
FIG. 7 provides the calculated H-bond interaction energy (kJmol$^{-1}$) between water and heteroatom compound compared with water dimer.
Figure 8A:
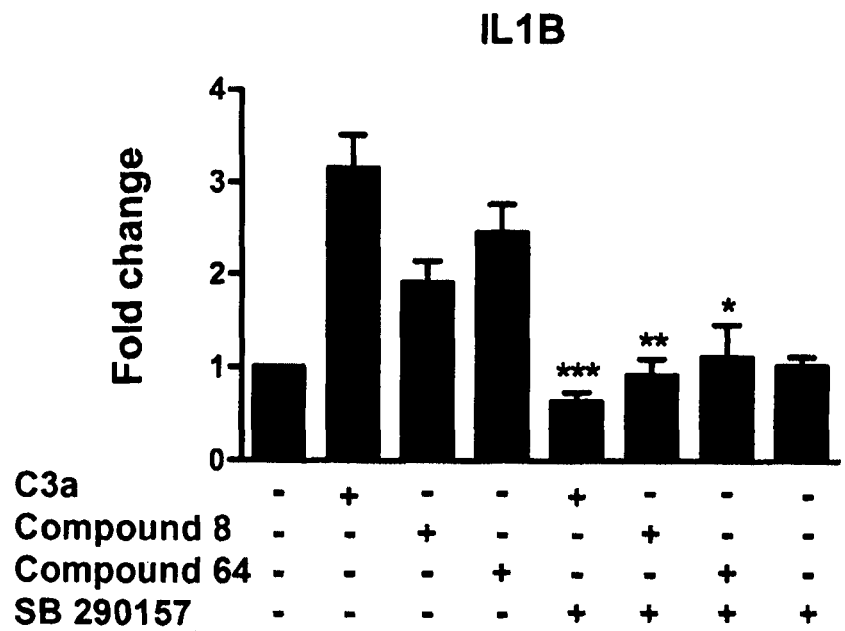
FIG. 8 provides graphical representations showing C3a, compounds 8 and 64 significantly induce gene expression of IL1B (A), IL8 (B), CCL3 (C), EGR1 (D), FOSB (E) and TNF (F), in HMDMs and this effect is prevented by C3a antagonist SB290157. HMDMs were treated with C3a or compounds 8 or 64 (300 nM, 30 minutes)±SB290167 (5 μM, 30 mins preincubation). Gene expression was detected using qRT-PCR and is shown as fold changes from control. The relative gene expression data points represent duplicates that were normalized against 18S housekeeping gene. Fold changes were calculated against control (untreated). Error bars represent mean±SEM of at least three independent experiments. *P<0.05; P<0.01; *P<0.005. Furthermore, when HMDMs were pre-treated with 200 ng/mL pertussis toxin overnight, before adding 300 nM of C3a or compounds 8 or 64 for 30 minutes, all of the responses were also ablated (not shown), confirming that induction of these genes was mediated via a Gi protein coupled receptor (e.g. C3aR) rather than some other off-target receptor.
Figure 8B:
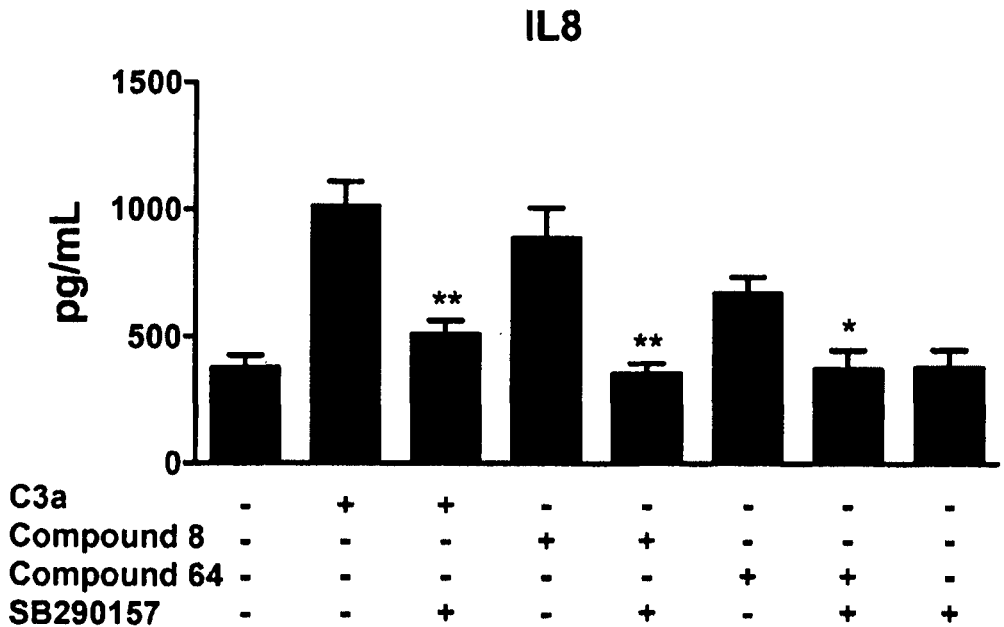
Figure 8C:
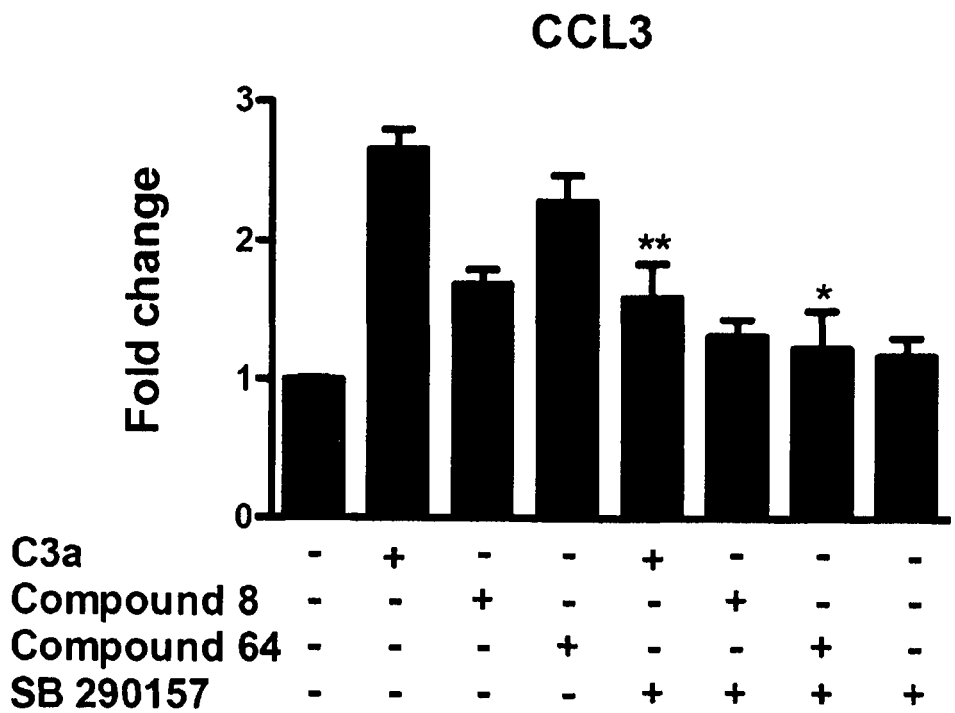
Figure 8D:
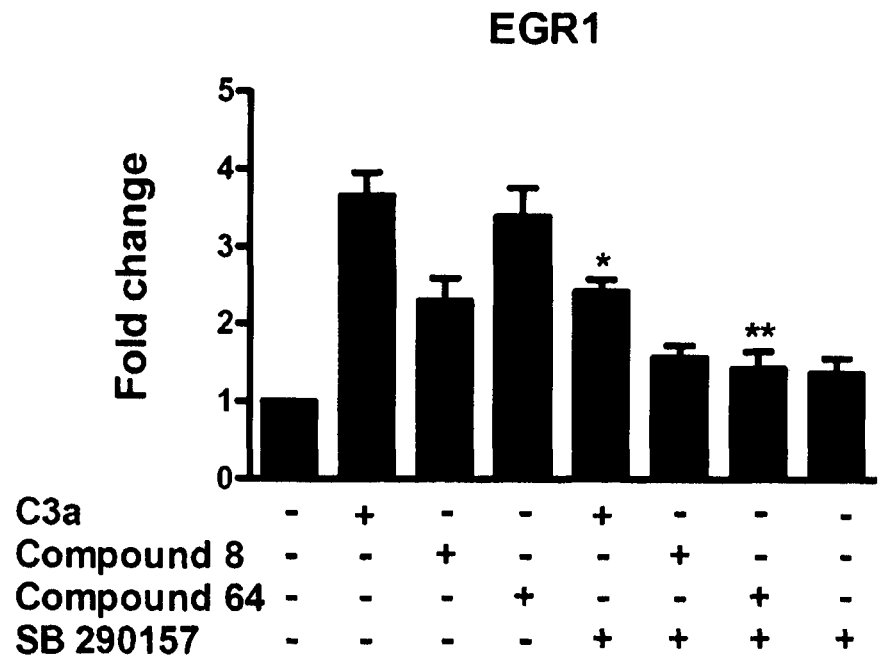
Figure 8E:
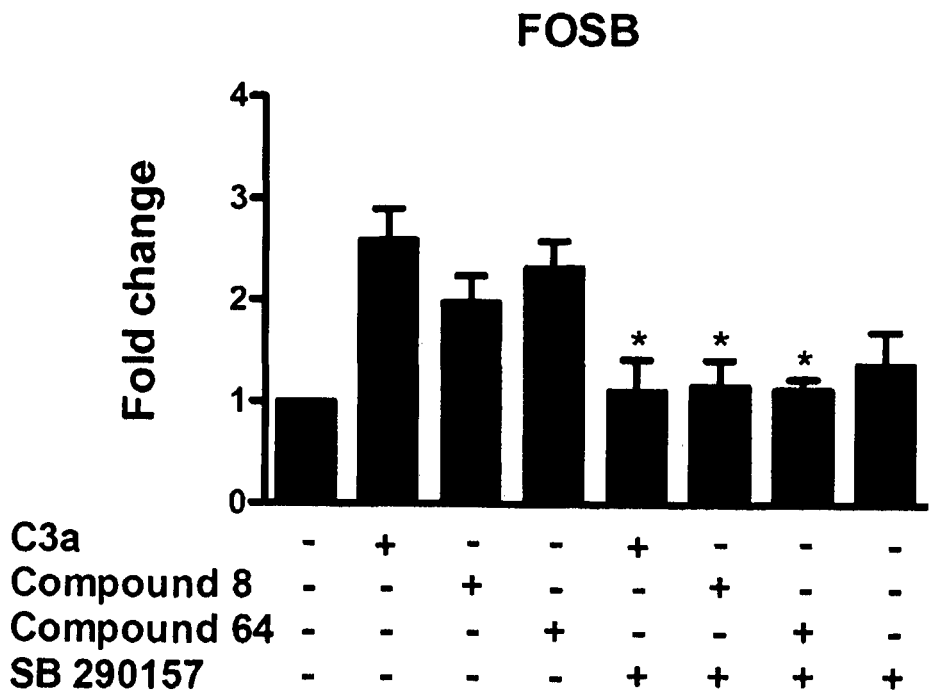
Figure 8F:
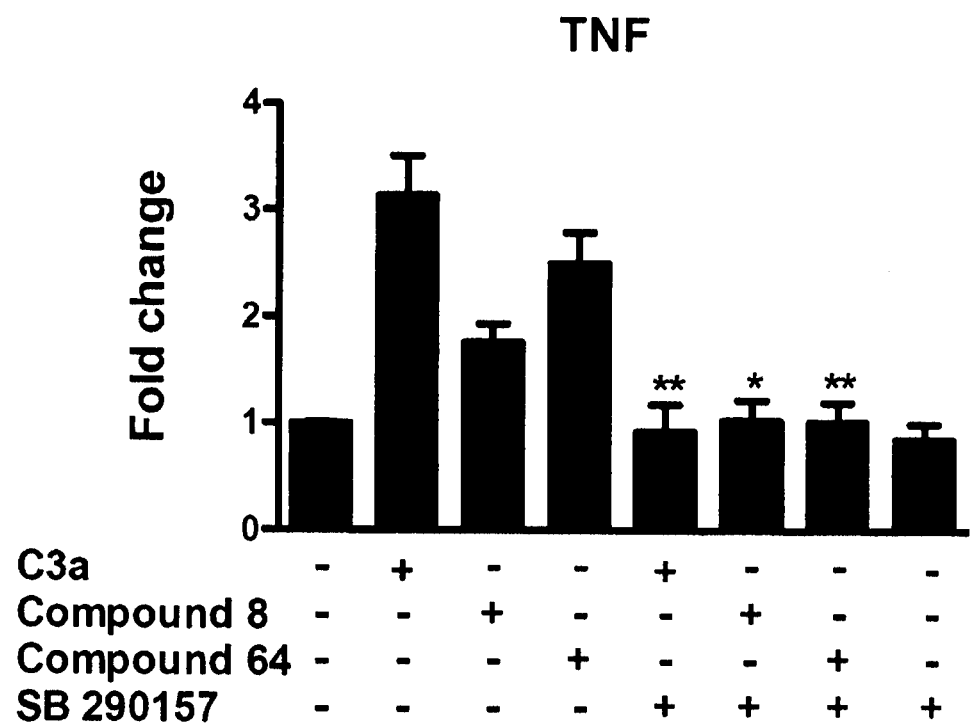

The heterocyclic ring present in all compounds comprising this invention is a very important feature offering a conformationally rigid template from which to append the various R groups and suitably positioned atoms to function as hydrogen bond acceptors. For example Compounds 64, 77, 59, 78, 61, 67, 60, 57, 58 and 97 are structurally identical except for the nature of the heterocyclic ring which allows comparison of just the contribution to receptor binding affinity that the ring offers. A linear correlation between receptor binding affinity (−Log IC$_{50}$) and the calculated hydrogen bond interaction energy with correlation coefficient of $R^2$=0.92 was observed, (Table 14, FIG. 6). This suggests that an increased H-bond interaction with the receptor C3aR would enhance binding. For simplicity the calculated H-bond interaction energy predicted between a specific heterocycle heteroatom and a water molecule was used for the comparison (FIG. 7). Energies were calculated for models minimised by ab initio MP2 methods at the 6-311++G(3d,3p) level of theory with Gaussian 09 software. Additionally, increases in affinity can change the function of the ligands. For instance, when the furan ring of antagonist 57 was replaced with imidazole, which possesses a much better H-bond accepting atom (nitrogen instead of oxygen), the ligand was transformed to a potent full agonist 64.

While not wishing to be bound by theory, it is postulated that compounds having a hydrogen bond accepting heteroatom at positions Y or X have enhanced receptor binding because of hydrogen bond formation with a hydrogen bond donor in the C3a receptor. It is thought that this hydrogen bond interaction may activate the receptor and therefore, compounds in which X and/or Y are hydrogen bond accepting heteroatoms are likely to be agonists of the C3a receptor. On the other hand, those compounds that lack a hydrogen bond accepting heteroatom at positions X and/or Y, may not activate the receptor but still may bind to the receptor, blocking binding of the natural activating C3a, and thereby result in antagonist activity.

TABLE 14

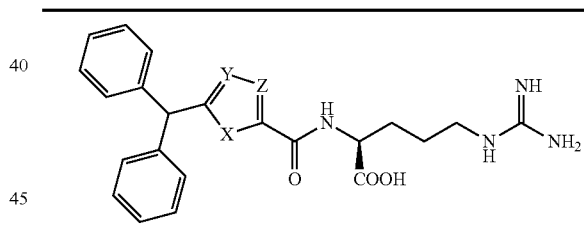

| Compound | X | Y | Z | H-bond interaction energy | −Log IC$_{50}$ |
|---|---|---|---|---|---|
| 64 | NH | N | C—Me | −34.0 | 8.0 |
| 77 | NH | N | CH | −34.0 | 8.2 |
| 59 | S | N | C—Me | −30.0 | 7.9 |
| 78 | S | N | CH | −30.0 | 8.4 |
| 61 | N | O | C—Me | −28.4 | 8.0 |
| 67 | N | N | O | −25.1 | 7.9 |
| 60 | S | CH | CH | −19.8 | 7.2 |
| 57 | O | CH | CH | −16.2 | 7.3 |
| 58 | O | N | C—Me | −15.7 | 7.0 |
| 97 | N | N—Me | C—Me | 0.0 | 5.9 |

Example 101

Regulation of Inflammatory Genes in Macrophages HMDM Isolation and Cell Culture

Human monocyte-derived macrophages (HMDMS) were isolated from buffy coat of anonymous donors provided by the Australian Red Cross Blood Service at Kelvin Grove, Queensland, Australia. White blood cells were separated from other blood components into different layers using Ficoll-Paque Plus Density Centrifugation (GE Healthcare Bio-Science, Uppsala, Sweden) according to manufacturer's instruction. The isolated white blood cells were repeatedly washed with ice-cold water to remove contaminating erythrocytes. $CD14^+$ monocytes were positively selected from white blood cells using $CD14^+$ Macs Magnetic Beads (Miltenyi biotech, Auburn, Calif., USA) after successive magnetic sorting and washings. $CD14^+$ monocytes ($1.5 \times 10^6$ cells/mL) were seeded in 10 mL of IMDM supplemented with 10% fetal calf serum (FBS), 10 U/mL streptomycin, 10 U/mL penicillin and 2 mmol L-glutamine (Invitrogen). To generate HMDMS, 104 U/mL of recombinant human macrophage colony stimulating factor (M-CSF) (Peprotech Inc., rocky Hill, N.J., USA) was added for differentiation. HMDMS were maintained at 37° C. in a humidified incubator with 5% $CO_2$ for a week to fully differentiate. At day 7, the adhered HMDMS were harvested by gentle scraping in saline solution.

HMDM Treatment

HMDMs ($2 \times 10^6$) in 2 mL of IMDM medium were transferred into each well on a 6-well plate. The cells were left to incubate for 6 h to allow adhesion before being serum starved in serum free IMDM to reduce background noise of the C3a treatment. In the time response experiment, cells were treated with 10 nM of C3a or agonist (compound 8 or 64) for 0.5, 1, 2 or 6 h. In concentration response experiments, cells were treated with 1, 10, 100 or 300 nM for 1 h. To prepare the samples for the microarray experiments, cells were treated with agonist at 100-300 nM for 30 min or 1 h in the absence or presence of the antagonist (e.g. SB-290157 or antagonists). Antagonist at 10 µM was pre-incubated for 30 minutes before the addition of C3a. Cells were washed with saline solution at the end of each treatment before the RNA extraction step.

RNA Extraction and Reverse Transcription

Total RNA was extracted from cells using RNeasy Mini Plus kit (Qiagen, USA) according to the manufacturer's instructions. The concentration of the RNA was determined by measuring absorbance at $\lambda=260/280$ nM on a nanodrop spectrophotometer (Thermo Scientific), according to the manufacturer's instructions.

Total RNA (2-5 µg) was reverse transcribed with Superscript III (Invitrogen, USA) using random oligo dT primer. Reagents were incubated (50 min, 50° C.; then 10 min, 70° C.) in thermal cyclers (Bio-Rad) to complete the reaction, cDNA samples were stored at −20° C. until further use. All RNA work was performed on ice (4° C.) to prevent degradation of the RNA samples.

Intracellular Calcium Mobilization Assay

HMDMs were seeded into black-wall, clear bottom 96-well plates (Corning Incorporated, NY) at 50,000 cells/well and left to incubate at 37° C. with 5% CO2 overnight for cells to adhere. The medium was removed before being washed with the assay buffer (1×HBSS, 20 mM HEPES, 2.5 mM probenecid, pH 7.4). To each well was added 100 µL of dye-loading buffer made up of 12 mL calcium buffer, 1% FBS, 25 µL of Fluo-3 dye (final concentration of 4 µM) and 25 µL of 20% pluronic acid. The plate was covered in aluminium foil to protect the light-sensitive dye and left to incubate at 37° C. for 1 h. The dye-loading buffer was removed before the cells were washed with the assay buffer to remove excess loading dye. To each well was added 50 µL of fresh assay buffer before the plate was loaded into a FLIPR (Fluorescent Imaging Plate Reader) that can inject treatments and measure any calcium release. To generate agonist plots, calcium release was monitored for 300 seconds. To generate antagonist plots, calcium release was recorded for 900 seconds, which at the same time would allow incubation for the antagonists. After the initial incubation period, an agonist would be added and the response was recorded for 300 seconds. Intracellular release of calcium was recorded via fluorescence measurements at wavelength of 485 nm for excitation and 520 nm for emission.

Quantitative RT-PCR cDNA (0.5 µg) samples were prepared with 5 µL SYBR® Green PCR master mix (Applied Biosystems™, CA, USA), 2 µL relevant primers (2 µM) and 1 µL $dH_2O$ before being analysed using an ABI 7900HT Fast Real-Time PCR System (Applied Biosystems™, CA, USA) according to the manufacturer's specifications. Fluorescence data was collected during the extension phase (60° C.). The concentration response data for each sample was then normalised against the same data for control housekeeping gene, (18S) to quantify and generate gene expression data. All samples were done in at least duplicate. Primers were designed using the Primer-BLAST software (National Center for Biotechnology Information, USA). Primers contained, amplicons that cross exon-exon boundaries to prevent amplification of genomic DNA. Primer sequences were checked for similar matches with other known human cDNAs using the standard nucleotide-nucleotide Basic Local Alignment Search Tool (BLASTN) to prevent non-specific binding.

As shown in FIG. 8, C3aR agonists compounds 8 and 64 induced expression of inflammatory genes IL1B, IL8, TNF, CCL3, FOSB and EGR1 in human monocyte derived macrophages. These effects are comparable and are all inhibited by C3aR antagonists or blocked by pertussis toxin (Gi protein decoupler).

Enzyme-Linked Immunosorbent Assay (ELISA)

Human renal cortical tissue (10 g) was minced finely, washed several times and agitated for 20 minutes at 37° C. in a Krebs-Henseleit buffer (KHB) containing collagenase type II (1 mg/mL), Cold KHB was added and the solution passed through a 297 µm sieve (50 Mesh, Sigma). After washing three times the tubular fragments were re-suspended in 45% percoll-KHB and centrifuged at 20000×g. A high density band, previously shown to be tubule fragments, was removed and cultured in a serum free, hormonally defined DMEM/F12 media (containing 10 ng/mL epidermal growth factor, 5 µg/mL insulin, 5 mg/mL transferrin, 50 nM hydrocortisone, 50 µM prostaglandin E1, 50 nM selenium and 5 pM triiodothyronine). All experiments were performed on confluent passage 2 HTEC made quiescent by two washes followed by incubation for 24 h in serum and growth factor free DMEM/F12 media. These cells were incubated with C3aR agonists and antagonists.

Supernatant and lysates from cell culture treatment samples were collected and stored separately at −20° C. until further use. Human IL1B, IL8, IL6 and TNF levels were determined using the respective OptEIA™ ELISA kit (BD Biosciences, San Diego, USA) according to the manufacturer's instructions. The readings were recorded on a FLUOstar Optima (BMG LabTechnologies, Offenburg, Germany).

The results for the agonist induced effects are exemplified by compound 8 as shown in Table 15. They demonstrate that compound 8 induces secretion of inflammatory cytokines from primary human kidney cells (this secretion was blocked by C3aR antagonists).

TABLE 15

Induction of cytokines by C3a agonist compound 8 in human kidney tubule cells

| Induction at 40 μM Compound 8 (μM) | 2-fold Fibronectin (ng/ml) | 40-fold IL-6 (ng/ml) | 75-fold TNF (pg/ml) | 75-fold IL-8 (ng/ml) | 80-fold GMCSF (pg/ml/ml) |
|---|---|---|---|---|---|
| 0   | 75.2 ± 29  | 2.4 ± 0.4  | 10.1 ± 2  | 1.8 ± 0.3 | 71.3 ± 23 |
| 1   | 89.6 ± 11  | 2.5 ± 0.1  | 9.9 ± 1   | 1.9 ± 0.4 | 74.6 ± 7.1 |
| 2.5 | 89.0 ± 5   | 8.2 ± 0.6  | 12.3 ± 1  | 5.7 ± 2   | 142.8 ± 10.9 |
| 5   | 149.5 ± 21 | 30.9 ± 2.5 | 76.6 ± 13 | 31.5 ± 5  | 738.0 ± 127.6 |
| 10  | 172.9 ± 20 | 33.5 ± 5   | 117.8 ± 53| 30.4 ± 8  | 1056 ± 147.8 |
| 20  | 200.9 ± 28 | 55.8 ± 12  | 277.9 ± 28| 76.4 ± 18 | 2853 ± 399 |
| 40  | 148.0 ± 32 | 96.9 ± 29  | 757.8 ± 13| 135.0 ± 9 | 5790 ± 726 |

REFERENCES

Boos, L.; Campbell, I. L.; Ames, R.; Wetsel, R. A.; Barnum, S. R., Deletion of the complement anaphylatoxin C3a receptor attenuates, whereas ectopic expression of C3a in the brain exacerbates, experimental autoimmune encephalomyelitis. *J Immunol* 2004, 173, 4708-4714.

Boos, L.; Szalai, A. J.; Barnum, S. R., C3a expressed in the central nervous system protects against LPS-induced shock. *Neurosci Lett* 2005, 387, 68-71.

Drouin, S. M.; Corry, D. B.; Kildsgaard, J.; Wetsel, R. A., Cutting edge: the absence of C3 demonstrates a role for complement in Th2 effector functions in a murine model of pulmonary allergy. *J Immunol* 2001, 167, 4141-4145.

Drouin, S. M.; Corry, D. B.; Hollman, T. J.; Kildsgaard, J.; Wetsel, R. A., Absence of the complement anaphylatoxin C3a receptor suppresses Th2 effector functions in a murine model of pulmonary allergy. *J Immunol* 2002, 169, 5926-5933.

Engstrom, G., Hedblad, B., Janzon, L. & Lindgarde, F. Weight gain in relation to plasma levels of complement factor 3: results from a population-based cohort study. *Diabetologia* 48, 2525-2531 (2005).

Garrett, M. C.; Otten, M. L.; Starke, R. M.; Komotar, R. J.; Magotti, P.; Lambris, J. D.; Rynkowski, M. A.; Connolly, E. S., Synergistic neuroprotective effects of C3a and C5a receptor blockade following intracerebral hemorrhage. *Brain Res* 2009, 1298, 171-177.

Hernandez, D.; Vilar, G.; Riego, E.; Canedo, L. M.; Cuevas, C.; Albericio, F.; Alvarez, M. Synthesis of IB-01211, a cyclic peptide containing 2,4-concatenated thia- and oxazoles, via Hantzsch macrocyclization. *Organic letters* 2007, 9, 809-11.

Humbles, A. A.; Lu, B.; Nilsson, C. A.; Lilly, C.; Israel, E.; Fujiwara, Y.; Gerard, N. P.; Gerard, C., A role for the C3a anaphylatoxin receptor in the effector phase of asthma. *Nature* 2000, 406, 998-1001.

Hutamekalin P, Takeda K, Tani M, Tsuga Y, Ogawa N, Mizutani N, Yoshino S. Effect of the C3a-receptor antagonist SB 290157 on anti-OVA polyclonal antibody-induced arthritis. *J Pharmacol Sci.* 2010, 112, 56-63.

Jacob, A.; Bao, L.; Brorson, J.; Quigg, R. J.; Alexander, J. J., C3aR inhibition reduces neurodegeneration in experimental lupus. *Lupus* 2009, 19, 73-82.

Kawamoto, S.; Yalcindag, A.; Laouini, D.; Brodeur, S.; Bryce, P.; Lu, B.; Humbles, A. A.; Oettgen, H.; Gerard, C.; Geha, R. S., The anaphylatoxin C3a downregulates the Th2 response to epicutaneously introduced antigen. *J Clin Invest* 2004, 114, 399-407.

Kildsgaard, J.; Hollmann, T. J.; Matthews, K. W.; Bian, K.; Murad, F.; Wetsel, R. A., Cutting edge: targeted disruption of the C3a receptor gene demonstrates a novel protective anti-inflammatory role for C3a in endotoxin-shock. *J Immunol* 2000, 165, 5406-5409.

Kirschfink, M., Targeting complement in therapy. *Immunol Rev* 2001, 180, 177-189.

Malmsten, M.; Schtmdtchen, A. Antimicrobial C3a —Biology, biophysics, and evolution. *Curr. Top. Innate Immunity* 2007, 598, 141-158.

Mamane, Y., et al. The C3a Anaphylatoxin Receptor Is a Key Mediator of Insulin Resistance and Functions by Modulating Adipose Tissue Macrophage Infiltration and Activation. *Diabetes* 58, 2006-2017 (2009). (a)

Mamane, Y.; Chung Chan, C.; Lavallee, G.; Morin, N.; Xu, L. J.; Huang, J.; Gordon, R.; Thomas, W.; Lamb, J.; Schadt, E. E.; Kennedy, B. P.; Mancini, J. A., The C3a anaphylatoxin receptor is a key mediator of insulin resistance and functions by modulating adipose tissue macrophage infiltration and activation. *Diabetes* 2009, 58, 2006-2017. (b)

Masters, S L; Simon, A; Aksentijevich, I; Horror Autoinflammaticus: The Molecular Pathophysiology of Autoinflammatory Disease, *Ann. Rev. Immunol.* 2009, 27, 621-668.

Mizutani, N.; Nabe, T.; Yoshino, S., Complement C3a regulates late asthmatic response and airway hyperresponsiveness in mice. *J Immunol* 2009, 183, 4039-4046.

Mocco, J.; Mack, W. J.; Ducruet, A. F.; Sosunov, S. A.; Sughrue, M. E.; Hassid, B. G.; Nair, M. N.; Laufer, I.; Komotar, R. J.; Claire, M.; Holland, H.; Pinsky, D. J.; Connolly, E. S., Jr., Complement component C3 mediates inflammatory injury following focal cerebral ischemia. *Circ Res* 2006, 99, 209-217.

Mueller-Ortiz, S. L.; Hohmann, T. J.; Haviland, D. L.; Wetsel, R. A., Ablation of the complement C3a anaphylatoxin receptor causes enhanced killing of *Pseudomonas aeruginosa* in a mouse model of pneumonia. *Am J Physiol Lung Cell Mol Physiol* 2006, 291, L157-165.

Nordahl, E. A.; Rydengard, V.; Nyberg, P.; Nitsche, D. P.; Morgelin, M.; Malmsten, M.; Bjorck, L.; Schmidtchen, A. Activation of the complement system generates antibacterial peptides. *Proc. Natl. Acad. Sci. USA* 2004, 101, 16879-16884.

van Oostrom, A., Alipour, A., Plokker, T. W. M., Sniderman, A. D. & Cabezas, M. C. The metabolic syndrome in relation to complement component 3 and postprandial lipemia in patients from an outpatient lipid clinic and healthy volunteers. *Atherosclerosis* 190, 167-173 (2007).

Pasupuleti, M.; Walse, B. r.; Svensson, B.; Malmsten, M.; Schmidtchen, A., Rational Design of Antimicrobial C3a Analogues with Enhanced Effects against Staphylococci Using an Integrated Structure and Function-Based Approach. *Biochemistry* 2008, 47, 9057-9070.
Patani, G. A and LaVoie, E. J., Bioisosterism: A rational approach in Drug Design. *Chem. Rev.,* 96, 3147-3176 (1996).
Peterfy, H.; Toth, G.; Pecht, I.; Erdei, A. C3a-derived peptide binds to the type I Fc epsilon R and inhibits proximal-coupling signal processes and cytokine secretion by mast cells. *Int. Immunol.* 2008, 20, 1239-1245.
Peterlin-Magic, L. & Kikelj, D. Arginine Mimetics. *Tetrahedron,* 2001, 57, 7073-7105.
Phillips, C. M., et al. Complement component 3 polymorphisms interact with polyunsaturated fatty acids to modulate risk of metabolic syndrome. *Am J Clin Nutr* 90, 1665-1673 (2009).
Phillips, A. J.; Uto, Y.; Wipf, P.; Reno, M. J.; Williams, D. R. Synthesis of functionalized oxazolines and oxazoles with DAST and Deoxo-Fluor. *Organic letters* 2000, 2, 1165-8.
Rahpeymai, Y.; Hietala, M. A.; Wilhelmsson, U.; Fotheringham, A.; Davies, I.; Nilsson, A. K.; Zwirner, J.; Wetsel, R. A.; Gerard, C.; Pekny, M.; Pekna, M., Complement: a novel factor in basal and ischemia-induced neurogenesis. *EMBO J.* 2006, 25, 1364-1374.
Rynkowski, M. A.; Kim, G. H.; Garrett, M. C.; Zacharia, B. E.; Often, M. L.; Sosunov, S. A.; Komotar, R. J.; Hassid, B. G.; Ducruet, A. F.; Lambris, J. D.; Connolly, E. S., C3a receptor antagonist attenuates brain injury after intracerebral hemorrhage. *J Cereb Blood Flow Metab* 2009, 29, 98-107.
Sonesson, A.; Ringstad, L.; Nordahl, E. A.; Malmsten, M.; Morgelin, M.; Schmidtchen, A. Antifungal activity of C3a and C3a-derived peptides against *Candida. Biochim. Biophys., Acta-Biomembranes* 2007, 1768, 346-353.
Tang, Z.; Lu, B.; Hatch, E.; Sacks, S. H.; Sheerin, N. S., C3a mediates epithelial-to-mesenchymal transition in proteinuric nephropathy. *J Am Soc Nephrol* 2009, 20, 593-603.
Wagner, B.; Schumann, D.; Linne, U.; Koert, U.; Marahiel, M. A. Rational design of bacitracin A derivatives by incorporating natural product derived heterocycles. *Journal of the American Chemical Society* 2006, 128, 10513-20.
Wenderfer, S. E.; Wang, H.; Ke, B.; Wetsel, R. A.; Braun, M. C., C3a receptor deficiency accelerates the onset of renal injury in the MRL/lpr mouse. *Mol Immunol* 2009, 46, 1397-1404.
Zipfel, P. F.; Skerka, C. Complement regulators and inhibitory proteins *Nature Rev Immunol.* 2009, 9, 729-740.

The invention claimed is:

1. A compound of formula (I):

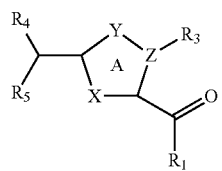

(I)

wherein the ring A is selected from one of the following:

wherein X is N or CH;
Y is O, S, NH, N($C_{1-3}$alkyl) or $CH_2$; and
Z is N or C, provided that when Z is N, $R_3$ is absent;

wherein X is O, S, NH, N($C_{1-3}$alkyl) or $CH_2$;
Y is N; and
Z is N or C, provided that when Z is N, $R_3$ is absent;

wherein X is N or CH;
Y is N or CH; and
Z is O, S, N or CH, provided that when Z is O or S, $R_3$ is absent;

$R_1$ is selected from arginine or arginine mimetics;
$R_3$ is selected from hydrogen, halogen, alkyl, alkenyl, cycloalkyl, cycloalkenyl, aryl, heterocyclyl or heteroaryl;
$R_4$ is selected from alkyl, alkenyl, —$(CH_2)_m$cycloalkyl, —$(CH_2)_m$aryl, —$(CH)_m$heterocyclyl, —$(CH_2)_m$heteroaryl, —$(CH_2)_m$NHC(=NH)$NH_2$, —$(CH_2)_m$$CONH_2$, —$(CH_2)_m$$CO_2H$, —$(CH_2)_m$$SR_6$, —$(CH_2)_m$$OR_6$,
$R_5$ is selected from alkyl, alkenyl, cycloalkyl, cycloalkenyl, aryl, heterocyclyl, heteroaryl or —$NHR_7$,
$R_6$ is selected from hydrogen, alkyl, cycloalkyl, aryl, heterocyclyl or heteroaryl;
$R_7$ is selected from —C(O)$R_8$, —C(O)O$R_8$, —C(O)NH$R_8$ or —S(O)$_2$$R_8$;
$R_8$ is selected from alkyl, alkenyl, —(CHR$_9$)$_p$cycloalkyl, —(CHR$_9$)$_p$cycloalkenyl, —(CHR$_9$)$_p$aryl, —(CHR$_9$)$_p$heterocyclyl or —(CHR$_9$)$_p$heteroaryl;
$R_9$ is selected from hydrogen, alkyl, alkenyl, cycloalkyl, cycloalkenyl, aryl, heterocyclyl or heteroaryl;
m is 0 or an integer from 1 to 6; and
p is 0 or an integer from 1 to 6;
wherein each cycloalkyl, cycloalkenyl, aryl, heteroaryl and heterocyclyl group may be optionally substituted with one or more optional substituents;
or a pharmaceutically acceptable salt thereof.

2. A compound of formula (I) according to claim 1 which is a compound of formula (II):

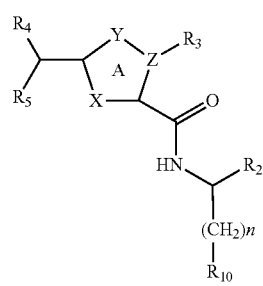

(II)

wherein $R_{10}$ is selected from guanidine or a guanidine mimetic;

$R_2$ is selected from $CO_2H$ and a carboxylic acid bioisostere;

n is an integer from 1 to 4;

A, X, Y, Z, $R_3$, $R_4$ and $R_5$ are as defined for formula (I).

3. A compound according to claim 1 wherein the ring A is selected from one of:

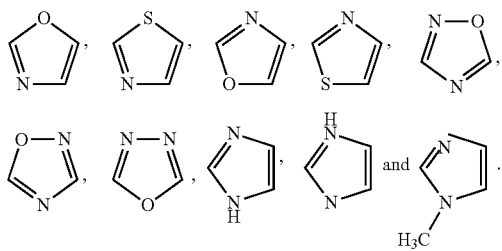

4. A compound according to claim 3 wherein the ring A is selected from one of:

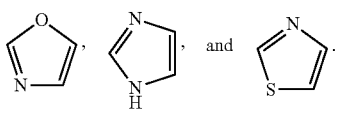

5. A compound according to claim 2 wherein $R_{10}$ is selected from:

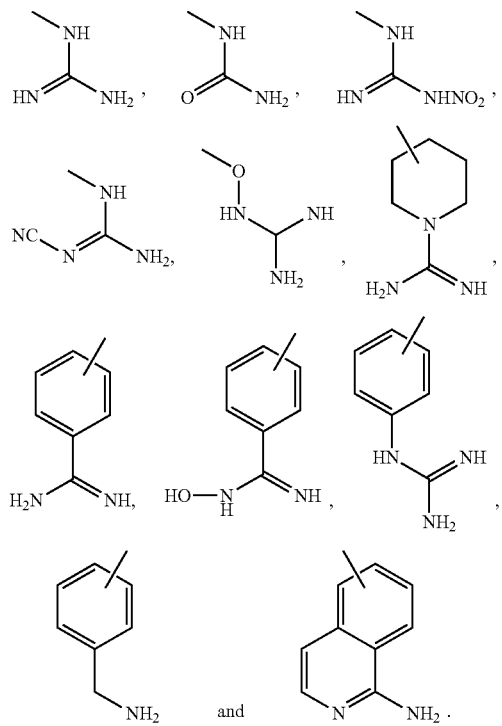

6. A compound according to claim 5 wherein $R_{10}$ is

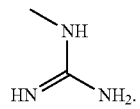

7. A compound according to claim 2 wherein $R_2$ is selected from $-CO_2H$, $-C(OH)(CF_3)_2$, $-C(O)NHSO_2aryl$, $-C(O)NHSO_2alkyl$,

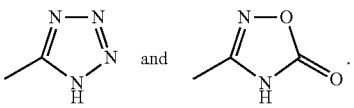

8. A compound according to claim 7 wherein $R_2$ is $CO_2H$.

9. A compound according to claim 1 wherein $R_3$ is selected from hydrogen, $-C_{1-6}$alkyl, $-C_{2-6}$alkenyl, $-C_{5-6}$cycloalkyl, cycloalkenyl, aryl, and 5 or 6 membered heterocyclyl and heteroaryl.

10. A compound according to claim 9 wherein $R_3$ is hydrogen.

11. A compound according to claim 9 wherein $R_3$ is selected from methyl, ethyl, propyl, isopropyl, cyclohexyl, cyclohexenyl, cyclohexadienyl and phenyl.

12. A compound according to claim 1 wherein $R_4$ is selected from $-CH_3$, cyclohexyl, phenyl, $-(CH_2)_2NHC(=NH)NH_2$, $-CH_2-CONH_2$, $-CH_2CO_2H$, $-CH_2SH$, $-(CH_2)_2CONH_2$, $-(CH_2)_2CO_2H$, $-CH_2(4$-imidazolyl$)$, $-CH(CH_3)CH_2CH_3$, $-CH_2CH(CH_3)_2$, $-(CH_2)_2SCH_3$, $-CH_2Ph$, $-CH_2OH$, $-CH(CH_3)OH$, $-CH_2(3$-indolyl$)$, $-CH_2(4$-hydroxyphenyl$)$, $-CH(CH_3)_2$ and $-(CH_2)$cyclohexyl.

13. A compound according to claim 12 wherein $R_4$ is selected from $-CH_2CH(CH_3)_2$ and $-CH(CH_3)CH_2CH_3$.

14. A compound according to claim 1 wherein $R_5$ is selected from $-NHC(O)R_8$, $-NHC(O)OR_8$, $-NHC(O)NHR_8$ and $-NHSO_2R_8$.

15. A compound according to claim 14 wherein $R_8$ is selected from $C_{1-6}$alkyl, cycloalkyl, cycloalkenyl, aryl, heterocyclyl, heteroaryl, $-CH_2$cycloalkyl, $-CH_2$cycloalkenyl, $-CH_2$aryl, $-CH_2$heterocyclyl, $-CH_2$heteroaryl and $-CH(CH_3)$aryl, wherein each cycloalkyl, cycloalkenyl, aryl, heterocyclyl and heteroaryl are optionally substituted with one or more of $C_{1-6}$alkyl, $-NHC_{1-6}$alkyl, $-N(C_{1-6}$alkyl$)_2$, halogen, $-C(O)$phenyl, -Ophenyl, $-CF_3$, $-N=N$-phenyl and OH.

16. A compound according to claim 2 wherein n is 2 or 3.

17. A compound according to claim 1 wherein m is 0, 1, 2 or 3.

18. A compound according to claim 1 wherein p is 0, 1 or 2.

19. A pharmaceutical composition comprising a compound of formula (I) according to claim 1 or a pharmaceutically acceptable salt thereof and one or more pharmaceutically acceptable carriers, diluents or excipients.

20. A method of modulating C3a receptor comprising exposing the receptor to a compound of formula (I) according to claim 1 or a pharmaceutically acceptable salt thereof.

21. A method of treating, delaying the onset of or reducing the risk of an inflammatory disease, obesity, Type 2 diabetes, metabolic syndrome and associated metabolic or cardiovascular disorders, infectious diseases, or inflammatory complications arising from infection, comprising administering to a subject an effective amount of a compound of formula (I) according to claim 1 or a pharmaceutically acceptable salt thereof.

22. A method of stimulating an immune response in a subject comprising administering to a subject an effective amount of a compound of formula (I) according to claim 1 or a pharmaceutically acceptable salt thereof.

23. A compound according to claim 1 which is Boc-leucine oxazole-arginine-OH:

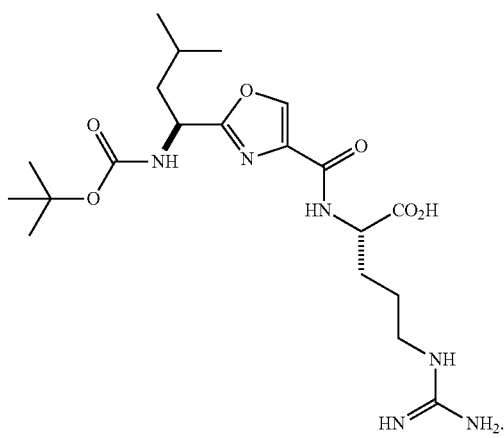 [SMILES: CC(C)C[C@H](NC(=O)OC(C)(C)C)c1nc(C(=O)N[C@@H](CCCNC(=N)N)C(=O)O)co1]

24. A compound according to claim 1 which is 3-Indole carboxylic acid-Leucine-Oxazole-Arginine-OH:

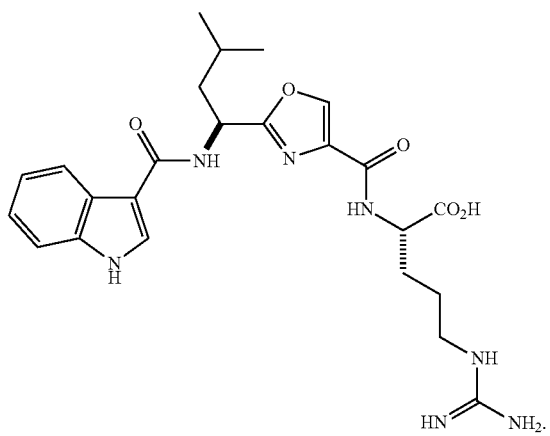 [SMILES: CC(C)C[C@H](NC(=O)c1c[nH]c2ccccc12)c1nc(C(=O)N[C@@H](CCCNC(=N)N)C(=O)O)co1]

25. A pharmaceutically acceptable salt according to claim 1 where the cation has the following structure:

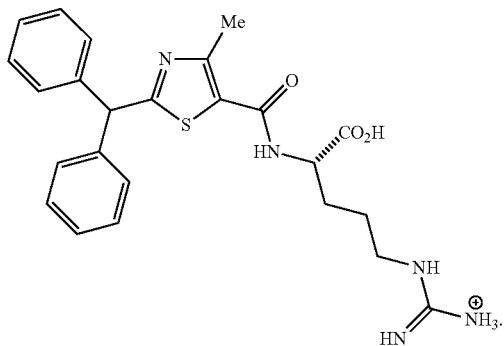

26. A compound according to claim 1 which is 2-Benzhydryl-1,5-Dimethyl imidazole-4-carboxyl-Arginine:

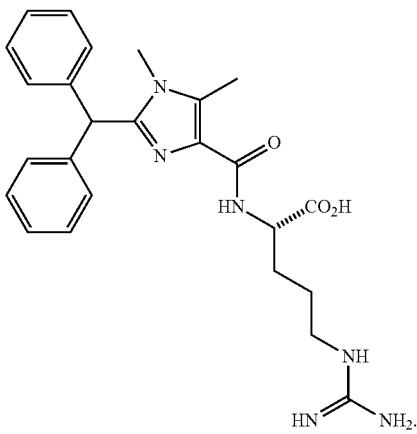 [SMILES: Cc1c(C(=O)N[C@@H](CCCNC(=N)N)C(=O)O)nc(C(c2ccccc2)c2ccccc2)n1C]

* * * * *